US007825222B2

(12) United States Patent
Aversa et al.

(10) Patent No.: US 7,825,222 B2
(45) Date of Patent: Nov. 2, 2010

(54) THERAPEUTIC BINDING MOLECULES

(75) Inventors: Gregorio Aversa, Vancouver (CA); Frank Kolbinger, Neuenburg (DE); Josè M Carballido Herrera, Perchtoldsdorf (AT); András Aszódi, Vienna (AT); José W Saldanha, Enfield (GB); Bruce M Hall, Strathfield (AU)

(73) Assignee: Novartis AG, Basel (CH)

( * ) Notice: Subject to any disclaimer, the term of this patent is extended or adjusted under 35 U.S.C. 154(b) by 853 days.

(21) Appl. No.: 11/297,317

(22) Filed: Dec. 8, 2005

(65) Prior Publication Data

US 2006/0088525 A1 Apr. 27, 2006

Related U.S. Application Data

(63) Continuation of application No. 10/666,332, filed on Sep. 18, 2003, now abandoned, and a continuation-in-part of application No. 10/467,546, filed as application No. PCT/EP02/01420 on Feb. 11, 2002, now abandoned.

(30) Foreign Application Priority Data

Dec. 2, 2001 (GB) ................................ 0103389.3

(51) Int. Cl.
*C07K 16/00* (2006.01)
*C07K 16/46* (2006.01)

(52) U.S. Cl. ............................. 530/388.1; 530/388.15; 530/387.3; 424/130.1

(58) Field of Classification Search ....................... None
See application file for complete search history.

(56) References Cited

U.S. PATENT DOCUMENTS 5,759,808 A 6/1998 Casterman et al.

FOREIGN PATENT DOCUMENTS

WO 98/11918 3/1998
WO WO 02/072832 A2 9/2002

OTHER PUBLICATIONS

Janeway et al. Immunobiology, 3rd Ed. Garland Press, 1997, p. 3:7-3:11.*

Fundamental Immunology, William E. Paul, MD 3rd ed. 1993, p. 242.*

Portolano et al., J. Immunology, 1993, vol. 150. p. 880-887.*

Aversa et al., "Use of Monoclonal Antibodies to Study in vivo and in vitro Activated Lymphocytes", Transplantation Proceedings, vol. 21, No. 1, part 1, pp. 349-350 (1989).

Aversa et al., "A Monoclonal Antibodi (A6) Recognizing a Unique Epitope Restricted to CD45RO and—RB Isoforms of the Leukocyte Common Antigen Family Identifies Functional T Cell Subsets", Cellular Immunology, vol. 158, No. 2, pp. 314-328 (1994).

Kolbinger et al., "Humanization of a Mouse Anti-Human IgE Antibody: A Potential Therapeutic for IgE-Mediated Allergies", Protein Engineering, vol. 6, No. 8, pp. 971-980 (1993).

Petersen et al., "Autoreactive and immunoregulatory T-Cell Subsets in Insulin-Dependent Diabetes Mellitus", Diabetologia, vol. 42, pp. 443-449 (1999).

Trowbridge et al., "NL6 CD45: An Emerging Role as a Protein Tyrosine Phosphatase Required for Lymphocyte Activation and Development", Annu. Rev. Immunol., vol. 12, pp. 85-116 (1994).

Sewell et al., "CD45 Workshop Panel Report", Proc 6th Intern Workshop and Conference held in Kobe, JP, Nov. 10-14, 1996, pp. 499-505 (1996).

Aversa et al., "Cell Surface Markers of T-Cell Activation", Transplantation Reviews, vol. 5, No. 1, pp. 9-30 (1991).

Morimoto et al., "T18 CD45 Cluster Report", Proc 5th Intern Workshop and Conference held in Boston, US, Nov. 3-7, 1993, pp. 386-398 (1993).

Sasaki et al., "New Insights into the Transmembrane Protein Tyrosine Phosphatase CD45", Intern. J. Biochem. & Cell Biol., vol. 33, pp. 1041-1046 (2001).

Dunn-Walters et al., "Effect of Somatic Hypermutation on Potential N-glycosylation Sites in Human Immunoglobulin Heavy Chain Vaiable Regions", Molecular Immunology, 2000 vol. 37 pp. 107-113.

Friend et al., "Phase I Study of an Engineered Aglycosylated Humanized CD3 Antibody in Renal Transplant Rejection", Transplantation, 1999 vol. 68 No. 11 pp. 1632-1637.

Gregori et al., "Anti-CD45RO/RB mAb a New Tool for Tolerance Induction", The FASEB Journal, 2003 vol. 17 No. 7 p. C63.

* cited by examiner

*Primary Examiner*—Michael Szperka
*Assistant Examiner*—Yunsoo Kim

(57) ABSTRACT

A molecule comprising at least one antigen binding site, comprising in sequence the hypervariable regions CDR1, CDR2 and CDR3, said CDR1 having the amino acid sequence Asn-Tyr-Ile-Ile-His (NYIIH), said CDR2 having the amino acid sequence Tyr-Phe-Asn-Pro-Tyr-Asn-His-Gly-Thr-Lys-Tyr-Asn-Glu-Lys-Phe-Lys-Gly (YFNPYNHGT-KYNEKFKG) and said CDR3 having the amino acid sequence Ser-Gly-Pro-Tyr-Ala-Trp-Phe-Asp-Thr (SG-PYAWFDT); e.g. further comprising in sequence the hypervariable regions CDR1', CDR2' and CDR3', CDR1' having the amino acid sequence Arg-Ala-Ser-Gln-Asn-Ile-Gly-Thr-Ser-Ile-Gln (RASQNIGTSIQ), CDR2' having the amino acid sequence Ser-Ser-Ser-Glu-Ser-Ile-Ser (SSSESIS) and CDR3' having the amino acid sequence Gln-Gln-Ser-Asn-Thr-Trp-Pro-Phe-Thr (QQSNTWPFT), e.g. a chimeric or humanised antibody, useful as a pharmaceutical.

13 Claims, 5 Drawing Sheets

THERAPEUTIC BINDING MOLECULES

FIELD OF THE INVENTION

The present invention relates to organic compounds, such as to binding molecules against CD45 antigen isoforms, such as for example monoclonal antibodies (mAbs).

BACKGROUND OF THE INVENTION

One approach in the treatment of a variety of diseases is to achieve the elimination or the inactivation of pathogenic leukocytes and the potential for induction of tolerance to inactivate pathological immune responses.

Organ, cell and tissue transplant rejection and the various autoimmune diseases are thought to be primarily the result of T-cell mediated immune response triggered by helper T-cells which are capable of recognizing specific antigens which are captured, processed and presented to the helper T cells by antigen presenting cell (APC) such as macrophages and dendritic cells, in the form of an antigen-MHC complex, i.e. the helper T-cell when recognizing specific antigens is stimulated to produce cytokines such as IL-2 and to express or upregulate some cytokine receptors and other activation molecules and to proliferate. Some of these activated helper T-cells may act directly or indirectly, i.e. assisting effector cytotoxic T-cells or B cells, to destroy cells or tissues expressing the selected antigen. After the termination of the immune response some of the mature clonally selected cells remain as memory helper and memory cytotoxic T-cells, which circulate in the body and rapidly recognize the antigen if appearing again. If the antigen triggering this response is an innocuous environmental antigen the result is allergy, if the antigen is not a foreign antigen, but a self antigen, it can result is autoimmune disease; if the antigen is an antigen from a transplanted organ, the result can be graft rejection.

The immune system has developed to recognize self from non-self. This property enables an organism to survive in an environment exposed to the daily challenges of pathogens. This specificity for non-self and tolerance towards self arises during the development of the T cell repertoire in the thymus through processes of positive and negative selection, which also comprise the recognition and elimination of autoreactive T cells. This type of tolerance is referred to as central tolerance. However, some of these autoreactive cells escape this selective mechanism and pose a potential hazard for the development of autoimmune diseases. To control the autoreactive T cells that have escaped to the periphery, the immune system has peripheral regulatory mechanisms that provide protection against autoimmunity. These mechanisms are a basis for peripheral tolerance.

Cell surface antigens recognized by specific mAbs are generally designated by a CD (Cluster of Differentiation) number assigned by successive International Leukocyte Typing workshops and the term CD45 applied herein refers to the cell surface leukocyte common antigen CD45; and an mAb to that antigen is designated herein as "anti-CD45".

Antibodies against the leukocyte common antigen (LCA) or CD45 are a major component of anti-lymphocyte globulin (ALG). CD45 belongs to the family of transmembrane tyrosine phosphatases and is both a positive and negative regulator of cell activation, depending upon receptor interaction. The phosphatase activity of CD45 appears to be required for activation of Src-family kinases associated with antigen receptor of B and T lymphocytes (Trowbridge I S et al, Annu Rev Immunol. 1994; 12:85-116). Thus, in T cell activation, CD45 is essential for signal 1 and CD45-deficient cells have profound defects in TCR-mediated activation events.

The CD45 antigen exists in different isoforms comprising a family of transmembrane glycoproteins. Distinct isoforms of CD45 differ in their extracellular domain structure which arise from alternative splicing of 3 variable exons coding for part of the CD45 extracellular region (Streuli M F. et al, J. Exp. Med. 1987; 166:1548-1566). The various isoforms of CD45 have different extra-cellular domains, but have the same transmembrane and cytoplasmic segments having two homologous, highly conserved phosphatase domains of approximately 300 residues. Different isoform combinations are differentially expressed on subpopulations of T and B lymphocytes (Thomas M L. et al, Immunol. Today 1988; 9:320-325). Some monoclonal antibodies recognize an epitope common to all the different isoforms, while other mAbs have a restricted (CD45R) specificity, dependent on which of the alternatively spliced exons (A, B or C) they recognize. For example, monoclonal antibodies recognizing the product of exon A are consequently designated CD45RA, those recognizing the various isoforms containing exon B have been designated CD45RB (Beverley PCL et al, Immunol. Supp. 1988; 1:3-5). Antibodies such as UCHL1 selectively bind to the 180 kDa isoform CD45RO (without any of the variable exons A, B or C) which appears to be restricted to a subset of activated T cells, memory cells and cortical thymocytes and is not detected on B cells (Terry L A et al, Immunol. 1988; 64:331-336).

DESCRIPTION OF THE INVENTION

Figure 1:
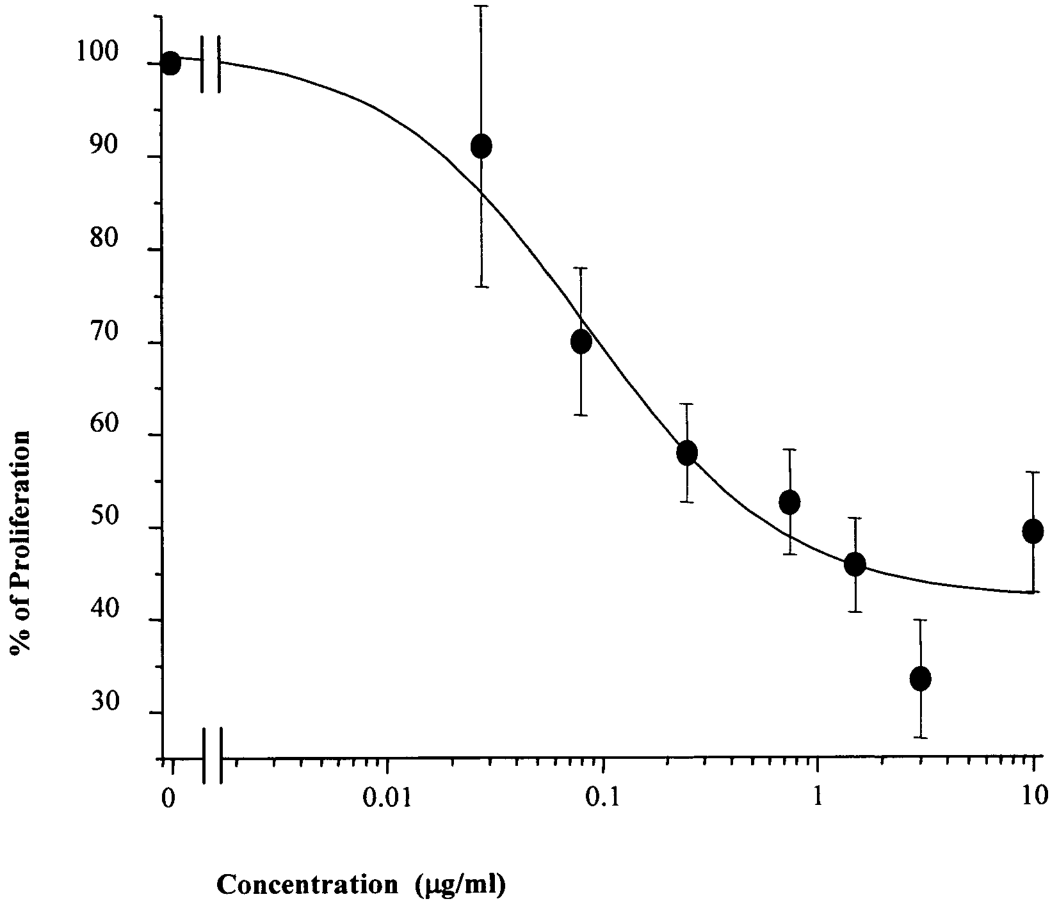
FIG. 1 shows that the inhibition of primary MLR by the "candidate mAb" is dose-dependent in the range of 0.001 and 10 μg/ml. "Concentration" is concentration of the "candidate mAb".
Figure 2:
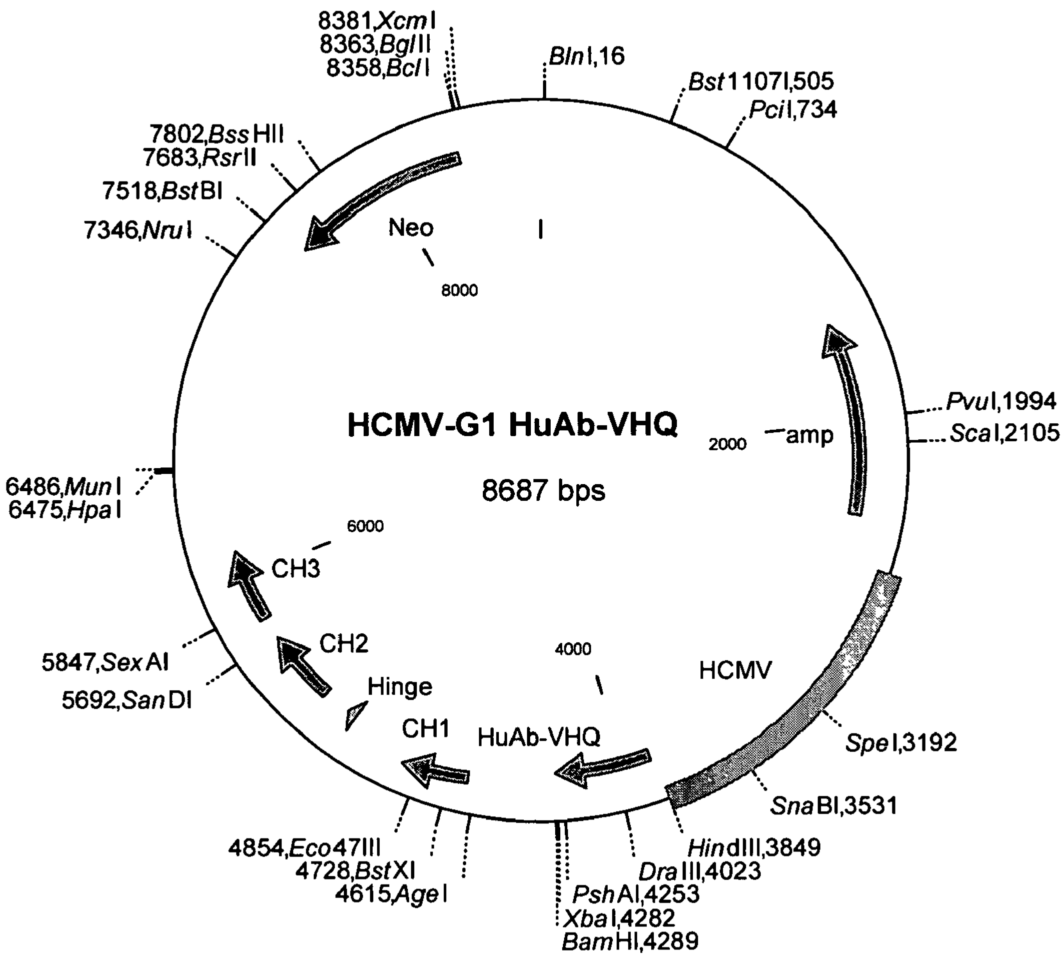
FIG. 2 shows the plasmid map of the expression vector HCMV-G1 HuAb-VHQ comprising the heavy chain having the nucleotide sequence SEQ ID NO:12 (3921-4274) in the complete expression vector nucleotide sequence SEQ ID NO:15.
Figure 3:
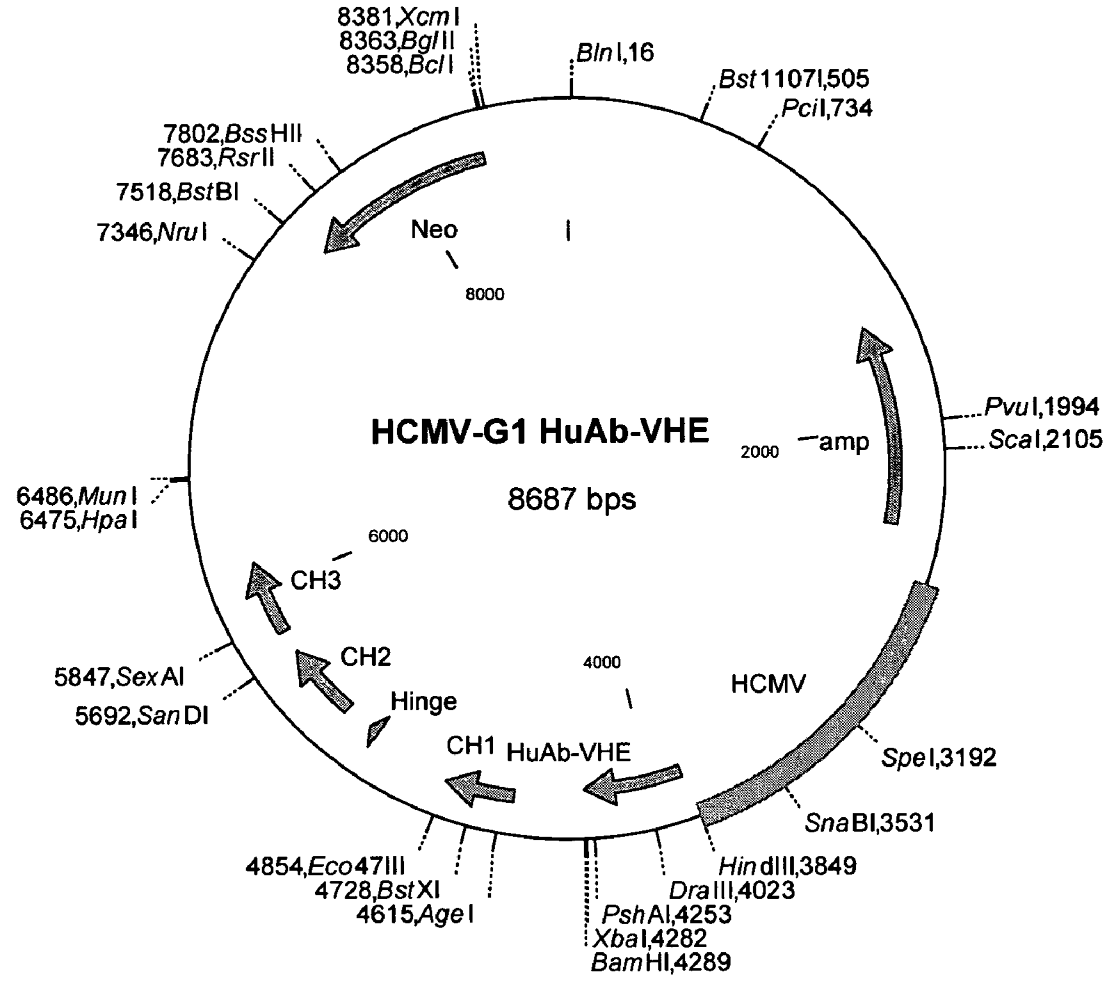
FIG. 3 shows the plasmid map of the expression vector HCMV-G1 HuAb-VHE comprising the heavy chain having the nucleotide sequence SEQ ID NO:11 (3921-4274) in the complete expression vector nucleotide sequence SEQ ID NO:16.
Figure 4:
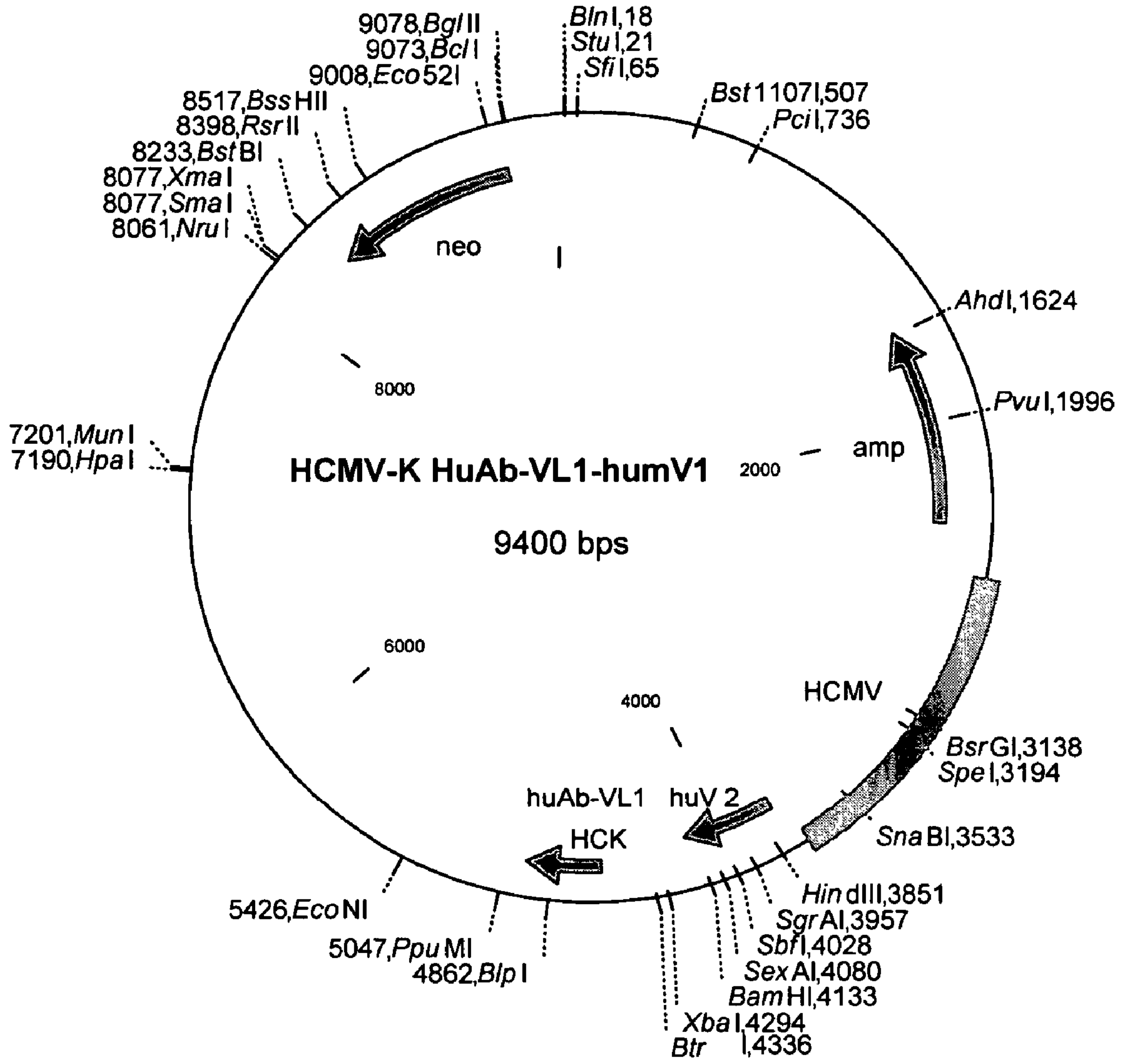
FIG. 4 shows the plasmid map of the expression vector HCMV-K HuAb-humV1 comprising the light chain having the nucleotide sequence SEQ ID NO:14 (3964-4284) in the complete expression vector nucleotide sequence SEQ ID NO:17.
Figure 5:
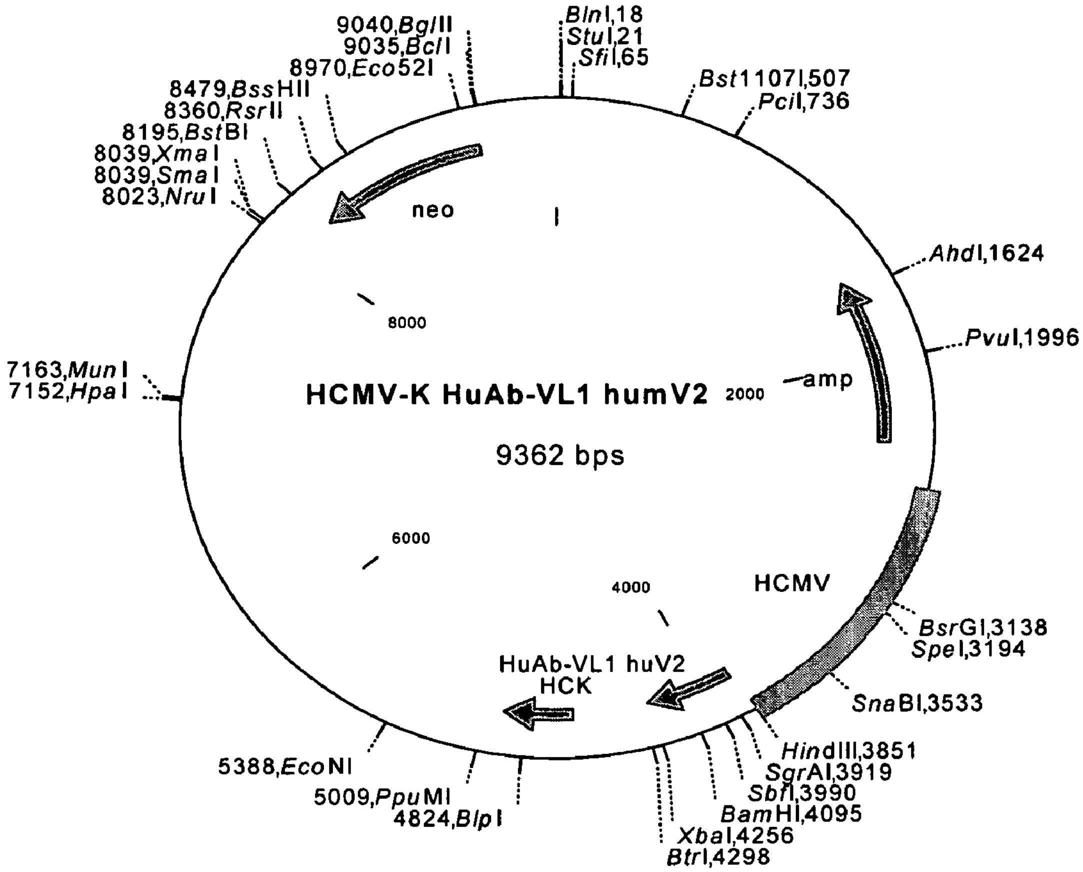
FIG. 5 shows the plasmid map of the expression vector HCMV-K HuAb-humV2 comprising the light chain having the nucleotide sequence SEQ ID NO:13 (3926-4246) in the complete expression vector nucleotide sequence SEQ ID NO:18.

We have now found a binding molecule which comprises a polypeptide sequence which binds to CD45RO and CD45RB, hereinafter also designated as a "CD45RO/RB binding molecule". These binding molecule according to the invention may induce immunosuppression, inhibit primary T cell responses and induce T cell tolerance. Furthermore, the binding molecules of the invention inhibit primary mixed lymphocyte responses (MLR). Cells derived from cultures treated with CD45RO/RB binding molecules preferredly also have impaired proliferative responses in secondary MLR even in the absence of CD45RO/RB binding molecules in the secondary MLR. Such impaired proliferative responses in secondary MLR are an indication of the ability of binding molecules of the invention to induce tolerance.

Furthermore, it is found that in vivo administration of CD45RO/RB binding molecule to severe combined immunodeficiency (SCID) mice undergoing xeno-GVHD following injection with human PBMC may prolong mice survival, compared to control treated mice, even though circulating human T cells may still be detected in CD45RO/RB binding molecule treated mice. CD45RB/RO binding molecule may also suppress the inflammatory process that mediates human allograft skin rejection.

By "CD45RO/RB binding molecule" is meant any molecule capable of binding specifically to the CD45RB and CD45RO isoforms of the CD45 antigen, either alone or associated with other molecules. The binding reaction may be shown by standard methods (qualitative assay) including for example any kind of binding assay such as direct or indirect immunofluorescence together with fluorescence microscopy or cytofluorimetric (FACS) analysis, enzyme-linked immunosorbent assay (ELISA) or radioimmunoassay in which binding of the molecule to cells expressing a particular CD45 isoform can be visualized. In addition, the binding of this molecule may result in the alteration of the function of the cells expressing these isoforms. For example inhibition of primary or secondary mixed lymphocyte response (MLR) may be determined, such as an in vitro assay or a bioassay for determining the inhibition of primary or secondary MLR in the presence and in the absence of a CD46RO/RB binding molecule and determining the differences in primary MLR inhibition.

Alternatively, the in vitro functional modulatory effects can also be determined by measuring the PBMC or T cells or $CD4^+$ T cells proliferation, production of cytokines, change in the expression of cell surface molecules e.g. following cell activation in MLR, or following stimulation with specific antigen such as tetanus toxoid or other antigens, or with polyclonal stimulators such as phytohemagglutinin (PHA) or anti-CD3 and anti-CD28 antibodies or phorbol esters and $Ca^{2+}$ ionophores. The cultures are set up in a similar manner as described for MLR except that instead of allogeneic cells as stimulators soluble antigen or polyclonal stimulators such as those mentioned above are used. T cell proliferation is measured preferably as described above by $^3$H-thymidine incorporation.

Cytokine production is measured preferably by sandwich ELISA where a cytokine capture antibody is coated on the surface of a 96-well plate, the supernatants from the cultures are added and incubated for 1 hr at room temperature and a detecting antibody specific for the particular cytokine is then added, following a second-step antibody conjugated to an enzyme such as Horseradish peroxidase followed by the corresponding substrate and the absorbance is measured in a plate reader. The change in cell surface molecules may be preferably measured by direct or indirect immunofluorescence after staining the target cells with antibodies specific for a particular cell surface molecule. The antibody can be either directly labeled with flourochrome or a fluorescently labeled second step antibody specific for the first antibody can be used, and the cells are analysed with a cytofluorimeter.

The binding molecule of the invention has a binding specificity for both CD45RO and CD45RB ("CD45RB/RO binding molecule").

Preferably the binding molecule binds to CD45RO isoforms with a dissociation constant (Kd)<20 nM, preferably with a Kd<15 nM or <10 nM, more preferably with a Kd<5 nM. Preferably the binding molecule binds to CD45RB isoforms with a Kd<50 nM, preferably with a Kd<15 nM or <10 nM, more preferably with a Kd<5 nM.

In a further preferred embodiment the binding molecule of the invention binds those CD45 isoforms which 1) include the A and B epitopes but not the C epitope of the CD45 molecule; and/or 2) include the B epitope but not the A and not the C epitope of the CD45 molecule; and/or 3) do not include any of the A, B or C epitopes of the CD45 molecule.

In yet a further preferred embodiment the binding molecule of the invention does not bind CD45 isoforms which include 1) all of the A, B and C epitopes of the CD45 molecule; and/or 2) both the B and C epitopes but not the A epitope of the CD45 molecule.

In further preferred embodiments the binding molecule of the invention further 1) recognises memory and in vivo alloactivated T cells; and/or 2) binds to its target on human T cells, such as for example PEER cells; wherein said binding preferably is with a Kd<15 nM, more preferably with a Kd<10 nM, most preferably with a Kd<5 nM; and/or 3) inhibits in vitro alloreactive T cell function, preferably with an $IC_{50}$ of about less than 100 nM, preferably less than 50 nM or 30 nM, more preferably with an $IC_{50}$ of about 10 or 5 nM, most preferably with an $IC_{50}$ of about 0.5 nM or even 0.1 nM; and/or 4) induces cell death through apoptosis in human T lymphocytes; and/or 5) induces alloantigen-specific T cell tolerance in vitro; and/or 6) prevents lethal xenogeneic graft versus host disease (GvHD) induced in SCID mice by injection of human PBMC when administered in an effective amount; and/or 7) binds to T lymphocytes, monocytes, stem cells, natural killer cells and/or granulocytes, but not to platelets or B lymphocytes; and/or 8) supports the differentiation of T cells with a characteristic T regulatory cell (Treg) phenotype; and/or 9) induces T regulatory cells capable of suppressing naïve T cell activation; and/or 10) suppresses the inflammatory process that mediates human allograft skin rejection, in particular, suppresses the inflammatory process that mediates human allograft skin rejection in vivo in SCID mice transplanted with human skin and engrafted with mononuclear splenocytes.

In a further preferred embodiment the binding molecule of the invention binds to the same epitope as the monoclonal antibody "A6" as described by Aversa et al., Cellular Immunology 158, 314-328 (1994).

Due to the above-described binding properties and biological activities, such binding molecules of the invention are particularly useful in medicine for therapy and/or prophylaxis. Diseases in which binding molecules of the invention are particularly useful include autoimmune diseases, transplant rejection, psoriasis, inflammatory bowel disease and allergies, as will be further set out below.

We have found that a molecule comprising a polypeptide of SEQ ID NO: 1 and a polypeptide of SEQ ID NO: 2 is a CD45RO/RB binding molecule. We also have found the hypervariable regions CDR1', CDR2' and CDR3' in a CD45RO/RB binding molecule of SEQ ID NO:1, CDR1' having the amino acid sequence Arg-Ala-Ser-Gln-Asn-Ile-Gly-Thr-Ser-Ile-Gln (RASQNIGTSIQ), CDR2' having the amino acid sequence Ser-Ser-Ser-Glu-Ser-Ile-Ser (SSSESIS) and CDR3' having the amino acid sequence Gln-Gln-Ser-Asn-Thr-Trp-Pro-Phe-Thr (QQSNTWPFT).

We also have found the hypervariable regions CDR1, CDR2 and CDR3 in a CD45RO/RB binding molecule of SEQ ID NO:2, CDR1 having the amino acid sequence Asn-Tyr-Ile-Ile-His (NYIIH), CDR2 having the amino acid sequence Tyr-Phe-Asn-Pro-Tyr-Asn-His-Gly-Thr-Lys-Tyr-Asn-Glu-Lys-Phe-Lys-Gly (YFNPYNHGTKYNEKFKG) and CDR3 having the amino acid sequence Ser-Gly-Pro-Tyr-Ala-Trp-Phe-Asp-Thr (SGPYAWFDT).

CDRs are 3 specific complementary determining regions which are also called hypervariable regions which essentially determine the antigen binding characteristics. These CDRs are part of the variable region, e.g. of SEQ ID NO: 1 or SEQ ID NO: 2, respectively, wherein these CDRs alternate with framework regions (FR's) e.g. constant regions. A SEQ ID NO: 1 is part of a light chain, e.g. of SEQ ID NO: 3, and a SEQ ID NO:2 is part of a heavy chain, e.g. of SEQ ID NO: 4, in a chimeric antibody according to the present invention. The CDRs of a heavy chain together with the CDRs of an associated light chain essentially constitute the antigen binding site of a molecule of the present invention. It is known that the contribution made by a light chain variable region to the energetics of binding is small compared to that made by the associated heavy chain variable region and that isolated heavy chain variable regions have an antigen binding activity on their own. Such molecules are commonly referred to as single domain antibodies.

In one aspect the present invention provides a molecule comprising at least one antigen binding site, e.g. a CD45RO/RB binding molecule, comprising in sequence the hypervariable regions CDR1, CDR2 and CDR3, said CDR1 having the amino acid sequence Asn-Tyr-Ile-Ile-His (NYIIH), said CDR2 having the amino acid sequence Tyr-Phe-Ash-Pro-Tyr-Asn-His-Gly-Thr-Lys-Tyr-Asn-Glu-Lys-Phe-Lys-Gly (YFNPYNHGTKYNEKFKG) and said CDR3 having the amino acid sequence Ser-Gly-Pro-Tyr-Ala-Trp-Phe-Asp-Thr (SGPYAWFDT); e.g. and direct equivalents thereof.

In another aspect the present invention provides a molecule comprising at least one antigen binding site, e.g. a CD45RO/RB binding molecule, comprising a) a first domain comprising in sequence the hypervariable regions CDR1, CDR2 and CDR3, said CDR1 having the amino acid sequence Asn-Tyr-Ile-Ile-His (NYIIH), said CDR2 having the amino acid sequence Tyr-Phe-Asn-Pro-Tyr-Asn-His-Gly-Thr-Lys-Tyr-Asn-Glu-Lys-Phe-Lys-Gly (YFNPYNHGTKYNEKFKG) and said CDR3 having the amino acid sequence Ser-Gly-Pro-Tyr-Ala-Trp-Phe-Asp-Thr (SGPYAWFDT); and b) a second domain comprising in sequence the hypervariable regions CDR1', CDR2' and CDR3', CDR1' having the amino acid sequence Arg-Ala-Ser-Gln-Asn-Ile-Gly-Thr-Ser-Ile-Gln (RASQNIGTSIQ), CDR2' having the amino acid sequence Ser-Ser-Ser-Glu-Ser-Ile-Ser (SSSESIS) and CDR3' having the amino acid sequence Gln-Gln-Ser-Asn-Thr-Trp-Pro-Phe-Thr (QQSNTWPFT), e.g. and direct equivalents thereof.

In a preferred embodiment the first domain comprising in sequence the hypervariable regions CDR1, CDR2 and CDR3 is an immunoglobulin heavy chain, and the second domain comprising in sequence the hypervariable regions CDR1', CDR2' and CDR3' is an immunoglobulin light chain.

In another aspect the present invention provides a molecule, e.g. a CD45RO/RB binding molecule, comprising a polypeptide of SEQ ID NO: 1 and/or a polypeptide of SEQ ID NO: 2, preferably comprising in one domain a polypeptide of SEQ ID NO: 1 and in another domain a polypeptide of SEQ ID NO: 2, e.g. a chimeric monoclonal antibody, and in another aspect A molecule, e.g. a CD45RO/RB binding molecule, comprising a polypeptide of SEQ ID NO: 3 and/or a polypeptide of SEQ ID NO: 4, preferably comprising in one domain a polypeptide of SEQ ID NO: 3 and in another domain a polypeptide of SEQ ID NO: 4, e.g. a chimeric monoclonal antibody.

When the antigen binding site comprises both the first and second domains or a polypeptide of SEQ ID NO: 1 or SEQ ID NO:3, respectively, and a polypeptide of SEQ ID NO: 2 or of SEQ ID NO:4, respectively, these may be located on the same polypeptide, or, preferably each domain may be on a different chain, e.g. the first domain being part of an heavy chain, e.g. immunoglobulin heavy chain, or fragment thereof and the second domain being part of a light chain, e.g. an immunoglobulin light chain or fragment thereof.

We have further found that a CD45RO/RB binding molecule according to the present invention is a CD45RO/RB binding molecule in mammalian, e.g. human, body environment. A CD45RO/RB binding molecule according to the present invention can thus be designated as a monoclonal antibody (mAb), wherein the binding activity is determined mainly by the CDR regions as described above, e.g. said CDR regions being associated with other molecules without binding specificity, such as framework, e.g. constant regions, which are substantially of human origin.

In another aspect the present invention provides a CD45RO/RB binding molecule which is not the monoclonal antibody "A6" as described by Aversa et al., Cellular Immunology 158, 314-328 (1994), which is incorporated by reference for the passages characterizing A6.

In another aspect the present invention provides a CD45RO/RB binding molecule according to the present invention which is a chimeric, a humanised or a fully human monoclonal antibody.

Examples of a CD45RO/RB binding molecules include chimeric or humanised antibodies e.g. derived from antibodies as produced by B-cells or hybridomas and or any fragment thereof, e.g. F(ab')2 and Fab fragments, as well as single chain or single domain antibodies. A single chain antibody consists of the variable regions of antibody heavy and light chains covalently bound by a peptide linker, usually consisting of from 10 to 30 amino acids, preferably from 15 to 25 amino acids. Therefore, such a structure does not include the constant part of the heavy and light chains and it is believed that the small peptide spacer should be less antigenic than a whole constant part. By a chimeric antibody is meant an antibody in which the constant regions of heavy and light chains or both are of human origin while the variable domains of both heavy and light chains are of non-human (e.g. murine) origin. By a humanised antibody is meant an antibody in which the hypervariable regions (CDRs) are of non-human (e.g. murine) origin while all or substantially all the other part, e.g. the constant regions and the highly conserved parts of the variable regions are of human origins. A humanised antibody may however retain a few amino acids of the murine sequence in the parts of the variable regions adjacent to the hypervariable regions.

Hypervariable regions, i.e. CDR's according to the present invention may be associated with any kind of framework regions, e.g. constant parts of the light and heavy chains, of human origin. Suitable framework regions are e.g. described in "Sequences of proteins of immunological interest", Kabat, E. A. et al, US department of health and human services, Public health service, National Institute of health. Preferably the constant part of a human heavy chain may be of the IgG1 type, including subtypes, preferably the constant part of a human light chain may be of the κ or λ type, more preferably of the κ type. A preferred constant part of a heavy chain is a polypeptide of SEQ ID NO: 4 (without the CDR1', CDR2' and CDR3' sequence parts which are specified above) and a preferred constant part of a light chain is a polypeptide of SEQ ID NO: 3 (without the CDR1, CDR2 and CDR3 sequence parts which are specified above).

We also have found a humanised antibody comprising a light chain variable region of amino acid SEQ ID NO:7 or of amino acid SEQ ID NO:8, which comprises CDR1', CDR2' and CDR3' according to the present invention and a heavy chain variable region of SEQ:ID NO:9 or of SEQ:ID NO:10, which comprises CDR1, CDR2 and CDR3 according to the present invention.

In another aspect the present invention provides a humanised antibody comprising a polypeptide of SEQ ID NO:9 or of SEQ ID NO:10 and a polypeptide of SEQ ID NO:7 or of SEQ ID NO:8.

In another aspect the present invention provides a humanised antibody comprising

- a polypeptide of SEQ ID NO:9 and a polypeptide of SEQ ID NO:7,
- a polypeptide of SEQ ID NO:9 and a polypeptide of SEQ ID NO:8,
- a polypeptide of SEQ ID NO:10 and a polypeptide of SEQ ID NO:7, or
- a polypeptide of SEQ ID NO:10 and a polypeptide of SEQ ID NO:8.

A polypeptide according to the present invention, e.g. of a herein specified sequence, e.g. of CDR1, CDR2, CDR3, CDR1', CDR2', CDR3', or of a SEQ ID NO:1, SEQ ID NO:2, SEQ ID NO:3, SEQ ID NO:4, SEQ ID NO:7, SEQ ID NO:8, SEQ ID NO:9 or SEQ ID NO:10 includes direct equivalents of said (poly)peptide (sequence); e.g. including a functional derivative of said polypeptide. Said functional derivative may include covalent modifications of a specified sequence, and/or said functional derivative may include amino acid sequence variants of a specified sequence.

"Polypeptide", if not otherwise specified herein, includes any peptide or protein comprising amino acids joined to each other by peptide bonds, having an amino acid sequence starting at the N-terminal extremity and ending at the C-terminal extremity. Preferably the polypeptide of the present invention is a monoclonal antibody, more preferred is a chimeric (V-grafted) or humanised (CDR-grafted) monoclonal antibody. The humanised (CDR-grafted) monoclonal antibody may or may not include further mutations introduced into the framework (FR) sequences of the acceptor antibody.

A functional derivative of a polypeptide as used herein includes a molecule having a qualitative biological activity in common with a polypeptide to the present invention, i.e. having the ability to bind to CD45RO and CD45RB. A functional derivative includes fragments and peptide analogs of a polypeptide according to the present invention. Fragments comprise regions within the sequence of a polypeptide according to the present invention, e.g. of a specified sequence. The term "derivative" is used to define amino acid sequence variants, and covalent modifications of a polypeptide according to the present invention. e.g. of a specified sequence. The functional derivatives of a polypeptide according to the present invention, e.g. of a specified sequence, preferably have at least about 65%, more preferably at least about 75%, even more preferably at least about 85%, most preferably at least about 95% overall sequence homology with the amino acid sequence of a polypeptide according to the present invention, e.g. of a specified sequence, and substantially retain the ability to bind to CD45RO and CD45RB.

The term "covalent modification" includes modifications of a polypeptide according to the present invention, e.g. of a specified sequence; or a fragment thereof with an organic proteinaceous or non-proteinaceous derivatizing agent, fusions to heterologous polypeptide sequences, and post-translational modifications. Covalent modified polypeptides, e.g. of a specified sequence, still have the ability bind to CD45RO and CD45RB by crosslinking. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deaminated to the corresponding glutamyl and aspartyl residues. Alternatively, these residues are deaminated under mildly acidic conditions. Other post-translational modifications include hydroxylation of proline and lysine, phosphorylation of hydroxyl groups of seryl, tyrosine or threonyl residues, methylation of the α-amino groups of lysine, arginine, and histidine side chains, see e.g. T. E. Creighton, Proteins: Structure and Molecular Properties, W. H. Freeman & Co., San Francisco, pp. 79-86 (1983). Covalent modifications e.g. include fusion proteins comprising a polypeptide according to the present invention, e.g. of a specified sequence and their amino acid sequence variants, such as immunoadhesins, and N-terminal fusions to heterologous signal sequences.

"Homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known.

"Amino acid(s)" refer to all naturally occurring L-α-amino acids, e.g. and including D-amino acids. The amino acids are identified by either the well known single-letter or three-letter designations.

The term "amino acid sequence variant" refers to molecules with some differences in their amino acid sequences as compared to a polypeptide according to the present invention, e.g. of a specified sequence. Amino acid sequence variants of a polypeptide according to the present invention, e.g. of a specified sequence, still have the ability to bind to CD45RO and CD45RB. Substitutional variants are those that have at least one amino acid residue removed and a different amino acid inserted in its place at the same position in a polypeptide according to the present invention, e.g. of a specified sequence. These substitutions may be single, where only one amino acid in the molecule has been substituted, or they may be multiple, where two or more amino acids have been substituted in the same molecule. Insertional variants are those with one or more amino acids inserted immediately adjacent to an amino acid at a particular position in a polypeptide according to the present invention, e.g. of a specified sequence. Immediately adjacent to an amino acid means connected to either the α-carboxy or α-amino functional group of the amino acid. Deletional variants are those with one or more amino acids in a polypeptide according to the present invention, e.g. of a specified sequence, removed. Ordinarily, deletional variants will have one or two amino acids deleted in a particular region of the molecule.

We also have found the polynucleotide sequences of

GGCCAGTCAGAACATTGGCACAAGCATACAGTG, encoding the amino acid sequence of CDR1,

TTCTTCTGAGTCTATCTCTGG; encoding the amino acid sequence of CDR 2,

ACAAAGTAATACCTGGCCATTCACGTT encoding the amino acid sequence of CDR 3,

TTATATTATCCACTG, encoding the amino acid sequence of CDR1',

TTTTAATCCTTACAATCATGGTACTAAG-TACAATGAGAAGTTCAAAGGCAG encoding the amino acid sequence of CDR2', AGGACCCTATGC-CTGGTTTGACACCTG encoding the amino acid sequence of CDR3', SEQ ID NO:5 encoding a polypeptide of SEQ ID NO: 1, i.e. the variable region of a light chain of an mAb according to the present invention;

SEQ ID NO:6 encoding a polypeptide of SEQ ID NO:2, i.e. the variable region of the heavy chain of an mAb according to the present invention;

SEQ ID NO:11 encoding a polypeptide of SEQ ID NO:9. i.e. a heavy chain variable region including CDR1, CDR2 and CDR3 according to the present invention;

SEQ ID NO:12 encoding a polypeptide of SEQ ID NO:10, i.e. a heavy chain variable region including CDR1, CDR2 and CDR3 according to the present invention;

SEQ ID NO:13 encoding a polypeptide of SEQ ID NO:7, i.e. a light chain variable region including CDR1', CDR2' and CDR3' according to the present invention; and SEQ ID NO:14 encoding a polypeptide of SEQ ID NO:8, i.e. a light chain variable region including CDR1', CDR2' and CDR3' according to the present invention.

In another aspect the present invention provides isolated polynucleotides comprising polynucleotides encoding a CD45RO/RB-biding molecule, e.g. encoding the amino acid sequence of CDR1, CDR2 and CDR3 according to the present invention and/or, preferably and, polynucleotides encoding the amino acid sequence of CDR1', CDR2' and CDR3' according to the present invention; and Polynucleotides comprising a polynucleotide of SEQ ID NO: 5 and/or, preferably and, a polynucleotide of SEQ ID NO: 6; and Polynucleotides comprising polynucleotides encoding a polypeptide of SEQ ID NO:7 or SEQ ID NO:8 and a polypeptide of SEQ ID NO:9 or SEQ ID NO:10; e.g. encoding a polypeptide of SEQ ID NO:7 and a polypeptide of SEQ ID NO:9, a polypeptide of SEQ ID NO:7 and a polypeptide of SEQ ID NO:10, a polypeptide of SEQ ID NO:8 and a polypeptide of SEQ ID NO:9, or a polypeptide of SEQ ID NO:8 and a polypeptide of SEQ ID NO:10; and Polynucleotides comprising a polynucleotide of SEQ ID NO:11 or of SEQ ID NO:12 and a polynucleotide of SEQ ID NO:13 or a polynucleotide of SEQ ID NO:14, preferably comprising a polynucleotide of SEQ ID NO:11 and a polynucleotide of SEQ ID NO:13, a polynucleotide of SEQ ID NO:11 and a polynucleotide of SEQ ID NO:14, a polynucleotide of SEQ ID NO:12 and a polynucleotide of SEQ ID NO:13, or a polynucleotide of SEQ ID NO:12 and a polynucleotide of SEQ ID NO:14.

"Polynucleotide", if not otherwise specified herein, includes any polyribonucleotide or polydeoxyribonucleotide, which may be unmodified RNA or DNA, or modified RNA or DNA, including without limitation single and double stranded RNA, and RNA that is a mixture of single- and double-stranded regions.

A polynucleotide according to the present invention, e.g. a polynucleotide encoding the amino acid sequence CDR1, CDR2, CDR3, CDR1', CDR2', CDR3', or of SEQ ID NO:1, SEQ ID NO:2, SEQ ID NO:3, SEQ ID NO:4, SEQ ID NO:7, SEQ ID NO:8, SEQ ID NO:9 or SEQ ID NO:10, respectively, such as a polynucleotide of SEQ ID NO:5, SEQ ID NO:6, SEQ ID NO:11, SEQ ID NO:12, SEQ ID NO:13 or SEQ ID NO:14, respectively, includes allelic variants thereof and/or their complements; e.g. including a polynucleotide that hybridizes to the nucleotide sequence of SEQ ID NO: 5, SEQ ID NO:6, SEQ ID NO:11, SEQ ID NO:12, SEQ ID NO:13 or SEQ ID NO:14, respectively; e.g. encoding a polypeptide having at least 80% identity to SEQ ID NO:1, SEQ ID NO:2, SEQ ID NO:3, SEQ ID NO:4, SEQ ID NO:7, SEQ ID NO:8, SEQ ID NO:9 or SEQ ID NO:10, respectively, e.g. including a functional derivative of said polypeptide, e.g. said functional derivative having at least 65% homology with SEQ ID NO:1, SEQ ID NO:2, SEQ ID NO:3, SEQ ID NO:4, SEQ ID NO:7, SEQ ID NO:8, SEQ ID NO:9 or SEQ ID NO:10, respectively, e.g. said functional derivative including covalent modifications of SEQ ID NO:1, SEQ ID NO:2, SEQ ID NO:3, SEQ ID NO:4, SEQ ID NO:7, SEQ ID NO:8, SEQ ID NO:9 or SEQ ID NO:10, respectively, e.g. said functional derivative including amino acid sequence variants of SEQ ID NO:1, SEQ ID NO:2, SEQ ID NO:3, SEQ ID NO:4, SEQ ID NO:7, SEQ ID NO:8, SEQ ID NO:9 or SEQ ID NO:10, respectively; e.g. a SEQ ID NO:5, SEQ ID NO:6, SEQ ID NO:11, SEQ ID NO:12, SEQ ID NO:13 or SEQ ID NO:14, respectively includes a sequence, which as a result of the redundancy (degeneracy) of the genetic code, also encodes a polypeptide of SEQ ID NO:1, SEQ ID NO:2, SEQ ID NO:3, SEQ ID NO:4, SEQ ID NO:7, SEQ ID NO:8, SEQ ID NO:9 or SEQ ID NO:10, respectively, or encodes a polypeptide with an amino acid sequence which has at least 80% identity with the amino acid sequence of SEQ ID NO:1, SEQ ID NO:2, SEQ ID NO:3, SEQ ID NO:4, SEQ ID NO:7, SEQ ID NO:8, SEQ ID NO:9 or SEQ ID NO:10, respectively.

A CD45RO/RB binding molecule, e.g. which is a chimeric or humanised antibody, may be produced by recombinant DNA techniques. Thus, one or more DNA molecules encoding the CD45RO/RB may be constructed, placed under appropriate control sequences and transferred into a suitable host (organism) for expression by an appropriate vector.

In another aspect the present invention provides a polynucleotide which encodes a single, heavy and/or a light chain of a CD45RO/RB binding molecule according to the present invention; and the use of a polynucleotide according to the present invention for the production of a CD45RO/RB binding molecule according to the present invention by recombinant means.

A CD45RO/RB binding molecule may be obtained according, e.g. analogously, to a method as conventional together with the information provided herein, e.g. with the knowledge of the amino acid sequence of the hypervariable or variable regions and the polynucleotide sequences encoding these regions. A method for constructing a variable domain gene is e.g. described in EP 239 400 and may be briefly summarized as follows: A gene encoding a variable region of a mAb of whatever specificity may be cloned. The DNA segments encoding the frame work and hypervariable regions are determined and the DNA segments encoding the hypervariable regions are removed. Double stranded synthetic CDR cassettes are prepared by DNA synthesis according to the CDR and CDR' sequences as specified herein. These cassettes are provided with sticky ends so that they can be ligated at junctions of a desired framework of human origin. Polynucleotides encoding single chain antibodies may also be prepared according to, e.g. analogously, to a method as conventional. A polynucleotide according to the present invention thus prepared may be conveniently transferred into an appropriate expression vector.

Appropriate cell lines may be found according, e.g. analogously, to a method as conventional. Expression vectors, e.g. comprising suitable promoter(s) and genes encoding heavy and light chain constant parts are known e.g. and are commercially available. Appropriate hosts are known or may be found according, e.g. analogously, to a method as conventional and include cell culture or transgenic animals.

In another aspect the present invention provides an expression vector comprising a polynucleotide encoding a CD45RO/RB binding molecule according to the present invention, e.g. of sequence SEQ ID NO:15, SEQ ID NO:16, SEQ ID NO:17 or SEQ ID NO:18.

In another aspect the present invention provides

An expression system comprising a polynucleotide according to the present invention wherein said expression system or part thereof is capable of producing a CD45RO/RB binding molecule according to the present invention, when said expression system or part thereof is present in a compatible host cell; and An isolated host cell which comprises an expression system as defined above.

We have further found that a CD45RO/RB binding molecule according to the present invention inhibit primary alloimmune responses in a dose-dependent fashion as determined by in vitro MLR. The results indicate that the cells which had been alloactivated in the presence of a CD45RO/RB binding molecule according to the present invention are impaired in their responses to alloantigen. This confirms the indication that a CD45RO/RB binding molecule according to the present invention can act directly on the effector alloreactive T cells and modulate their function. In addition, the functional properties of T cells derived from the primary MLR were further studied in restimulation experiments in secondary MLR, using specific stimulator cells or third-party stimulators to assess the specificity of the observed functional effects. We have found that the cells derived from primary MLRs in which a CD45RO/RB binding molecule according to the present invention is present, were impaired in their ability to respond to subsequent optimal stimulation with specific stimulator cells, although there was no antibody added to the secondary cultures. The specificity of the inhibition was demonstrated by the ability of cells treated with a CD45RO/RB binding molecule according to the present invention to respond normally to stimulator cells from unrelated third-party donors. Restimulation experiments using T cells derived from primary MLR cultures thus indicate that the cells which had been alloactivated a CD45RO/RB binding molecule according to the present invention are hyporesponsive, i.e. tolerant, to the original alloantigen. Further biological activities are described in examples 7, and 9 to 12.

Furthermore we have found that cell proliferation in cells pre-treated with a CD45RO/RB binding molecule according to the present invention could be rescued by exogenous IL-2. This indicates that treatment of alloreactive T cells with a CD45RO/RB binding molecule according to the present invention induces a state of tolerance. Indeed, the reduced proliferative responses observed in cells treated with a CD45RO/RB binding molecule according to the present invention, was due to impairment of T cell function, and these cells were able to respond to exogenous IL-2, indicating that these cells are in an anergic, true unresponsive state. The specificity of this response was shown by the ability of cells treated with a CD45RO/RB binding molecule according to the present invention to proliferate normally to unrelated donor cells to the level of the control treated cells.

In addition experiments indicate that the binding of a CD45RO/RB binding molecule according to the present invention to CD45RO and CD45RB may inhibit the memory responses of peripheral blood mononuclear cells (PBMC) from immunized donors to specific recall antigen. Binding of a CD45RO/RB binding molecule according to the present invention to CD45RO and CD45RB thus is also effective in inhibiting memory responses to soluble Ag. The ability of a CD45RO/RB binding molecule according to the present invention to inhibit recall responses to tetanus in PBMC from immunized donors indicate that a CD45RO/RB binding molecule according to the present invention is able to target and modulate the activation of memory T cells. E.g. these data indicate that a CD45RO/RB binding molecule according to the present invention in addition to recognizing alloreactive and activated T cells is able to modulate their function, resulting in induction of T cell anergy. This property may be important in treatment of ongoing immune responses to autoantigens and allergens and possibly to alloantigens as seen in autoimmune diseases, allergy and chronic rejection, and diseases, such as psoriasis, inflammatory bowel disease, where memory responses play a role in the maintenance of disease state. It is believed to be an important feature in a disease situation, such as in autoimmune diseases in which memory responses to autoantigens may play a major role for the disease maintenance.

We have also found that a CD45RO/RB binding molecule according to the present invention may modulate T cell proliferative responses in a mixed lymphocyte response (MLR) in vivo, i.e. a CD45RO/RB binding molecule according to the present invention was found to have corresponding inhibitory properties in vivo testing.

A CD45RO/RB binding molecule according to the present invention may thus have immunosuppressive and tolerogenic properties and may be useful for in vivo and ex-vivo tolerance induction to alloantigens, autoantigens, allergens and bacterial flora antigens, e.g. a CD45RO/RB binding molecule according to the present invention may be useful in the treatment and prophylaxis of diseases e.g. including autoimmune diseases, such as, but not limited to, rheumatoid arthritis, autoimmune thyroditis, Graves disease, type I and type II diabetes, multiple sclerosis, systemic lupus erythematosus, Sjögren syndrome, scleroderma, autoimmune gastritis, glomerulonephritis, transplant rejection, e.g. organ and tissue allograft and xenograft rejection, graft versus host disease (GVHD), and also psoriasis, inflammatory bowel disease and allergies.

In another aspect the present invention provides the use of a CD45RO/RB binding molecule according to the present invention as a pharmaceutical, e.g. in the treatment and prophylaxis of autoimmune diseases, transplant rejection, psoriasis, inflammatory bowel disease and allergies.

In another aspect the present invention provides a CD45RO/RB binding molecule according to the present invention for the production of a medicament in the treatment and prophylaxis of diseases associated with autoimmune diseases, transplant rejection, psoriasis, inflammatory bowel disease and allergies.

In another aspect the present invention provides a pharmaceutical composition comprising a CD45RO/RB binding molecule according to the present invention in association with at least one pharmaceutically acceptable carrier or diluent.

A pharmaceutical composition may comprise further, e.g. active, ingredients, e.g. other immunomodulatory antibodies such as, but not confined to anti-ICOS, anti-CD154, anti-CD134L or recombinant proteins such as, but not confined to rCTLA4 (CD152), rOX40 (CD134), or immunomodulatory compounds such as, but not confined to cyclosporin A, FTY720, RAD, rapamycin, FK506, 15-deoxyspergualin, steroids.

In another aspect the present invention provides a method of treatment and/or prophylaxis of diseases associated with autoimmune diseases, transplant rejection, psoriasis, inflammatory bowel disease and allergies comprising administering to a subject in need of such treatment and/or prophylaxis an effective amount of a CD45RO/RB binding molecule according to the present invention, e.g. in the form of a pharmaceutical composition according to the present invention.

Autoimmune diseases to be treated with binding molecule of the present invention further include, but are not limited to, rheumatoid arthritis, autoimmune thyroditis, Graves disease, type I and type II diabetes, multiple sclerosis, systemic lupus erythematosus, Sjögren syndrome, scleroderma, autoimmune gastritis, glomerulonephritis; transplant rejection, e.g. organ and tissue allograft and xenograft rejection and graft-versus-host disease (GVHD).

EXAMPLES

The invention will be more fully understood by reference to the following examples. They should not, however, be construed as limiting the scope of the invention. In the following examples all temperatures are in degree Celsius.

The “candidate mAb” or “chimeric antibody” is a CD45RO/RB binding molecule according to the present invention comprising light chain of SEQ ID NO:3 and heavy chain of SEQ ID NO:4.

The “humanised antibody” is a CD45RO/RB binding molecule according to the present invention comprising a polypeptide of SEQ ID NO:8 and polypeptide of SEQ ID NO:9 or a polypeptide of SEQ ID NO:8 and a polypeptide of SEQ ID NO:10.

The following abbreviations are used:

| | |
|---|---|
| APC | antigen presenting cell |
| c.p.m. | counts per minute |
| ELISA | enzyme linked immuno-sorbant assay |
| FACS | fluorescence activated cell sorting |
| Fc | fragment crystallizable |
| F(ab')2 | fragment antigen-binding; bivalent |
| FITC | fluorescein isothiocyanate |
| FBS | foetal bovine serum |
| GVHD | graft-vs-host disease |
| HCMV | human cytomegalovirus promoter |
| IFN-γ | interferon gamma |

-continued

| | |
|---|---|
| IgE | immunoglobulin isotype E |
| IgG | immunoglobulin isotype G |
| IL-2 | interleukin-2 |
| IU | international units |
| MLR | mixed lymphocyte reaction |
| MLC | mixed lymphocyte culture |
| MP1 | matrix protein 1 from hemophilus influenza |
| PBS | phosphate-buffered saline |
| PBL | peripheral blood leukocytes |
| PBMC | peripheral blood mononuclear cells |
| PCR | polymerase chain reaction |
| SCID | severe combined immunodeficiency |
| $T_{reg}$ | T regulatory cells |
| xGVHD | xeno-graft-vs-host disease |

Example 1

Primary Mixed Lymphocyte Response (MLR)

Cells

Blood samples are obtained from healthy human donors. Peripheral blood mononuclear cells (PBMC) are isolated by centrifugation over Ficoll-Hypaque (Pharmacia LKB) from leukocytes from whole peripheral blood, leukopheresis or buffy coats with known blood type, but unknown HLA type. In some MLR experiments, PBMC are directly used as the stimulator cells after the irradiation at 40 Gy. In the other experiments, T cells were depleted from PBMC by using CD2 or CD3 Dynabeads (Dynal, Oslo, Norway). Beads and contaminating cells are removed by magnetic field. T cell-depleted PBMC are used as simulator cells after the irradiation.

PBMC, $CD3^+$ T cells or $CD4^+$ T cells are used as the responder cells in MLR. Cells are prepared from different donors to stimulator cells. $CD3^+$ T cells are purified by negative selection using anti-CD16 mAb (Zymed, Calif.), goat anti-mouse IgG Dynabeads, anti-CD14 Dynabeads, CD19 Dynabeads. In addition anti-CD8 Dynabeads are used to purify $CD4^+$ T cells. The cells obtained are analyzed by FACScan or FACSCalibur (Becton Dickinson & Co., Calif.) and the purity of the cells obtained was >75%. Cells are suspended in RPMI1640 medium, supplemented with 10% heat-inactivated FBS, penicillin, streptomycin and L-glutamine.

Reagents

The chimeric anti-CD45R0/RB mAb “candidate mAb” and an isotype matched control chimeric antibody is also generated. Mouse (Human) control $IgG_1$ antibody specific for KLH (keyhole limpet hemocyanin) or recombinant human IL-10 is purchased from BD Pharmingen (San Diego, Calif.). Anti-human CD154 mAb 5c8 is according to Lederman et al 1992.

Primary Mixed Lymphocyte Response (MLR)

Aliquots of $1\times10^5$ PBMC or $5\times10^4$ of $CD3^+$ or $CD4^+$ cells are mixed with $1\times10^5$ irradiated PBMC or $5\times10^4$ T cells-depleted irradiated (50 Gy) PBMC in the each well of 96-well culture plates (Costar, Cambridge, Mass.) in the presence of the indicated mAb or absence of Ab. In some experiments, $F(ab')_2$ fragment of goat anti-mouse Ig or goat anti-human Ig specific for Fc portion (Jackson ImmunoResearch, West Grove, Pa.) is added at 10 μg/ml in addition to the candidate mAb To ensure optimal in vitro cross-linking of the target CD45 molecules. The mixed cells are cultured for 4 or 5 days at 37° C. in 5% $CO_2$ and proliferation is determined by pulsing the cells with $^3$H-thymidine for the last 16-20 hours of culture. Other experiments are similar to those described above, but with the following exceptions: 1) Medium used is EX-VIVO (Bio-Whittaker) containing 10% FBS and 1% human plasma; 2) Anti-mouse total IgG (5 µg/ml) is used as secondary cross-linking step; 3) Irradiation of stimulator cells is 60 Gy.

Primary MLR is performed in the presence of the "candidate mAb" or control chimeric $IgG_1$ (10 µg/ml) both with a second step reagent, $F(ab')_2$ fragment of goat anti-human Ig specific for Fc portion (10 µg/ml). Percentage inhibition by the "candidate mAb" is calculated in comparison with the cell proliferation in the presence of control $IgG_1$. Results are shown in TABLE 1 below:

TABLE 1

Inhibition of primary MLR by 10 µg/ml of a candidate mAb according to the present invention

| Responder | Stimulator (Irr. PBMC) | % of Inhibition |
|---|---|---|
| #211 CD4 | #219 CD3 | 63.51 |
| #220 CD4 | #219 CD3 depl. | 63.07 |
| #227 CD4 | #220 CD3 depl. | 65.96 |
| #229 CD4 | #219 CD3 depl. | 50.76 |
| | Average ± SD | 60.83 ± 6.83* |

*Significantly different from control value (P < 0.001)

A candidate mAb according to the present invention inhibits primary MLR as can be seen from TABLE 1. The average inhibitory effect is 60.83±6.83% in four different donors-derived $CD4^+$ T cells and statistically significant.

The inhibition of primary MLR by the "candidate mAb" is shown to be dose-dependent in the range of 0.001 and 10 µg/ml of the "candidate mAb" as shown in FIG. 1.

The $IC_{50}$ for the inhibition of primary MLR by a "candidate mAb" is determined from the results of three separate MLR experiments using one donor PBMC as responder cells. Thus, responder $CD4^+$ T cells from Donor #229 and #219 and irradiated PBMC depleted of T cells as stimulators are mixed in the presence of a "candidate mAb" or control chimeric Ab with 10 µg/ml of $F(ab')_2$ fragment of goat anti-human Ig. Experiments are repeated 3 times and percentage of proliferation in the presence of a "candidate mAb" is calculated in comparison with the T cell proliferation in the presence of control Ab. $IC_{50}$ value is determined using Origin (V. 6.0®). The cellular activity $IC_{50}$ value is calculated to be 0.87±0.35 nM (0.13±0.052 µg/ml).

Example 2

Secondary MLR

In order to assess whether a "candidate mAb" induces unresponsiveness of $CD4^+$ T cells to specific alloantigens, secondary MLR is performed in the absence of any antibodies after the primary MLC. $CD4^+$ T cells are cultured with irradiated allogeneic stimulator cells (T cells-depleted PBMC) in the presence of the indicated antibody in 96-well culture plates for 10 days (primary MLC). Then, cells are collected, layered on a Ficoll-Hypaque gradient to remove dead cells, washed twice with RPMI, and restimulated with the same stimulator, $3^{rd}$ party stimulator cells or IL-2 (50 U/ml). The cells are cultured for 3 days and the proliferative response is determined by pulsing the cells with $^3$H-thymidine for the last 16-20 hours of culture.

Specifically, $CD4^+$ T cells are cultured with irradiated allogeneic stimulator cells (T cells-depleted PBMC taken from other donors) in the presence of 10 µg/ml of the "candidate mAb", control IgG1 chimeric Ab and $F(ab')_2$ fragment of goat anti-human Ig. Primary MLR proliferation is determined on day 5. For secondary MLR, the responder and stimulator cells are cultured for 10 days in the presence of the "candidate mAb", then the cells are harvested, washed twice in RPMI1640 and restimulated with specific stimulator, third-party stimulators or IL-2 (50 U/ml) in the absence of any Ab. Cell proliferation is determined on day 3. Results set out in TABLE 2:

TABLE 2

| Responder CD4+ T cells Donor # | % Inhibition of $2^{ry}$ MLR |
|---|---|
| #211 | 49.90* |
| #220 | 59.33* |
| #227 | 58.68* |

*Significantly different from control value (p =< 0.001 determined by t-test, SigmaStat V.2.03).
#p =< 0.046

In order to test whether the impaired proliferation is due to unresponsiveness as a consequence of the treatment with a "candidate mAb", the cells derived from primary MLR are cultured in the presence of IL-2 (50 U/ml). Addition of IL-2 results in the rescue of proliferative responses of the T cells which had been treated with a "candidate mAb" in primary MLR, to levels similar to those observed in the presence of $IgG_1$ control Ab. These data indicate that the impaired secondary response in T cells treated with a "candidate mAb" is due to functional alteration of the responder T cells which become unresponsive to the specific stimulator cells.

Percentage inhibition is calculated according to the following formula:

$$\frac{\text{c.p.m. with control } Ab - \text{c.p.m. with "candidate } mAb}{\text{c.p.m. with control } Ab} \times 100$$

Statistical analysis is performed using SigmaStat (Vers. 2.03).

The data is analyzed by two-way ANOVA followed by Dunnett method. In all test procedures probabilities<0.05 are considered as significant. In some experiments t-test is used (SigmaStat V.2.03).

Example 3

In Vivo Survival Studies in SCID-Mice

Engraftment of hu-PBL in SCID Mice

Human peripheral blood mononuclear cells (PBMC) are injected intraperitoneally into SCID mice C.B 17/GbmsTac-Prkdc$^{scid}$ Lyse$^{bg}$ mice (Taconic, Germantown, N.Y.) in an amount sufficient to induce a lethal xenogeneic graft-versus-host disease (xGvHD) in >90% of the mice within 4 weeks after cell transfer. Such treated SCID mice are hereinafter designated as hu-PBL-SCID mice Mab-Treatment of hu-PBL-SCID Mice Hu-PBL-SCID mice are treated with a "candidate mAb" or mouse or chimeric isotype matched mAb controls at day 0, immediately after PBMC injection, at day 3, day 7 and at weekly intervals thereafter. Mabs are delivered subcutaneously in 100 µl PBS at a final concentration of 5 mg/kg body weight. The treatment was stopped when all control mice were dead.

Evaluation of Treatment Results

The main criterion to assess the efficacy of a "candidate mAb" in this study was the survival of the hu-PBL-SCID mice. The significance of the results is evaluated by the statistical method of survival analysis using the Log-rank test (Mantel method) with the help of the Systat v9.01 software. The method of survival analysis is a non-parametric test, which not only consider whether a particular mouse is still alive but also whether if it was sacrificed for reasons irrelevant to the treatment/disease such as the requirement of perform in vitro analysis with its organs/cells. Biopsies of liver, lung, kidney and spleen are obtained from dead mice for further evaluation. In addition, hu-PBL-SCID mice are weighed at the beginning (before cell transfer) and throughout (every two days) the experiment as an indirect estimation of their health status. Linear regression lines were generated using the body weight versus days post-PBMC transfer values obtained from each mouse and subsequently, their slopes (control versus anti-CD45 treated mice) were compared using the non-parametric Mann-Whitney test.

Results

All hu-PBL-SCID mice treated with mouse mAb controls had infiltrated human leukocytes in the lung, liver and spleen and died (4/4) within ca. 2 to 3 weeks after cell transfer. Death is a likely consequence of xGvHD. Control mAb-treated mice furthermore lost weight in a linear manner, ca. 10% and more within 3 weeks.

All hu-PBL-SCID mice treated with a "candidate mAb" survived (4/4) without any apparent sign of disease more than 4 weeks, even although "candidate mAb"-treatment was stopped after 3 weeks. "Candidate mAb"-treated mice increased weight in a linear manner, up to ca. 5% within 4 weeks.

Example 4

Expression of Antibodies of the Invention

Expression of Humanised Antibody Comprising a SEQ ID NO:7, SEQ ID NO:8, SEQ ID NO:9, or SEQ ID NO:10

Expression vectors according to the plasmid map shown in FIGS. 2 to 5 are constructed, comprising the corresponding nucleotides encoding the amino acid sequence of humanised light chain variable region humV1 (SEQ ID NO:7), humanised light chain variable region humV2 (SEQ ID NO:8), humanised heavy chain variable region VHE (SEQ ID NO:9), or humanised heavy chain variable region VHQ (SEQ ID NO:10), respectively. These expression vectors have the DNA (nucleotide) sequences SEQ ID NO 15, SEQ ID NO 16, SEQ ID NO 17, or SEQ ID NO 18, respectively.

Construction of Humanised Antibody Heavy and Light Chain Expression Vectors

Human kappa light chain expression vectors for versions VLh and VLm

In order to construct the final expression vector encoding for the complete humanised light chain of human kappa isotype, DNA fragments encoding the complete light chain variable regions (VLh and VLm) were excised from the VLh and VLm containing PCR-Script cloning vectors (Stratagene) (VLm region) using HindIII and BglII. The gel-purified fragments were then subcloned into the HindIII and BamHI sites of C21-HCMV Kappa expression vector which was created during construction of the humanised anti-IgE antibody TESC-21 (Kolbinger et al 1993) and which originally received from M. Bendig (MRC Collaborative Centre, London, UK) (Maeda et al. 1991). The ligation products were purified by phenol/chloroform extraction, and electroporated into electrocoporation-competent Epicurian Coli® XL1-Blue strain (Cat. N° #200228, Stratagene). After plating on LB/amp agar plates overnight at 37° C., each 12 colonies were picked to prepare plasmid DNA from a 3 ml culture using the BioRobot 9600 (Qiagen). This yielded the light chain expression vectors for the humanised antibody versions VLh and VLm, respectively, as further described in the Figures.

Human Gamma-1 Heavy Chain Expression Vectors for VHQ

For the construction of the VHQ expression vector, a stepwise approach was taken. First, the complete variable region of VHQ was assembled by PCR according to the methology as described in Kolbinger et al 1993 (Protein Eng. November 1993; 6(8):971-80) and subcloned into the C21-HCMV-gamma-1 expression from which the C21 insert had been removed using the same enzymes. A HindIII/BamHI fragment of PCRScript clone VHQ containing the complete variable region was then subcloned into expression vector C21-HCMV-gamma-1 cleaved with the same enzymes. This yielded the final expression vector for the humanised antibody version VHQ.

Human Gamma-1 Heavy Chain Expression Vectors for VHE

The construction of the final VHE expression vector encoding for the complete humanised heavy chain of human gamma-1 isotype was achieved by directly ligating a HindIII and BamHI restricted PCR fragment encoding the variable region into the HindIII and BamHI sites of C21-HCMV gamma-1 expression vector which was created during construction of the humanised anti-IgE antibody TESC-21 (Kolbinger et al 1993) and which was also originally received from M. Bendig (MRC Collaborative Centre, London, UK) (Maeda et al. 1991).

Transient Expression in COS Cells

The following transfection protocol is adapted for adherent COS cells in 150 mm cell culture dishes, using SuperFect™ Transfection Reagent (Cat. N° 301305, Qiagen). The four different expression vectors described above are used for transient transfection of cells. For expression of humanised antibody, each of two clones containing heavy chain inserts (VHE or VHQ, respectively) are co-transfected into cells with each of the two clones encoding for the light chains (humV1 or humV2, respectively), in total 4 different combinations of heavy and light chain expression vectors (VHE/humV1, VHE/humV2, VHQ/humV1 and VHQ/humV2). Before transfection, the plasmids are linearized with the restriction endonuclease PvuI which cleaves in the region encoding the resistance gene for ampicillin. The day before transfection, $4\times10^6$ COS cells in 30 ml of fresh culture medium are seeded in 150 mm cell culture dishes. Seeding at this cell density generally yielded 80% confluency after 24 hours. On the day of transfection, four different combinations of linearized heavy- and light-chain DNA expression vectors (15 μg each) are diluted in a total volume of 900 μl of fresh medium without serum and antibiotics. 180 μl of SuperFect Transfection Reagent is then mixed thoroughly with the DNA solution. The DNA mixture is incubated for 10 min at room temperature to allow complex formation. While complex formation takes place, the growth medium is removed from COS cell cultures, and cells are washed once with PBS. 9 ml of fresh culture medium (containing 10% FBS and antibiotics) are then added to each reaction tube containing the transfection complexes and well mixed. The final preparation is immediately transferred to each of 4 cultures to be transfected and gently mixed. Cell cultures are then incubated with the DNA complexes for 3 hours at 37° C. and 5% CO2. After incubation, the medium containing transfection complexes is removed and replaced with 30 ml of fresh culture medium. At 48 hr post transfection, the culture supernatants are harvested.

Concentration of Culture Supernatants

For ELISA and FACS analysis, the culture supernatants collected from COS cells transfected with heavy- and light-chain plasmids are concentrated as follows. 10 ml of each supernatant are added to Centriprep YM-50 Centrifugal Filter Devices (Cat. N° 4310, Millipore) as described by the manufacturer. The Centriprep filters are centrifuged for 10 min at 3000 rpm at room temperature. The centrifugation step is then repeated again with the remaining 20 ml of supernatant using only 5 min of centrifugation and supervising the concentration evolution. The intermediate 500 μl of concentrated supernatant is recovered, transferred to new Microcon Centrifugal Filter Devices (Cat. N° 42412, Microcon) and further concentrated following the manufacturer's protocol. The concentrated supernatants are centrifuged four times for 24 min at 3000 rpm at room temperature, one time for 10 min at 6000 rpm and then, three times for 5 min, always supervising the concentration evolution. The final volume of concentrated conditioned medium achieved is 100-120 μl corresponding to a 250 to 300-fold concentration of original culture medium and is stored at 4° C. until use. For comparison and control, culture medium from untransfected cells is similarly concentrated, using the same centrifugation protocol described above.

Generation of Stable Sp2/0 Myeloma Transfectants Secreting Humanised Anti-CD45RO/RB Antibodies The mouse myeloma cell line Sp2/0 (ATCC, CRL-1581) is electroporated with vectors encoding heavy (VHE or VHQ) and light (humV1 or humV2) chain of the CD45RO/RB binding humanised antibodies. Four different combinations of heavy and light chain expression vectors (VHE/humV1, VHE/humV2, VHQ/humV1 and VHQ/humV2) are transfected according to the following protocol: 20 μg supercoiled DNA of each plasmid is mixed in an electroporation cuvette (0.4 cm gap) with $8\times10^6$ live Sp2/0 cells suspended in DMEM/10% FCS culture medium. Electroporation settings are 1500 V, 25 μF using a BioRad GenePulser instrument. After electroporation, cells are cultured for 20 h in culture medium (DMEM supplemented with 10% FCS penicillin, streptomycin and L-glutamine). On day two the selection drug G418 (Cat. N° 10131-019, Gibco) is added to a final concentration of 1 mg active drug/ml and the cells are distributed into one 96-well plate, 200 μl each well with approx. $10^5$ cells per well. Ten to 15 days later, G418-surviving clones are expanded in G418-containing medium. Secretion of humanised mAbs from these transfectants is assessed by ELISA, using a coating antibody goat anti-human IgG/Fcγ (Cat. N° 109-005-098, Jackson Labs) and a peroxidase-coupled antibody against human kappa light chain (Cat. N° A-7164, Sigma). Transfectants, which score positive in this assay are selected for a comparison of productivity on a per cell per day basis, again using ELISA (see below). The best clone of each transfectant is selected for immediate subcloning by limiting dilution, using a seeding density of 1 cell per well. Productivity of G418-surviving subclones is again determined as described above. Subclones are expanded in G418-containing selection medium, until the culture volume reaches 150 ml, at which stage the culture is continued without G418 in flasks destined to feed roller bottles.

After the first transfection and selection, stable transfectants grow out of the 96-well plates at a frequency of 20.8% for VHE/humV1, 11.5% for VHQ/humV1, 18.8% for VHE/humV2 and 7.3% for VHQ/humV2. After two rounds of subcloning the best two producers are clone 1.33.25 (3.87 pg/cell/day) and clone 1.33.26 (3.43 pg/cell/day) for VHE/humV1 and clone 12.1.4 (1.19 pg/cell/day) and clone 12.1.20 (1.05 pg/cell/day) for VHQ/humV1. The stable Sp2/0 transfectants for VHE/humV1 and VHQ/humV1 are subsequently expanded for antibody production and purification.

The antibodies are purified from supernatants of stably transfected SP2/0 myeloma cell lines containing 10% FCS by a combination of affinity chromatography using an immobilized anti-human IgGFc matrix and size-exclusion chromatography. If required, endotoxin is removed using an Acticlean Etox column (Sterogene Bioseparations).

Example 5

Determination of Recombinant Human IgG Expression by ELISA

To determine IgG concentrations of recombinant human antibody expressed in the culture supernatants, a sandwich ELISA protocol has been developed and optimized using human IgG as standard. Flat bottom 96-well microtiter plates (Cat. N° 4-39454, Nunc Immunoplate Maxisorp) are coated overnight at 4° C. with 100 μl of goat anti-human IgG (whole molecule, Cat. N° I1011, SIGMA) at the final concentration of 0.5 pg/ml in PBS. Wells are then washed 3 times with washing buffer (PBS containing 0.05% Tween 20) and blocked for 1.5 hours at 37° C. with blocking buffer (0.5% BSA in PBS). After 3 washing cycles, the antibody samples and the standard human IgG (Cat. No. 14506, SIGMA) are prepared by serial 1.5-fold dilution in blocking buffer. 100 ||l of diluted samples or standard are transferred in duplicate to the coated plate and incubated for 1 hour at room temperature. After incubation, the plates are washed 3 times with washing buffer and subsequently incubated for 1 hour with 100 μl of horseradish peroxidase-conjugated goat anti-human IgG kappa-light chain (Cat. N° A-7164, SIGMA) diluted at 1/4000 in blocking buffer. Control wells received 100 μl of blocking buffer or concentrated normal culture medium. After washing, the colorimetric quantification of bound peroxidase in the sample and standard wells is performed, using a TMB Peroxidase EIA Substrate Kit (Cat. N° 172-1067, Bio-Rad) according to the manufacturer's instructions. The peroxidase mixture is added at 100 μl per well and incubated for 30 min at room temperature in the dark. The colorimetric reaction is stopped by addition of 100 μl of 1 M sulfuric acid and the absorbance in each well is read at 450 nm, using an ELISA plate reader (Model 3350-UV, BioRad).

With a correlation coefficient of 0.998 for the IgG standard curve, the following concentrations are determined for the four different culture concentrates (ca. 250-300 fold concentrated) obtained from transfected COS cells:

VHE/humV1 supernatant=8.26 μg/ml
VHE/humV2 supernatant=6.27 μg/ml
VHQ/humV1 supernatant=5.3 μg/ml
VHQ/humV2 supernatant=5.56 μg/ml

Example 6

FACS Competition Analysis

Binding Affinity

The human T-cell line PEER is chosen as the target cell for FACS analysis because it expressed the CD45 antigen on its cell surface. To analyze the binding affinity of humanised antibody supernatants, competition experiments using FITC-labeled chimeric antibody as a reference are performed and compared with the inhibition of purified mouse antibody and of chimeric antibody. PEER cell cultures are centrifuged for 10 seconds at 3000 rpm and the medium is removed. Cells are resuspended in FACS buffer (PBS containing 1% FBS and 0.1% sodium azide) and seeded into 96-well round-bottom microtiter plate at a cell density of $1\times10^5$ cells per well. The plate is centrifuged and the supernatant is discarded. For blocking studies, 25 μl of concentrated untransfected medium or isotype matched control antibody (negative controls), unlabeled mouse antibody or chimeric antibody (positive controls) as well as concentrated supernatant containing the various combinations of humanised antibody (samples), is first added in each well at the indicated concentrations in the text. After 1 hour of incubation at 4° C., PEER cells are washed with 200 μl of FACS buffer by centrifugation. Cells are subsequently incubated for 1 hour at 4° C. with chimeric antibody conjugated with FITC in 25 μl of FACS buffer at the final concentration of 20 μg/ml. Cells are washed and resuspended in 300 μl of FACS buffer containing 2 μg/ml propidium iodide which allows gating of viable cells. The cell preparations are analyzed on a flow cytometer (FACSCalibur, Becton Dickinson).

FACS analyses indicate a dose-dependent blockade of fluorochrome-labeled chimeric antibody by the concentrated humanised antibody culture supernatants. No dose-dependent blockade of chimeric antibody binding is seen with the isotype matched control antibody, indicating that the blocking effect by the different humanised antibody combinations is epitope specific and that epitope specificity appears to be retained after the humanisation process.

Undiluted supernatant from the above mentioned SP2/0 transfectants or chimeric antibody (positive controls) or isotype matched control antibody (negative controls) at 2 μg/ml in culture medium are incubated with $1.5\times10^5$ PEER cells in 100 μl for 30 min at 4° C. Then, 100 μl PBS containing FITC-labeled chimeric antibody is added to each sample and incubation at 4° C. continues for another 30 minutes. After washing, cells are resuspended in FACS-PBS containing 1 μg/ml 7-Amino-Actinomycin D and analyzed by flow cytometry using a Becton Dickinson FACSCalibur instrument and the CellQuest Pro Software. Gating was on live cells, i.e. 7-Amino-Actinomycin D—negative events.

FACS analyses show that unlabeled humanised CD45RB/RO binding molecules, e.g. VHE/humV1 and VHQ/humV1 but not the isotype matched control antibody compete with FITC-labeled chimeric antibody for binding to the human CD45-positive T cell line PEER.

Example 7

Biological Activities of CD45RB/RO Binding Molecules

In this study, we have addressed whether CD45RB/RO binding chimeric antibody, when present in cultures of polyclonally activated primary human T cells (i) supports the differentiation of T cells with a characteristic Treg phenotype, (ii) prevents or enhances apoptosis following T cell activation, and (iii) affects expression of subset-specific antigens and receptors after restimulation.

CD45RB/RO Binding Chimeric Antibody Enhances Cell Death in Polyclonally Activated T Cells Primary T cells (mixture of CD4+ and CD8+ T subsets) were subjected to activation by anti-CD3 plus anti-CD28 mAb (200 ng/ml each) in the presence or absence (=control) of CD45RB/RO binding chimeric antibody. Excess antibodies were removed by washing on day 2. 7-amino-actinomycin D (7-MD) as a DNA-staining dye taken up by apoptotic and necrotic cells was used to measure cell death following activation. The results show that activation of T cells in the presence of CD45RB/RO binding chimeric antibody increased the fraction of 7-MD positive cells than two-fold on day 2 after activation. On day 7, the portion of 7-MD positive cells was again similar in CD45RB/RO binding chimeric antibody-treated and control cultures.

CD45RB/RO Binding Chimeric Antibody but not Control mAb Treated T Cells Display a T Regulatory Cell (Treg) Phenotype Increased expression of CD25 and the negative regulatory protein CTLA-4 (CD152) is a marker of Treg cells. Functional suppression of primary and secondary T cell responses by CD45RB/RO binding chimeric antibody may be due to the induction of Treg cells. To address this issue, T cells were activated by anti-CD3+CD28 mAbs and cultured in the presence of CD45RB/RO binding chimeric antibody or anti-LPS control mAb. The time course of CTLA-4 and CD25 expression reveals marked differences between controls and CD45RB/RO binding chimeric antibody-treated T cells on days 1 and 3 after secondary stimulation, indicating a Treg phenotype.

Intracellular CTLA-4 Expression is Sustained in the Presence of CD45RB/RO Binding Chimeric Antibody It has been reported that substantial amounts of CTLA-4 can also be found intracellularly. Therefore, in parallel to surface CTLA-4 staining, intracellular CTLA-4 expression was analyzed. Moderate differences between T cell cultures were seen on day 4 after stimulation. After prolonged culture, however, high levels of intracellular CTLA-4 were sustained only in CD45RB/RO binding chimeric antibody-treated but not in control T cells.

CD45RB/RO Binding Chimeric Antibody-Treated T Cells Become Double Positive for CD4 and CD8

Following stimulation, T cells induce and upregulate the expression of several surface receptors, such as CD25, CD152 (CTLA-4), CD154 (CD40-Ligand) and others. In contrast, the level of expression of CD4 or CD8 is thought to stay relatively constant. We reproducibly observed a strong increase of both CD4 and CD8 antigens on CD45RB/RO binding chimeric antibody-treated but not on control Ab-treated T cells after activation. The emergence of a CD4/CD8 double-positive T cell population seems to be due to the upregulation of CD4 on the CD8+ subset and conversely, CD8 on the CD4+ subset. This contrasts with a moderately low percentage of double positive T cells in control cultures.

High IL-2 Receptor Alpha-Chain, but Very Low Beta-Chain Expression by CD45RB/RO Binding Chimeric Antibody-Treated T Cells Treg cells are known to be constitutively positive for CD25, the IL-2 receptor alpha-chain. The regulation of other subunits of the trimeric IL-2 receptor on Treg cells is not known. Recently we have compared the expression of the beta-chain of IL-2 receptor, e.g. CD122, on T cells activated and propagated in the presence or absence of CD45RB/RO binding chimeric antibody. The results show that CD45RB/RO binding chimeric antibody-treated T cells have about ten-fold lower CD122 expression as compared to T cells in control cultures. This difference may indicate that Treg cells require factors other than IL-2 to proliferate.

Example 8

Sequences of the Invention

CDR Sequences of the Invention are Underlined

SEQ ID NO:1

Part of the Amino Acid Sequence of Chimeric Light Chain

DILLTQSPAILSVSPGERVSFSCRASQNIGTSIQWYQQRTNGSPRLLIR
SSSESISGIPSRFSGSGSGTDFTLSINSVESEDIADYYCQQSNTWPFTFG
SGTKLEIK

SEQ ID NO:2

Part of the Amino Acid Sequence of Chimeric Heavy Chain

EVQLQQSGPELVKPGASVKMSCKASGYTFTNYIIHWVKQEPGQGLEWIG
YFNPYNHGTKYNEKFKGRATLTADKSSNTAYMDLSSLTSEDSAIYYCAR
SGPYAWFDTWGQGTTVTVSS

SEQ ID NO:3

Amino Acid Sequence of Chimeric Light Chain

DILLTQSPAILSVSPGERVSFSCRASQNIGTSIQWYQQRTNGSPRLLIR
SSSESISGIPSRFSGSGSGTDFTLSINSVESEDIADYYCQQSNTWPFT
FGSGTKLEIKRTVAAPSVFIFPPSDEQLKSGTASVVCLLNNFYPREAKVQ
WKVDNALQSGNSQESVTEQDSKDSTYSLSSTLTLSKADYEKHKVYACEVT
HQGLSSPVTKSFNRGEC

SEQ ID NO:4

Amino Acid Sequence of Chimeric Heavy Chain

EVQLQQSGPELVKPGASVKMSCKASGYTFTNYIIHWVKQEPGQGLEWIG
YFNPYNHGTKYNEKFKGRATLTADKSSNTAYMDLSSLTSEDSAIYYCAR
SGPYAWFDTWGQGTTVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPK
PKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLS
PGK

SEQ ID NO:5

Nucleotide Sequence Encoding a Polypeptide of SEQ ID NO:1

GACATTCTGCTGACCCAGTCTCCAGCCATCCTGTCTGTGAGTCCAGGAGA
AAGAGTCAGTTTCTCCTGCAGGGCCAGTCAGAACATTGGCACAAGCATAC

-continued

AGTGGTATCAACAAAGAACAAATGGTTCTCCAAGGCTTCTCATAAGGTCT
TCTTCTGAGTCTATCTCTGGGATCCCTTCCAGGTTTAGTGGCAGTGGATC
AGGGACAGATTTTACTCTTAGCATCAACAGTGTGGAGTCTGAAGATATTG
CAGATTATTACTGTCAACAAAGTAATACCTGGCCATTCACGTTCGGCTCG
GGGACCAAGCTTGAAATCAAA

SEQ ID NO:6

Nucleotide Sequence Encoding a Polypeptide of SEQ ID NO:2

GAGGTGCAGCTGCAGCAGTCAGGACCTGAACTGGTAAAGCCTGGGGCTTC
AGTGAAGATGTCCTGCAAGGCCTCTGGATACACATTCACTAATTATATTA
TCCACTGGGTGAAGCAGGAGCCTGGTCAGGGCCTTGAATGGATTGGATAT
TTTAATCCTTACAATCATGGTACTAAGTACAATGAGAAGTTCAAAGGCAG
GGCCACACTAACTGCAGACAAATCCTCCAACACAGCCTACATGGACCTCA
GCAGCCTGACCTCTGAGGACTCTGCGATCTACTACTGTGCAAGATCAGGA
CCCTATGCCTGGTTTGACACCTGGGGCCAAGGGACCACGGTCACCGTCTC
CTCA

SEQ ID NO:7

Part of Amino Acid Sequence of Humanised Light Chain Designated humV2 (humV2=VLm)

DILLTQSPAT LSLSPGERAT FSCRASQNIG TSIQWYQQKT
NGAPRLLIRS SSESISGIPS RFSGSGSGTD FTLTISSLEP
EDFAVYYCQQ SNTWPFTFGQ GTKLEIK

SEQ ID NO:8

Part of Amino Acid Sequence of Humanised Light Chain Designated humV1 (humV1=VLh)

DILLTQSPAT LSLSPGERAT LSCRASQNIG TSIQWYQQKP
GQAPRLLIRS SSESISGIPS RFSGSGSGTD FTLTISSLEP
EDFAVYYCQQ SNTWPFTFGQ GTKLEIK

SEQ ID NO:9

Part of Amino Acid Sequence of Humanised Heavy Chain Designated VHE

EVQLVESGAE VKKPGASVKV SCKASGYTFT NYIIHWVKQE
PGQGLEWIGY FNPYNHGTKY NEKFKGRATL TANKSISTAY
MELSSLRSED TAVYYCARSG PYAWFDTWGQ GTTVTVSS

SEQ ID NO:10

Part of Amino Acid Sequence of Humanised Heavy Chain Designated VHQ

QVQLVESGAE VKKPGASVKV SCKASGYTFT NYIIHWVKQE

PGQGLEWIGY FNPYNHGTKY NEKFKGRATL TANKSISTAY

MELSSLRSED TAVYYCARSG PYAWFDTWGQ GTTVTVSS

SEQ ID NO:11

Nucleotide Sequence Encoding Amino Acid Sequence SEQ ID NO:9

GAGGTGCAGCTGGTGGAGTCAGGAGCCGAAGTGAAAAAGCCTGGGGCTTCAGTGAAG

GTGTCCTGCAAGGCCTCTGGATACACATTCACTAATTATATTATCCACTGGGTGAAGCA

GGAGCCTGGTCAGGGCCTTGAATGGATTGGATATTTTAATCCTTACAATCATGGTACTA

AGTACAATGAGAAGTTCAAAGGCAGGGCCACACTAACTGCAAACAAATCCATCAGCACA

GCCTACATGGAGCTCAGCAGCCTGCGCTCTGAGGACACTGCGGTCTACTACTGTGCAA

GATCAGGACCCTATGCCTGGTTTGACACCTGGGGCCAAGGGACCACGGTCACCGTCTC

CTCA

SEQ ID NO:12

Nucleotide Sequence Encoding Amino Acid Sequence SEQ ID NO:10

CAGGTGCAGCTGGTGGAGTCAGGAGCCGAAGTGAAAAAGCCTGGGGCTTCAGTGAAG

GTGTCCTGCAAGGCCTCTGGATACACATTCACTAATTATATTATCCACTGGGTGAAGCA

GGAGCCTGGTCAGGGCCTTGAATGGATTGGATATTTTAATCCTTACAATCATGGTACTA

AGTACAATGAGAAGTTCAAAGGCAGGGCCACACTAACTGCAAACAAATCCATCAGCACA

GCCTACATGGAGCTCAGCAGCCTGCGCTCTGAGGACACTGCGGTCTACTACTGTGCAA

GATCAGGACCCTATGCCTGGTTTGACACCTGGGGCCAAGGGACCACGGTCACCGTCTC

CTCA

SEQ ID NO:13

Nucleotide Sequence Encoding Amino Acid Sequence SEQ ID NO:7

GACATTCTGCTGACCCAGTCTCCAGCCACCCTGTCTCTGAGTCCAGGAGAAAGAGCCA

CTTTCTCCTGCAGGGCCAGTCAGAACATTGGCACAAGCATACAGTGGTATCAACAAAAA

ACAAATGGTGCTCCAAGGCTTCTCATAAGGTCTTCTTCTGAGTCTATCTCTGGGATCCC

TTCCAGGTTTAGTGGCAGTGGATCAGGGACAGATTTTACTCTTACCATCAGCAGTCTGG

AGCCTGAAGATTTTGCAGTGTATTACTGTCAACAAAGTAATACCTGGCCATTCACGTTC

GGCCAGGGGACCAAGCTGGAGATCAAA

SEQ ID NO:14

Nucleotide Sequence Encoding Amino Acid Sequence SEQ ID NO:8

GACATTCTGCTGACCCAGTCTCCAGCCACCCTGTCTCTGAGTCCAGGAGAAAGAGCCA

CTCTCTCCTGCAGGGCCAGTCAGAACATTGGCACAAGCATACAGTGGTATCAACAAAAA

CCAGGTCAGGCTCCAAGGCTTCTCATAAGGTCTTCTTCTGAGTCTATCTCTGGGATCCC

TTCCAGGTTTAGTGGCAGTGGATCAGGGACAGATTTTACTCTTACCATCAGCAGTCTGG

AGCCTGAAGATTTTGCAGTGTATTACTGTCAACAAAGTAATACCTGGCCATTCACGTTC

GGCCAGGGGACCAAGCTGGAGATCAAA

SEQ ID NO:15

Nucleotide Sequence of the Expression Vector HCMV-G1 HuAb-VHQ (Complete DNA Sequence of a Humanised Heavy Chain Expression Vector Comprising SEQ ID NO:12 (VHQ) from 3921-4274)

```
   1 AGCTTTTTGC AAAAGCCTAG GCCTCCAAAA AAGCCTCCTC
     ACTACTTCTG

  51 GAATAGCTCA GAGGCCGAGG CGGCCTCGGC CTCTGCATAA
     ATAAAAAAAA

 101 TTAGTCAGCC ATGGGGCGGA GAATGGGCGG AACTGGGCGG
     AGTTAGGGGC

 151 GGGATGGGCG GAGTTAGGGG CGGGACTATG GTTGCTGACT
     AATTGAGATG

 201 CATGCTTTGC ATACTTCTGC CTGCTGGGGA GCCTGGTTGC
     TGACTAATTG

 251 AGATGCATGC TTTGCATACT TCTGCCTGCT GGGGAGCCTG
     GGGACTTTCC

 301 ACACCCTAAC TGACACACAT TCCACAGCTG CCTCGCGCGT
     TTCGGTGATG

 351 ACGGTGAAAA CCTCTGACAC ATGCAGCTCC CGGAGACGGT
     CACAGCTTGT

 401 CTGTAAGCGG ATGCCGGGAG CAGACAAGCC CGTCAGGGCG
     CGTCAGCGGG

 451 TGTTGGCGGG TGTCGGGGCG CAGCCATGAC CCAGTCACGT
     AGCGATAGCG

 501 GAGTGTATAC TGGCTTAACT ATGCGGCATC AGAGCAGATT
     GTACTGAGAG

 551 TGCACCATAT GCGGTGTGAA ATACCGCACA GATGCGTAAG
     GAGAAAATAC

 601 CGCATCAGGC GCTCTTCCGC TTCCTCGCTC ACTGACTCGC
     TGCGCTCGGT

 651 CGTTCGGCTG CGGCGAGCGG TATCAGCTCA CTCAAAGGCG
     GTAATACGGT

 701 TATCCACAGA ATCAGGGGAT AACGCAGGAA AGAACATGTG
     AGCAAAAGGC

 751 CAGCAAAAGG CCAGGAACCG TAAAAAGGCC GCGTTGCTGG
     CGTTTTTCCA

 801 TAGGCTCCGC CCCCCTGACG AGCATCACAA AAATCGACGC
     TCAAGTCAGA

 851 GGTGGCGAAA CCCGACAGGA CTATAAAGAT ACCAGGCGTT
     TCCCCCTGGA

 901 AGCTCCCTCG TGCGCTCTCC TGTTCCGACC CTGCCGCTTA
     CCGGATACCT
```

-continued

```
 951 GTCCGCCTTT CTCCCTTCGG GAAGCGTGGC GCTTTCTCAT
     AGCTCACGCT

1001 GTAGGTATCT CAGTTCGGTG TAGGTCGTTC GCTCCAAGCT
     GGGCTGTGTG

1051 CACGAACCCC CCGTTCAGCC CGACCGCTGC GCCTTATCCG
     GTAACTATCG

1101 TCTTGAGTCC AACCCGGTAA GACACGACTT ATCGCCACTG
     GCAGCAGCCA

1151 CTGGTAACAG GATTAGCAGA GCGAGGTATG TAGGCGGTGC
     TACAGAGTTC

1201 TTGAAGTGGT GGCCTAACTA CGGCTACACT AGAAGGACAG
     TATTTGGTAT

1251 CTGCGCTCTG CTGAAGCCAG TTACCTTCGG AAAAAGAGTT
     GGTAGCTCTT

1301 GATCCGGCAA ACAAACCACC GCTGGTAGCG GTGGTTTTTT
     TGTTTGCAAG

1351 CAGCAGATTA CGCGCAGAAA AAAAGGATCT CAAGAAGATC
     CTTTGATCTT

1401 TTCTACGGGG TCTGACGCTC AGTGGAACGA AAACTCACGT
     TAAGGGATTT

1451 TGGTCATGAG ATTATCAAAA AGGATCTTCA CCTAGATCCT
     TTTAAATTAA

1501 AAATGAAGTT TTAAATCAAT CTAAAGTATA TATGAGTAAA
     CTTGGTCTGA

1551 CAGTTACCAA TGCTTAATCA GTGAGGCACC TATCTCAGCG
     ATCTGTCTAT

1601 TTCGTTCATC CATAGTTGCC TGACTCCCCG TCGTGTAGAT
     AACTACGATA

1651 CGGGAGGGCT TACCATCTGG CCCCAGTGCT GCAATGATAC
     CGCGAGACCC

1701 ACGCTCACCG GCTCCAGATT TATCAGCAAT AAACCAGCCA
     GCCGGAAGGG

1751 CCGAGCGCAG AAGTGGTCCT GCAACTTTAT CCGCCTCCAT
     CCAGTCTATT

1801 AATTGTTGCC GGGAAGCTAG AGTAAGTAGT TCGCCAGTTA
     ATAGTTTGCG

1851 CAACGTTGTT GCCATTGCTG CAGGCATCGT GGTGTCACGC
     TCGTCGTTTG

1901 GTATGGCTTC ATTCAGCTCC GGTTCCCAAC GATCAAGGCG
     AGTTACATGA

1951 TCCCCCATGT TGTGCAAAAA AGCGGTTAGC TCCTTCGGTC
     CTCCGATCGT
```

-continued

```
2001 TGTCAGAAGT AAGTTGGCCG CAGTGTTATC ACTCATGGTT
     ATGGCAGCAC

2051 TGCATAATTC TCTTACTGTC ATGCCATCCG TAAGATGCTT
     TTCTGTGACT

2101 GGTGAGTACT CAACCAAGTC ATTCTGAGAA TAGTGTATGC
     GGCGACCGAG

2151 TTGCTCTTGC CCGGCGTCAA CACGGGATAA TACCGCGCCA
     CATAGCAGAA

2201 CTTTAAAAGT GCTCATCATT GGAAAACGTT CTTCGGGGCG
     AAAACTCTCA

2251 AGGATCTTAC CGCTGTTGAG ATCCAGTTCG ATGTAACCCA
     CTCGTGCACC

2301 CAACTGATCT TCAGCATCTT TTACTTTCAC CAGCGTTTCT
     GGGTGAGCAA

2351 AAACAGGAAG GCAAAATGCC GCAAAAAAGG GAATAAGGGC
     GACACGGAAA

2401 TGTTGAATAC TCATACTCTT CCTTTTTCAA TATTATTGAA
     GCATTTATCA

2451 GGGTTATTGT CTCATGAGCG GATACATATT TGAATGTATT
     TAGAAAAATA

2501 AACAAATAGG GGTTCCGCGC ACATTTCCCC GAAAAGTGCC
     ACCTGACGTC

2551 TAAGAAACCA TTATTATCAT GACATTAACC TATAAAAATA
     GGCGTATCAC

2601 GAGGCCCTTT CGTCTTCAAG AATTCAGCTT GGCTGCAGTG
     AATAATAAAA

2651 TGTGTGTTTG TCCGAAATAC GCGTTTTGAG ATTTCTGTCG
     CCGACTAAAT

2701 TCATGTCGCG CGATAGTGGT GTTTATCGCC GATAGAGATG
     GCGATATTGG

2751 AAAAATCGAT ATTTGAAAAT ATGGCATATT GAAAATGTCG
     CCGATGTGAG

2801 TTTCTGTGTA ACTGATATCG CCATTTTTCC AAAAGTGATT
     TTTGGGCATA

2851 CGCGATATCT GGCGATAGCG CTTATATCGT TTACGGGGGA
     TGGCGATAGA

2901 CGACTTTGGT GACTTGGGCG ATTCTGTGTG TCGCAAATAT
     CGCAGTTTCG

2951 ATATAGGTGA CAGACGATAT GAGGCTATAT CGCCGATAGA
     GGCGACATCA

3001 AGCTGGCACA TGGCCAATGC ATATCGATCT ATACATTGAA
     TCAATATTGG

3051 CCATTAGCCA TATTATTCAT TGGTTATATA GCATAAATCA
     ATATTGGCTA

3101 TTGGCCATTG CATACGTTGT ATCCATATCA TAATATGTAC
     ATTTATATTG

3151 GCTCATGTCC AACATTACCG CCATGTTGAC ATTGATTATT
     GACTAGTTAT

3201 TAATAGTAAT CAATTACGGG GTCATTAGTT CATAGCCCAT
     ATATGGAGTT

3251 CCGCGTTACA TAACTTACGG TAAATGGCCC GCCTGGCTGA
     CCGCCCAACG

3301 ACCCCCGCCC ATTGACGTCA ATAATGACGT ATGTTCCCAT
     AGTAACGCCA
```

-continued

```
3351 ATAGGGACTT TCCATTGACG TCAATGGGTG GAGTATTTAC
     GGTAAACTGC

3401 CCACTTGGCA GTACATCAAG TGTATCATAT GCCAAGTACG
     CCCCCTATTG

3451 ACGTCAATGA CGGTAAATGG CCCGCCTGGC ATTATGCCCA
     GTACATGACC

3501 TTATGGGACT TTCCTACTTG GCAGTACATC TACGTATTAG
     TCATCGCTAT

3551 TACCATGGTG ATGCGGTTTT GGCAGTACAT CAATGGGCGT
     GGATAGCGGT

3601 TTGACTCACG GGGATTTCCA AGTCTCCACC CCATTGACGT
     CAATGGGAGT

3651 TTGTTTTGGC ACCAAAATCA ACGGGACTTT CCAAAATGTC
     GTAACAACTC

3701 CGCCCCATTG ACGCAAATGG GCGGTAGGCG TGTACGGTGG
     GAGGTCTATA

3751 TAAGCAGAGC TCGTTTAGTG AACCGTCAGA TCGCCTGGAG
     ACGCCATCCA

3801 CGCTGTTTTG ACCTCCATAG AAGACACCGG GACCGATCCA
     GCCTCCGCAA

3851 GCTTGCCGCC ACCATGGACT GGACCTGGAG GGTGTTCTGC
     CTGCTGGCCG

3901 TGGCCCCCGG CGCCCACAGC CAGGTGCAGC TGGTGGAGTC
     AGGAGCCGAA

3951 GTGAAAAAGC CTGGGGCTTC AGTGAAGGTG TCCTGCAAGG
     CCTCTGGATA

4001 CACATTCACT AATTATATTA TCCACTGGGT GAAGCAGGAG
     CCTGGTCAGG

4051 GCCTTGAATG GATTGGATAT TTTAATCCTT ACAATCATGG
     TACTAAGTAC

4101 AATGAGAAGT TCAAAGGCAG GGCCACACTA ACTGCAAACA
     AATCCATCAG

4151 CACAGCCTAC ATGGAGCTCA GCAGCCTGCG CTCTGAGGAC
     ACTGCGGTCT

4201 ACTACTGTGC AAGATCAGGA CCCTATGCCT GGTTTGACAC
     CTGGGGCCAA

4251 GGGACCACGG TCACCGTCTC CTCAGGTGAG TTCTAGAAGG
     ATCCCAAGCT

4301 AGCTTTCTGG GGCAGGCCAG GCCTGACCTT GGCTTTGGGG
     CAGGGAGGGG

4351 GCTAAGGTGA GGCAGGTGGC GCCAGCCAGG TGCACACCCA
     ATGCCCATGA

4401 GCCCAGACAC TGGACGCTGA ACCTCGCGGA CAGTTAAGAA
     CCCAGGGGCC

4451 TCTGCGCCCT GGGCCCAGCT CTGTCCCACA CCGCGGTCAC
     ATGGCACCAC

4501 CTCTCTTGCA GCCTCCACCA AGGGCCCATC GGTCTTCCCC
     CTGGCACCCT

4551 CCTCCAAGAG CACCTCTGGG GGCACAGCGG CCCTGGGCTG
     CCTGGTCAAG

4601 GACTACTTCC CCGAACCGGT GACGGTGTCG TGGAACTCAG
     GCGCCCTGAC
```

-continued

4651 CAGCGGCGTG CACACCTTCC CGGCTGTCCT ACAGTCCTCA
GGACTCTACT

4701 CCCTCAGCAG CGTGGTGACC GTGCCCTCCA GCAGCTTGGG
CACCCAGACC

4751 TACATCTGCA ACGTGAATCA CAAGCCCAGC AACACCAAGG
TGGACAAGAA

4801 AGTTGGTGAG AGGCCAGCAC AGGGAGGGAG GGTGTCTGCT
GGAAGCCAGG

4851 CTCAGCGCTC CTGCCTGGAC GCATCCCGGC TATGCAGCCC
CAGTCCAGGG

4901 CAGCAAGGCA GGCCCCGTCT GCCTCTTCAC CCGGAGGCCT
CTGCCCGCCC

4951 CACTCATGCT CAGGGAGAGG GTCTTCTGGC TTTTTCCCCA
GGCTCTGGGC

5001 AGGCACAGGC TAGGTGCCCC TAACCCAGGC CCTGCACACA
AAGGGGCAGG

5051 TGCTGGGCTC AGACCTGCCA AGAGCCATAT CCGGGAGGAC
CCTGCCCCTG

5101 ACCTAAGCCC ACCCCAAAGG CCAAACTCTC CACTCCCTCA
GCTCGGACAC

5151 CTTCTCTCCT CCCAGATTCC AGTAACTCCC AATCTTCTCT
CTGCAGAGCC

5201 CAAATCTTGT GACAAAACTC ACACATGCCC ACCGTGCCCA
GGTAAGCCAG

5251 CCCAGGCCTC GCCCTCCAGC TCAAGGCGGG ACAGGTGCCC
TAGAGTAGCC

5301 TGCATCCAGG GACAGGCCCC AGCCGGGTGC TGACACGTCC
ACCTCCATCT

5351 CTTCCTCAGC ACCTGAACTC CTGGGGGGAC CGTCAGTCTT
CCTCTTCCCC

5401 CCAAAACCCA AGGACACCCT CATGATCTCC CGGACCCCTG
AGGTCACATG

5451 CGTGGTGGTG GACGTGAGCC ACGAAGACCC TGAGGTCAAG
TTCAACTGGT

5501 ACGTGGACGG CGTGGAGGTG CATAATGCCA AGACAAAGCC
GCGGGAGGAG

5551 CAGTACAACA GCACGTACCG TGTGGTCAGC GTCCTCACCG
TCCTGCACCA

5601 GGACTGGCTG AATGGCAAGG AGTACAAGTG CAAGGTCTCC
AACAAAGCCC

5651 TCCCAGCCCC CATCGAGAAA ACCATCTCCA AAGCCAAAGG
TGGGACCCGT

5701 GGGGTGCGAG GGCCACATGG ACAGAGGCCG GCTCGGCCCA
CCCTCTGCCC

5751 TGAGAGTGAC CGCTGTACCA ACCTCTGTCC CTACAGGGCA
GCCCCGAGAA

5801 CCACAGGTGT ACACCCTGCC CCCATCCCGG GATGAGCTGA
CCAAGAACCA

5851 GGTCAGCCTG ACCTGCCTGG TCAAAGGCTT CTATCCCAGC
GACATCGCCG

5901 TGGAGTGGGA GAGCAATGGG CAGCCGGAGA ACAACTACAA
GACCACGCCT

5951 CCCGTGCTGG ACTCCGACGG CTCCTTCTTC CTCTACAGCA
AGCTCACCGT

-continued

6001 GGACAAGAGC AGGTGGCAGC AGGGGAACGT CTTCTCATGC
TCCGTGATGC

6051 ATGAGGCTCT GCACAACCAC TACACGCAGA AGAGCCTCTC
CCTGTCTCCG

6101 GGTAAATGAG TGCGACGGCC GGCAAGCCCC CGCTCCCCGG
GCTCTCGCGG

6151 TCGCACGAGG ATGCTTGGCA CGTACCCCCT GTACATACTT
CCCGGGCGCC

6201 CAGCATGGAA ATAAAGCACC CAGCGCTGCC CTGGGCCCCT
GCGAGACTGT

6251 GATGGTTCTT TCCACGGGTC AGGCCGAGTC TGAGGCCTGA
GTGGCATGAG

6301 ATCTGATATC ATCGATGAAT TCGAGCTCGG TACCCGGGGA
TCGATCCAGA

6351 CATGATAAGA TACATTGATG AGTTTGGACA AACCACAACT
AGAATGCAGT

6401 GAAAAAAATG CTTTATTTGT GAAATTTGTG ATGCTATTGC
TTTATTTGTA

6451 ACCATTATAA GCTGCAATAA ACAAGTTAAC AACAACAATT
GCATTCATTT

6501 TATGTTTCAG GTTCAGGGGG AGGTGTGGGA GGTTTTTTAA
AGCAAGTAAA

6551 ACCTCTACAA ATGTGGTATG GCTGATTATG ATCTCTAGTC
AAGGCACTAT

6601 ACATCAAATA TTCCTTATTA ACCCCTTTAC AAATTAAAAA
GCTAAAGGTA

6651 CACAATTTTT GAGCATAGTT ATTAATAGCA GACACTCTAT
GCCTGTGTGG

6701 AGTAAGAAAA AACAGTATGT TATGATTATA ACTGTTATGC
CTACTTATAA

6751 AGGTTACAGA ATATTTTTCC ATAATTTTCT TGTATAGCAG
TGCAGCTTTT

6801 TCCTTTGTGG TGTAAATAGC AAAGCAAGCA AGAGTTCTAT
TACTAAACAC

6851 AGCATGACTC AAAAAACTTA GCAATTCTGA AGGAAAGTCC
TTGGGGTCTT

6901 CTACCTTTCT CTTCTTTTTT GGAGGAGTAG AATGTTGAGA
GTCAGCAGTA

6951 GCCTCATCAT CACTAGATGG CATTTCTTCT GAGCAAAACA
GGTTTTCCTC

7001 ATTAAAGGCA TTCCACCACT GCTCCCATTC ATCAGTTCCA
TAGGTTGGAA

7051 TCTAAAATAC ACAAACAATT AGAATCAGTA GTTTAACACA
TTATACACTT

7101 AAAAATTTTA TATTTACCTT AGAGCTTTAA ATCTCTGTAG
GTAGTTTGTC

7151 CAATTATGTC ACACCACAGA AGTAAGGTTC CTTCACAAAG
ATCCGGGACC

7201 AAAGCGGCCA TCGTGCCTCC CCACTCCTGC AGTTCGGGGG
CATGGATGCG

7251 CGGATAGCCG CTGCTGGTTT CCTGGATGCC GACGGATTTG
CACTGCCGGT

-continued

```
7301 AGAACTCCGC GAGGTCGTCC AGCCTCAGGC AGCAGCTGAA
     CCAACTCGCG

7351 AGGGGATCGA GCCCGGGGTG GGCGAAGAAC TCCAGCATGA
     GATCCCCGCG

7401 CTGGAGGATC ATCCAGCCGG CGTCCCGGAA AACGATTCCG
     AAGCCCAACC

7451 TTTCATAGAA GGCGGCGGTG GAATCGAAAT CTCGTGATGG
     CAGGTTGGGC

7501 GTCGCTTGGT CGGTCATTTC GAACCCCAGA GTCCCGCTCA
     GAAGAACTCG

7551 TCAAGAAGGC GATAGAAGGC GATGCGCTGC GAATCGGGAG
     CGGCGATACC

7601 GTAAAGCACG AGGAAGCGGT CAGCCCATTC GCCGCCAAGC
     TCTTCAGCAA

7651 TATCACGGGT AGCCAACGCT ATGTCCTGAT AGCGGTCCGC
     CACACCCAGC

7701 CGGCCACAGT CGATGAATCC AGAAAAGCGG CCATTTTCCA
     CCATGATATT

7751 CGGCAAGCAG GCATCGCCAT GGGTCACGAC GAGATCCTCG
     CCGTCGGGCA

7801 TGCGCGCCTT GAGCCTGGCG AACAGTTCGG CTGGCGCGAG
     CCCCTGATGC

7851 TCTTCGTCCA GATCATCCTG ATCGACAAGA CCGGCTTCCA
     TCCGAGTACG

7901 TGCTCGCTCG ATGCGATGTT TCGCTTGGTG GTCGAATGGG
     CAGGTAGCCG

7951 GATCAAGCGT ATGCAGCCGC CGCATTGCAT CAGCCATGAT
     GGATACTTTC

8001 TCGGCAGGAG CAAGGTGAGA TGACAGGAGA TCCTGCCCCG
     GCACTTCGCC

8051 CAATAGCAGC CAGTCCCTTC CCGCTTCAGT GACAACGTCG
     AGCACAGCTG

8101 CGCAAGGAAC GCCCGTCGTG GCCAGCCACG ATAGCCGCGC
     TGCCTCGTCC

8151 TGCAGTTCAT TCAGGGCACC GGACAGGTCG GTCTTGACAA
     AAAGAACCGG

8201 GCGCCCCTGC GCTGACAGCC GGAACACGGC GGCATCAGAG
     CAGCCGATTG

8251 TCTGTTGTGC CCAGTCATAG CCGAATAGCC TCTCCACCCA
     AGCGGCCGGA

8301 GAACCTGCGT GCAATCCATC TTGTTCAATC ATGCGAAACG
     ATCCTCATCC

8351 TGTCTCTTGA TCAGATCTTG ATCCCCTGCG CCATCAGATC
     CTTGGCGGCA

8401 AGAAAGCCAT CCAGTTTACT TTGCAGGGCT TCCCAACCTT
     ACCAGAGGGC

8451 GCCCCAGCTG GCAATTCCGG TTCGCTTGCT GTCCATAAAA
     CCGCCCAGTC

8501 TAGCTATCGC CATGTAAGCC CACTGCAAGC TACCTGCTTT
     CTCTTTGCGC

8551 TTGCGTTTTC CCTTGTCCAG ATAGCCCAGT AGCTGACATT
     CATCCGGGGT
```

-continued

```
8601 CAGCACCGTT TCTGCGGACT GGCTTTCTAC GTGTTCCGCT
     TCCTTTAGCA

8651 GCCCTTGCGC CCTGAGTGCT TGCGGCAGCG TGAAGCT
```

SEQ ID NO:16

Nucleotide Sequence of the Expression Vector HCMV-G1 HuAb-VHE (Complete DNA Sequence of a Humanised Heavy Chain Expression Vector Comprising SEQ ID NO: 11 (VHE) from 3921-4274)

```
   1 AGCTTTTTGC AAAAGCCTAG GCCTCCAAAA AAGCCTCCTC
     ACTACTTCTG

  51 GAATAGCTCA GAGGCCGAGG CGGCCTCGGC CTCTGCATAA
     ATAAAAAAAA

 101 TTAGTCAGCC ATGGGGCGGA GAATGGGCGG AACTGGGCGG
     AGTTAGGGGC

 151 GGGATGGGCG GAGTTAGGGG CGGGACTATG GTTGCTGACT
     AATTGAGATG

 201 CATGCTTTGC ATACTTCTGC CTGCTGGGGA GCCTGGTTGC
     TGACTAATTG

 251 AGATGCATGC TTTGCATACT TCTGCCTGCT GGGGAGCCTG
     GGGACTTTCC

 301 ACACCCTAAC TGACACACAT TCCACAGCTG CCTCGCGCGT
     TTCGGTGATG

 351 ACGGTGAAAA CCTCTGACAC ATGCAGCTCC CGGAGACGGT
     CACAGCTTGT

 401 CTGTAAGCGG ATGCCGGGAG CAGACAAGCC CGTCAGGGCG
     CGTCAGCGGG

 451 TGTTGGCGGG TGTCGGGGCG CAGCCATGAC CCAGTCACGT
     AGCGATAGCG

 501 GAGTGTATAC TGGCTTAACT ATGCGGCATC AGAGCAGATT
     GTACTGAGAG

 551 TGCACCATAT GCGGTGTGAA ATACCGCACA GATGCGTAAG
     GAGAAAATAC

 601 CGCATCAGGC GCTCTTCCGC TTCCTCGCTC ACTGACTCGC
     TGCGCTCGGT

 651 CGTTCGGCTG CGGCGAGCGG TATCAGCTCA CTCAAAGGCG
     GTAATACGGT

 701 TATCCACAGA ATCAGGGGAT AACGCAGGAA AGAACATGTG
     AGCAAAAGGC

 751 CAGCAAAAGG CCAGGAACCG TAAAAAGGCC GCGTTGCTGG
     CGTTTTTCCA

 801 TAGGCTCCGC CCCCCTGACG AGCATCACAA AAATCGACGC
     TCAAGTCAGA

 851 GGTGGCGAAA CCCGACAGGA CTATAAAGAT ACCAGGCGTT
     TCCCCCTGGA

 901 AGCTCCCTCG TGCGCTCTCC TGTTCCGACC CTGCCGCTTA
     CCGGATACCT

 951 GTCCGCCTTT CTCCCTTCGG GAAGCGTGGC GCTTTCTCAT
     AGCTCACGCT

1001 GTAGGTATCT CAGTTCGGTG TAGGTCGTTC GCTCCAAGCT
     GGGCTGTGTG

1051 CACGAACCCC CCGTTCAGCC CGACCGCTGC GCCTTATCCG
     GTAACTATCG
```

-continued

1101 TCTTGAGTCC AACCCGGTAA GACACGACTT ATCGCCACTG GCAGCAGCCA

1151 CTGGTAACAG GATTAGCAGA GCGAGGTATG TAGGCGGTGC TACAGAGTTC

1201 TTGAAGTGGT GGCCTAACTA CGGCTACACT AGAAGGACAG TATTTGGTAT

1251 CTGCGCTCTG CTGAAGCCAG TTACCTTCGG AAAAAGAGTT GGTAGCTCTT

1301 GATCCGGCAA ACAAACCACC GCTGGTAGCG GTGGTTTTTT TGTTTGCAAG

1351 CAGCAGATTA CGCGCAGAAA AAAAGGATCT CAAGAAGATC CTTTGATCTT

1401 TTCTACGGGG TCTGACGCTC AGTGGAACGA AAACTCACGT TAAGGGATTT

1451 TGGTCATGAG ATTATCAAAA AGGATCTTCA CCTAGATCCT TTTAAATTAA

1501 AAATGAAGTT TTAAATCAAT CTAAAGTATA TATGAGTAAA CTTGGTCTGA

1551 CAGTTACCAA TGCTTAATCA GTGAGGCACC TATCTCAGCG ATCTGTCTAT

1601 TTCGTTCATC CATAGTTGCC TGACTCCCCG TCGTGTAGAT AACTACGATA

1651 CGGGAGGGCT TACCATCTGG CCCCAGTGCT GCAATGATAC CGCGAGACCC

1701 ACGCTCACCG GCTCCAGATT TATCAGCAAT AAACCAGCCA GCCGGAAGGG

1751 CCGAGCGCAG AAGTGGTCCT GCAACTTTAT CCGCCTCCAT CCAGTCTATT

1801 AATTGTTGCC GGGAAGCTAG AGTAAGTAGT TCGCCAGTTA ATAGTTTGCG

1851 CAACGTTGTT GCCATTGCTG CAGGCATCGT GGTGTCACGC TCGTCGTTTG

1901 GTATGGCTTC ATTCAGCTCC GGTTCCCAAC GATCAAGGCG AGTTACATGA

1951 TCCCCCATGT TGTGCAAAAA AGCGGTTAGC TCCTTCGGTC CTCCGATCGT

2001 TGTCAGAAGT AAGTTGGCCG CAGTGTTATC ACTCATGGTT ATGGCAGCAC

2051 TGCATAATTC TCTTACTGTC ATGCCATCCG TAAGATGCTT TTCTGTGACT

2101 GGTGAGTACT CAACCAAGTC ATTCTGAGAA TAGTGTATGC GGCGACCGAG

2151 TTGCTCTTGC CCGGCGTCAA CACGGGATAA TACCGCGCCA CATAGCAGAA

2201 CTTTAAAAGT GCTCATCATT GGAAAACGTT CTTCGGGGCG AAAACTCTCA

2251 AGGATCTTAC CGCTGTTGAG ATCCAGTTCG ATGTAACCCA CTCGTGCACC

2301 CAACTGATCT TCAGCATCTT TTACTTTCAC CAGCGTTTCT GGGTGAGCAA

2351 AAACAGGAAG GCAAAATGCC GCAAAAAAGG GAATAAGGGC GACACGGAAA

-continued

2401 TGTTGAATAC TCATACTCTT CCTTTTTCAA TATTATTGAA GCATTTATCA

2451 GGGTTATTGT CTCATGAGCG GATACATATT TGAATGTATT TAGAAAAATA

2501 AACAAATAGG GGTTCCGCGC ACATTTCCCC GAAAAGTGCC ACCTGACGTC

2551 TAAGAAACCA TTATTATCAT GACATTAACC TATAAAAATA GGCGTATCAC

2601 GAGGCCCTTT CGTCTTCAAG AATTCAGCTT GGCTGCAGTG AATAATAAAA

2651 TGTGTGTTTG TCCGAAATAC GCGTTTTGAG ATTTCTGTCG CCGACTAAAT

2701 TCATGTCGCG CGATAGTGGT GTTTATCGCC GATAGAGATG GCGATATTGG

2751 AAAAATCGAT ATTTGAAAAT ATGGCATATT GAAAATGTCG CCGATGTGAG

2801 TTTCTGTGTA ACTGATATCG CCATTTTTCC AAAAGTGATT TTTGGGCATA

2851 CGCGATATCT GGCGATAGCG CTTATATCGT TTACGGGGGA TGGCGATAGA

2901 CGACTTTGGT GACTTGGGCG ATTCTGTGTG TCGCAAATAT CGCAGTTTCG

2951 ATATAGGTGA CAGACGATAT GAGGCTATAT CGCCGATAGA GGCGACATCA

3001 AGCTGGCACA TGGCCAATGC ATATCGATCT ATACATTGAA TCAATATTGG

3051 CCATTAGCCA TATTATTCAT TGGTTATATA GCATAAATCA ATATTGGCTA

3101 TTGGCCATTG CATACGTTGT ATCCATATCA TAATATGTAC ATTTATATTG

3151 GCTCATGTCC AACATTACCG CCATGTTGAC ATTGATTATT GACTAGTTAT

3201 TAATAGTAAT CAATTACGGG GTCATTAGTT CATAGCCCAT ATATGGAGTT

3251 CCGCGTTACA TAACTTACGG TAAATGGCCC GCCTGGCTGA CCGCCCAACG

3301 ACCCCCGCCC ATTGACGTCA ATAATGACGT ATGTTCCCAT AGTAACGCCA

3351 ATAGGGACTT TCCATTGACG TCAATGGGTG GAGTATTTAC GGTAAACTGC

3401 CCACTTGGCA GTACATCAAG TGTATCATAT GCCAAGTACG CCCCCTATTG

3451 ACGTCAATGA CGGTAAATGG CCCGCCTGGC ATTATGCCCA GTACATGACC

3501 TTATGGGACT TTCCTACTTG GCAGTACATC TACGTATTAG TCATCGCTAT

3551 TACCATGGTG ATGCGGTTTT GGCAGTACAT CAATGGGCGT GGATAGCGGT

3601 TTGACTCACG GGGATTTCCA AGTCTCCACC CCATTGACGT CAATGGGAGT

3651 TTGTTTTGGC ACCAAAATCA ACGGGACTTT CCAAAATGTC GTAACAACTC

3701 CGCCCCATTG ACGCAAATGG GCGGTAGGCG TGTACGGTGG GAGGTCTATA

-continued

3751 TAAGCAGAGC TCGTTTAGTG AACCGTCAGA TCGCCTGGAG ACGCCATCCA

3801 CGCTGTTTTG ACCTCCATAG AAGACACCGG GACCGATCCA GCCTCCGCAA

3851 GCTTGCCGCC ACCATGGACT GGACCTGGAG GGTGTTCTGC CTGCTGGCCG

3901 TGGCCCCCGG CGCCCACAGC GAGGTGCAGC TGGTGGAGTC AGGAGCCGAA

3951 GTGAAAAAGC CTGGGGCTTC AGTGAAGGTG TCCTGCAAGG CCTCTGGATA

4001 CACATTCACT AATTATATTA TCCACTGGGT GAAGCAGGAG CCTGGTCAGG

4051 GCCTTGAATG GATTGGATAT TTTAATCCTT ACAATCATGG TACTAAGTAC

4101 AATGAGAAGT TCAAAGGCAG GGCCACACTA ACTGCAAACA AATCCATCAG

4151 CACAGCCTAC ATGGAGCTCA GCAGCCTGCG CTCTGAGGAC ACTGCGGTCT

4201 ACTACTGTGC AAGATCAGGA CCCTATGCCT GGTTTGACAC CTGGGGCCAA

4251 GGGACCACGG TCACCGTCTC CTCAGGTGAG TTCTAGAAGG ATCCCAAGCT

4301 AGCTTTCTGG GGCAGGCCAG GCCTGACCTT GGCTTTGGGG CAGGGAGGGG

4351 GCTAAGGTGA GGCAGGTGGC GCCAGCCAGG TGCACACCCA ATGCCCATGA

4401 GCCCAGACAC TGGACGCTGA ACCTCGCGGA CAGTTAAGAA CCCAGGGGCC

4451 TCTGCGCCCT GGGCCCAGCT CTGTCCCACA CCGCGGTCAC ATGGCACCAC

4501 CTCTCTTGCA GCCTCCACCA AGGGCCCATC GGTCTTCCCC CTGGCACCCT

4551 CCTCCAAGAG CACCTCTGGG GGCACAGCGG CCCTGGGCTG CCTGGTCAAG

4601 GACTACTTCC CCGAACCGGT GACGGTGTCG TGGAACTCAG GCGCCCTGAC

4651 CAGCGGCGTG CACACCTTCC CGGCTGTCCT ACAGTCCTCA GGACTCTACT

4701 CCCTCAGCAG CGTGGTGACC GTGCCCTCCA GCAGCTTGGG CACCCAGACC

4751 TACATCTGCA ACGTGAATCA CAAGCCCAGC AACACCAAGG TGGACAAGAA

4801 AGTTGGTGAG AGGCCAGCAC AGGGAGGGAG GGTGTCTGCT GGAAGCCAGG

4851 CTCAGCGCTC CTGCCTGGAC GCATCCCGGC TATGCAGCCC CAGTCCAGGG

4901 CAGCAAGGCA GGCCCCGTCT GCCTCTTCAC CCGGAGGCCT CTGCCCGCCC

4951 CACTCATGCT CAGGGAGAGG GTCTTCTGGC TTTTTCCCCA GGCTCTGGGC

5001 AGGCACAGGC TAGGTGCCCC TAACCCAGGC CCTGCACACA AAGGGGCAGG

5051 TGCTGGGCTC AGACCTGCCA AGAGCCATAT CCGGGAGGAC CCTGCCCCTG

-continued

5101 ACCTAAGCCC ACCCCAAAGG CCAAACTCTC CACTCCCTCA GCTCGGACAC

5151 CTTCTCTCCT CCCAGATTCC AGTAACTCCC AATCTTCTCT CTGCAGAGCC

5201 CAAATCTTGT GACAAAACTC ACACATGCCC ACCGTGCCCA GGTAAGCCAG

5251 CCCAGGCCTC GCCCTCCAGC TCAAGGCGGG ACAGGTGCCC TAGAGTAGCC

5301 TGCATCCAGG GACAGGCCCC AGCCGGGTGC TGACACGTCC ACCTCCATCT

5351 CTTCCTCAGC ACCTGAACTC CTGGGGGGAC CGTCAGTCTT CCTCTTCCCC

5401 CCAAAACCCA AGGACACCCT CATGATCTCC CGGACCCCTG AGGTCACATG

5451 CGTGGTGGTG GACGTGAGCC ACGAAGACCC TGAGGTCAAG TTCAACTGGT

5501 ACGTGGACGG CGTGGAGGTG CATAATGCCA AGACAAAGCC GCGGGAGGAG

5551 CAGTACAACA GCACGTACCG TGTGGTCAGC GTCCTCACCG TCCTGCACCA

5601 GGACTGGCTG AATGGCAAGG AGTACAAGTG CAAGGTCTCC AACAAAGCCC

5651 TCCCAGCCCC CATCGAGAAA ACCATCTCCA AAGCCAAAGG TGGGACCCGT

5701 GGGGTGCGAG GGCCACATGG ACAGAGGCCG GCTCGGCCCA CCCTCTGCCC

5751 TGAGAGTGAC CGCTGTACCA ACCTCTGTCC CTACAGGGCA GCCCCGAGAA

5801 CCACAGGTGT ACACCCTGCC CCCATCCCGG GATGAGCTGA CCAAGAACCA

5851 GGTCAGCCTG ACCTGCCTGG TCAAAGGCTT CTATCCCAGC GACATCGCCG

5901 TGGAGTGGGA GAGCAATGGG CAGCCGGAGA ACAACTACAA GACCACGCCT

5951 CCCGTGCTGG ACTCCGACGG CTCCTTCTTC CTCTACAGCA AGCTCACCGT

6001 GGACAAGAGC AGGTGGCAGC AGGGGAACGT CTTCTCATGC TCCGTGATGC

6051 ATGAGGCTCT GCACAACCAC TACACGCAGA AGAGCCTCTC CCTGTCTCCG

6101 GGTAAATGAG TGCGACGGCC GGCAAGCCCC CGCTCCCCGG GCTCTCGCGG

6151 TCGCACGAGG ATGCTTGGCA CGTACCCCCT GTACATACTT CCCGGGCGCC

6201 CAGCATGGAA ATAAAGCACC CAGCGCTGCC CTGGGCCCCT GCGAGACTGT

6251 GATGGTTCTT TCCACGGGTC AGGCCGAGTC TGAGGCCTGA GTGGCATGAG

6301 ATCTGATATC ATCGATGAAT TCGAGCTCGG TACCCGGGGA TCGATCCAGA

6351 CATGATAAGA TACATTGATG AGTTTGGACA AACCACAACT AGAATGCAGT

-continued

```
6401 GAAAAAAATG CTTTATTTGT GAAATTTGTG ATGCTATTGC
     TTTATTTGTA

6451 ACCATTATAA GCTGCAATAA ACAAGTTAAC AACAACAATT
     GCATTCATTT

6501 TATGTTTCAG GTTCAGGGGG AGGTGTGGGA GGTTTTTTAA
     AGCAAGTAAA

6551 ACCTCTACAA ATGTGGTATG GCTGATTATG ATCTCTAGTC
     AAGGCACTAT

6601 ACATCAAATA TTCCTTATTA ACCCCTTTAC AAATTAAAAA
     GCTAAAGGTA

6651 CACAATTTTT GAGCATAGTT ATTAATAGCA GACACTCTAT
     GCCTGTGTGG

6701 AGTAAGAAAA AACAGTATGT TATGATTATA ACTGTTATGC
     CTACTTATAA

6751 AGGTTACAGA ATATTTTTCC ATAATTTTCT TGTATAGCAG
     TGCAGCTTTT

6801 TCCTTTGTGG TGTAAATAGC AAAGCAAGCA AGAGTTCTAT
     TACTAAACAC

6851 AGCATGACTC AAAAAACTTA GCAATTCTGA AGGAAAGTCC
     TTGGGGTCTT

6901 CTACCTTTCT CTTCTTTTTT GGAGGAGTAG AATGTTGAGA
     GTCAGCAGTA

6951 GCCTCATCAT CACTAGATGG CATTTCTTCT GAGCAAAACA
     GGTTTTCCTC

7001 ATTAAAGGCA TTCCACCACT GCTCCCATTC ATCAGTTCCA
     TAGGTTGGAA

7051 TCTAAAATAC ACAAACAATT AGAATCAGTA GTTTAACACA
     TTATACACTT

7101 AAAAATTTTA TATTTACCTT AGAGCTTTAA ATCTCTGTAG
     GTAGTTTGTC

7151 CAATTATGTC ACACCACAGA AGTAAGGTTC CTTCACAAAG
     ATCCGGGACC

7201 AAAGCGGCCA TCGTGCCTCC CCACTCCTGC AGTTCGGGGG
     CATGGATGCG

7251 CGGATAGCCG CTGCTGGTTT CCTGGATGCC GACGGATTTG
     CACTGCCGGT

7301 AGAACTCCGC GAGGTCGTCC AGCCTCAGGC AGCAGCTGAA
     CCAACTCGCG

7351 AGGGGATCGA GCCCGGGGTG GGCGAAGAAC TCCAGCATGA
     GATCCCCGCG

7401 CTGGAGGATC ATCCAGCCGG CGTCCCGGAA AACGATTCCG
     AAGCCCAACC

7451 TTTCATAGAA GGCGGCGGTG GAATCGAAAT CTCGTGATGG
     CAGGTTGGGC

7501 GTCGCTTGGT CGGTCATTTC GAACCCCAGA GTCCCGCTCA
     GAAGAACTCG

7551 TCAAGAAGGC GATAGAAGGC GATGCGCTGC GAATCGGGAG
     CGGCGATACC

7601 GTAAAGCACG AGGAAGCGGT CAGCCCATTC GCCGCCAAGC
     TCTTCAGCAA

7651 TATCACGGGT AGCCAACGCT ATGTCCTGAT AGCGGTCCGC
     CACACCCAGC
```

-continued

```
7701 CGGCCACAGT CGATGAATCC AGAAAAGCGG CCATTTTCCA
     CCATGATATT

7751 CGGCAAGCAG GCATCGCCAT GGGTCACGAC GAGATCCTCG
     CCGTCGGGCA

7801 TGCGCGCCTT GAGCCTGGCG AACAGTTCGG CTGGCGCGAG
     CCCCTGATGC

7851 TCTTCGTCCA GATCATCCTG ATCGACAAGA CCGGCTTCCA
     TCCGAGTACG

7901 TGCTCGCTCG ATGCGATGTT TCGCTTGGTG GTCGAATGGG
     CAGGTAGCCG

7951 GATCAAGCGT ATGCAGCCGC CGCATTGCAT CAGCCATGAT
     GGATACTTTC

8001 TCGGCAGGAG CAAGGTGAGA TGACAGGAGA TCCTGCCCCG
     GCACTTCGCC

8051 CAATAGCAGC CAGTCCCTTC CCGCTTCAGT GACAACGTCG
     AGCACAGCTG

8101 CGCAAGGAAC GCCCGTCGTG GCCAGCCACG ATAGCCGCGC
     TGCCTCGTCC

8151 TGCAGTTCAT TCAGGGCACC GGACAGGTCG GTCTTGACAA
     AAAGAACCGG

8201 GCGCCCCTGC GCTGACAGCC GGAACACGGC GGCATCAGAG
     CAGCCGATTG

8251 TCTGTTGTGC CCAGTCATAG CCGAATAGCC TCTCCACCCA
     AGCGGCCGGA

8301 GAACCTGCGT GCAATCCATC TTGTTCAATC ATGCGAAACG
     ATCCTCATCC

8351 TGTCTCTTGA TCAGATCTTG ATCCCCTGCG CCATCAGATC
     CTTGGCGGCA

8401 AGAAAGCCAT CCAGTTTACT TTGCAGGGCT TCCCAACCTT
     ACCAGAGGGC

8451 GCCCCAGCTG GCAATTCCGG TTCGCTTGCT GTCCATAAAA
     CCGCCCAGTC

8501 TAGCTATCGC CATGTAAGCC CACTGCAAGC TACCTGCTTT
     CTCTTTGCGC

8551 TTGCGTTTTC CCTTGTCCAG ATAGCCCAGT AGCTGACATT
     CATCCGGGGT

8601 CAGCACCGTT TCTGCGGACT GGCTTTCTAC GTGTTCCGCT
     TCCTTTAGCA

8651 GCCCTTGCGC CCTGAGTGCT TGCGGCAGCG TGAAGCT
```

SEQ ID NO:17

Nucleotide Sequence of the Expression Vector HCMV-K HuAb-VL1 hum V1 (Complete DNA Sequence of a Humanised Light Chain Expression Vector Comprising SEQ ID NO: 14 (humV1=VLh) from 3964-4284)

```
  1 CTAGCTTTTT GCAAAAGCCT AGGCCTCCAA AAAAGCCTCC
    TCACTACTTC

 51 TGGAATAGCT CAGAGGCCGA GGCGGCCTCG GCCTCTGCAT
    AAATAAAAAA

101 AATTAGTCAG CCATGGGGCG GAGAATGGGC GGAACTGGGC
    GGAGTTAGGG
```

-continued

151 GCGGGATGGG CGGAGTTAGG GGCGGGACTA TGGTTGCTGA CTAATTGAGA

201 TGCATGCTTT GCATACTTCT GCCTGCTGGG GAGCCTGGTT GCTGACTAAT

251 TGAGATGCAT GCTTTGCATA CTTCTGCCTG CTGGGGAGCC TGGGGACTTT

301 CCACACCCTA ACTGACACAC ATTCCACAGC TGCCTCGCGC GTTTCGGTGA

351 TGACGGTGAA AACCTCTGAC ACATGCAGCT CCCGGAGACG GTCACAGCTT

401 GTCTGTAAGC GGATGCCGGG AGCAGACAAG CCCGTCAGGG CGCGTCAGCG

451 GGTGTTGGCG GGTGTCGGGG CGCAGCCATG ACCCAGTCAC GTAGCGATAG

501 CGGAGTGTAT ACTGGCTTAA CTATGCGGCA TCAGAGCAGA TTGTACTGAG

551 AGTGCACCAT ATGCGGTGTG AAATACCGCA CAGATGCGTA AGGAGAAAAT

601 ACCGCATCAG GCGCTCTTCC GCTTCCTCGC TCACTGACTC GCTGCGCTCG

651 GTCGTTCGGC TGCGGCGAGC GGTATCAGCT CACTCAAAGG CGGTAATACG

701 GTTATCCACA GAATCAGGGG ATAACGCAGG AAAGAACATG TGAGCAAAAG

751 GCCAGCAAAA GGCCAGGAAC CGTAAAAAGG CCGCGTTGCT GGCGTTTTTC

801 CATAGGCTCC GCCCCCCTGA CGAGCATCAC AAAAATCGAC GCTCAAGTCA

851 GAGGTGGCGA AACCCGACAG GACTATAAAG ATACCAGGCG TTTCCCCCTG

901 GAAGCTCCCT CGTGCGCTCT CCTGTTCCGA CCCTGCCGCT TACCGGATAC

951 CTGTCCGCCT TTCTCCCTTC GGGAAGCGTG GCGCTTTCTC ATAGCTCACG

1001 CTGTAGGTAT CTCAGTTCGG TGTAGGTCGT TCGCTCCAAG CTGGGCTGTG

1051 TGCACGAACC CCCCGTTCAG CCCGACCGCT GCGCCTTATC CGGTAACTAT

1101 CGTCTTGAGT CCAACCCGGT AAGACACGAC TTATCGCCAC TGGCAGCAGC

1151 CACTGGTAAC AGGATTAGCA GAGCGAGGTA TGTAGGCGGT GCTACAGAGT

1201 TCTTGAAGTG GTGGCCTAAC TACGGCTACA CTAGAAGGAC AGTATTTGGT

1251 ATCTGCGCTC TGCTGAAGCC AGTTACCTTC GGAAAAAGAG TTGGTAGCTC

1301 TTGATCCGGC AAACAAACCA CCGCTGGTAG CGGTGGTTTT TTTGTTTGCA

1351 AGCAGCAGAT TACGCGCAGA AAAAAAGGAT CTCAAGAAGA TCCTTTGATC

1401 TTTTCTACGG GGTCTGACGC TCAGTGGAAC GAAAACTCAC GTTAAGGGAT

-continued

1451 TTTGGTCATG AGATTATCAA AAAGGATCTT CACCTAGATC CTTTTAAATT

1501 AAAAATGAAG TTTTAAATCA ATCTAAAGTA TATATGAGTA AACTTGGTCT

1551 GACAGTTACC AATGCTTAAT CAGTGAGGCA CCTATCTCAG CGATCTGTCT

1601 ATTTCGTTCA TCCATAGTTG CCTGACTCCC CGTCGTGTAG ATAACTACGA

1651 TACGGGAGGG CTTACCATCT GGCCCCAGTG CTGCAATGAT ACCGCGAGAC

1701 CCACGCTCAC CGGCTCCAGA TTTATCAGCA ATAAACCAGC CAGCCGGAAG

1751 GGCCGAGCGC AGAAGTGGTC CTGCAACTTT ATCCGCCTCC ATCCAGTCTA

1801 TTAATTGTTG CCGGGAAGCT AGAGTAAGTA GTTCGCCAGT TAATAGTTTG

1851 CGCAACGTTG TTGCCATTGC TGCAGGCATC GTGGTGTCAC GCTCGTCGTT

1901 TGGTATGGCT TCATTCAGCT CCGGTTCCCA ACGATCAAGG CGAGTTACAT

1951 GATCCCCCAT GTTGTGCAAA AAAGCGGTTA GCTCCTTCGG TCCTCCGATC

2001 GTTGTCAGAA GTAAGTTGGC CGCAGTGTTA TCACTCATGG TTATGGCAGC

2051 ACTGCATAAT TCTCTTACTG TCATGCCATC CGTAAGATGC TTTTCTGTGA

2101 CTGGTGAGTA CTCAACCAAG TCATTCTGAG AATAGTGTAT GCGGCGACCG

2151 AGTTGCTCTT GCCCGGCGTC AACACGGGAT AATACCGCGC CACATAGCAG

2201 AACTTTAAAA GTGCTCATCA TTGGAAAACG TTCTTCGGGG CGAAAACTCT

2251 CAAGGATCTT ACCGCTGTTG AGATCCAGTT CGATGTAACC CACTCGTGCA

2301 CCCAACTGAT CTTCAGCATC TTTTACTTTC ACCAGCGTTT CTGGGTGAGC

2351 AAAAACAGGA AGGCAAAATG CCGCAAAAAA GGGAATAAGG GCGACACGGA

2401 AATGTTGAAT ACTCATACTC TTCCTTTTTC AATATTATTG AAGCATTTAT

2451 CAGGGTTATT GTCTCATGAG CGGATACATA TTTGAATGTA TTTAGAAAAA

2501 TAAACAAATA GGGGTTCCGC GCACATTTCC CCGAAAAGTG CCACCTGACG

2551 TCTAAGAAAC CATTATTATC ATGACATTAA CCTATAAAAA TAGGCGTATC

2601 ACGAGGCCCT TTCGTCTTCA AGAATTCAGC TTGGCTGCAG TGAATAATAA

2651 AATGTGTGTT TGTCCGAAAT ACGCGTTTTG AGATTTCTGT CGCCGACTAA

2701 ATTCATGTCG CGCGATAGTG GTGTTTATCG CCGATAGAGA TGGCGATATT

-continued

2751 GGAAAAATCG ATATTTGAAA ATATGGCATA TTGAAAATGT CGCCGATGTG

2801 AGTTTCTGTG TAACTGATAT CGCCATTTTT CCAAAAGTGA TTTTTGGGCA

2851 TACGCGATAT CTGGCGATAG CGCTTATATC GTTTACGGGG GATGGCGATA

2901 GACGACTTTG GTGACTTGGG CGATTCTGTG TGTCGCAAAT ATCGCAGTTT

2951 CGATATAGGT GACAGACGAT ATGAGGCTAT ATCGCCGATA GAGGCGACAT

3001 CAAGCTGGCA CATGGCCAAT GCATATCGAT CTATACATTG AATCAATATT

3051 GGCCATTAGC CATATTATTC ATTGGTTATA TAGCATAAAT CAATATTGGC

3101 TATTGGCCAT TGCATACGTT GTATCCATAT CATAATATGT ACATTTATAT

3151 TGGCTCATGT CCAACATTAC CGCCATGTTG ACATTGATTA TTGACTAGTT

3201 ATTAATAGTA ATCAATTACG GGGTCATTAG TTCATAGCCC ATATATGGAG

3251 TTCCGCGTTA CATAACTTAC GGTAAATGGC CCGCCTGGCT GACCGCCCAA

3301 CGACCCCCGC CCATTGACGT CAATAATGAC GTATGTTCCC ATAGTAACGC

3351 CAATAGGGAC TTTCCATTGA CGTCAATGGG TGGAGTATTT ACGGTAAACT

3401 GCCCACTTGG CAGTACATCA AGTGTATCAT ATGCCAAGTA CGCCCCCTAT

3451 TGACGTCAAT GACGGTAAAT GGCCCGCCTG GCATTATGCC CAGTACATGA

3501 CCTTATGGGA CTTTCCTACT TGGCAGTACA TCTACGTATT AGTCATCGCT

3551 ATTACCATGG TGATGCGGTT TTGGCAGTAC ATCAATGGGC GTGGATAGCG

3601 GTTTGACTCA CGGGGATTTC CAAGTCTCCA CCCCATTGAC GTCAATGGGA

3651 GTTTGTTTTG GCACCAAAAT CAACGGGACT TTCCAAAATG TCGTAACAAC

3701 TCCGCCCCAT TGACGCAAAT GGGCGGTAGG CGTGTACGGT GGGAGGTCTA

3751 TATAAGCAGA GCTCGTTTAG TGAACCGTCA GATCGCCTGG AGACGCCATC

3801 CACGCTGTTT TGACCTCCAT AGAAGACACC GGGACCGATC CAGCCTCCGC

3851 AAGCTTGATA TCGAATTCCT GCAGCCCGGG GGATCCGCCC GCTTGCCGCC

3901 ACCATGGAGA CCCCCGCCCA GCTGCTGTTC CTGCTGCTGC TGTGGCTGCC

3951 CGACACCACC GGCGACATTC TGCTGACCCA GTCTCCAGCC ACCCTGTCTC

4001 TGAGTCCAGG AGAAAGAGCC ACTCTCTCCT GCAGGGCCAG TCAGAACATT

-continued

4051 GGCACAAGCA TACAGTGGTA TCAACAAAAA CCAGGTCAGG CTCCAAGGCT

4101 TCTCATAAGG TCTTCTTCTG AGTCTATCTC TGGGATCCCT TCCAGGTTTA

4151 GTGGCAGTGG ATCAGGGACA GATTTTACTC TTACCATCAG CAGTCTGGAG

4201 CCTGAAGATT TTGCAGTGTA TTACTGTCAA CAAAGTAATA CCTGGCCATT

4251 CACGTTCGGC CAGGGGACCA AGCTGGAGAT CAAACGTGAG TATTCTAGAA

4301 AGATCCTAGA ATTCTAAACT CTGAGGGGGT CGGATGACGT GGCCATTCTT

4351 TGCCTAAAGC ATTGAGTTTA CTGCAAGGTC AGAAAAGCAT GCAAAGCCCT

4401 CAGAATGGCT GCAAAGAGCT CCAACAAAAC AATTTAGAAC TTTATTAAGG

4451 AATAGGGGGA AGCTAGGAAG AAACTCAAAA CATCAAGATT TTAAATACGC

4501 TTCTTGGTCT CCTTGCTATA ATTATCTGGG ATAAGCATGC TGTTTTCTGT

4551 CTGTCCCTAA CATGCCCTGT GATTATCCGC AAACAACACA CCCAAGGGCA

4601 GAACTTTGTT ACTTAAACAC CATCCTGTTT GCTTCTTTCC TCAGGAACTG

4651 TGGCTGCACC ATCTGTCTTC ATCTTCCCGC CATCTGATGA GCAGTTGAAA

4701 TCTGGAACTG CCTCTGTTGT GTGCCTGCTG AATAACTTCT ATCCCAGAGA

4751 GGCCAAAGTA CAGTGGAAGG TGGATAACGC CCTCCAATCG GGTAACTCCC

4801 AGGAGAGTGT CACAGAGCAG GACAGCAAGG ACAGCACCTA CAGCCTCAGC

4851 AGCACCCTGA CGCTGAGCAA AGCAGACTAC GAGAAACACA AAGTCTACGC

4901 CTGCGAAGTC ACCCATCAGG GCCTGAGCTC GCCCGTCACA AAGAGCTTCA

4951 ACAGGGGAGA GTGTTAGAGG GAGAAGTGCC CCCACCTGCT CCTCAGTTCC

5001 AGCCTGACCC CCTCCCATCC TTTGGCCTCT GACCCTTTTT CCACAGGGGA

5051 CCTACCCCTA TTGCGGTCCT CCAGCTCATC TTTCACCTCA CCCCCCTCCT

5101 CCTCCTTGGC TTTAATTATG CTAATGTTGG AGGAGAATGA ATAAATAAAG

5151 TGAATCTTTG CACCTGTGGT TTCTCTCTTT CCTCATTTAA TAATTATTAT

5201 CTGTTGTTTA CCAACTACTC AATTTCTCTT ATAAGGGACT AAATATGTAG

5251 TCATCCTAAG GCGCATAACC ATTTATAAAA ATCATCCTTC ATTCTATTTT

5301 ACCCTATCAT CCTCTGCAAG ACAGTCCTCC CTCAAACCCA CAAGCCTTCT

-continued

```
5351 GTCCTCACAG TCCCCTGGGC CATGGTAGGA GAGACTTGCT
     TCCTTGTTTT

5401 CCCCTCCTCA GCAAGCCCTC ATAGTCCTTT TTAAGGGTGA
     CAGGTCTTAC

5451 AGTCATATAT CCTTTGATTC AATTCCCTGA GAATCAACCA
     AAGCAAATTT

5501 TTCAAAAGAA GAAACCTGCT ATAAAGAGAA TCATTCATTG
     CAACATGATA

5551 TAAAATAACA ACACAATAAA AGCAATTAAA TAAACAAACA
     ATAGGGAAAT

5601 GTTTAAGTTC ATCATGGTAC TTAGACTTAA TGGAATGTCA
     TGCCTTATTT

5651 ACATTTTTAA ACAGGTACTG AGGGACTCCT GTCTGCCAAG
     GGCCGTATTG

5701 AGTACTTTCC ACAACCTAAT TTAATCCACA CTATACTGTG
     AGATTAAAAA

5751 CATTCATTAA AATGTTGCAA AGGTTCTATA AAGCTGAGAG
     ACAAATATAT

5801 TCTATAACTC AGCAATCCCA CTTCTAGATG ACTGAGTGTC
     CCCACCCACC

5851 AAAAAACTAT GCAAGAATGT TCAAAGCAGC TTTATTTACA
     AAAGCCAAAA

5901 ATTGGAAATA GCCCGATTGT CCAACAATAG AATGAGTTAT
     TAAACTGTGG

5951 TATGTTTATA CATTAGAATA CCCAATGAGG AGAATTAACA
     AGCTACAACT

6001 ATACCTACTC ACACAGATGA ATCTCATAAA AATAATGTTA
     CATAAGAGAA

6051 ACTCAATGCA AAAGATATGT TCTGTATGTT TTCATCCATA
     TAAAGTTCAA

6101 AACCAGGTAA AAATAAAGTT AGAAATTTGG ATGGAAATTA
     CTCTTAGCTG

6151 GGGGTGGGCG AGTTAGTGCC TGGGAGAAGA CAAGAAGGGG
     CTTCTGGGGT

6201 CTTGGTAATG TTCTGTTCCT CGTGTGGGGT TGTGCAGTTA
     TGATCTGTGC

6251 ACTGTTCTGT ATACACATTA TGCTTCAAAA TAACTTCACA
     TAAAGAACAT

6301 CTTATACCCA GTTAATAGAT AGAAGAGGAA TAAGTAATAG
     GTCAAGACCA

6351 CGCAGCTGGT AAGTGGGGGG GCCTGGGATC AAATAGCTAC
     CTGCCTAATC

6401 CTGCCCTCTT GAGCCCTGAA TGAGTCTGCC TTCCAGGGCT
     CAAGGTGCTC

6451 AACAAAACAA CAGGCCTGCT ATTTTCCTGG CATCTGTGCC
     CTGTTTGGCT

6501 AGCTAGGAGC ACACATACAT AGAAATTAAA TGAAACAGAC
     CTTCAGCAAG

6551 GGGACAGAGG ACAGAATTAA CCTTGCCCAG ACACTGGAAA
     CCCATGTATG

6601 AACACTCACA TGTTTGGGAA GGGGGAAGGG CACATGTAAA
     TGAGGACTCT
```

-continued

```
6651 TCCTCATTCT ATGGGGCACT CTGGCCCTGC CCCTCTCAGC
     TACTCATCCA

6701 TCCAACACAC CTTTCTAAGT ACCTCTCTCT GCCTACACTC
     TGAAGGGGTT

6751 CAGGAGTAAC TAACACAGCA TCCCTTCCCT CAAATGACTG
     ACAATCCCTT

6801 TGTCCTGCTT TGTTTTTCTT TCCAGTCAGT ACTGGGAAAG
     TGGGGAAGGA

6851 CAGTCATGGA GAAACTACAT AAGGAAGCAC CTTGCCCTTC
     TGCCTCTTGA

6901 GAATGTTGAT GAGTATCAAA TCTTTCAAAC TTTGGAGGTT
     TGAGTAGGGG

6951 TGAGACTCAG TAATGTCCCT TCCAATGACA TGAACTTGCT
     CACTCATCCC

7001 TGGGGGCCAA ATTGAACAAT CAAAGGCAGG CATAATCCAG
     CTATGAATTC

7051 TAGGATCGAT CCAGACATGA TAAGATACAT TGATGAGTTT
     GGACAAACCA

7101 CAACTAGAAT GCAGTGAAAA AAATGCTTTA TTTGTGAAAT
     TTGTGATGCT

7151 ATTGCTTTAT TTGTAACCAT TATAAGCTGC AATAAACAAG
     TTAACAACAA

7201 CAATTGCATT CATTTTATGT TTCAGGTTCA GGGGGAGGTG
     TGGGAGGTTT

7251 TTTAAAGCAA GTAAAACCTC TACAAATGTG GTATGGCTGA
     TTATGATCTC

7301 TAGTCAAGGC ACTATACATC AAATATTCCT TATTAACCCC
     TTTACAAATT

7351 AAAAAGCTAA AGGTACACAA TTTTTGAGCA TAGTTATTAA
     TAGCAGACAC

7401 TCTATGCCTG TGTGGAGTAA GAAAAAACAG TATGTTATGA
     TTATAACTGT

7451 TATGCCTACT TATAAAGGTT ACAGAATATT TTTCCATAAT
     TTTCTTGTAT

7501 AGCAGTGCAG CTTTTTCCTT TGTGGTGTAA ATAGCAAAGC
     AAGCAAGAGT

7551 TCTATTACTA AACACAGCAT GACTCAAAAA ACTTAGCAAT
     TCTGAAGGAA

7601 AGTCCTTGGG GTCTTCTACC TTTCTCTTCT TTTTTGGAGG
     AGTAGAATGT

7651 TGAGAGTCAG CAGTAGCCTC ATCATCACTA GATGGCATTT
     CTTCTGAGCA

7701 AAACAGGTTT TCCTCATTAA AGGCATTCCA CCACTGCTCC
     CATTCATCAG

7751 TTCCATAGGT TGGAATCTAA AATACACAAA CAATTAGAAT
     CAGTAGTTTA

7801 ACACATTATA CACTTAAAAA TTTTATATTT ACCTTAGAGC
     TTTAAATCTC

7851 TGTAGGTAGT TTGTCCAATT ATGTCACACC ACAGAAGTAA
     GGTTCCTTCA

7901 CAAAGATCCG GGACCAAAGC GGCCATCGTG CCTCCCCACT
     CCTGCAGTTC
```

-continued

```
7951 GGGGGCATGG ATGCGCGGAT AGCCGCTGCT GGTTTCCTGG
     ATGCCGACGG

8001 ATTTGCACTG CCGGTAGAAC TCCGCGAGGT CGTCCAGCCT
     CAGGCAGCAG

8051 CTGAACCAAC TCGCGAGGGG ATCGAGCCCG GGGTGGGCGA
     AGAACTCCAG

8101 CATGAGATCC CCGCGCTGGA GGATCATCCA GCCGGCGTCC
     CGGAAAACGA

8151 TTCCGAAGCC CAACCTTTCA TAGAAGGCGG CGGTGGAATC
     GAAATCTCGT

8201 GATGGCAGGT TGGGCGTCGC TTGGTCGGTC ATTTCGAACC
     CCAGAGTCCC

8251 GCTCAGAAGA ACTCGTCAAG AAGGCGATAG AAGGCGATGC
     GCTGCGAATC

8301 GGGAGCGGCG ATACCGTAAA GCACGAGGAA GCGGTCAGCC
     CATTCGCCGC

8351 CAAGCTCTTC AGCAATATCA CGGGTAGCCA ACGCTATGTC
     CTGATAGCGG

8401 TCCGCCACAC CCAGCCGGCC ACAGTCGATG AATCCAGAAA
     AGCGGCCATT

8451 TTCCACCATG ATATTCGGCA AGCAGGCATC GCCATGGGTC
     ACGACGAGAT

8501 CCTCGCCGTC GGGCATGCGC GCCTTGAGCC TGGCGAACAG
     TTCGGCTGGC

8551 GCGAGCCCCT GATGCTCTTC GTCCAGATCA TCCTGATCGA
     CAAGACCGGC

8601 TTCCATCCGA GTACGTGCTC GCTCGATGCG ATGTTTCGCT
     TGGTGGTCGA

8651 ATGGGCAGGT AGCCGGATCA AGCGTATGCA GCCGCCGCAT
     TGCATCAGCC

8701 ATGATGGATA CTTTCTCGGC AGGAGCAAGG TGAGATGACA
     GGAGATCCTG

8751 CCCCGGCACT TCGCCCAATA GCAGCCAGTC CCTTCCCGCT
     TCAGTGACAA

8801 CGTCGAGCAC AGCTGCGCAA GGAACGCCCG TCGTGGCCAG
     CCACGATAGC

8851 CGCGCTGCCT CGTCCTGCAG TTCATTCAGG GCACCGGACA
     GGTCGGTCTT

8901 GACAAAAAGA ACCGGGCGCC CCTGCGCTGA CAGCCGGAAC
     ACGGCGGCAT

8951 CAGAGCAGCC GATTGTCTGT TGTGCCCAGT CATAGCCGAA
     TAGCCTCTCC

9001 ACCCAAGCGG CCGGAGAACC TGCGTGCAAT CCATCTTGTT
     CAATCATGCG

9051 AAACGATCCT CATCCTGTCT CTTGATCAGA TCTTGATCCC
     CTGCGCCATC

9101 AGATCCTTGG CGGCAAGAAA GCCATCCAGT TTACTTTGCA
     GGGCTTCCCA

9151 ACCTTACCAG AGGGCGCCCC AGCTGGCAAT TCCGGTTCGC
     TTGCTGTCCA

9201 TAAAACCGCC CAGTCTAGCT ATCGCCATGT AAGCCCACTG
     CAAGCTACCT
```

-continued

```
9251 GCTTTCTCTT TGCGCTTGCG TTTTCCCTTG TCCAGATAGC
     CCAGTAGCTG

9301 ACATTCATCC GGGGTCAGCA CCGTTTCTGC GGACTGGCTT
     TCTACGTGTT

9351 CCGCTTCCTT TAGCAGCCCT TGCGCCCTGA GTGCTTGCGG
     CAGCGTGAAG
```

SEQ ID NO:18

Nucleotide Sequence of the Expression Vector HCMV-K HuAb-VL1 hum V2 (Complete DNA Sequence of a Humanised Light Chain Expression Vector Comprising SEQ ID NO: 13 (humV2=VLm) from 3926-4246)

```
  1 CTAGCTTTTT GCAAAAGCCT AGGCCTCCAA AAAAGCCTCC
    TCACTACTTC

 51 TGGAATAGCT CAGAGGCCGA GGCGGCCTCG GCCTCTGCAT
    AAATAAAAAA

101 AATTAGTCAG CCATGGGGCG GAGAATGGGC GGAACTGGGC
    GGAGTTAGGG

151 GCGGGATGGG CGGAGTTAGG GGCGGGACTA TGGTTGCTGA
    CTAATTGAGA

201 TGCATGCTTT GCATACTTCT GCCTGCTGGG GAGCCTGGTT
    GCTGACTAAT

251 TGAGATGCAT GCTTTGCATA CTTCTGCCTG CTGGGGAGCC
    TGGGGACTTT

301 CCACACCCTA ACTGACACAC ATTCCACAGC TGCCTCGCGC
    GTTTCGGTGA

351 TGACGGTGAA AACCTCTGAC ACATGCAGCT CCCGGAGACG
    GTCACAGCTT

401 GTCTGTAAGC GGATGCCGGG AGCAGACAAG CCCGTCAGGG
    CGCGTCAGCG

451 GGTGTTGGCG GGTGTCGGGG CGCAGCCATG ACCCAGTCAC
    GTAGCGATAG

501 CGGAGTGTAT ACTGGCTTAA CTATGCGGCA TCAGAGCAGA
    TTGTACTGAG

551 AGTGCACCAT ATGCGGTGTG AAATACCGCA CAGATGCGTA
    AGGAGAAAAT

601 ACCGCATCAG GCGCTCTTCC GCTTCCTCGC TCACTGACTC
    GCTGCGCTCG

651 GTCGTTCGGC TGCGGCGAGC GGTATCAGCT CACTCAAAGG
    CGGTAATACG

701 GTTATCCACA GAATCAGGGG ATAACGCAGG AAAGAACATG
    TGAGCAAAAG

751 GCCAGCAAAA GGCCAGGAAC CGTAAAAAGG CCGCGTTGCT
    GGCGTTTTTC

801 CATAGGCTCC GCCCCCCTGA CGAGCATCAC AAAAATCGAC
    GCTCAAGTCA

851 GAGGTGGCGA AACCCGACAG GACTATAAAG ATACCAGGCG
    TTTCCCCCTG

901 GAAGCTCCCT CGTGCGCTCT CCTGTTCCGA CCCTGCCGCT
    TACCGGATAC

951 CTGTCCGCCT TTCTCCCTTC GGGAAGCGTG GCGCTTTCTC
    ATAGCTCACG
```

-continued

```
1001 CTGTAGGTAT CTCAGTTCGG TGTAGGTCGT TCGCTCCAAG
     CTGGGCTGTG

1051 TGCACGAACC CCCCGTTCAG CCCGACCGCT GCGCCTTATC
     CGGTAACTAT

1101 CGTCTTGAGT CCAACCCGGT AAGACACGAC TTATCGCCAC
     TGGCAGCAGC

1151 CACTGGTAAC AGGATTAGCA GAGCGAGGTA TGTAGGCGGT
     GCTACAGAGT

1201 TCTTGAAGTG GTGGCCTAAC TACGGCTACA CTAGAAGGAC
     AGTATTTGGT

1251 ATCTGCGCTC TGCTGAAGCC AGTTACCTTC GGAAAAAGAG
     TTGGTAGCTC

1301 TTGATCCGGC AAACAAACCA CCGCTGGTAG CGGTGGTTTT
     TTTGTTTGCA

1351 AGCAGCAGAT TACGCGCAGA AAAAAAGGAT CTCAAGAAGA
     TCCTTTGATC

1401 TTTTCTACGG GGTCTGACGC TCAGTGGAAC GAAAACTCAC
     GTTAAGGGAT

1451 TTTGGTCATG AGATTATCAA AAAGGATCTT CACCTAGATC
     CTTTTAAATT

1501 AAAAATGAAG TTTTAAATCA ATCTAAAGTA TATATGAGTA
     AACTTGGTCT

1551 GACAGTTACC AATGCTTAAT CAGTGAGGCA CCTATCTCAG
     CGATCTGTCT

1601 ATTTCGTTCA TCCATAGTTG CCTGACTCCC CGTCGTGTAG
     ATAACTACGA

1651 TACGGGAGGG CTTACCATCT GGCCCCAGTG CTGCAATGAT
     ACCGCGAGAC

1701 CCACGCTCAC CGGCTCCAGA TTTATCAGCA ATAAACCAGC
     CAGCCGGAAG

1751 GGCCGAGCGC AGAAGTGGTC CTGCAACTTT ATCCGCCTCC
     ATCCAGTCTA

1801 TTAATTGTTG CCGGGAAGCT AGAGTAAGTA GTTCGCCAGT
     TAATAGTTTG

1851 CGCAACGTTG TTGCCATTGC TGCAGGCATC GTGGTGTCAC
     GCTCGTCGTT

1901 TGGTATGGCT TCATTCAGCT CCGGTTCCCA ACGATCAAGG
     CGAGTTACAT

1951 GATCCCCCAT GTTGTGCAAA AAAGCGGTTA GCTCCTTCGG
     TCCTCCGATC

2001 GTTGTCAGAA GTAAGTTGGC CGCAGTGTTA TCACTCATGG
     TTATGGCAGC

2051 ACTGCATAAT TCTCTTACTG TCATGCCATC CGTAAGATGC
     TTTTCTGTGA

2101 CTGGTGAGTA CTCAACCAAG TCATTCTGAG AATAGTGTAT
     GCGGCGACCG

2151 AGTTGCTCTT GCCCGGCGTC AACACGGGAT AATACCGCGC
     CACATAGCAG

2201 AACTTTAAAA GTGCTCATCA TTGGAAAACG TTCTTCGGGG
     CGAAAACTCT

2251 CAAGGATCTT ACCGCTGTTG AGATCCAGTT CGATGTAACC
     CACTCGTGCA
```

-continued

```
2301 CCCAACTGAT CTTCAGCATC TTTTACTTTC ACCAGCGTTT
     CTGGGTGAGC

2351 AAAAACAGGA AGGCAAAATG CCGCAAAAAA GGGAATAAGG
     GCGACACGGA

2401 AATGTTGAAT ACTCATACTC TTCCTTTTTC AATATTATTG
     AAGCATTTAT

2451 CAGGGTTATT GTCTCATGAG CGGATACATA TTTGAATGTA
     TTTAGAAAAA

2501 TAAACAAATA GGGGTTCCGC GCACATTTCC CCGAAAAGTG
     CCACCTGACG

2551 TCTAAGAAAC CATTATTATC ATGACATTAA CCTATAAAAA
     TAGGCGTATC

2601 ACGAGGCCCT TTCGTCTTCA AGAATTCAGC TTGGCTGCAG
     TGAATAATAA

2651 AATGTGTGTT TGTCCGAAAT ACGCGTTTTG AGATTTCTGT
     CGCCGACTAA

2701 ATTCATGTCG CGCGATAGTG GTGTTTATCG CCGATAGAGA
     TGGCGATATT

2751 GGAAAAATCG ATATTTGAAA ATATGGCATA TTGAAAATGT
     CGCCGATGTG

2801 AGTTTCTGTG TAACTGATAT CGCCATTTTT CCAAAAGTGA
     TTTTTGGGCA

2851 TACGCGATAT CTGGCGATAG CGCTTATATC GTTTACGGGG
     GATGGCGATA

2901 GACGACTTTG GTGACTTGGG CGATTCTGTG TGTCGCAAAT
     ATCGCAGTTT

2951 CGATATAGGT GACAGACGAT ATGAGGCTAT ATCGCCGATA
     GAGGCGACAT

3001 CAAGCTGGCA CATGGCCAAT GCATATCGAT CTATACATTG
     AATCAATATT

3051 GGCCATTAGC CATATTATTC ATTGGTTATA TAGCATAAAT
     CAATATTGGC

3101 TATTGGCCAT TGCATACGTT GTATCCATAT CATAATATGT
     ACATTTATAT

3151 TGGCTCATGT CCAACATTAC CGCCATGTTG ACATTGATTA
     TTGACTAGTT

3201 ATTAATAGTA ATCAATTACG GGGTCATTAG TTCATAGCCC
     ATATATGGAG

3251 TTCCGCGTTA CATAACTTAC GGTAAATGGC CCGCCTGGCT
     GACCGCCCAA

3301 CGACCCCCGC CCATTGACGT CAATAATGAC GTATGTTCCC
     ATAGTAACGC

3351 CAATAGGGAC TTTCCATTGA CGTCAATGGG TGGAGTATTT
     ACGGTAAACT

3401 GCCCACTTGG CAGTACATCA AGTGTATCAT ATGCCAAGTA
     CGCCCCCTAT

3451 TGACGTCAAT GACGGTAAAT GGCCCGCCTG GCATTATGCC
     CAGTACATGA

3501 CCTTATGGGA CTTTCCTACT TGGCAGTACA TCTACGTATT
     AGTCATCGCT

3551 ATTACCATGG TGATGCGGTT TTGGCAGTAC ATCAATGGGC
     GTGGATAGCG
```

-continued

```
3601 GTTTGACTCA CGGGGATTTC CAAGTCTCCA CCCCATTGAC
     GTCAATGGGA

3651 GTTTGTTTTG GCACCAAAAT CAACGGGACT TTCCAAAATG
     TCGTAACAAC

3701 TCCGCCCCAT TGACGCAAAT GGGCGGTAGG CGTGTACGGT
     GGGAGGTCTA

3751 TATAAGCAGA GCTCGTTTAG TGAACCGTCA GATCGCCTGG
     AGACGCCATC

3801 CACGCTGTTT TGACCTCCAT AGAAGACACC GGGACCGATC
     CAGCCTCCGC

3851 AAGCTTGCCG CCACCATGGA GACCCCCGCC CAGCTGCTGT
     TCCTGCTGCT

3901 GCTGTGGCTG CCCGACACCA CCGGCGACAT TCTGCTGACC
     CAGTCTCCAG

3951 CCACCCTGTC TCTGAGTCCA GGAGAAAGAG CCACTTTCTC
     CTGCAGGGCC

4001 AGTCAGAACA TTGGCACAAG CATACAGTGG TATCAACAAA
     AAACAAATGG

4051 TGCTCCAAGG CTTCTCATAA GGTCTTCTTC TGAGTCTATC
     TCTGGGATCC

4101 CTTCCAGGTT TAGTGGCAGT GGATCAGGGA CAGATTTTAC
     TCTTACCATC

4151 AGCAGTCTGG AGCCTGAAGA TTTTGCAGTG TATTACTGTC
     AACAAAGTAA

4201 TACCTGGCCA TTCACGTTCG GCCAGGGGAC CAAGCTGGAG
     ATCAAACGTG

4251 AGTATTCTAG AAAGATCCTA GAATTCTAAA CTCTGAGGGG
     GTCGGATGAC

4301 GTGGCCATTC TTTGCCTAAA GCATTGAGTT TACTGCAAGG
     TCAGAAAAGC

4351 ATGCAAAGCC CTCAGAATGG CTGCAAAGAG CTCCAACAAA
     ACAATTTAGA

4401 ACTTTATTAA GGAATAGGGG GAAGCTAGGA AGAAACTCAA
     AACATCAAGA

4451 TTTTAAATAC GCTTCTTGGT CTCCTTGCTA TAATTATCTG
     GGATAAGCAT

4501 GCTGTTTTCT GTCTGTCCCT AACATGCCCT GTGATTATCC
     GCAAACAACA

4551 CACCCAAGGG CAGAACTTTG TTACTTAAAC ACCATCCTGT
     TTGCTTCTTT

4601 CCTCAGGAAC TGTGGCTGCA CCATCTGTCT TCATCTTCCC
     GCCATCTGAT

4651 GAGCAGTTGA AATCTGGAAC TGCCTCTGTT GTGTGCCTGC
     TGAATAACTT

4701 CTATCCCAGA GAGGCCAAAG TACAGTGGAA GGTGGATAAC
     GCCCTCCAAT

4751 CGGGTAACTC CCAGGAGAGT GTCACAGAGC AGGACAGCAA
     GGACAGCACC

4801 TACAGCCTCA GCAGCACCCT GACGCTGAGC AAAGCAGACT
     ACGAGAAACA

4851 CAAAGTCTAC GCCTGCGAAG TCACCCATCA GGGCCTGAGC
     TCGCCCGTCA
```

-continued

```
4901 CAAAGAGCTT CAACAGGGGA GAGTGTTAGA GGGAGAAGTG
     CCCCCACCTG

4951 CTCCTCAGTT CCAGCCTGAC CCCCTCCCAT CCTTTGGCCT
     CTGACCCTTT

5001 TTCCACAGGG GACCTACCCC TATTGCGGTC CTCCAGCTCA
     TCTTTCACCT

5051 CACCCCCCTC CTCCTCCTTG GCTTTAATTA TGCTAATGTT
     GGAGGAGAAT

5101 GAATAAATAA AGTGAATCTT TGCACCTGTG GTTTCTCTCT
     TTCCTCATTT

5151 AATAATTATT ATCTGTTGTT TACCAACTAC TCAATTTCTC
     TTATAAGGGA

5201 CTAAATATGT AGTCATCCTA AGGCGCATAA CCATTTATAA
     AAATCATCCT

5251 TCATTCTATT TTACCCTATC ATCCTCTGCA AGACAGTCCT
     CCCTCAAACC

5301 CACAAGCCTT CTGTCCTCAC AGTCCCCTGG GCCATGGTAG
     GAGAGACTTG

5351 CTTCCTTGTT TTCCCCTCCT CAGCAAGCCC TCATAGTCCT
     TTTTAAGGGT

5401 GACAGGTCTT ACAGTCATAT ATCCTTTGAT TCAATTCCCT
     GAGAATCAAC

5451 CAAAGCAAAT TTTTCAAAAG AAGAAACCTG CTATAAAGAG
     AATCATTCAT

5501 TGCAACATGA TATAAAATAA CAACACAATA AAAGCAATTA
     AATAAACAAA

5551 CAATAGGGAA ATGTTTAAGT TCATCATGGT ACTTAGACTT
     AATGGAATGT

5601 CATGCCTTAT TTACATTTTT AAACAGGTAC TGAGGGACTC
     CTGTCTGCCA

5651 AGGGCCGTAT TGAGTACTTT CCACAACCTA ATTTAATCCA
     CACTATACTG

5701 TGAGATTAAA AACATTCATT AAAATGTTGC AAAGGTTCTA
     TAAAGCTGAG

5751 AGACAAATAT ATTCTATAAC TCAGCAATCC CACTTCTAGA
     TGACTGAGTG

5801 TCCCCACCCA CCAAAAAACT ATGCAAGAAT GTTCAAAGCA
     GCTTTATTTA

5851 CAAAAGCCAA AAATTGGAAA TAGCCCGATT GTCCAACAAT
     AGAATGAGTT

5901 ATTAAACTGT GGTATGTTTA TACATTAGAA TACCCAATGA
     GGAGAATTAA

5951 CAAGCTACAA CTATACCTAC TCACACAGAT GAATCTCATA
     AAAATAATGT

6001 TACATAAGAG AAACTCAATG CAAAAGATAT GTTCTGTATG
     TTTTCATCCA

6051 TATAAAGTTC AAAACCAGGT AAAAATAAAG TTAGAAATTT
     GGATGGAAAT

6101 TACTCTTAGC TGGGGGTGGG CGAGTTAGTG CCTGGGAGAA
     GACAAGAAGG

6151 GGCTTCTGGG GTCTTGGTAA TGTTCTGTTC CTCGTGTGGG
     GTTGTGCAGT
```

-continued

6201 TATGATCTGT GCACTGTTCT GTATACACAT TATGCTTCAA AATAACTTCA

6251 CATAAAGAAC ATCTTATACC CAGTTAATAG ATAGAAGAGG AATAAGTAAT

6301 AGGTCAAGAC CACGCAGCTG GTAAGTGGGG GGGCCTGGGA TCAAATAGCT

6351 ACCTGCCTAA TCCTGCCCTC TTGAGCCCTG AATGAGTCTG CCTTCCAGGG

6401 CTCAAGGTGC TCAACAAAAC AACAGGCCTG CTATTTTCCT GGCATCTGTG

6451 CCCTGTTTGG CTAGCTAGGA GCACACATAC ATAGAAATTA AATGAAACAG

6501 ACCTTCAGCA AGGGGACAGA GGACAGAATT AACCTTGCCC AGACACTGGA

6551 AACCCATGTA TGAACACTCA CATGTTTGGG AAGGGGGAAG GGCACATGTA

6601 AATGAGGACT CTTCCTCATT CTATGGGGCA CTCTGGCCCT GCCCCTCTCA

6651 GCTACTCATC CATCCAACAC ACCTTTCTAA GTACCTCTCT CTGCCTACAC

6701 TCTGAAGGGG TTCAGGAGTA ACTAACACAG CATCCCTTCC CTCAAATGAC

6751 TGACAATCCC TTTGTCCTGC TTTGTTTTTC TTTCCAGTCA GTACTGGGAA

6801 AGTGGGGAAG GACAGTCATG GAGAAACTAC ATAAGGAAGC ACCTTGCCCT

6851 TCTGCCTCTT GAGAATGTTG ATGAGTATCA AATCTTTCAA ACTTTGGAGG

6901 TTTGAGTAGG GGTGAGACTC AGTAATGTCC CTTCCAATGA CATGAACTTG

6951 CTCACTCATC CCTGGGGGCC AAATTGAACA ATCAAAGGCA GGCATAATCC

7001 AGCTATGAAT TCTAGGATCG ATCCAGACAT GATAAGATAC ATTGATGAGT

7051 TTGGACAAAC CACAACTAGA ATGCAGTGAA AAAAATGCTT TATTTGTGAA

7101 ATTTGTGATG CTATTGCTTT ATTTGTAACC ATTATAAGCT GCAATAAACA

7151 AGTTAACAAC AACAATTGCA TTCATTTTAT GTTTCAGGTT CAGGGGGAGG

7201 TGTGGGAGGT TTTTTAAAGC AAGTAAAACC TCTACAAATG TGGTATGGCT

7251 GATTATGATC TCTAGTCAAG GCACTATACA TCAAATATTC CTTATTAACC

7301 CCTTTACAAA TTAAAAAGCT AAAGGTACAC AATTTTTGAG CATAGTTATT

7351 AATAGCAGAC ACTCTATGCC TGTGTGGAGT AAGAAAAAAC AGTATGTTAT

7401 GATTATAACT GTTATGCCTA CTTATAAAGG TTACAGAATA TTTTTCCATA

7451 ATTTTCTTGT ATAGCAGTGC AGCTTTTTCC TTTGTGGTGT AAATAGCAAA

-continued

7501 GCAAGCAAGA GTTCTATTAC TAAACACAGC ATGACTCAAA AAACTTAGCA

7551 ATTCTGAAGG AAAGTCCTTG GGGTCTTCTA CCTTTCTCTT CTTTTTTGGA

7601 GGAGTAGAAT GTTGAGAGTC AGCAGTAGCC TCATCATCAC TAGATGGCAT

7651 TTCTTCTGAG CAAAACAGGT TTTCCTCATT AAAGGCATTC CACCACTGCT

7701 CCCATTCATC AGTTCCATAG GTTGGAATCT AAAATACACA AACAATTAGA

7751 ATCAGTAGTT TAACACATTA TACACTTAAA AATTTTATAT TTACCTTAGA

7801 GCTTTAAATC TCTGTAGGTA GTTTGTCCAA TTATGTCACA CCACAGAAGT

7851 AAGGTTCCTT CACAAAGATC CGGGACCAAA GCGGCCATCG TGCCTCCCCA

7901 CTCCTGCAGT TCGGGGGCAT GGATGCGCGG ATAGCCGCTG CTGGTTTCCT

7951 GGATGCCGAC GGATTTGCAC TGCCGGTAGA ACTCCGCGAG GTCGTCCAGC

8001 CTCAGGCAGC AGCTGAACCA ACTCGCGAGG GGATCGAGCC CGGGGTGGGC

8051 GAAGAACTCC AGCATGAGAT CCCCGCGCTG GAGGATCATC CAGCCGGCGT

8101 CCCGGAAAAC GATTCCGAAG CCCAACCTTT CATAGAAGGC GGCGGTGGAA

8151 TCGAAATCTC GTGATGGCAG GTTGGGCGTC GCTTGGTCGG TCATTTCGAA

8201 CCCCAGAGTC CCGCTCAGAA GAACTCGTCA AGAAGGCGAT AGAAGGCGAT

8251 GCGCTGCGAA TCGGGAGCGG CGATACCGTA AAGCACGAGG AAGCGGTCAG

8301 CCCATTCGCC GCCAAGCTCT TCAGCAATAT CACGGGTAGC CAACGCTATG

8351 TCCTGATAGC GGTCCGCCAC ACCCAGCCGG CCACAGTCGA TGAATCCAGA

8401 AAAGCGGCCA TTTTCCACCA TGATATTCGG CAAGCAGGCA TCGCCATGGG

8451 TCACGACGAG ATCCTCGCCG TCGGGCATGC GCGCCTTGAG CCTGGCGAAC

8501 AGTTCGGCTG GCGCGAGCCC CTGATGCTCT TCGTCCAGAT CATCCTGATC

8551 GACAAGACCG GCTTCCATCC GAGTACGTGC TCGCTCGATG CGATGTTTCG

8601 CTTGGTGGTC GAATGGGCAG GTAGCCGGAT CAAGCGTATG CAGCCGCCGC

8651 ATTGCATCAG CCATGATGGA TACTTTCTCG GCAGGAGCAA GGTGAGATGA

8701 CAGGAGATCC TGCCCCGGCA CTTCGCCCAA TAGCAGCCAG TCCCTTCCCG

8751 CTTCAGTGAC AACGTCGAGC ACAGCTGCGC AAGGAACGCC CGTCGTGGCC

-continued

```
8801 AGCCACGATA GCCGCGCTGC CTCGTCCTGC AGTTCATTCA
     GGGCACCGGA

8851 CAGGTCGGTC TTGACAAAAA GAACCGGGCG CCCCTGCGCT
     GACAGCCGGA

8901 ACACGGCGGC ATCAGAGCAG CCGATTGTCT GTTGTGCCCA
     GTCATAGCCG

8951 AATAGCCTCT CCACCCAAGC GGCCGGAGAA CCTGCGTGCA
     ATCCATCTTG

9001 TTCAATCATG CGAAACGATC CTCATCCTGT CTCTTGATCA
     GATCTTGATC

9051 CCCTGCGCCA TCAGATCCTT GGCGGCAAGA AAGCCATCCA
     GTTTACTTTG

9101 CAGGGCTTCC CAACCTTACC AGAGGGCGCC CCAGCTGGCA
     ATTCCGGTTC

9151 GCTTGCTGTC CATAAAACCG CCCAGTCTAG CTATCGCCAT
     GTAAGCCCAC

9201 TGCAAGCTAC CTGCTTTCTC TTTGCGCTTG CGTTTTCCCT
     TGTCCAGATA

9251 GCCCAGTAGC TGACATTCAT CCGGGGTCAG CACCGTTTCT
     GCGGACTGGC

9301 TTTCTACGTG TTCCGCTTCC TTTAGCAGCC CTTGCGCCCT
     GAGTGCTTGC

9351 GGCAGCGTGA AG
```

Example 9

In vitro Efficacy of CD45RO/RB Binding Humanised Antibodies

To determine the efficacy of the CD45RO/RB binding humanised antibodies VHE/humV1 and VHQ/humV1 in comparison to the chimeric antibody the ability to induce apoptosis in human T cells and also the ability to inhibit human T cell proliferation is analysed.

Cells and Reagents

Peripheral blood mononuclear cells (PBMC) are isolated from leukopheresis samples of healthy human donors with known blood type, but unknown HLA type by centrifugation over Ficoll-Hypaque (Pharmacia LKB). PBMC used as stimulators are first depleted of T and NK cells by using CD3-coated ferromagnetic beads (Miltenyi). Beads and contaminating cells are removed by magnetic field. T cell-depleted PBMC are used as stimulator cells after irradiation (50 Gy). $CD4^+$ T cells are used as responder cells in MLR and are isolated from PBMC with a CD4 T cell negative selection kit (Miltenyi).

The obtained cells are analyzed by FACScan or FACSCalibur (Becton Dickinson & Co., Calif.) and the purity of the obtained cells is >75%. Cells are suspended in RPMI1640 medium supplemented with 10% heat-inactivated FCS, penicillin, streptomycin and L-glutamine.

Apoptosis Assays

Human PBMC of three healthy voluntary donors are cultured in growth medium (RPMI1640+10% FCS) overnight (<16 h) in the presence of CD45RO/RB binding chimeric mAb, humanized antibodies (VHE/humV1 and VHQ/humV1) or anti-LPS control mAb. If indicated, a cross-linking reagent, $F(ab')_2$-fragment of goat anti-human IgG (Cat. No. 109-006-098, JacksonLab) is included at a μg/ml concentration being twice as high as the sample's anti-CD45 antibodies concentration. The PBS-concentration in all wells introduced by the antibody reagents is kept constant among all samples, namely at 20% (v/v) for samples without cross-linker or at 40% (v/v) for samples with cross-linker. Earlier experiments demonstrate that the amount of PBS does not affect the readout.

After overnight culture in the presence of the antibodies, the samples are subjected to flow cytometry analyses and stained with the apoptosis marker AnnexinV-FITC (Cat. No. 556419, BD/Pharmingen) and the T cell marker CD2-PE (Cat. No. 556609, BD/Pharmingen). The samples are run in a Becton Dickinson FACSCalibur instrument and the data are analyzed using the CellQuest Pro Software.

From the data collected, curves are fitted using the software Origin v7.0300 The equation used for fitting is

("Sigmoid-Logistic")

$A_1$: final value (for fitting sessions set to "shared" and "floating")

$A_2$: initial value (for fitting sessions set to "shared" and "floating")

p: power $X_0$: $ED_{50}$; $IC_{50}$ (see below).

In the absence of cross-linker, VHE/humV1 is most effective, with an $ED_{50}$ value of 148±71 nM, followed by VHQ/humV1 with 377±219 nM. CD45RO/RB binding chimeric antibody is less effective with an $ED_{50}$ value of 2440±1205 nM.

In the presence of a cross-linking antiserum, the $ED_{50}$ values are shifted dramatically towards higher efficacy by at least two orders of magnitude. In addition, the presence of cross-linker permitted higher levels of apoptosis at very high antibody concentrations, now reaching up to 80%, whereas the absence of cross-linker only allowed for up to 50% of apoptosis. In the presence of cross-linker, the curves (antibody concentration/% apoptosis) are bi-modal with two plateaus: the first plateau is reached at low antibody concentrations (~5 nM), where the apoptosis level corresponds to the maximum level obtained in the absence of cross-linker. The second plateau is reached at high antibody concentrations (~500 nM) and apoptosis is observed within 70-80% of the T cell population.

Both CD45R0/RB binding humanised mAb are equally effective and better or equal compared to CD45R0/RB binding chimeric mAb with respect to their ability to induce apoptosis in primary human T cells.

Mixed Lymphocyte Reaction Assays

One $\times 10^5$ PBMC or $5\times10^4$ of $CD4^+$ cells are mixed with 1× or $5\times10^4$ T cells-depleted irradiated (50 Gy) PBMC in each well of 96-well culture plates in the presence or absence of the different concentrations of mAb.

The mixed cells are cultured for 5 days and proliferation is determined by pulsing the cells with $^3H$-thymidine for the last 16-20 hours of culture. MLR inhibition at each antibody concentration is expressed as percentage inhibition as described in Example 2.

The effect of increasing concentrations of VHE/humV1 and VHQ/humV1 on MLR is evaluated in three responder: stimulator combinations. All antibodies inhibit the MLR in a dose-dependent manner. The $IC_{50}$ values (see above) are similar for the humanized Ab VHE/humV1 (7±7 nM) and VHQ/humV1 (39±54 nM). Both humanised antibodies are more potent in inhibiting MLR than the parental chimeric antibody ($IC_{50}$ of 347±434 nM). As usually seen with MLR experiments, donor variability is high in these experiments.

Example 10

Specificity of CD45RB/RO Binding Molecule

The CD45 molecule is expressed on all leukocytes. However, different CD45 isoforms are expressed by the various leukocyte subsets. In order to determine the leukocyte subset reactivity of CD45RB/RO binding chimeric antibody molecule immunofluorescent labeling of human leukocytes with subset-specific markers and simultaneous immunofluorescent labeling with a dye-conjugated CD45RB/RO binding chimeric antibody is performed, followed by flow cytometry analysis. Briefly, specific subsets of a freshly isolated preparation of human peripheral blood mononuclear cells (PBMC), human platelets, human peripheral blood neutrophils or human bone-marrow derived hematopoietic stem cells are identified by incubation with phycoerythrin-coupled antibodies against CD2 (T lymphocytes), CD14 (monocytes), CD19 (B lymphocytes), CD34 (stem cells), CD42a (platelets), CD56 (natural killer cells) or CD66b (granulocytes). Simultaneous binding of a FITC-labeled chimeric CD45RB/RO binding molecule is detected on T lymphocytes, monocytes, stem cells, natural killer cells and granulocytes, but not on platelets or B lymphocytes.

Example 11

In Vitro Induction of Suppressor T Cells (T Regulatory Cells) and of Functionally Paralyzed T Cells To demonstrate the ability of a CD45RO/RB binding chimeric antibody to induce suppressor T cells, the antibody is included at various concentrations during the generation of CD8+ T cell lines reactive with the antigen matrix protein 1 (MP1) of hemophilus influenza. These lines are generated through repeated co-culture of CD8+ human lymphocytes with CD14+ human monocytes pulsed with the antigen. Later on, CD14+ monocytes can be replaced with a human leukocyte antigen-2 positive cell line as an MP1 antigen-presenting cell (APC). If such MP1-specific CD8+ T cells from a culture including CD45RO/RB binding chimeric antibody are mixed with freshly isolated human CD8+ T cells and this mixture of cells is stimulated with the MP1 antigen on APC, the addition of CD8+ T cells from the culture in the presence of CD45RO/RB binding molecule is able to reduce the IFN-γ production in an antibody-dose-dependent fashion. No CD45RO/RB binding chimeric antibody is present during this IFN-γ assay culture, indicating that the pre-treatment with the CD45RO/RB mAb has induced CD8+ T cells capable of suppressing the activation of freshly isolated T cells. Because of this induction of suppressor T regulatory cells by the CD45RO/RB binding chimeric antibody, the antibody may be useful in diseases, where a dysregulated and/or activated T cell population is thought to contribute to the pathology. Examples of such diseases include autoimmune diseases, transplant rejection, psoriasis, inflammatory bowel disease and allergies.

To demonstrate the ability of a chimeric CD45RO/RB binding molecule to render T cells hyporesponsive (anergic) to further stimulation, i.e. to functionally paralyze T cells, the antibody is included during the generation of CD8+ T cell lines reactive with the antigen matrix protein 1 (MP1) of hemophilus influenza as outlined above. Paralysis is assessed by activating the T cells (exposed prior to CD45RO/RB binding chimeric antibody) with MP1 antigen presented by APC. No CD45RO/RB binding molecule is present in this culture. CD8+ T cells not exposed to CD45RO/RB binding chimeric antibody previously produce IFN-γ upon the mentioned stimulus. In contrast, CD8+ T cells pre-treated with CD45RO/RB binding chimeric antibody show a markedly reduced to inexistent production of this cytokine in response to the antigen-stimulus, demonstrating the CD45RO/RB binding chimeric antibody's ability to functionally paralyze human T cells. Because of this induction of functional T cell hyporesponsiveness by the CD45RO/RB binding molecule, the antibody may be used in diseases, such autoimmune diseases, transplant rejection, psoriasis, inflammatory bowel disease or allergies, where an activated T cell population is thought to contribute to the pathology.

Example 12

In Vivo Studies in SCID-hu Skin Mice

In this study, the utility of the CD45RB/RO binding chimeric antibody in a Psoriasis model system is tested. Human skin from normal individuals is transplanted to SCID (SCID-hu Skin) mice and the inflammatory process is mimicked by transferring mononuclear cells of unrelated donors into the SCID-hu Skin mice.

Transplantation of Human Adult Skin in SCID Mice (SCID-hu Skin Mice)

Two small pieces (1 $cm^2$) of human adult skin (obtained from the West Hungarian Regional Tissue Bank; WHRTB, Gyor) consisting of the entire epidermis, the papillary dermis and part of the reticular dermis, are transplanted at the right and left upper-back sides of SCID mice C.B 17/GbmsTac-Prkdc$^{scid}$ Lyst$^{bg}$ mice (Taconic, Germantown, N.Y.) in replacement of mouse skin. The quality of the grafts is monitored during 5-6 weeks following transplantation and successfully transplanted mice (SCID-hu Skin mice, generally >85%) are selected for in vivo testing of CD45RB/RO binding chimeric antibody.

Engraftment of Human Mononuclear Cells in SCID Mice

Mononuclear splenocytes (Spl) are isolated from human adult spleen biopsies (WHRTB, Gyor) after cell suspension (using a cell dissociation sieve equipped with a size 50 mesh) and standard density gradient procedures. Aliquots of ~$5\times10^8$ Spl are re-suspended in 1.5 ml of RPMI-10% FCS and injected intraperitoneally (i.p.), on experimental day 0, into the SCID-hu Skin mice. These Spl numbers have been found in previous experiments to be sufficient to induce a lethal xeno-GvHD in >90% of the mice within 4-6 weeks after cell transfer.

Antibody Treatment of SCID-hu Skin Mice

SCID-hu Skin mice, reconstituted with human Spl, are treated with CD45RB/RO binding chimeric antibody or with anti-LPS control mAb at day 0, immediately after mononuclear cell injection, at days 3 and 7 and at weekly intervals thereafter. Antibodies are delivered subcutaneously (s.c.) in 100 μl PBS at a final concentration of 1 mg/kg body weight (b.w.).

Evaluation of Anti-CD45 Treatment

The efficacy of CD45RB/RO binding chimeric antibody is assessed by the survival of the transplanted mice and by monitoring the rejection of the skin grafts. The significance of the results is evaluated by the statistical method of survival analysis using the Log-rank test (Mantel method) with the help of Systat v10 software. At the end of the experiment biopsies of human skin grafts and mouse liver, lung, kidney and spleen are obtained from sacrificed mice for histological purposes. All mice are weighed at the beginning (before cell transfer) and throughout the experiment (every two days) as an indirect estimation of their health status. Linear regression lines are generated using the body weight versus days post-PBMC transfer values obtained from each mouse and subsequently, their slopes (control versus anti-CD45 treated mice) are compared using the non parametric Mann-Whitney test.

Results

The human skin grafts are very well tolerated by the SCID mice. Initially, the grafts undergo a period of keratinocyte hyperproliferation resulting in the formation of hyperkeratotic crusts. About 5 weeks after transplantation, the crusts fall off the grafts and reveal a tissue containing all the characteristic structures observed in normal human skin. During this process, the human skin grafts fuse with the adjacent mouse skin and generate a network of freshly grown human vessels that connect the grafts with the underlying mouse tissue. The circulating human Spl transferred into SCID-hu Skin mice (at experimental day 0, approx. 6 weeks after skin transplantation) infiltrate the skin grafts and after recognition of alloantigen molecules expressed on the human skin mount an inflammatory response that in some cases completely destroy the graft.

Treatment of these mice with CD45RB/RO binding chimeric antibody suppresses the inflammatory process and prevents the rejection of the human skin grafts. In contrast, the sample obtained from the control treated mouse shows a massive infiltration with multiple signs of necrosis and a dramatic destruction of the epidermis. This process is easily monitored by eye and documented by simple photography of the mice.

Six out of six SCID-hu Skin mice transferred with allogeneic human Spl and treated with control anti-LPS mAb show a strong inflammatory response clearly visible by eye 23 days after mononuclear cell transfer. All mice show considerable lesions, including erythema, scaling and pronounced pustules. In contrast the skin grafts of all mice treated with CD45RB/RO binding chimeric antibody have a normal appearance. The dramatic differences between the two groups of mice is specifically due to the antibody treatment since the human skin of all mice have an identical look at the beginning of the experiment. This aspect is not changed until the second week after cell transfer, the time at which the control group started to developed skin lesions. The experiment is terminated at day 34 after mononuclear cell transfer. By that time, one of the control mice is already dead (day 30) and four other are sacrificed (days 27, 27, 27 and 30) due to a strong xeno-GvHD. The pathologic reactions observed in the antibody control treated mice also correlates with a loss of body weight in these animals.

In contrast, the CD45RB/RO binding chimeric antibody treated group displays a healthy status during the whole experimentation time.

The invention claimed is:

1. An isolated antibody which binds CD45RB/CD45RO comprising the polypeptide of SEQ ID NO:8 and the polypeptide of SEQ ID NO: 31.

2. An isolated antibody which binds CD45RB/CD45RO comprising:

a) a first domain comprising the hypervariable regions CDR1, CDR2 and CDR3, said CDR1 having the amino acid sequence Asn-Tyr-Ile-Ile-His (NYIIH) (SEQ ID NO:22), said CDR2 having the amino acid sequence Tyr-Phe-Asn-Pro-Tyr-Asn-His-Gly-Thr-Lys-Tyr-Asn-Glu-Lys-Phe-Lys-Gly (YFNPYNHGTKYNEKFKG) (SEQ ID NO:23) and said CDR3 having the amino acid sequence Ser-Gly-Pro-Tyr-Ala-Trp-Phe-Asp-Thr (SGPYAWFDT) (SEQ ID NO:24); and b) a second domain comprising the hypervariable regions CDR1', CDR2' and CDR3', said CDR1' having the amino acid sequence Arg-Ala-Ser-Gln-Asn-Ile-Gly-Thr-Ser-Ile-Gln (RASQNIGTSIQ) (SEQ ID NO:19), CDR2' having the amino acid sequence Ser-Ser-Ser-Glu-Ser-Ile-Ser (SSSESIS) (SEQ ID NO:20) and CDR3' having the amino acid sequence Gln-Gln-Ser-Asn-Thr-Trp-Pro-Phe-Thr (QQSNTWPFT) (SEQ ID NO:21).

3. The isolated antibody according to claim 2, which is a chimeric or humanised monoclonal antibody.

4. The isolated antibody according to claim 2, comprising the polypeptide of SEQ ID NO: 31.

5. The isolated antibody according to claim 2, comprising the polypeptide of SEQ ID NO:8.

6. The isolated antibody according to claim 4 which is a chimeric monoclonal antibody.

7. An isolated antibody which binds CD45RB/CD45RO which is a humanised antibody comprising the polypeptide of SEQ ID NO:8 and the polypeptide of SEQ ID NO: 31.

8. A pharmaceutical composition comprising the antibody according to claim 1 in association with at least one pharmaceutically acceptable carrier or diluent.

9. A pharmaceutical composition comprising the antibody according to claim 2 in association with at least one pharmaceutically acceptable carrier or diluent.

10. The isolated antibody according to claim 1, which is a chimeric or humanised monoclonal antibody.

11. An isolated antibody that binds CD45RB/CD45RO comprising the polypeptide of SEQ ID NO: 31.

12. The isolated antibody according to claim 11, which is a chimeric or humanised monoclonal antibody.

13. A pharmaceutical composition comprising an isolated antibody according to claim 11, in association with at least one pharmaceutically acceptable carrier or diluent.

* * * * *

SEQUENCE LISTING

```
<160> NUMBER OF SEQ ID NOS: 49

<210> SEQ ID NO 1
<211> LENGTH: 107
<212> TYPE: PRT
<213> ORGANISM: Artificial
<220> FEATURE:
<223> OTHER INFORMATION: Part of the amino acid sequence of chimeric
      light chain

<400> SEQUENCE: 1

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Asn Ile Gly Thr Ser
            20                  25                  30

Ile Gln Trp Tyr Gln Gln Arg Thr Asn Gly Ser Pro Arg Leu Leu Ile
        35                  40                  45

Arg Ser Ser Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Thr Trp Pro Phe
                85                  90                  95

Thr Phe Gly Ser Gly Thr Lys Leu Glu Ile Lys
            100                 105


<210> SEQ ID NO 2
<211> LENGTH: 118
<212> TYPE: PRT
```

-continued

```
<213> ORGANISM: Artificial
<220> FEATURE:
<223> OTHER INFORMATION: Part of the amino acid sequence of chimeric
      heavy chain

<400> SEQUENCE: 2

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Ile Ile His Trp Val Lys Gln Glu Pro Gly Gln Gly Leu Glu Trp Ile
        35                  40                  45

Gly Tyr Phe Asn Pro Tyr Asn His Gly Thr Lys Tyr Asn Glu Lys Phe
    50                  55                  60

Lys Gly Arg Ala Thr Leu Thr Ala Asp Lys Ser Ser Asn Thr Ala Tyr
65                  70                  75                  80

Met Asp Leu Ser Ser Leu Thr Ser Glu Asp Ser Ala Ile Tyr Tyr Cys
                85                  90                  95

Ala Arg Ser Gly Pro Tyr Ala Trp Phe Asp Thr Trp Gly Gln Gly Thr
            100                 105                 110

Thr Val Thr Val Ser Ser
        115


<210> SEQ ID NO 3
<211> LENGTH: 214
<212> TYPE: PRT
<213> ORGANISM: Artificial
<220> FEATURE:
<223> OTHER INFORMATION: Amino acid sequence of chimeric light chain

<400> SEQUENCE: 3

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Asn Ile Gly Thr Ser
            20                  25                  30

Ile Gln Trp Tyr Gln Gln Arg Thr Asn Gly Ser Pro Arg Leu Leu Ile
        35                  40                  45

Arg Ser Ser Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Thr Trp Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

-continued

```
Phe Asn Arg Gly Glu Cys
    210


<210> SEQ ID NO 4
<211> LENGTH: 448
<212> TYPE: PRT
<213> ORGANISM: Artificial
<220> FEATURE:
<223> OTHER INFORMATION: Amino acid sequence of chimeric heavy chain

<400> SEQUENCE: 4

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Ile Ile His Trp Val Lys Gln Glu Pro Gly Gln Gly Leu Glu Trp Ile
        35                  40                  45

Gly Tyr Phe Asn Pro Tyr Asn His Gly Thr Lys Tyr Asn Glu Lys Phe
    50                  55                  60

Lys Gly Arg Ala Thr Leu Thr Ala Asp Lys Ser Ser Asn Thr Ala Tyr
65                  70                  75                  80

Met Asp Leu Ser Ser Leu Thr Ser Glu Asp Ser Ala Ile Tyr Tyr Cys
                85                  90                  95

Ala Arg Ser Gly Pro Tyr Ala Trp Phe Asp Thr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

-continued

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 5
<211> LENGTH: 321
<212> TYPE: DNA
<213> ORGANISM: Artificial
<220> FEATURE:
<223> OTHER INFORMATION: Nucleotide sequence encoding a polypeptide of SEQ ID NO:1

<400> SEQUENCE: 5
gacattctgc tgacccagtc tccagccatc ctgtctgtga gtccaggaga aagagtcagt 60
ttctcctgca gggccagtca gaacattggc acaagcatac agtggtatca acaaagaaca 120
aatggttctc caaggcttct cataaggtct tcttctgagt ctatctctgg gatcccttcc 180
aggtttagtg gcagtggatc agggacagat tttactctta gcatcaacag tgtggagtct 240
gaagatattg cagattatta ctgtcaacaa agtaatacct ggccattcac gttcggctcg 300
gggaccaagc ttgaaatcaa a 321

<210> SEQ ID NO 6
<211> LENGTH: 354
<212> TYPE: DNA
<213> ORGANISM: Artificial
<220> FEATURE:
<223> OTHER INFORMATION: Nucleotide sequence encoding a polypeptide of SEQ ID NO:2

<400> SEQUENCE: 6
gaggtgcagc tgcagcagtc aggacctgaa ctggtaaagc ctggggcttc agtgaagatg 60
tcctgcaagg cctctggata cacattcact aattatatta tccactgggt gaagcaggag 120
cctggtcagg gccttgaatg gattggatat tttaatcctt acaatcatgg tactaagtac 180
aatgagaagt tcaaaggcag ggccacacta actgcagaca aatcctccaa cacagcctac 240
atggacctca gcagcctgac ctctgaggac tctgcgatct actactgtgc aagatcagga 300
ccctatgcct ggtttgacac ctggggccaa gggaccacgg tcaccgtctc ctca 354

<210> SEQ ID NO 7
<211> LENGTH: 107
<212> TYPE: PRT
<213> ORGANISM: Artificial
<220> FEATURE:
<223> OTHER INFORMATION: Part of amino acid sequence of humanised light chain designated humV2 (humV2 = VLm)

<400> SEQUENCE: 7

Asp Ile Leu Leu Thr Gln Ser Pro Ala Thr Leu Ser Leu Ser Pro Gly
1               5                   10                  15

-continued

```
Glu Arg Ala Thr Phe Ser Cys Arg Ala Ser Gln Asn Ile Gly Thr Ser
            20                  25                  30

Ile Gln Trp Tyr Gln Gln Lys Thr Asn Gly Ala Pro Arg Leu Leu Ile
        35                  40                  45

Arg Ser Ser Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Thr Trp Pro Phe
                85                  90                  95

Thr Phe Gly Gln Gly Thr Lys Leu Glu Ile Lys
            100                 105


<210> SEQ ID NO 8
<211> LENGTH: 107
<212> TYPE: PRT
<213> ORGANISM: Artificial
<220> FEATURE:
<223> OTHER INFORMATION: Part of amino acid sequence of humanised
      light chain designated humV1 (humV1 = VLh)

<400> SEQUENCE: 8

Asp Ile Leu Leu Thr Gln Ser Pro Ala Thr Leu Ser Leu Ser Pro Gly
1               5                   10                  15

Glu Arg Ala Thr Leu Ser Cys Arg Ala Ser Gln Asn Ile Gly Thr Ser
            20                  25                  30

Ile Gln Trp Tyr Gln Gln Lys Pro Gly Gln Ala Pro Arg Leu Leu Ile
        35                  40                  45

Arg Ser Ser Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Thr Trp Pro Phe
85                  90                  95

Thr Phe Gly Gln Gly Thr Lys Leu Glu Ile Lys
                100                 105


<210> SEQ ID NO 9
<211> LENGTH: 118
<212> TYPE: PRT
<213> ORGANISM: Artificial
<220> FEATURE:
<223> OTHER INFORMATION: Part of amino acid sequence of humanised heavy
      chain designated VHE

<400> SEQUENCE: 9

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ile Ile His Trp Val Lys Gln Glu Pro Gly Gln Gly Leu Glu Trp Ile
        35                  40                  45

Gly Tyr Phe Asn Pro Tyr Asn His Gly Thr Lys Tyr Asn Glu Lys Phe
    50                  55                  60

Lys Gly Arg Ala Thr Leu Thr Ala Asn Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95
```

-continued

```
Ala Arg Ser Gly Pro Tyr Ala Trp Phe Asp Thr Trp Gly Gln Gly Thr
            100                 105                 110

Thr Val Thr Val Ser Ser
        115


<210> SEQ ID NO 10
<211> LENGTH: 118
<212> TYPE: PRT
<213> ORGANISM: Artificial
<220> FEATURE:
<223> OTHER INFORMATION: Part of amino acid sequence of humanised heavy
      chain designated VHQ

<400> SEQUENCE: 10

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ile Ile His Trp Val Lys Gln Glu Pro Gly Gln Gly Leu Glu Trp Ile
        35                  40                  45

Gly Tyr Phe Asn Pro Tyr Asn His Gly Thr Lys Tyr Asn Glu Lys Phe
    50                  55                  60

Lys Gly Arg Ala Thr Leu Thr Ala Asn Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Pro Tyr Ala Trp Phe Asp Thr Trp Gly Gln Gly Thr
            100                 105                 110

Thr Val Thr Val Ser Ser
        115


<210> SEQ ID NO 11
<211> LENGTH: 354
<212> TYPE: DNA
<213> ORGANISM: Artificial
<220> FEATURE:
<223> OTHER INFORMATION: Nucleotide sequence encoding amino acid
      sequence SEQ ID NO:9

<400> SEQUENCE: 11

gaggtgcagc tggtggagtc aggagccgaa gtgaaaaagc ctggggcttc agtgaaggtg      60

tcctgcaagg cctctggata cacattcact aattatatta tccactgggt gaagcaggag     120

cctggtcagg gccttgaatg gattggatat tttaatcctt acaatcatgg tactaagtac     180

aatgagaagt tcaaaggcag ggccacacta actgcaaaca aatccatcag cacagcctac     240

atggagctca gcagcctgcg ctctgaggac actgcggtct actactgtgc aagatcagga     300

ccctatgcct ggtttgacac ctggggccaa gggaccacgg tcaccgtctc ctca           354


<210> SEQ ID NO 12
<211> LENGTH: 354
<212> TYPE: DNA
<213> ORGANISM: Artificial
<220> FEATURE:
<223> OTHER INFORMATION: Nucleotide sequence encoding amino acid
      sequence SEQ ID NO:10

<400> SEQUENCE: 12

caggtgcagc tggtggagtc aggagccgaa gtgaaaaagc ctggggcttc agtgaaggtg      60

tcctgcaagg cctctggata cacattcact aattatatta tccactgggt gaagcaggag     120
```

-continued

```
cctggtcagg gccttgaatg gattggatat tttaatcctt acaatcatgg tactaagtac    180

aatgagaagt tcaaaggcag ggccacacta actgcaaaca aatccatcag cacagcctac    240

atggagctca gcagcctgcg ctctgaggac actgcggtct actactgtgc aagatcagga    300

ccctatgcct ggtttgacac ctggggccaa gggaccacgg tcaccgtctc ctca          354
```

<210> SEQ ID NO 13
<211> LENGTH: 321
<212> TYPE: DNA
<213> ORGANISM: Artificial
<220> FEATURE:
<223> OTHER INFORMATION: Nucleotide sequence encoding amino acid sequence SEQ ID NO:7

<400> SEQUENCE: 13

```
gacattctgc tgacccagtc tccagccacc ctgtctctga gtccaggaga aagagccact     60

ttctcctgca gggccagtca gaacattggc acaagcatac agtggtatca acaaaaaaca    120

aatggtgctc caaggcttct cataaggtct tcttctgagt ctatctctgg gatcccttcc    180

aggtttagtg gcagtggatc agggacagat tttactctta ccatcagcag tctggagcct    240

gaagattttg cagtgtatta ctgtcaacaa agtaatacct ggccattcac gttcggccag    300

gggaccaagc tggagatcaa a                                              321
```

<210> SEQ ID NO 14
<211> LENGTH: 321
<212> TYPE: DNA
<213> ORGANISM: Artificial
<220> FEATURE:
<223> OTHER INFORMATION: Nucleotide sequence encoding amino acid sequence SEQ ID NO:8

<400> SEQUENCE: 14

```
gacattctgc tgacccagtc tccagccacc ctgtctctga gtccaggaga aagagccact     60

ctctcctgca gggccagtca gaacattggc acaagcatac agtggtatca acaaaaacca    120

ggtcaggctc caaggcttct cataaggtct tcttctgagt ctatctctgg gatcccttcc    180

aggtttagtg gcagtggatc agggacagat tttactctta ccatcagcag tctggagcct    240

gaagattttg cagtgtatta ctgtcaacaa agtaatacct ggccattcac gttcggccag    300

gggaccaagc tggagatcaa a                                              321
```

<210> SEQ ID NO 15
<211> LENGTH: 8687
<212> TYPE: DNA
<213> ORGANISM: Artificial
<220> FEATURE:
<223> OTHER INFORMATION: Nucleotide sequence of the expression vector HCMV-G1 HuA6-VHQ (Complete DNA Sequence of a humanised heavy chain expression vector comprising SEQ ID NO:12 (VHQ) from 3921-4274)

<400> SEQUENCE: 15

```
agctttttgc aaaagcctag gcctccaaaa aagcctcctc actacttctg gaatagctca     60

gaggccgagg cggcctcggc ctctgcataa ataaaaaaaa ttagtcagcc atggggcgga    120

gaatgggcgg aactgggcgg agttaggggc gggatgggcg gagttagggg cgggactatg    180

gttgctgact aattgagatg catgctttgc atacttctgc ctgctgggga gcctggttgc    240

tgactaattg agatgcatgc tttgcatact tctgcctgct ggggagcctg gggactttcc    300

acaccctaac tgacacacat tccacagctg cctcgcgcgt ttcggtgatg acggtgaaaa    360
```

-continued

```
cctctgacac atgcagctcc cggagacggt cacagcttgt ctgtaagcgg atgccgggag    420
cagacaagcc cgtcagggcg cgtcagcggg tgttggcggg tgtcggggcg cagccatgac    480
ccagtcacgt agcgatagcg gagtgtatac tggcttaact atgcggcatc agagcagatt    540
gtactgagag tgcaccatat gcggtgtgaa ataccgcaca gatgcgtaag gagaaaatac    600
cgcatcaggc gctcttccgc ttcctcgctc actgactcgc tgcgctcggt cgttcggctg    660
cggcgagcgg tatcagctca ctcaaaggcg gtaatacggt tatccacaga atcaggggat    720
aacgcaggaa agaacatgtg agcaaaaggc cagcaaaagg ccaggaaccg taaaaaggcc    780
gcgttgctgg cgtttttcca taggctccgc ccccctgacg agcatcacaa aaatcgacgc    840
tcaagtcaga ggtggcgaaa cccgacagga ctataaagat accaggcgtt tccccctgga    900
agctccctcg tgcgctctcc tgttccgacc ctgccgctta ccggatacct gtccgccttt    960
ctcccttcgg gaagcgtggc gctttctcat agctcacgct gtaggtatct cagttcggtg   1020
taggtcgttc gctccaagct gggctgtgtg cacgaacccc ccgttcagcc cgaccgctgc   1080
gccttatccg gtaactatcg tcttgagtcc aacccggtaa gacacgactt atcgccactg   1140
gcagcagcca ctggtaacag gattagcaga gcgaggtatg taggcggtgc tacagagttc   1200
ttgaagtggt ggcctaacta cggctacact agaaggacag tatttggtat ctgcgctctg   1260
ctgaagccag ttaccttcgg aaaaagagtt ggtagctctt gatccggcaa acaaaccacc   1320
gctggtagcg gtggtttttt tgtttgcaag cagcagatta cgcgcagaaa aaaaggatct   1380
caagaagatc ctttgatctt ttctacgggg tctgacgctc agtggaacga aaactcacgt   1440
taagggattt tggtcatgag attatcaaaa aggatcttca cctagatcct tttaaattaa   1500
aaatgaagtt ttaaatcaat ctaaagtata tatgagtaaa cttggtctga cagttaccaa   1560
tgcttaatca gtgaggcacc tatctcagcg atctgtctat ttcgttcatc catagttgcc   1620
tgactccccg tcgtgtagat aactacgata cgggagggct taccatctgg ccccagtgct   1680
gcaatgatac cgcgagaccc acgctcaccg gctccagatt tatcagcaat aaaccagcca   1740
gccggaaggg ccgagcgcag aagtggtcct gcaactttat ccgcctccat ccagtctatt   1800
aattgttgcc gggaagctag agtaagtagt tcgccagtta atagtttgcg caacgttgtt   1860
gccattgctg caggcatcgt ggtgtcacgc tcgtcgtttg gtatggcttc attcagctcc   1920
ggttcccaac gatcaaggcg agttacatga tcccccatgt tgtgcaaaaa agcggttagc   1980
tccttcggtc ctccgatcgt tgtcagaagt aagttggccg cagtgttatc actcatggtt   2040
atggcagcac tgcataattc tcttactgtc atgccatccg taagatgctt ttctgtgact   2100
ggtgagtact caaccaagtc attctgagaa tagtgtatgc ggcgaccgag ttgctcttgc   2160
ccggcgtcaa cacgggataa taccgcgcca catagcagaa ctttaaaagt gctcatcatt   2220
ggaaaacgtt cttcggggcg aaaactctca aggatcttac cgctgttgag atccagttcg   2280
atgtaaccca ctcgtgcacc caactgatct tcagcatctt ttactttcac cagcgtttct   2340
gggtgagcaa aaacaggaag gcaaaatgcc gcaaaaaagg gaataagggc gacacggaaa   2400
tgttgaatac tcatactctt cctttttcaa tattattgaa gcatttatca gggttattgt   2460
ctcatgagcg gatacatatt tgaatgtatt tagaaaaata aacaaatagg ggttccgcgc   2520
acatttcccc gaaaagtgcc acctgacgtc taagaaacca ttattatcat gacattaacc   2580
tataaaaata ggcgtatcac gaggcccttt cgtcttcaag aattcagctt ggctgcagtg   2640
aataataaaa tgtgtgtttg tccgaaatac gcgttttgag atttctgtcg ccgactaaat   2700
tcatgtcgcg cgatagtggt gtttatcgcc gatagagatg gcgatattgg aaaaatcgat   2760
```

-continued

```
atttgaaaat atggcatatt gaaaatgtcg ccgatgtgag tttctgtgta actgatatcg   2820
ccatttttcc aaaagtgatt tttgggcata cgcgatatct ggcgatagcg cttatatcgt   2880
ttacggggga tggcgataga cgactttggt gacttgggcg attctgtgtg tcgcaaatat   2940
cgcagtttcg atataggtga cagacgatat gaggctatat cgccgataga ggcgacatca   3000
agctggcaca tggccaatgc atatcgatct atacattgaa tcaatattgg ccattagcca   3060
tattattcat tggttatata gcataaatca atattggcta ttggccattg catacgttgt   3120
atccatatca taatatgtac atttatattg gctcatgtcc aacattaccg ccatgttgac   3180
attgattatt gactagttat taatagtaat caattacggg gtcattagtt catagcccat   3240
atatggagtt ccgcgttaca taacttacgg taaatggccc gcctggctga ccgcccaacg   3300
acccccgccc attgacgtca ataatgacgt atgttcccat agtaacgcca atagggactt   3360
tccattgacg tcaatgggtg gagtatttac ggtaaactgc ccacttggca gtacatcaag   3420
tgtatcatat gccaagtacg ccccctattg acgtcaatga cggtaaatgg cccgcctggc   3480
attatgccca gtacatgacc ttatgggact ttcctacttg gcagtacatc tacgtattag   3540
tcatcgctat taccatggtg atgcggtttt ggcagtacat caatgggcgt ggatagcggt   3600
ttgactcacg gggatttcca agtctccacc ccattgacgt caatgggagt ttgttttggc   3660
accaaaatca acgggacttt ccaaaatgtc gtaacaactc cgccccattg acgcaaatgg   3720
gcggtaggcg tgtacggtgg gaggtctata taagcagagc tcgtttagtg aaccgtcaga   3780
tcgcctggag acgccatcca cgctgttttg acctccatag aagacaccgg gaccgatcca   3840
gcctccgcaa gcttgccgcc accatggact ggacctggag ggtgttctgc ctgctggccg   3900
tggcccccgg cgcccacagc caggtgcagc tggtggagtc aggagccgaa gtgaaaaagc   3960
ctggggcttc agtgaaggtg tcctgcaagg cctctggata cacattcact aattatatta   4020
tccactgggt gaagcaggag cctggtcagg gccttgaatg gattggatat tttaatcctt   4080
acaatcatgg tactaagtac aatgagaagt tcaaaggcag ggccacacta actgcaaaca   4140
aatccatcag cacagcctac atggagctca gcagcctgcg ctctgaggac actgcggtct   4200
actactgtgc aagatcagga ccctatgcct ggtttgacac ctggggccaa gggaccacgg   4260
tcaccgtctc ctcaggtgag ttctagaagg atcccaagct agctttctgg ggcaggccag   4320
gcctgacctt ggctttgggg cagggagggg gctaaggtga ggcaggtggc gccagccagg   4380
tgcacaccca atgcccatga gcccagacac tggacgctga acctcgcgga cagttaagaa   4440
cccaggggcc tctgcgccct gggcccagct ctgtcccaca ccgcggtcac atggcaccac   4500
ctctcttgca gcctccacca agggcccatc ggtcttcccc ctggcaccct cctccaagag   4560
cacctctggg ggcacagcgg ccctgggctg cctggtcaag gactacttcc ccgaaccggt   4620
gacggtgtcg tggaactcag gcgccctgac cagcggcgtg cacaccttcc cggctgtcct   4680
acagtcctca ggactctact ccctcagcag cgtggtgacc gtgccctcca gcagcttggg   4740
cacccagacc tacatctgca acgtgaatca caagcccagc aacaccaagg tggacaagaa   4800
agttggtgag aggccagcac agggagggag ggtgtctgct ggaagccagg ctcagcgctc   4860
ctgcctggac gcatcccggc tatgcagccc cagtccaggg cagcaaggca ggccccgtct   4920
gcctcttcac ccggaggcct ctgcccgccc cactcatgct cagggagagg gtcttctggc   4980
tttttcccca ggctctgggc aggcacaggc taggtgcccc taacccaggc cctgcacaca   5040
aaggggcagg tgctgggctc agacctgcca agagccatat ccgggaggac cctgcccctg   5100
```

-continued

```
acctaagccc accccaaagg ccaaactctc cactccctca gctcggacac cttctctcct   5160
cccagattcc agtaactccc aatcttctct ctgcagagcc caaatcttgt gacaaaactc   5220
acacatgccc accgtgccca ggtaagccag cccaggcctc gccctccagc tcaaggcggg   5280
acaggtgccc tagagtagcc tgcatccagg gacaggcccc agccgggtgc tgacacgtcc   5340
acctccatct cttcctcagc acctgaactc ctggggggac cgtcagtctt cctcttcccc   5400
ccaaaaccca aggacaccct catgatctcc cggacccctg aggtcacatg cgtggtggtg   5460
gacgtgagcc acgaagaccc tgaggtcaag ttcaactggt acgtggacgg cgtggaggtg   5520
cataatgcca agacaaagcc gcgggaggag cagtacaaca gcacgtaccg tgtggtcagc   5580
gtcctcaccg tcctgcacca ggactggctg aatggcaagg agtacaagtg caaggtctcc   5640
aacaaagccc tcccagcccc catcgagaaa accatctcca aagccaaagg tgggacccgt   5700
ggggtgcgag ggccacatgg acagaggccg gctcggccca ccctctgccc tgagagtgac   5760
cgctgtacca acctctgtcc ctacagggca gccccgagaa ccacaggtgt acaccctgcc   5820
cccatcccgg gatgagctga ccaagaacca ggtcagcctg acctgcctgg tcaaaggctt   5880
ctatcccagc gacatcgccg tggagtggga gagcaatggg cagccggaga acaactacaa   5940
gaccacgcct cccgtgctgg actccgacgg ctccttcttc ctctacagca agctcaccgt   6000
ggacaagagc aggtggcagc aggggaacgt cttctcatgc tccgtgatgc atgaggctct   6060
gcacaaccac tacacgcaga agagcctctc cctgtctccg ggtaaatgag tgcgacggcc   6120
ggcaagcccc cgctccccgg gctctcgcgg tcgcacgagg atgcttggca cgtaccccct   6180
gtacatactt cccgggcgcc cagcatggaa ataaagcacc cagcgctgcc ctgggcccct   6240
gcgagactgt gatggttctt tccacgggtc aggccgagtc tgaggcctga gtggcatgag   6300
atctgatatc atcgatgaat tcgagctcgg tacccgggga tcgatccaga catgataaga   6360
tacattgatg agtttggaca aaccacaact agaatgcagt gaaaaaaatg ctttatttgt   6420
gaaatttgtg atgctattgc tttatttgta accattataa gctgcaataa acaagttaac   6480
aacaacaatt gcattcattt tatgtttcag gttcaggggg aggtgtggga ggttttttaa   6540
agcaagtaaa acctctacaa atgtggtatg gctgattatg atctctagtc aaggcactat   6600
acatcaaata ttccttatta acccctttac aaattaaaaa gctaaaggta cacaattttt   6660
gagcatagtt attaatagca gacactctat gcctgtgtgg agtaagaaaa aacagtatgt   6720
tatgattata actgttatgc ctacttataa aggttacaga atatttttcc ataattttct   6780
tgtatagcag tgcagctttt tcctttgtgg tgtaaatagc aaagcaagca agagttctat   6840
tactaaacac agcatgactc aaaaaactta gcaattctga aggaaagtcc ttggggtctt   6900
ctacctttct cttctttttt ggaggagtag aatgttgaga gtcagcagta gcctcatcat   6960
cactagatgg catttcttct gagcaaaaca ggttttcctc attaaaggca ttccaccact   7020
gctcccattc atcagttcca taggttggaa tctaaaatac acaaacaatt agaatcagta   7080
gtttaacaca ttatacactt aaaaatttta tatttacctt agagctttaa atctctgtag   7140
gtagtttgtc caattatgtc acaccacaga agtaaggttc cttcacaaag atccgggacc   7200
aaagcggcca tcgtgcctcc ccactcctgc agttcggggg catggatgcg cggatagccg   7260
ctgctggttt cctggatgcc gacggatttg cactgccggt agaactccgc gaggtcgtcc   7320
agcctcaggc agcagctgaa ccaactcgcg aggggatcga gcccggggtg ggcgaagaac   7380
tccagcatga gatccccgcg ctggaggatc atccagccgg cgtcccggaa aacgattccg   7440
aagcccaacc tttcatagaa ggcggcggtg gaatcgaaat ctcgtgatgg caggttgggc   7500
```

-continued

```
gtcgcttggt cggtcatttc gaaccccaga gtcccgctca gaagaactcg tcaagaaggc   7560

gatagaaggc gatgcgctgc gaatcgggag cggcgatacc gtaaagcacg aggaagcggt   7620

cagcccattc gccgccaagc tcttcagcaa tatcacgggt agccaacgct atgtcctgat   7680

agcggtccgc cacacccagc cggccacagt cgatgaatcc agaaaagcgg ccattttcca   7740

ccatgatatt cggcaagcag gcatcgccat gggtcacgac gagatcctcg ccgtcgggca   7800

tgcgcgcctt gagcctggcg aacagttcgg ctggcgcgag cccctgatgc tcttcgtcca   7860

gatcatcctg atcgacaaga ccggcttcca tccgagtacg tgctcgctcg atgcgatgtt   7920

tcgcttggtg gtcgaatggg caggtagccg gatcaagcgt atgcagccgc cgcattgcat   7980

cagccatgat ggatactttc tcggcaggag caaggtgaga tgacaggaga tcctgccccg   8040

gcacttcgcc caatagcagc cagtcccttc ccgcttcagt gacaacgtcg agcacagctg   8100

cgcaaggaac gcccgtcgtg gccagccacg atagccgcgc tgcctcgtcc tgcagttcat   8160

tcagggcacc ggacaggtcg gtcttgacaa aaagaaccgg gcgcccctgc gctgacagcc   8220

ggaacacggc ggcatcagag cagccgattg tctgttgtgc ccagtcatag ccgaatagcc   8280

tctccaccca agcggccgga gaacctgcgt gcaatccatc ttgttcaatc atgcgaaacg   8340

atcctcatcc tgtctcttga tcagatcttg atcccctgcg ccatcagatc cttggcggca   8400

agaaagccat ccagtttact ttgcagggct tcccaacctt accagagggc gccccagctg   8460

gcaattccgg ttcgcttgct gtccataaaa ccgcccagtc tagctatcgc catgtaagcc   8520

cactgcaagc tacctgcttt ctctttgcgc ttgcgttttc ccttgtccag atagcccagt   8580

agctgacatt catccggggt cagcaccgtt tctgcggact ggctttctac gtgttccgct   8640

tcctttagca gcccttgcgc cctgagtgct tgcggcagcg tgaagct                 8687
```

<210> SEQ ID NO 16
<211> LENGTH: 8687
<212> TYPE: DNA
<213> ORGANISM: Artificial
<220> FEATURE:
<223> OTHER INFORMATION: Nucleotide sequence of the expression vector HCMV-G1 HuA6-VHE (Complete DNA Sequence of a humanised heavy chain expression vector comprising SEQ ID NO: 11 (VHE) from 3921-4274)

<400> SEQUENCE: 16

```
agctttttgc aaaagcctag gcctccaaaa aagcctcctc actacttctg gaatagctca     60

gaggccgagg cggcctcggc ctctgcataa ataaaaaaaa ttagtcagcc atggggcgga    120

gaatgggcgg aactgggcgg agttaggggc gggatgggcg gagttagggg cgggactatg    180

gttgctgact aattgagatg catgctttgc atacttctgc ctgctgggga gcctggttgc    240

tgactaattg agatgcatgc tttgcatact tctgcctgct ggggagcctg gggactttcc    300

acaccctaac tgacacacat tccacagctg cctcgcgcgt ttcggtgatg acggtgaaaa    360

cctctgacac atgcagctcc cggagacggt cacagcttgt ctgtaagcgg atgccgggag    420

cagacaagcc cgtcagggcg cgtcagcggg tgttggcggg tgtcggggcg cagccatgac    480

ccagtcacgt agcgatagcg gagtgtatac tggcttaact atgcggcatc agagcagatt    540

gtactgagag tgcaccatat gcggtgtgaa ataccgcaca gatgcgtaag gagaaaatac    600

cgcatcaggc gctcttccgc ttcctcgctc actgactcgc tgcgctcggt cgttcggctg    660

cggcgagcgg tatcagctca ctcaaaggcg gtaatacggt tatccacaga atcaggggat    720

aacgcaggaa agaacatgtg agcaaaaggc cagcaaaagg ccaggaaccg taaaaaggcc    780
```

-continued

```
gcgttgctgg cgtttttcca taggctccgc ccccctgacg agcatcacaa aaatcgacgc    840
tcaagtcaga ggtggcgaaa cccgacagga ctataaagat accaggcgtt tccccctgga    900
agctccctcg tgcgctctcc tgttccgacc ctgccgctta ccggatacct gtccgccttt    960
ctcccttcgg gaagcgtggc gctttctcat agctcacgct gtaggtatct cagttcggtg   1020
taggtcgttc gctccaagct gggctgtgtg cacgaacccc ccgttcagcc cgaccgctgc   1080
gccttatccg gtaactatcg tcttgagtcc aacccggtaa gacacgactt atcgccactg   1140
gcagcagcca ctggtaacag gattagcaga gcgaggtatg taggcggtgc tacagagttc   1200
ttgaagtggt ggcctaacta cggctacact agaaggacag tatttggtat ctgcgctctg   1260
ctgaagccag ttaccttcgg aaaaagagtt ggtagctctt gatccggcaa acaaaccacc   1320
gctggtagcg gtggtttttt tgtttgcaag cagcagatta cgcgcagaaa aaaaggatct   1380
caagaagatc ctttgatctt ttctacgggg tctgacgctc agtggaacga aaactcacgt   1440
taagggattt tggtcatgag attatcaaaa aggatcttca cctagatcct tttaaattaa   1500
aaatgaagtt ttaaatcaat ctaaagtata tatgagtaaa cttggtctga cagttaccaa   1560
tgcttaatca gtgaggcacc tatctcagcg atctgtctat ttcgttcatc catagttgcc   1620
tgactccccg tcgtgtagat aactacgata cgggagggct taccatctgg ccccagtgct   1680
gcaatgatac cgcgagaccc acgctcaccg gctccagatt tatcagcaat aaaccagcca   1740
gccggaaggg ccgagcgcag aagtggtcct gcaactttat ccgcctccat ccagtctatt   1800
aattgttgcc gggaagctag agtaagtagt tcgccagtta atagtttgcg caacgttgtt   1860
gccattgctg caggcatcgt ggtgtcacgc tcgtcgtttg gtatggcttc attcagctcc   1920
ggttcccaac gatcaaggcg agttacatga tcccccatgt tgtgcaaaaa agcggttagc   1980
tccttcggtc ctccgatcgt tgtcagaagt aagttggccg cagtgttatc actcatggtt   2040
atggcagcac tgcataattc tcttactgtc atgccatccg taagatgctt ttctgtgact   2100
ggtgagtact caaccaagtc attctgagaa tagtgtatgc ggcgaccgag ttgctcttgc   2160
ccggcgtcaa cacgggataa taccgcgcca catagcagaa ctttaaaagt gctcatcatt   2220
ggaaaacgtt cttcggggcg aaaactctca aggatcttac cgctgttgag atccagttcg   2280
atgtaaccca ctcgtgcacc caactgatct tcagcatctt ttactttcac cagcgtttct   2340
gggtgagcaa aaacaggaag gcaaaatgcc gcaaaaaagg gaataagggc gacacggaaa   2400
tgttgaatac tcatactctt cctttttcaa tattattgaa gcatttatca gggttattgt   2460
ctcatgagcg gatacatatt tgaatgtatt tagaaaaata aacaaatagg ggttccgcgc   2520
acatttcccc gaaaagtgcc acctgacgtc taagaaacca ttattatcat gacattaacc   2580
tataaaaata ggcgtatcac gaggcccttt cgtcttcaag aattcagctt ggctgcagtg   2640
aataataaaa tgtgtgtttg tccgaaatac gcgttttgag atttctgtcg ccgactaaat   2700
tcatgtcgcg cgatagtggt gtttatcgcc gatagagatg gcgatattgg aaaaatcgat   2760
atttgaaaat atggcatatt gaaaatgtcg ccgatgtgag tttctgtgta actgatatcg   2820
ccatttttcc aaaagtgatt tttgggcata cgcgatatct ggcgatagcg cttatatcgt   2880
ttacggggga tggcgataga cgactttggt gacttgggcg attctgtgtg tcgcaaatat   2940
cgcagtttcg atataggtga cagacgatat gaggctatat cgccgataga ggcgacatca   3000
agctggcaca tggccaatgc atatcgatct atacattgaa tcaatattgg ccattagcca   3060
tattattcat tggttatata gcataaatca atattggcta ttggccattg catacgttgt   3120
```

-continued atccatatca taatatgtac atttatattg gctcatgtcc aacattaccg ccatgttgac 3180
attgattatt gactagttat taatagtaat caattacggg gtcattagtt catagcccat 3240
atatggagtt ccgcgttaca taacttacgg taaatggccc gcctggctga ccgcccaacg 3300
acccccgccc attgacgtca ataatgacgt atgttcccat agtaacgcca atagggactt 3360
tccattgacg tcaatgggtg gagtatttac ggtaaactgc ccacttggca gtacatcaag 3420
tgtatcatat gccaagtacg ccccctattg acgtcaatga cggtaaatgg cccgcctggc 3480
attatgccca gtacatgacc ttatgggact ttcctacttg gcagtacatc tacgtattag 3540
tcatcgctat taccatggtg atgcggtttt ggcagtacat caatgggcgt ggatagcggt 3600
ttgactcacg gggatttcca agtctccacc ccattgacgt caatgggagt ttgttttggc 3660
accaaaatca acgggacttt ccaaaatgtc gtaacaactc cgccccattg acgcaaatgg 3720
gcggtaggcg tgtacggtgg gaggtctata taagcagagc tcgtttagtg aaccgtcaga 3780
tcgcctggag acgccatcca cgctgttttg acctccatag aagacaccgg gaccgatcca 3840
gcctccgcaa gcttgccgcc accatggact ggacctggag ggtgttctgc ctgctggccg 3900
tggcccccgg cgcccacagc gaggtgcagc tggtggagtc aggagccgaa gtgaaaaagc 3960
ctggggcttc agtgaaggtg tcctgcaagg cctctggata cacattcact aattatatta 4020
tccactgggt gaagcaggag cctggtcagg gccttgaatg gattggatat tttaatcctt 4080
acaatcatgg tactaagtac aatgagaagt tcaaaggcag ggccacacta actgcaaaca 4140
aatccatcag cacagcctac atggagctca gcagcctgcg ctctgaggac actgcggtct 4200
actactgtgc aagatcagga ccctatgcct ggtttgacac ctggggccaa gggaccacgg 4260
tcaccgtctc ctcaggtgag ttctagaagg atcccaagct agctttctgg ggcaggccag 4320
gcctgacctt ggctttgggg cagggagggg gctaaggtga ggcaggtggc gccagccagg 4380
tgcacaccca atgcccatga gcccagacac tggacgctga acctcgcgga cagttaagaa 4440
cccaggggcc tctgcgccct gggcccagct ctgtcccaca ccgcggtcac atggcaccac 4500
ctctcttgca gcctccacca agggcccatc ggtcttcccc ctggcaccct cctccaagag 4560
cacctctggg ggcacagcgg ccctgggctg cctggtcaag gactacttcc ccgaaccggt 4620
gacggtgtcg tggaactcag gcgccctgac cagcggcgtg cacaccttcc cggctgtcct 4680
acagtcctca ggactctact ccctcagcag cgtggtgacc gtgccctcca gcagcttggg 4740
cacccagacc tacatctgca acgtgaatca caagcccagc aacaccaagg tggacaagaa 4800
agttggtgag aggccagcac agggagggag ggtgtctgct ggaagccagg ctcagcgctc 4860
ctgcctggac gcatcccggc tatgcagccc cagtccaggg cagcaaggca ggccccgtct 4920
gcctcttcac ccggaggcct ctgcccgccc cactcatgct cagggagagg gtcttctggc 4980
tttttcccca ggctctgggc aggcacaggc taggtgcccc taacccaggc cctgcacaca 5040
aaggggcagg tgctgggctc agacctgcca agagccatat ccgggaggac cctgcccctg 5100
acctaagccc accccaaagg ccaaactctc cactccctca gctcggacac cttctctcct 5160
cccagattcc agtaactccc aatcttctct ctgcagagcc caaatcttgt gacaaaactc 5220
acacatgccc accgtgccca ggtaagccag cccaggcctc gccctccagc tcaaggcggg 5280
acaggtgccc tagagtagcc tgcatccagg gacaggcccc agccgggtgc tgacacgtcc 5340
acctccatct cttcctcagc acctgaactc ctggggggac cgtcagtctt cctcttcccc 5400
ccaaaaccca aggacaccct catgatctcc cggacccctg aggtcacatg cgtggtggtg 5460
gacgtgagcc acgaagaccc tgaggtcaag ttcaactggt acgtggacgg cgtggaggtg 5520

-continued

```
cataatgcca agacaaagcc gcgggaggag cagtacaaca gcacgtaccg tgtggtcagc   5580
gtcctcaccg tcctgcacca ggactggctg aatggcaagg agtacaagtg caaggtctcc   5640
aacaaagccc tcccagcccc catcgagaaa accatctcca aagccaaagg tgggacccgt   5700
ggggtgcgag ggccacatgg acagaggccg gctcggccca ccctctgccc tgagagtgac   5760
cgctgtacca acctctgtcc ctacagggca gccccgagaa ccacaggtgt acaccctgcc   5820
cccatcccgg gatgagctga ccaagaacca ggtcagcctg acctgcctgg tcaaaggctt   5880
ctatcccagc gacatcgccg tggagtggga gagcaatggg cagccggaga acaactacaa   5940
gaccacgcct cccgtgctgg actccgacgg ctccttcttc ctctacagca agctcaccgt   6000
ggacaagagc aggtggcagc aggggaacgt cttctcatgc tccgtgatgc atgaggctct   6060
gcacaaccac tacacgcaga agagcctctc cctgtctccg ggtaaatgag tgcgacggcc   6120
ggcaagcccc cgctccccgg gctctcgcgg tcgcacgagg atgcttggca cgtaccccct   6180
gtacatactt cccgggcgcc cagcatggaa ataaagcacc cagcgctgcc ctgggcccct   6240
gcgagactgt gatggttctt tccacgggtc aggccgagtc tgaggcctga gtggcatgag   6300
atctgatatc atcgatgaat tcgagctcgg tacccgggga tcgatccaga catgataaga   6360
tacattgatg agtttggaca aaccacaact agaatgcagt gaaaaaaatg ctttatttgt   6420
gaaatttgtg atgctattgc tttatttgta accattataa gctgcaataa acaagttaac   6480
aacaacaatt gcattcattt tatgtttcag gttcaggggg aggtgtggga ggttttttaa   6540
agcaagtaaa acctctacaa atgtggtatg gctgattatg atctctagtc aaggcactat   6600
acatcaaata ttccttatta acccctttac aaattaaaaa gctaaaggta cacaattttt   6660
gagcatagtt attaatagca gacactctat gcctgtgtgg agtaagaaaa aacagtatgt   6720
tatgattata actgttatgc ctacttataa aggttacaga atatttttcc ataatttttct  6780
tgtatagcag tgcagctttt tcctttgtgg tgtaaatagc aaagcaagca agagttctat   6840
tactaaacac agcatgactc aaaaaactta gcaattctga aggaaagtcc ttggggtctt   6900
ctacctttct cttctttttt ggaggagtag aatgttgaga gtcagcagta gcctcatcat   6960
cactagatgg catttcttct gagcaaaaca ggttttcctc attaaaggca ttccaccact   7020
gctcccattc atcagttcca taggttggaa tctaaaatac acaaacaatt agaatcagta   7080
gtttaacaca ttatacactt aaaaatttta tatttacctt agagctttaa atctctgtag   7140
gtagtttgtc caattatgtc acaccacaga agtaaggttc cttcacaaag atccgggacc   7200
aaagcggcca tcgtgcctcc ccactcctgc agttcggggg catggatgcg cggatagccg   7260
ctgctggttt cctggatgcc gacggatttg cactgccggt agaactccgc gaggtcgtcc   7320
agcctcaggc agcagctgaa ccaactcgcg aggggatcga gcccggggtg ggcgaagaac   7380
tccagcatga gatccccgcg ctggaggatc atccagccgg cgtcccggaa aacgattccg   7440
aagcccaacc tttcatagaa ggcggcggtg gaatcgaaat ctcgtgatgg caggttgggc   7500
gtcgcttggt cggtcatttc gaaccccaga gtcccgctca gaagaactcg tcaagaaggc   7560
gatagaaggc gatgcgctgc gaatcgggag cggcgatacc gtaaagcacg aggaagcggt   7620
cagcccattc gccgccaagc tcttcagcaa tatcacgggt agccaacgct atgtcctgat   7680
agcggtccgc cacacccagc cggccacagt cgatgaatcc agaaaagcgg ccattttcca   7740
ccatgatatt cggcaagcag gcatcgccat gggtcacgac gagatcctcg ccgtcgggca   7800
tgcgcgcctt gagcctggcg aacagttcgg ctggcgcgag cccctgatgc tcttcgtcca   7860
```

-continued

```
gatcatcctg atcgacaaga ccggcttcca tccgagtacg tgctcgctcg atgcgatgtt   7920

tcgcttggtg gtcgaatggg caggtagccg gatcaagcgt atgcagccgc cgcattgcat   7980

cagccatgat ggatactttc tcggcaggag caaggtgaga tgacaggaga tcctgccccg   8040

gcacttcgcc caatagcagc cagtcccttc ccgcttcagt gacaacgtcg agcacagctg   8100

cgcaaggaac gcccgtcgtg gccagccacg atagccgcgc tgcctcgtcc tgcagttcat   8160

tcagggcacc ggacaggtcg gtcttgacaa aaagaaccgg gcgcccctgc gctgacagcc   8220

ggaacacggc ggcatcagag cagccgattg tctgttgtgc ccagtcatag ccgaatagcc   8280

tctccaccca agcggccgga gaacctgcgt gcaatccatc ttgttcaatc atgcgaaacg   8340

atcctcatcc tgtctcttga tcagatcttg atcccctgcg ccatcagatc cttggcggca   8400

agaaagccat ccagtttact ttgcagggct tcccaacctt accagagggc gccccagctg   8460

gcaattccgg ttcgcttgct gtccataaaa ccgcccagtc tagctatcgc catgtaagcc   8520

cactgcaagc tacctgcttt ctctttgcgc ttgcgttttc ccttgtccag atagcccagt   8580

agctgacatt catccggggt cagcaccgtt tctgcggact ggctttctac gtgttccgct   8640

tcctttagca gcccttgcgc cctgagtgct tgcggcagcg tgaagct                 8687
```

<210> SEQ ID NO 17
<211> LENGTH: 9400
<212> TYPE: DNA
<213> ORGANISM: Artificial
<220> FEATURE:
<223> OTHER INFORMATION: Nucleotide sequence of the expression vector HCMV-K HuAb-VL1 humV1 (Complete DNA Sequence of a humanised light chain expression vector comprising SEQ ID NO: 14 (humV1=VLh) from 3964-4284

<400> SEQUENCE: 17

```
ctagcttttt gcaaaagcct aggcctccaa aaaagcctcc tcactacttc tggaatagct     60

cagaggccga ggcggcctcg gcctctgcat aaataaaaaa aattagtcag ccatggggcg    120

gagaatgggc ggaactgggc ggagttaggg gcgggatggg cggagttagg ggcgggacta    180

tggttgctga ctaattgaga tgcatgcttt gcatacttct gcctgctggg gagcctggtt    240

gctgactaat tgagatgcat gctttgcata cttctgcctg ctggggagcc tggggacttt    300

ccacacccta actgacacac attccacagc tgcctcgcgc gtttcggtga tgacggtgaa    360

aacctctgac acatgcagct cccggagacg gtcacagctt gtctgtaagc ggatgccggg    420

agcagacaag cccgtcaggg cgcgtcagcg ggtgttggcg ggtgtcgggg cgcagccatg    480

acccagtcac gtagcgatag cggagtgtat actggcttaa ctatgcggca tcagagcaga    540

ttgtactgag agtgcaccat atgcggtgtg aaataccgca cagatgcgta aggagaaaat    600

accgcatcag gcgctcttcc gcttcctcgc tcactgactc gctgcgctcg gtcgttcggc    660

tgcggcgagc ggtatcagct cactcaaagg cggtaatacg gttatccaca gaatcagggg    720

ataacgcagg aaagaacatg tgagcaaaag gccagcaaaa ggccaggaac cgtaaaaagg    780

ccgcgttgct ggcgtttttc cataggctcc gcccccctga cgagcatcac aaaaatcgac    840

gctcaagtca gaggtggcga aacccgacag gactataaag ataccaggcg tttccccctg    900

gaagctccct cgtgcgctct cctgttccga ccctgccgct taccggatac ctgtccgcct    960

ttctcccttc gggaagcgtg gcgctttctc atagctcacg ctgtaggtat ctcagttcgg   1020

tgtaggtcgt tcgctccaag ctgggctgtg tgcacgaacc ccccgttcag cccgaccgct   1080

gcgccttatc cggtaactat cgtcttgagt ccaacccggt aagacacgac ttatcgccac   1140
```

-continued tggcagcagc cactggtaac aggattagca gagcgaggta tgtaggcggt gctacagagt 1200
tcttgaagtg gtggcctaac tacggctaca ctagaaggac agtatttggt atctgcgctc 1260
tgctgaagcc agttaccttc ggaaaaagag ttggtagctc ttgatccggc aaacaaacca 1320
ccgctggtag cggtggtttt tttgtttgca agcagcagat tacgcgcaga aaaaaaggat 1380
ctcaagaaga tcctttgatc ttttctacgg ggtctgacgc tcagtggaac gaaaactcac 1440
gttaagggat tttggtcatg agattatcaa aaaggatctt cacctagatc cttttaaatt 1500
aaaaatgaag ttttaaatca atctaaagta tatatgagta aacttggtct gacagttacc 1560
aatgcttaat cagtgaggca cctatctcag cgatctgtct atttcgttca tccatagttg 1620
cctgactccc cgtcgtgtag ataactacga tacgggaggg cttaccatct ggccccagtg 1680
ctgcaatgat accgcgagac ccacgctcac cggctccaga tttatcagca ataaaccagc 1740
cagccggaag ggccgagcgc agaagtggtc ctgcaacttt atccgcctcc atccagtcta 1800
ttaattgttg ccgggaagct agagtaagta gttcgccagt taatagtttg cgcaacgttg 1860
ttgccattgc tgcaggcatc gtggtgtcac gctcgtcgtt tggtatggct tcattcagct 1920
ccggttccca acgatcaagg cgagttacat gatcccccat gttgtgcaaa aaagcggtta 1980
gctccttcgg tcctccgatc gttgtcagaa gtaagttggc cgcagtgtta tcactcatgg 2040
ttatggcagc actgcataat tctcttactg tcatgccatc cgtaagatgc ttttctgtga 2100
ctggtgagta ctcaaccaag tcattctgag aatagtgtat gcggcgaccg agttgctctt 2160
gcccggcgtc aacacgggat aataccgcgc cacatagcag aactttaaaa gtgctcatca 2220
ttggaaaacg ttcttcgggg cgaaaactct caaggatctt accgctgttg agatccagtt 2280
cgatgtaacc cactcgtgca cccaactgat cttcagcatc ttttactttc accagcgttt 2340
ctgggtgagc aaaaacagga aggcaaaatg ccgcaaaaaa gggaataagg gcgacacgga 2400
aatgttgaat actcatactc ttcctttttc aatattattg aagcatttat cagggttatt 2460
gtctcatgag cggatacata tttgaatgta tttagaaaaa taaacaaata ggggttccgc 2520
gcacatttcc ccgaaaagtg ccacctgacg tctaagaaac cattattatc atgacattaa 2580
cctataaaaa taggcgtatc acgaggccct ttcgtcttca agaattcagc ttggctgcag 2640
tgaataataa aatgtgtgtt tgtccgaaat acgcgttttg agatttctgt cgccgactaa 2700
attcatgtcg cgcgatagtg gtgtttatcg ccgatagaga tggcgatatt ggaaaaatcg 2760
atatttgaaa atatggcata ttgaaaatgt cgccgatgtg agtttctgtg taactgatat 2820
cgccattttt ccaaaagtga tttttgggca tacgcgatat ctggcgatag cgcttatatc 2880
gtttacgggg gatggcgata gacgactttg gtgacttggg cgattctgtg tgtcgcaaat 2940
atcgcagttt cgatataggt gacagacgat atgaggctat atcgccgata gaggcgacat 3000
caagctggca catggccaat gcatatcgat ctatacattg aatcaatatt ggccattagc 3060
catattattc attggttata tagcataaat caatattggc tattggccat tgcatacgtt 3120
gtatccatat cataatatgt acatttatat tggctcatgt ccaacattac cgccatgttg 3180
acattgatta ttgactagtt attaatagta atcaattacg gggtcattag ttcatagccc 3240
atatatggag ttccgcgtta cataacttac ggtaaatggc ccgcctggct gaccgcccaa 3300
cgacccccgc ccattgacgt caataatgac gtatgttccc atagtaacgc caatagggac 3360
tttccattga cgtcaatggg tggagtattt acggtaaact gcccacttgg cagtacatca 3420
agtgtatcat atgccaagta cgccccctat tgacgtcaat gacggtaaat ggcccgcctg 3480
gcattatgcc cagtacatga ccttatggga ctttcctact tggcagtaca tctacgtatt 3540

-continued

```
agtcatcgct attaccatgg tgatgcggtt ttggcagtac atcaatgggc gtggatagcg   3600
gtttgactca cggggatttc caagtctcca ccccattgac gtcaatggga gtttgttttg   3660
gcaccaaaat caacgggact ttccaaaatg tcgtaacaac tccgccccat tgacgcaaat   3720
gggcggtagg cgtgtacggt gggaggtcta tataagcaga gctcgtttag tgaaccgtca   3780
gatcgcctgg agacgccatc cacgctgttt tgacctccat agaagacacc gggaccgatc   3840
cagcctccgc aagcttgata tcgaattcct gcagcccggg ggatccgccc gcttgccgcc   3900
accatggaga cccccgccca gctgctgttc ctgctgctgc tgtggctgcc cgacaccacc   3960
ggcgacattc tgctgaccca gtctccagcc accctgtctc tgagtccagg agaaagagcc   4020
actctctcct gcagggccag tcagaacatt ggcacaagca tacagtggta tcaacaaaaa   4080
ccaggtcagg ctccaaggct tctcataagg tcttcttctg agtctatctc tgggatccct   4140
tccaggttta gtggcagtgg atcagggaca gattttactc ttaccatcag cagtctggag   4200
cctgaagatt ttgcagtgta ttactgtcaa caaagtaata cctggccatt cacgttcggc   4260
caggggacca agctggagat caaacgtgag tattctagaa agatcctaga attctaaact   4320
ctgagggggt cggatgacgt ggccattctt tgcctaaagc attgagttta ctgcaaggtc   4380
agaaaagcat gcaaagccct cagaatggct gcaaagagct ccaacaaaac aatttagaac   4440
tttattaagg aataggggga agctaggaag aaactcaaaa catcaagatt ttaaatacgc   4500
ttcttggtct ccttgctata attatctggg ataagcatgc tgttttctgt ctgtccctaa   4560
catgccctgt gattatccgc aaacaacaca cccaagggca gaactttgtt acttaaacac   4620
catcctgttt gcttctttcc tcaggaactg tggctgcacc atctgtcttc atcttcccgc   4680
catctgatga gcagttgaaa tctggaactg cctctgttgt gtgcctgctg aataacttct   4740
atcccagaga ggccaaagta cagtggaagg tggataacgc cctccaatcg ggtaactccc   4800
aggagagtgt cacagagcag gacagcaagg acagcaccta cagcctcagc agcaccctga   4860
cgctgagcaa agcagactac gagaaacaca aagtctacgc ctgcgaagtc acccatcagg   4920
gcctgagctc gcccgtcaca aagagcttca acaggggaga gtgttagagg gagaagtgcc   4980
cccacctgct cctcagttcc agcctgaccc cctcccatcc tttggcctct gacccttttt   5040
ccacagggga cctaccccta ttgcggtcct ccagctcatc tttcacctca ccccccctcct   5100
cctccttggc tttaattatg ctaatgttgg aggagaatga ataaataaag tgaatctttg   5160
cacctgtggt ttctctcttt cctcatttaa taattattat ctgttgttta ccaactactc   5220
aatttctctt ataagggact aaatatgtag tcatcctaag gcgcataacc atttataaaa   5280
atcatccttc attctatttt accctatcat cctctgcaag acagtcctcc ctcaaaccca   5340
caagccttct gtcctcacag tcccctgggc catggtagga gagacttgct tccttgtttt   5400
cccctcctca gcaagccctc atagtccttt ttaagggtga caggtcttac agtcatatat   5460
cctttgattc aattccctga gaatcaacca aagcaaattt ttcaaaagaa gaaacctgct   5520
ataaagagaa tcattcattg caacatgata taaaataaca acacaataaa agcaattaaa   5580
taaacaaaca atagggaaat gtttaagttc atcatggtac ttagacttaa tggaatgtca   5640
tgccttattt acatttttaa acaggtactg agggactcct gtctgccaag ggccgtattg   5700
agtactttcc acaacctaat ttaatccaca ctatactgtg agattaaaaa cattcattaa   5760
aatgttgcaa aggttctata aagctgagag acaaatatat tctataactc agcaatccca   5820
cttctagatg actgagtgtc cccacccacc aaaaaactat gcaagaatgt tcaaagcagc   5880
```

-continued

```
tttatttaca aaagccaaaa attggaaata gcccgattgt ccaacaatag aatgagttat   5940
taaactgtgg tatgtttata cattagaata cccaatgagg agaattaaca agctacaact   6000
atacctactc acacagatga atctcataaa aataatgtta cataagagaa actcaatgca   6060
aaagatatgt tctgtatgtt ttcatccata taaagttcaa aaccaggtaa aaataaagtt   6120
agaaatttgg atggaaatta ctcttagctg ggggtgggcg agttagtgcc tgggagaaga   6180
caagaagggg cttctggggt cttggtaatg ttctgttcct cgtgtggggt tgtgcagtta   6240
tgatctgtgc actgttctgt atacacatta tgcttcaaaa taacttcaca taaagaacat   6300
cttataccca gttaatagat agaagaggaa taagtaatag gtcaagacca cgcagctggt   6360
aagtgggggg gcctgggatc aaatagctac ctgcctaatc ctgccctctt gagccctgaa   6420
tgagtctgcc ttccagggct caaggtgctc aacaaaacaa caggcctgct attttcctgg   6480
catctgtgcc ctgtttggct agctaggagc acacatacat agaaattaaa tgaaacagac   6540
cttcagcaag gggacagagg acagaattaa ccttgcccag acactggaaa cccatgtatg   6600
aacactcaca tgtttgggaa gggggaaggg cacatgtaaa tgaggactct tcctcattct   6660
atggggcact ctggccctgc ccctctcagc tactcatcca tccaacacac ctttctaagt   6720
acctctctct gcctacactc tgaaggggtt caggagtaac taacacagca tcccttccct   6780
caaatgactg acaatccctt tgtcctgctt tgtttttctt tccagtcagt actgggaaag   6840
tggggaagga cagtcatgga gaaactacat aaggaagcac cttgcccttc tgcctcttga   6900
gaatgttgat gagtatcaaa tctttcaaac tttggaggtt tgagtagggg tgagactcag   6960
taatgtccct tccaatgaca tgaacttgct cactcatccc tgggggccaa attgaacaat   7020
caaaggcagg cataatccag ctatgaattc taggatcgat ccagacatga taagatacat   7080
tgatgagttt ggacaaacca caactagaat gcagtgaaaa aaatgcttta tttgtgaaat   7140
ttgtgatgct attgctttat ttgtaaccat tataagctgc aataaacaag ttaacaacaa   7200
caattgcatt cattttatgt ttcaggttca gggggaggtg tgggaggttt tttaaagcaa   7260
gtaaaacctc tacaaatgtg gtatggctga ttatgatctc tagtcaaggc actatacatc   7320
aaatattcct tattaacccc tttacaaatt aaaaagctaa aggtacacaa tttttgagca   7380
tagttattaa tagcagacac tctatgcctg tgtggagtaa gaaaaaacag tatgttatga   7440
ttataactgt tatgcctact tataaaggtt acagaatatt tttccataat tttcttgtat   7500
agcagtgcag ctttttcctt tgtggtgtaa atagcaaagc aagcaagagt tctattacta   7560
aacacagcat gactcaaaaa acttagcaat tctgaaggaa agtccttggg gtcttctacc   7620
tttctcttct tttttggagg agtagaatgt tgagagtcag cagtagcctc atcatcacta   7680
gatggcattt cttctgagca aaacaggttt tcctcattaa aggcattcca ccactgctcc   7740
cattcatcag ttccataggt tggaatctaa aatacacaaa caattagaat cagtagttta   7800
acacattata cacttaaaaa ttttatattt accttagagc tttaaatctc tgtaggtagt   7860
ttgtccaatt atgtcacacc acagaagtaa ggttccttca caaagatccg ggaccaaagc   7920
ggccatcgtg cctccccact cctgcagttc gggggcatgg atgcgcggat agccgctgct   7980
ggtttcctgg atgccgacgg atttgcactg ccggtagaac tccgcgaggt cgtccagcct   8040
caggcagcag ctgaaccaac tcgcgagggg atcgagcccg gggtgggcga agaactccag   8100
catgagatcc ccgcgctgga ggatcatcca gccggcgtcc cggaaaacga ttccgaagcc   8160
caacctttca tagaaggcgg cggtggaatc gaaatctcgt gatggcaggt tgggcgtcgc   8220
ttggtcggtc atttcgaacc ccagagtccc gctcagaaga actcgtcaag aaggcgatag   8280
```

-continued

```
aaggcgatgc gctgcgaatc gggagcggcg ataccgtaaa gcacgaggaa gcggtcagcc   8340

cattcgccgc caagctcttc agcaatatca cgggtagcca acgctatgtc ctgatagcgg   8400

tccgccacac ccagccggcc acagtcgatg aatccagaaa agcggccatt ttccaccatg   8460

atattcggca agcaggcatc gccatgggtc acgacgagat cctcgccgtc gggcatgcgc   8520

gccttgagcc tggcgaacag ttcggctggc gcgagcccct gatgctcttc gtccagatca   8580

tcctgatcga caagaccggc ttccatccga gtacgtgctc gctcgatgcg atgtttcgct   8640

tggtggtcga atgggcaggt agccggatca agcgtatgca gccgccgcat tgcatcagcc   8700

atgatggata ctttctcggc aggagcaagg tgagatgaca ggagatcctg ccccggcact   8760

tcgcccaata gcagccagtc ccttcccgct tcagtgacaa cgtcgagcac agctgcgcaa   8820

ggaacgcccg tcgtggccag ccacgatagc cgcgctgcct cgtcctgcag ttcattcagg   8880

gcaccggaca ggtcggtctt gacaaaaaga accgggcgcc cctgcgctga cagccggaac   8940

acggcggcat cagagcagcc gattgtctgt tgtgcccagt catagccgaa tagcctctcc   9000

acccaagcgg ccggagaacc tgcgtgcaat ccatcttgtt caatcatgcg aaacgatcct   9060

catcctgtct cttgatcaga tcttgatccc ctgcgccatc agatccttgg cggcaagaaa   9120

gccatccagt ttactttgca gggcttccca accttaccag agggcgcccc agctggcaat   9180

tccggttcgc ttgctgtcca taaaaccgcc cagtctagct atcgccatgt aagcccactg   9240

caagctacct gctttctctt tgcgcttgcg ttttcccttg tccagatagc ccagtagctg   9300

acattcatcc ggggtcagca ccgtttctgc ggactggctt tctacgtgtt ccgcttcctt   9360

tagcagccct tgcgccctga gtgcttgcgg cagcgtgaag                        9400
```

<210> SEQ ID NO 18
<211> LENGTH: 9362
<212> TYPE: DNA
<213> ORGANISM: Artificial
<220> FEATURE:
<223> OTHER INFORMATION: Nucleotide sequence of the expression vector HCMV-K HuAb-VL1 humV2 (Complete DNA Sequence of a humanised light chain expression vector comprising SEQ ID NO: 13 (humV2=VLm) from 3926-4246)

<400> SEQUENCE: 18

```
ctagcttttt gcaaaagcct aggcctccaa aaaagcctcc tcactacttc tggaatagct     60

cagaggccga ggcggcctcg gcctctgcat aaataaaaaa aattagtcag ccatggggcg    120

gagaatgggc ggaactgggc ggagttaggg gcgggatggg cggagttagg ggcgggacta    180

tggttgctga ctaattgaga tgcatgcttt gcatacttct gcctgctggg gagcctggtt    240

gctgactaat tgagatgcat gctttgcata cttctgcctg ctggggagcc tggggacttt    300

ccacacccta actgacacac attccacagc tgcctcgcgc gtttcggtga tgacggtgaa    360

aacctctgac acatgcagct cccggagacg gtcacagctt gtctgtaagc ggatgccggg    420

agcagacaag cccgtcaggg cgcgtcagcg ggtgttggcg ggtgtcgggg cgcagccatg    480

acccagtcac gtagcgatag cggagtgtat actggcttaa ctatgcggca tcagagcaga    540

ttgtactgag agtgcaccat atgcggtgtg aaataccgca cagatgcgta aggagaaaat    600

accgcatcag gcgctcttcc gcttcctcgc tcactgactc gctgcgctcg gtcgttcggc    660

tgcggcgagc ggtatcagct cactcaaagg cggtaatacg gttatccaca gaatcagggg    720

ataacgcagg aaagaacatg tgagcaaaag gccagcaaaa ggccaggaac cgtaaaaagg    780

ccgcgttgct ggcgtttttc cataggctcc gcccccctga cgagcatcac aaaaatcgac    840
```

-continued

```
gctcaagtca gaggtggcga aacccgacag gactataaag ataccaggcg tttccccctg    900
gaagctccct cgtgcgctct cctgttccga ccctgccgct taccggatac ctgtccgcct    960
ttctcccttc gggaagcgtg gcgctttctc atagctcacg ctgtaggtat ctcagttcgg   1020
tgtaggtcgt tcgctccaag ctgggctgtg tgcacgaacc ccccgttcag cccgaccgct   1080
gcgccttatc cggtaactat cgtcttgagt ccaacccggt aagacacgac ttatcgccac   1140
tggcagcagc cactggtaac aggattagca gagcgaggta tgtaggcggt gctacagagt   1200
tcttgaagtg gtggcctaac tacggctaca ctagaaggac agtatttggt atctgcgctc   1260
tgctgaagcc agttaccttc ggaaaaagag ttggtagctc ttgatccggc aaacaaacca   1320
ccgctggtag cggtggtttt tttgtttgca agcagcagat tacgcgcaga aaaaaaggat   1380
ctcaagaaga tcctttgatc ttttctacgg ggtctgacgc tcagtggaac gaaaactcac   1440
gttaagggat tttggtcatg agattatcaa aaaggatctt cacctagatc cttttaaatt   1500
aaaaatgaag ttttaaatca atctaaagta tatatgagta aacttggtct gacagttacc   1560
aatgcttaat cagtgaggca cctatctcag cgatctgtct atttcgttca tccatagttg   1620
cctgactccc cgtcgtgtag ataactacga tacgggaggg cttaccatct ggccccagtg   1680
ctgcaatgat accgcgagac ccacgctcac cggctccaga tttatcagca ataaaccagc   1740
cagccggaag ggccgagcgc agaagtggtc ctgcaacttt atccgcctcc atccagtcta   1800
ttaattgttg ccgggaagct agagtaagta gttcgccagt taatagtttg cgcaacgttg   1860
ttgccattgc tgcaggcatc gtggtgtcac gctcgtcgtt tggtatggct tcattcagct   1920
ccggttccca acgatcaagg cgagttacat gatcccccat gttgtgcaaa aaagcggtta   1980
gctccttcgg tcctccgatc gttgtcagaa gtaagttggc cgcagtgtta tcactcatgg   2040
ttatggcagc actgcataat tctcttactg tcatgccatc cgtaagatgc ttttctgtga   2100
ctggtgagta ctcaaccaag tcattctgag aatagtgtat gcggcgaccg agttgctctt   2160
gcccggcgtc aacacgggat aataccgcgc cacatagcag aactttaaaa gtgctcatca   2220
ttggaaaacg ttcttcgggg cgaaaactct caaggatctt accgctgttg agatccagtt   2280
cgatgtaacc cactcgtgca cccaactgat cttcagcatc ttttactttc accagcgttt   2340
ctgggtgagc aaaaacagga aggcaaaatg ccgcaaaaaa gggaataagg gcgacacgga   2400
aatgttgaat actcatactc ttcctttttc aatattattg aagcatttat cagggttatt   2460
gtctcatgag cggatacata tttgaatgta tttagaaaaa taaacaaata ggggttccgc   2520
gcacatttcc ccgaaaagtg ccacctgacg tctaagaaac cattattatc atgacattaa   2580
cctataaaaa taggcgtatc acgaggccct ttcgtcttca agaattcagc ttggctgcag   2640
tgaataataa aatgtgtgtt tgtccgaaat acgcgttttg agatttctgt cgccgactaa   2700
attcatgtcg cgcgatagtg gtgtttatcg ccgatagaga tggcgatatt ggaaaaatcg   2760
atatttgaaa atatggcata ttgaaaatgt cgccgatgtg agtttctgtg taactgatat   2820
cgccattttt ccaaaagtga tttttgggca tacgcgatat ctggcgatag cgcttatatc   2880
gtttacgggg gatggcgata gacgactttg gtgacttggg cgattctgtg tgtcgcaaat   2940
atcgcagttt cgatataggt gacagacgat atgaggctat atcgccgata gaggcgacat   3000
caagctggca catggccaat gcatatcgat ctatacattg aatcaatatt ggccattagc   3060
catattattc attggttata tagcataaat caatattggc tattggccat tgcatacgtt   3120
gtatccatat cataatatgt acatttatat tggctcatgt ccaacattac cgccatgttg   3180
```

-continued

```
acattgatta ttgactagtt attaatagta atcaattacg gggtcattag ttcatagccc   3240

atatatggag ttccgcgtta cataacttac ggtaaatggc ccgcctggct gaccgcccaa   3300

cgacccccgc ccattgacgt caataatgac gtatgttccc atagtaacgc caatagggac   3360

tttccattga cgtcaatggg tggagtattt acggtaaact gcccacttgg cagtacatca   3420

agtgtatcat atgccaagta cgccccctat tgacgtcaat gacggtaaat ggcccgcctg   3480

gcattatgcc cagtacatga ccttatggga ctttcctact tggcagtaca tctacgtatt   3540

agtcatcgct attaccatgg tgatgcggtt ttggcagtac atcaatgggc gtggatagcg   3600

gtttgactca cggggatttc caagtctcca ccccattgac gtcaatggga gtttgttttg   3660

gcaccaaaat caacgggact ttccaaaatg tcgtaacaac tccgccccat tgacgcaaat   3720

gggcggtagg cgtgtacggt gggaggtcta tataagcaga gctcgtttag tgaaccgtca   3780

gatcgcctgg agacgccatc cacgctgttt tgacctccat agaagacacc gggaccgatc   3840

cagcctccgc aagcttgccg ccaccatgga gacccccgcc cagctgctgt tcctgctgct   3900

gctgtggctg cccgacacca ccggcgacat tctgctgacc cagtctccag ccaccctgtc   3960

tctgagtcca ggagaaagag ccactttctc ctgcagggcc agtcagaaca ttggcacaag   4020

catacagtgg tatcaacaaa aaacaaatgg tgctccaagg cttctcataa ggtcttcttc   4080

tgagtctatc tctgggatcc cttccaggtt tagtggcagt ggatcaggga cagattttac   4140

tcttaccatc agcagtctgg agcctgaaga ttttgcagtg tattactgtc aacaaagtaa   4200

tacctggcca ttcacgttcg gccaggggac caagctggag atcaaacgtg agtattctag   4260

aaagatccta gaattctaaa ctctgagggg gtcggatgac gtggccattc tttgcctaaa   4320

gcattgagtt tactgcaagg tcagaaaagc atgcaaagcc ctcagaatgg ctgcaaagag   4380

ctccaacaaa acaatttaga actttattaa ggaatagggg gaagctagga agaaactcaa   4440

aacatcaaga ttttaaatac gcttcttggt ctccttgcta taattatctg ggataagcat   4500

gctgttttct gtctgtccct aacatgccct gtgattatcc gcaaacaaca cacccaaggg   4560

cagaactttg ttacttaaac accatcctgt ttgcttcttt cctcaggaac tgtggctgca   4620

ccatctgtct tcatcttccc gccatctgat gagcagttga aatctggaac tgcctctgtt   4680

gtgtgcctgc tgaataactt ctatcccaga gaggccaaag tacagtggaa ggtggataac   4740

gccctccaat cgggtaactc ccaggagagt gtcacagagc aggacagcaa ggacagcacc   4800

tacagcctca gcagcaccct gacgctgagc aaagcagact acgagaaaca caaagtctac   4860

gcctgcgaag tcacccatca gggcctgagc tcgcccgtca caaagagctt caacagggga   4920

gagtgttaga gggagaagtg cccccacctg ctcctcagtt ccagcctgac cccctcccat   4980

cctttggcct ctgacccttt ttccacaggg gacctacccc tattgcggtc ctccagctca   5040

tctttcacct caccccccctc ctcctccttg gctttaatta tgctaatgtt ggaggagaat   5100

gaataaataa agtgaatctt tgcacctgtg gtttctctct ttcctcattt aataattatt   5160

atctgttgtt taccaactac tcaatttctc ttataaggga ctaaatatgt agtcatccta   5220

aggcgcataa ccatttataa aaatcatcct tcattctatt ttaccctatc atcctctgca   5280

agacagtcct ccctcaaacc cacaagcctt ctgtcctcac agtcccctgg gccatggtag   5340

gagagacttg cttccttgtt ttcccctcct cagcaagccc tcatagtcct ttttaagggt   5400

gacaggtctt acagtcatat atcctttgat tcaattccct gagaatcaac caaagcaaat   5460

ttttcaaaag aagaaacctg ctataaagag aatcattcat tgcaacatga tataaaataa   5520

caacacaata aaagcaatta aataaacaaa caatagggaa atgtttaagt tcatcatggt   5580
```

-continued

```
acttagactt aatggaatgt catgccttat ttacattttt aaacaggtac tgagggactc   5640
ctgtctgcca agggccgtat tgagtacttt ccacaaccta atttaatcca cactatactg   5700
tgagattaaa aacattcatt aaaatgttgc aaaggttcta taaagctgag agacaaatat   5760
attctataac tcagcaatcc cacttctaga tgactgagtg tccccaccca ccaaaaaact   5820
atgcaagaat gttcaaagca gctttattta caaaagccaa aaattggaaa tagcccgatt   5880
gtccaacaat agaatgagtt attaaactgt ggtatgttta tacattagaa tacccaatga   5940
ggagaattaa caagctacaa ctatacctac tcacacagat gaatctcata aaaataatgt   6000
tacataagag aaactcaatg caaaagatat gttctgtatg ttttcatcca tataaagttc   6060
aaaaccaggt aaaaataaag ttagaaattt ggatggaaat tactcttagc tgggggtggg   6120
cgagttagtg cctgggagaa gacaagaagg ggcttctggg gtcttggtaa tgttctgttc   6180
ctcgtgtggg gttgtgcagt tatgatctgt gcactgttct gtatacacat tatgcttcaa   6240
aataacttca cataaagaac atcttatacc cagttaatag atagaagagg aataagtaat   6300
aggtcaagac cacgcagctg gtaagtgggg gggcctggga tcaaatagct acctgcctaa   6360
tcctgccctc ttgagccctg aatgagtctg ccttccaggg ctcaaggtgc tcaacaaaac   6420
aacaggcctg ctattttcct ggcatctgtg ccctgtttgg ctagctagga gcacacatac   6480
atagaaatta aatgaaacag accttcagca aggggacaga ggacagaatt aaccttgccc   6540
agacactgga aacccatgta tgaacactca catgtttggg aagggggaag ggcacatgta   6600
aatgaggact cttcctcatt ctatggggca ctctggccct gcccctctca gctactcatc   6660
catccaacac acctttctaa gtacctctct ctgcctacac tctgaagggg ttcaggagta   6720
actaacacag catcccttcc ctcaaatgac tgacaatccc tttgtcctgc tttgtttttc   6780
tttccagtca gtactgggaa agtggggaag gacagtcatg gagaaactac ataaggaagc   6840
accttgccct tctgcctctt gagaatgttg atgagtatca aatctttcaa actttggagg   6900
tttgagtagg ggtgagactc agtaatgtcc cttccaatga catgaacttg ctcactcatc   6960
cctgggggcc aaattgaaca atcaaaggca ggcataatcc agctatgaat tctaggatcg   7020
atccagacat gataagatac attgatgagt ttggacaaac cacaactaga atgcagtgaa   7080
aaaaatgctt tatttgtgaa atttgtgatg ctattgcttt atttgtaacc attataagct   7140
gcaataaaca agttaacaac aacaattgca ttcattttat gtttcaggtt cagggggagg   7200
tgtgggaggt tttttaaagc aagtaaaacc tctacaaatg tggtatggct gattatgatc   7260
tctagtcaag gcactataca tcaaatattc cttattaacc cctttacaaa ttaaaaagct   7320
aaaggtacac aatttttgag catagttatt aatagcagac actctatgcc tgtgtggagt   7380
aagaaaaaac agtatgttat gattataact gttatgccta cttataaagg ttacagaata   7440
tttttccata attttcttgt atagcagtgc agctttttcc tttgtggtgt aaatagcaaa   7500
gcaagcaaga gttctattac taaacacagc atgactcaaa aaacttagca attctgaagg   7560
aaagtccttg gggtcttcta cctttctctt ctttttgga ggagtagaat gttgagagtc   7620
agcagtagcc tcatcatcac tagatggcat ttcttctgag caaaacaggt tttcctcatt   7680
aaaggcattc caccactgct cccattcatc agttccatag gttggaatct aaaatacaca   7740
aacaattaga atcagtagtt taacacatta tacacttaaa aattttatat ttaccttaga   7800
gctttaaatc tctgtaggta gtttgtccaa ttatgtcaca ccacagaagt aaggttcctt   7860
cacaaagatc cgggaccaaa gcggccatcg tgcctcccca ctcctgcagt tcgggggcat   7920
```

-continued

```
ggatgcgcgg atagccgctg ctggtttcct ggatgccgac ggatttgcac tgccggtaga   7980

actccgcgag gtcgtccagc ctcaggcagc agctgaacca actcgcgagg ggatcgagcc   8040

cggggtgggc gaagaactcc agcatgagat ccccgcgctg gaggatcatc cagccggcgt   8100

cccggaaaac gattccgaag cccaaccttt catagaaggc ggcggtggaa tcgaaatctc   8160

gtgatggcag gttgggcgtc gcttggtcgg tcatttcgaa ccccagagtc ccgctcagaa   8220

gaactcgtca agaaggcgat agaaggcgat gcgctgcgaa tcgggagcgg cgataccgta   8280

aagcacgagg aagcggtcag cccattcgcc gccaagctct tcagcaatat cacgggtagc   8340

caacgctatg tcctgatagc ggtccgccac acccagccgg ccacagtcga tgaatccaga   8400

aaagcggcca ttttccacca tgatattcgg caagcaggca tcgccatggg tcacgacgag   8460

atcctcgccg tcgggcatgc gcgccttgag cctggcgaac agttcggctg gcgcgagccc   8520

ctgatgctct tcgtccagat catcctgatc gacaagaccg gcttccatcc gagtacgtgc   8580

tcgctcgatg cgatgtttcg cttggtggtc gaatgggcag gtagccggat caagcgtatg   8640

cagccgccgc attgcatcag ccatgatgga tactttctcg gcaggagcaa ggtgagatga   8700

caggagatcc tgccccggca cttcgcccaa tagcagccag tcccttcccg cttcagtgac   8760

aacgtcgagc acagctgcgc aaggaacgcc cgtcgtggcc agccacgata gccgcgctgc   8820

ctcgtcctgc agttcattca gggcaccgga caggtcggtc ttgacaaaaa gaaccgggcg   8880

cccctgcgct gacagccgga acacggcggc atcagagcag ccgattgtct gttgtgccca   8940

gtcatagccg aatagcctct ccacccaagc ggccggagaa cctgcgtgca atccatcttg   9000

ttcaatcatg cgaaacgatc ctcatcctgt ctcttgatca gatcttgatc ccctgcgcca   9060

tcagatcctt ggcggcaaga aagccatcca gtttactttg cagggcttcc caaccttacc   9120

agagggcgcc ccagctggca attccggttc gcttgctgtc cataaaaccg cccagtctag   9180

ctatcgccat gtaagcccac tgcaagctac ctgctttctc tttgcgcttg cgttttccct   9240

tgtccagata gcccagtagc tgacattcat ccggggtcag caccgtttct gcggactggc   9300

tttctacgtg ttccgcttcc tttagcagcc cttgcgccct gagtgcttgc ggcagcgtga   9360

ag                                                                  9362
```

```
<210> SEQ ID NO 19
<211> LENGTH: 11
<212> TYPE: PRT
<213> ORGANISM: Artificial
<220> FEATURE:
<223> OTHER INFORMATION: hypervariable regions CDR1' in a CD45RO/RB
      binding molecule of SEQ ID NO:1

<400> SEQUENCE: 19

Arg Ala Ser Gln Asn Ile Gly Thr Ser Ile Gln
1               5                   10


<210> SEQ ID NO 20
<211> LENGTH: 7
<212> TYPE: PRT
<213> ORGANISM: Artificial
<220> FEATURE:
<223> OTHER INFORMATION: hypervariable region CDR2' in a CD45RO/RB
      binding molecule of SEQ ID NO:1

<400> SEQUENCE: 20

Ser Ser Ser Glu Ser Ile Ser
1               5
```

-continued

<210> SEQ ID NO 21
<211> LENGTH: 9
<212> TYPE: PRT
<213> ORGANISM: Artificial
<220> FEATURE:
<223> OTHER INFORMATION: hypervariable region CDR3' in a CD45RO/RB binding molecule of SEQ ID NO:1

<400> SEQUENCE: 21

Gln Gln Ser Asn Thr Trp Pro Phe Thr
1 5

<210> SEQ ID NO 22
<211> LENGTH: 5
<212> TYPE: PRT
<213> ORGANISM: Artificial
<220> FEATURE:
<223> OTHER INFORMATION: hypervariable region CDR1 in a CD45RO/RB binding molecule of SEQ ID NO:2

<400> SEQUENCE: 22

Asn Tyr Ile Ile His
1 5

<210> SEQ ID NO 23
<211> LENGTH: 17
<212> TYPE: PRT
<213> ORGANISM: Artificial
<220> FEATURE:
<223> OTHER INFORMATION: hypervariable region CDR2 in a CD45RO/RB binding molecule of SEQ ID NO:2

<400> SEQUENCE: 23

Tyr Phe Asn Pro Tyr Asn His Gly Thr Lys Tyr Asn Glu Lys Phe Lys
1 5 10 15

Gly

<210> SEQ ID NO 24
<211> LENGTH: 9
<212> TYPE: PRT
<213> ORGANISM: Artificial
<220> FEATURE:
<223> OTHER INFORMATION: hypervariable region CDR3 in a CD45RO/RB binding molecule of SEQ ID NO:2

<400> SEQUENCE: 24

Ser Gly Pro Tyr Ala Trp Phe Asp Thr
1 5

<210> SEQ ID NO 25
<211> LENGTH: 33
<212> TYPE: DNA
<213> ORGANISM: Artificial
<220> FEATURE:
<223> OTHER INFORMATION: polynucleotide sequence encoding the amino acid sequence of CDR1

<400> SEQUENCE: 25
ggccagtcag aacattggca caagcataca gtg 33

<210> SEQ ID NO 26
<211> LENGTH: 21
<212> TYPE: DNA
<213> ORGANISM: Artificial
<220> FEATURE:
<223> OTHER INFORMATION: polynucleotide sequence encoding the amino acid sequence of CDR2

-continued

<400> SEQUENCE: 26
ttcttctgag tctatctctg g 21

<210> SEQ ID NO 27
<211> LENGTH: 27
<212> TYPE: DNA
<213> ORGANISM: Artificial
<220> FEATURE:
<223> OTHER INFORMATION: polynucleotide sequence encoding the amino acid sequence of CDR3

<400> SEQUENCE: 27
acaaagtaat acctggccat tcacgtt 27

<210> SEQ ID NO 28
<211> LENGTH: 15
<212> TYPE: DNA
<213> ORGANISM: Artificial
<220> FEATURE:
<223> OTHER INFORMATION: polynucleotide sequence encoding the amino acid sequence of CDR1'

<400> SEQUENCE: 28
ttatattatc cactg 15

<210> SEQ ID NO 29
<211> LENGTH: 51
<212> TYPE: DNA
<213> ORGANISM: Artificial
<220> FEATURE:
<223> OTHER INFORMATION: polynucleotide sequence encoding the amino acid sequence of CDR2'

<400> SEQUENCE: 29
ttttaatcct tacaatcatg gtactaagta caatgagaag ttcaaaggca g 51

<210> SEQ ID NO 30
<211> LENGTH: 27
<212> TYPE: DNA
<213> ORGANISM: Artificial
<220> FEATURE:
<223> OTHER INFORMATION: polynucleotide sequence encoding the amino acid sequence of CDR3'

<400> SEQUENCE: 30
aggaccctat gcctggtttg acacctg 27

<210> SEQ ID NO 31
<211> LENGTH: 118
<212> TYPE: PRT
<213> ORGANISM: Artificial
<220> FEATURE:
<223> OTHER INFORMATION: Part of amino acid sequence of humanised heavy chain designated VHE-N73D

<400> SEQUENCE: 31

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ile Ile His Trp Val Lys Gln Glu Pro Gly Gln Gly Leu Glu Trp Ile
        35                  40                  45

Gly Tyr Phe Asn Pro Tyr Asn His Gly Thr Lys Tyr Asn Glu Lys Phe
    50                  55                  60
```

-continued

```
Lys Gly Arg Ala Thr Leu Thr Ala Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Pro Tyr Ala Trp Phe Asp Thr Trp Gly Gln Gly Thr
            100                 105                 110

Thr Val Thr Val Ser Ser
        115


<210> SEQ ID NO 32
<211> LENGTH: 118
<212> TYPE: PRT
<213> ORGANISM: Artificial
<220> FEATURE:
<223> OTHER INFORMATION: Part of amino acid sequence of humanised
      heavy chain designated VHQ-N73D

<400> SEQUENCE: 32

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ile Ile His Trp Val Lys Gln Glu Pro Gly Gln Gly Leu Glu Trp Ile
        35                  40                  45

Gly Tyr Phe Asn Pro Tyr Asn His Gly Thr Lys Tyr Asn Glu Lys Phe
    50                  55                  60

Lys Gly Arg Ala Thr Leu Thr Ala Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Pro Tyr Ala Trp Phe Asp Thr Trp Gly Gln Gly Thr
            100                 105                 110

Thr Val Thr Val Ser Ser
        115


<210> SEQ ID NO 33
<211> LENGTH: 321
<212> TYPE: DNA
<213> ORGANISM: Artificial
<220> FEATURE:
<223> OTHER INFORMATION: Nucleotide sequence encoding amino acid
      sequence SEQ ID NO: 8

<400> SEQUENCE: 33

gacattctgc tgacccagtc tccagccacc ctgtctctga gtccaggaga aagagccact      60

ctctcctgca gggccagtca gaacattggc acaagcatac agtggtatca acaaaaacca     120

ggtcaggctc caaggcttct cataaggtct tcttctgagt ctatctctgg gatcccttcc     180

aggtttagtg gcagtggatc agggacagat tttactctta ccatcagcag tctggagcct     240

gaagattttg cagtgtatta ctgtcaacaa agtaatacct ggccattcac gttcggccag     300

gggaccaagc ttgaaatcaa a                                               321


<210> SEQ ID NO 34
<211> LENGTH: 354
<212> TYPE: DNA
<213> ORGANISM: Artificial
<220> FEATURE:
<223> OTHER INFORMATION: Nucleotide sequence encoding amino acid
      sequence SEQ ID NO: 31
```

-continued

<400> SEQUENCE: 34

```
gaggtgcagc tggtggagtc aggagccgaa gtgaaaaagc ctggggcttc agtgaaggtg     60
tcctgcaagg cctctggata cacattcact aattatatta tccactgggt gaagcaggag    120
cctggtcagg gccttgaatg gattggatat tttaatcctt acaatcatgg tactaagtac    180
aatgagaagt tcaaaggcag ggccacacta actgcagaca aatccatcag cacagcctac    240
atggagctca gcagcctgcg ctctgaggac actgcggtct actactgtgc aagatcagga    300
ccctatgcct ggtttgacac ctggggccaa gggaccacgg tcaccgtctc ctca          354
```

<210> SEQ ID NO 35
<211> LENGTH: 354
<212> TYPE: DNA
<213> ORGANISM: Artificial
<220> FEATURE:
<223> OTHER INFORMATION: Nucleotide sequence encoding amino acid sequence SEQ ID NO: 32

<400> SEQUENCE: 35

```
caggtgcagc tggtggagtc aggagccgaa gtgaaaaagc ctggggcttc agtgaaggtg     60
tcctgcaagg cctctggata cacattcact aattatatta tccactgggt gaagcaggag    120
cctggtcagg gccttgaatg gattggatat tttaatcctt acaatcatgg tactaagtac    180
aatgagaagt tcaaaggcag ggccacacta actgcagaca aatccatcag cacagcctac    240
atggagctca gcagcctgcg ctctgaggac actgcggtct actactgtgc aagatcagga    300
ccctatgcct ggtttgacac ctggggccaa gggaccacgg tcaccgtctc ctca          354
```

<210> SEQ ID NO 36
<211> LENGTH: 8096
<212> TYPE: DNA
<213> ORGANISM: Artificial
<220> FEATURE:
<223> OTHER INFORMATION: Nucleotide sequence of expression vector LCVL1Sp20

<400> SEQUENCE: 36

```
ctagagtcct agagaggtct ggtggagcct gcaaaagtcc agctttcaaa ggaacacaga     60
agtatgtgta tggaatatta gaagatgttg cttttactct taagttggtt cctaggaaaa    120
atagttaaat actgtgactt taaaatgtga gagggttttc aagtactcat ttttttaaat    180
gtccaaaatt tttgtcaatc aatttgaggt cttgtttgtg tagaactgac attacttaaa    240
gtttaaccga ggaatgggag tgaggctctc tcatacccta ttcagaactg acttttaaca    300
ataataaatt aagtttaaaa tatttttaaa tgaattgagc aatgttgagt tggagtcaag    360
atggccgatc agaaccagaa cacctgcagc agctggcagg aagcaggtca tgtggcaagg    420
ctatttgggg aagggaaaat aaaaccacta ggtaaacttg tagctgtggt ttgaagaagt    480
ggttttgaaa cactctgtcc agccccacca aaccgaaagt ccaggctgag caaaacacca    540
cctgggtaat ttgcatttct aaaataagtt gaggattcag ccgaaactgg agaggtcctc    600
ttttaactta ttgagttcaa ccttttaatt ttagcttgag tagttctagt ttccccaaac    660
ttaagtttat cgacttctaa aatgtattta gaactcattt tcaaaattag gttatgtaag    720
aaattgaagg actttagtgt ctttaatttc taatatattt agaaaacttc ttaaaattac    780
tctattattc ttccctctga ttattggtct ccattcaatt cttttccaat acccgaagca    840
tttacagtga ctttgttcat gatctttttt agttgtttgt tttgccttac tattaagact    900
ttgacattct ggtcaaaacg gcttcacaaa tctttttcaa gaccactttc tgagtattca    960
```

-continued

```
ttttaggaga aatacttttt ttttaaatga atgcaattat ctaggacctg caggcatgct   1020
gttttctgtc tgtccctaac atgccctgtg attatccgca aacaacacac ccaagggcag   1080
aactttgtta cttaaacacc atcctgtttg cttctttcct caggaactgt ggctgcacca   1140
tctgtcttca tcttcccgcc atctgatgag cagttgaaat ctggaactgc ctctgttgtg   1200
tgcctgctga ataacttcta tcccagagag gccaaagtac agtggaaggt ggataacgcc   1260
ctccaatcgg gtaactccca ggagagtgtc acagagcagg acagcaagga cagcacctac   1320
agcctcagca gcaccctgac gctgagcaaa gcagactacg agaaacacaa agtctacgcc   1380
tgcgaagtca cccatcaggg cctgagctcg cccgtcacaa agagcttcaa caggggagag   1440
tgttagaggg agaagtgccc ccacctgctc ctcagttcca gcctgacccc ctcccatcct   1500
ttggcctctg accctttttc cacaggggac ctacccctat tgcggtcctc cagctcatct   1560
ttcacctcac ccccctcctc ctccttggct ttaattatgc taatgttgga ggagaatgaa   1620
taaataaagt gaatctttgc acctgtggtt tctctctttc ctcatttaat aattattatc   1680
tgttgtttta ccaactactc aatttctctt ataagggact aaatatgtag tcatcctaag   1740
gcgggatatc gagatctgaa gctgatccag acatgataag atacattgat gagtttggac   1800
aaaccacaac tagaatgcag tgaaaaaaat gctttatttg tgaaatttgt gatgctattg   1860
ctttatttgt aaccattata agctgcaata aacaagttaa caacaacaat tgcattcatt   1920
ttatgtttca ggttcagggg gaggtgtggg aggtttttta aagcaagtaa aacctctaca   1980
aatgtggtat ggctgattat gatctctagt caaggcacta tacatcaaat attccttatt   2040
aaccccttta caaattaaaa agctaaaggt acacaatttt tgagcatagt tattaatagc   2100
agacactcta tgcctgtgtg gagtaagaaa aaacagtatg ttatgattat aactgttatg   2160
cctacttata aaggttacag aatatttttc cataattttc ttgtatagca gtgcagcttt   2220
ttcctttgtg gtgtaaatag caaagcaagc aagagttcta ttactaaaca cagcatgact   2280
caaaaaactt agcaattctg aaggaaagtc cttggggtct tctacctttc tcttcttttt   2340
tggaggagta gaatgttgag agtcagcagt agcctcatca tcactagatg gcatttcttc   2400
tgagcaaaac aggttttcct cattaaaggc attccaccac tgctcccatt catcagttcc   2460
ataggttgga atctaaaata cacaaacaat tagaatcagt agtttaacac attatacact   2520
taaaaatttt atatttacct tagagcttta aatctctgta ggtagtttgt ccaattatgt   2580
cacaccacag aagtaaggtt ccttcacaaa gatccggacc aaagcggcca tcgtgcctcc   2640
ccactcctgc agttcggggg catggatgcg cggatagccg ctgctggttt cctggatgcc   2700
gacggatttg cactgccggt agaactccgc gaggtcgtcc agcctcaggc agcagctgaa   2760
ccaactcgcg aggggatcga gcatccccca tggtcttata aaaatgcata gctttaggag   2820
gggagcagag aacttgaaag catcttcctg ttagtctttc ttctcgtaga cttcaaactt   2880
atacttgatg cctttttcct cctggacctc agagaggacg cctgggtatt ctgggagaag   2940
tttatatttc cccaaatcaa tttctgggaa aaacgtgtca ctttcaaatt cctgcatgat   3000
ccttgtcaca aagagtctga ggtggcctgg ttgattcatg gcttcctggt aaacagaact   3060
gcctccgact atccaaacca tgtctacttt acttgccaat tccggttgtt caataagtct   3120
taaggcatca tccaaacttt tggcaagaaa atgagctcct cgtggtggtt ctttgagttc   3180
tctactgaga actatattaa ttctgtcctt taaaggtcga ttcttctcag gaatggagaa   3240
ccaggttttc ctacccataa tcaccagatt ctgtttacct tccactgaag aggttgtggt   3300
```

-continued

```
cattctttgg aagtacttga actcgttcct gagcggaggc cagggtcggt ctccgttctt   3360
gccaatcccc atattttggg acacggcgac gatgcagttc aatggtcgaa ccatgatggc   3420
agcggggata aaatcctacc agccttcacg ctaggattgc cgtcaagttt gggggtaccg   3480
agctcgaatt agctttttgc aaaagcctag gcctccaaaa aagcctcctc actacttctg   3540
gaatagctca gagggccgag gcggcctcgg cctctgcata aataaaaaaa attagtcagc   3600
catggggcgg agaatgggcg gaactgggcg gagttagggg cgggatgggc ggagttaggg   3660
gcgggactat ggttgctgac taattgagat gcatgctttg catacttctg cctgctgggg   3720
agcctgggga ctttccacac ctggttgctg actaattgag atgcatgctt tgcatacttc   3780
tgcctgctgg ggagcctggg gactttccac accctaactg acacacattc cacagctgcc   3840
tcgcgcgttt cggtgatgac ggtgaaaacc tctgacacat gcagctcccg gagacggtca   3900
cagcttgtct gtaagcggat gccgggagca gacaagcccg tcagggcgcg tcagcgggtg   3960
ttggcgggtg tcggggcgca gccatgaccc agtcacgtag cgatagcgga gtgtatactg   4020
gcttaactat gcggcatcag agcagattgt actgagagtg caccatatgc ggccgcatat   4080
gcggtgtgaa ataccgcaca gatgcgtaag gagaaaatac cgcatcaggc gctcttccgc   4140
ttcctcgctc actgactcgc tgcgctcggt cgttcggctg cggcgagcgg tatcagctca   4200
ctcaaaggcg gtaatacggt tatccacaga atcaggggat aacgcaggaa agaacatgtg   4260
agcaaaaggc cagcaaaagg ccaggaaccg taaaaaggcc gcgttgctgg cgtttttcca   4320
taggctccgc ccccctgacg agcatcacaa aaatcgacgc tcaagtcaga ggtggcgaaa   4380
cccgacagga ctataaagat accaggcgtt tccccctgga agctccctcg tgcgctctcc   4440
tgttccgacc ctgccgctta ccggatacct gtccgccttt ctcccttcgg gaagcgtggc   4500
gctttctcat agctcacgct gtaggtatct cagttcggtg taggtcgttc gctccaagct   4560
gggctgtgtg cacgaacccc ccgttcagcc cgaccgctgc gccttatccg gtaactatcg   4620
tcttgagtcc aacccggtaa gacacgactt atcgccactg gcagcagcca ctggtaacag   4680
gattagcaga gcgaggtatg taggcggtgc tacagagttc ttgaagtggt ggcctaacta   4740
cggctacact agaaggacag tatttggtat ctgcgctctg ctgaagccag ttaccttcgg   4800
aaaaagagtt ggtagctctt gatccggcaa acaaaccacc gctggtagcg gtggtttttt   4860
tgtttgcaag cagcagatta cgcgcagaaa aaaaggatct caagaagatc ctttgatctt   4920
ttctacgggg tctgacgctc agtggaacga aaactcacgt taagggattt tggtcatgag   4980
attatcaaaa aggatcttca cctagatcct tttaaattaa aaatgaagtt ttaaatcaat   5040
ctaaagtata tatgagtaaa cttggtctga cagttaccaa tgcttaatca gtgaggcacc   5100
tatctcagcg atctgtctat ttcgttcatc catagttgcc tgactccccg tcgtgtagat   5160
aactacgata cgggagggct taccatctgg ccccagtgct gcaatgatac cgcgagaccc   5220
acgctcaccg gctccagatt tatcagcaat aaaccagcca gccggaaggg ccgagcgcag   5280
aagtggtcct gcaactttat ccgcctccat ccagtctatt aattgttgcc gggaagctag   5340
agtaagtagt tcgccagtta atagtttgcg caacgttgtt gccattgctg caggcatcgt   5400
ggtgtcacgc tcgtcgtttg gtatggcttc attcagctcc ggttcccaac gatcaaggcg   5460
agttacatga tcccccatgt tgtgcaaaaa agcggttagc tccttcggtc ctccgatcgt   5520
tgtcagaagt aagttggccg cagtgttatc actcatggtt atggcagcac tgcataattc   5580
tcttactgtc atgccatccg taagatgctt ttctgtgact ggtgagtact caaccaagtc   5640
attctgagaa tagtgtatgc ggcgaccgag ttgctcttgc ccggcgtcaa cacgggataa   5700
```

-continued

```
taccgcgcca catagcagaa ctttaaaagt gctcatcatt ggaaaacgtt cttcggggcg   5760
aaaactctca aggatcttac cgctgttgag atccagttcg atgtaaccca ctcgtgcacc   5820
caactgatct tcagcatctt ttactttcac cagcgtttct gggtgagcaa aaacaggaag   5880
gcaaaatgcc gcaaaaaagg gaataagggc gacacggaaa tgttgaatac tcatactctt   5940
cctttttcaa tattattgaa gcatttatca gggttattgt ctcatgagcg gatacatatt   6000
tgaatgtatt tagaaaaata aacaaatagg ggttccgcgc acatttcccc gaaaagtgcc   6060
acctgacgtc taagaaacca ttattatcat gacattaacc tataaaaata ggcgtatcac   6120
gaggcccttt cgtcttcaag aattcagctg ctcgaggaag agctcaaacc catgctactc   6180
tctggcttga tggaagcaac gctttcatag ctgagctgtc ataaataata aagagatttt   6240
tttattaata ttgaaaagat gggttattta tgtaagactc tgtcttcatt ttaaaaacca   6300
caccttccag tagtattctg ttactgttct ggcaatcact gtgatcaaga agctacacgg   6360
tgagttgtgc ttctcagtcc taagggatac atctacaaga ggctcccata ctcgaagctc   6420
aggaaacatt gtagaaaagg aggcaaaaga ctgacagagc cagaggacca agaaatttgt   6480
tgtgaggttg tgtctcctac taacaatata agcaatatct ataaattgtt gatatcatgg   6540
ctactaaaat gtgagttgaa cgaggaggac acaaatgaac atgacaatca gaatgaggcc   6600
tctcacctgc aaaaaacact atagagaagc agataaagct gtcagcagaa gaggcgcacc   6660
tccttataga agaagcctac caggtttgat atatcagcct tgaaaaccta catagtattt   6720
acattatatc gagtctatga gacatattta gtaatgcata tgtatgtgtg tgtgtgcatg   6780
tatgtgtgta aatacatatg ttcatagaaa aatgtgtaaa aagagatcat gaatttaaga   6840
gagaactggg acaatttttt tcagggagtt gtaatcagga aagttaaggg aaaaatgttg   6900
taattaaaat tcaggctcag aaacaaacaa aggaaaagaa aaaaaaacaa caacaacaac   6960
aaaaaaacaa aacaaaggag aagctgtatg gccacaatag catctacagc taactgtgaa   7020
aggataatgg aacaagttat gtactgccta gagcagtatg atgcctaaat catctcgaca   7080
tggaggaaaa tagaacaaag acactctaca tagactatga tagaaatcaa aataaggtgt   7140
aagacataga acattagttt tgtttgttgt tcaaagagac tcacattccc acaaaaaaat   7200
ctgtgggatt ttacaggtct gcaataagct gctgacctga tgatttctgc agctgtgcct   7260
accctttgct gatttgcatg tacccaaagc atagcttact gacatgagga tttcttcata   7320
gtcaggtcac accctttgct ggagtcagaa tcacactgat cacacacagt catgagtgtg   7380
ctcactcagg tcctggcgtt gctgctgctg tggcttacag gtaatgaaga cagcactaga   7440
attttattga gcttcctgta cactgtgctg cttgtctctg tgaaaattct cttgtgaatt   7500
aatcatgtgg ggatctgttt tcaatttttc aattgtaggt acgcgttgtg acattctgct   7560
gacccagtct ccagccaccc tgtctctgag tccaggagaa agagccactc tctcctgcag   7620
ggccagtcag aacattggca caagcataca gtggtatcaa caaaaaccag gtcaggctcc   7680
aaggcttctc ataaggtctt cttctgagtc tatctctggg atcccttcca ggtttagtgg   7740
cagtggatca gggacagatt ttactcttac catcagcagt ctggagcctg aagattttgc   7800
agtgtattac tgtcaacaaa gtaatacctg gccattcacg ttcggccagg ggaccaagct   7860
tgaaatcaaa cgtaagtaga atccaaagtc tctttcttcc gttgtctatg tctgtggctt   7920
ctatgtctaa aaatgatgta taaaatctta ctctgaaacc agattctggc actctccaag   7980
gcaaagatac agagtaactc cgtaagcaaa gctgggaata ggctagacat gttctctgga   8040
```

-continued gaatgaatgc cagtgtaata attaacacaa gtgatagttt cagaaatgct ctagtt 8096

<210> SEQ ID NO 37
<211> LENGTH: 11563
<212> TYPE: DNA
<213> ORGANISM: Artificial
<220> FEATURE:
<223> OTHER INFORMATION: Nucleotide sequence of the expression vector HCVHEN73DSp20

<400> SEQUENCE: 37
ctagagaggt ctggtggagc ctgcaaaagt ccagctttca aaggaacaca gaagtatgtg 60
tatggaatat tagaagatgt tgcttttact cttaagttgg ttcctaggaa aaatagttaa 120
atactgtgac tttaaaatgt gagagggttt tcaagtactc atttttttaa atgtccaaaa 180
tttttgtcaa tcaatttgag gtcttgtttg tgtagaactg acattactta aagtttaacc 240
gaggaatggg agtgaggctc tctcataccc tattcagaac tgacttttaa caataataaa 300
ttaagtttaa aatattttta aatgaattga gcaatgttga gttggagtca agatggccga 360
tcagaaccag aacacctgca gcagctggca ggaagcaggt catgtggcaa ggctatttgg 420
ggaagggaaa ataaaaccac taggtaaact tgtagctgtg gtttgaagaa gtggttttga 480
aacactctgt ccagccccac caaaccgaaa gtccaggctg agcaaaacac cacctgggta 540
atttgcattt ctaaaataag ttgaggattc agccgaaact ggagaggtcc tcttttaact 600
tattgagttc aacctttaa ttttagcttg agtagttcta gtttccccaa acttaagttt 660
atcgacttct aaaatgtatt taagctttct ggggcaggcc aggcctgacc ttggctttgg 720
ggcagggagg gggctaaggt gaggcaggtg gcgccagcca ggtgcacacc caatgcccat 780
gagcccagac actggacgct gaacctcgcg gacagttaag aacccagggg cctctgcgcc 840
ctgggcccag ctctgtccca caccgcggtc acatggcacc acctctcttg cagcctccac 900
caagggccca tcggtcttcc ccctggcacc ctcctccaag agcacctctg ggggcacagc 960
ggccctgggc tgcctggtca aggactactt ccccgaaccg gtgacggtgt cgtggaactc 1020
aggcgccctg accagcggcg tgcacacctt cccggctgtc ctacagtcct caggactcta 1080
ctccctcagc agcgtggtga ccgtgccctc cagcagcttg ggcacccaga cctacatctg 1140
caacgtgaat cacaagccca gcaacaccaa ggtggacaag agagttggtg agaggccagc 1200
acagggaggg agggtgtctg ctggaagcca ggctcagcgc tcctgcctgg acgcatcccg 1260
gctatgcagt cccagtccag ggcagcaagg caggccccgt ctgcctcttc acccggaggc 1320
ctctgcccgc cccactcatg ctcagggaga gggtcttctg gctttttccc caggctctgg 1380
gcaggcacag gctaggtgcc cctaacccag gccctgcaca caaaggggca ggtgctgggc 1440
tcagacctgc caagagccat atccgggagg accctgcccc tgacctaagc ccaccccaaa 1500
ggccaaactc tccactccct cagctcggac accttctctc ctcccagatt ccagtaactc 1560
ccaatcttct ctctgcagag cccaaatctt gtgacaaaac tcacacatgc ccaccgtgcc 1620
caggtaagcc agcccaggcc tcgccctcca gctcaaggcg ggacaggtgc cctagagtag 1680
cctgcatcca gggacaggcc ccagccgggt gctgacacgt ccacctccat ctcttcctca 1740
gcacctgaac tcctgggggg accgtcagtc ttcctcttcc ccccaaaacc caaggacacc 1800
ctcatgatct cccggacccc tgaggtcaca tgcgtggtgg tggacgtgag ccacgaagac 1860
cctgaggtca agttcaactg gtacgtggac ggcgtggagg tgcataatgc caagacaaag 1920
ccgcgggagg agcagtacaa cagcacgtac cgtgtggtca gcgtcctcac cgtcctgcac 1980

-continued

```
caggactggc tgaatggcaa ggagtacaag tgcaaggtct ccaacaaagc cctcccagcc   2040
cccatcgaga aaaccatctc caaagccaaa ggtgggaccc gtggggtgcg agggccacat   2100
ggacagaggc cggctcggcc caccctctgc cctgagagtg accgctgtac caacctctgt   2160
ccctacaggg cagccccgag aaccacaggt gtacaccctg cccccatccc gggaggagat   2220
gaccaagaac caggtcagcc tgacctgcct ggtcaaaggc ttctatccca gcgacatcgc   2280
cgtggagtgg gagagcaatg ggcagccgga gaacaactac aagaccacgc ctcccgtgct   2340
ggactccgac ggctccttct tcctctatag caagctcacc gtggacaaga gcaggtggca   2400
gcaggggaac gtcttctcat gctccgtgat gcatgaggct ctgcacaacc actacacgca   2460
gaagagcctc tccctgtccc cgggtaaatg agtgcgacgg ccggcaagcc cccgctcccc   2520
gggctctcgc ggtcgcacga ggatgcttgg cacgtacccc gtctacatac ttcccaggca   2580
cccagcatgg aaataaagca cccaccactg ccctgggccc ctgcgagact gtgatggttc   2640
tttccacggg tcaggccgag tctgaggcct gagtggcatg agggaggcag agcgggtccc   2700
actgtcccca cactggccca ggctgtgcag gtgtgcctgg gccgcctagg gtggggctca   2760
gccaggggct gccctcggca gggtggggga tttgccagcg tggccctccc tccagcagca   2820
gctgccctgg gctgggccac gagaagccct aggagcccct ggggacagac acacagcccc   2880
tgcctctgta ggagactgtc ctgtcctgtg agcgccctgt cctccgaccc cgatgcccac   2940
tcgggggcat gcctagtcca tgcgcgtagg gacaggccct ccctcaccca tctacccccca   3000
cggcactaac ccctggcagc cctgcccagc ctcgcacccg catggggaca caaccgactc   3060
cggggacatg cactctcggg ccctgtggag ggactggtgc agatgcccac acacacactc   3120
agcccagacc cgttcaacaa accccgcact gaggttggtc gagcgggagt gcggccagag   3180
cctgcctcgg ccgtcaggga ggactcccgg gctcactcga aggaggtgcc accatttcag   3240
ctttggtagc ttttcttctt cttttaaatt ttctaaagct cattaattgt ctttgatgtt   3300
tcttttgtga tgacaataaa atatcctttt taagtcttgt acttcgtgat gggagccgcc   3360
ttcctgtgtc cacgcgcctc ctgcccccgg tgggaagcac ggtcaggagg aggctggtcc   3420
agctgcacct cgggggctcc ctgcactcgc cccccgcctc ctgcagccac acgcattgcc   3480
cgagcgaccc tccctggccc ctgtcactac atggacccct ggggcttctc ctcttttcta   3540
catggatgca gtttctcctc ctgctgggca cggtgctgcc tgccctggtc actctgcggg   3600
ggacagggcc tccagggaaa gctgggtcga ggctgggagc tggctcaggc tggccaggca   3660
gagccacagg gagggccttc cagaaccaac catggtccga agcgagaggt gggtgtcaga   3720
tccagacatg ataagataca ttgatgagtt tggacaaacc acaactagaa tgcagtgaaa   3780
aaaatgcttt atttgtgaaa tttgtgatgc tattgcttta tttgtaacca ttataagctg   3840
caataaacaa gttaacaaca acaattgcat tcattttatg tttcaggttc agggggaggt   3900
gtgggaggtt ttttaaagca agtaaaacct ctacaaatgt ggtatggctg attatgatct   3960
ctagtcaagg cactatacat caaatattcc ttattaaccc ctttacaaat taaaaagcta   4020
aaggtacaca atttttgagc atagttatta atagcagaca ctctatgcct gtgtggagta   4080
agaaaaaaca gtatgttatg attataactg ttatgcctac ttataaaggt tacagaatat   4140
ttttccataa ttttcttgta tagcagtgca gctttttcct ttgtggtgta aatagcaaag   4200
caagcaagag ttctattact aaacacagca tgactcaaaa aacttagcaa ttctgaagga   4260
aagtccttgg ggtcttctac ctttctcttc ttttttggag gagtagaatg ttgagagtca   4320
gcagtagcct catcatcact agatggcatt tcttctgagc aaaacaggtt ttcctcatta   4380
```

-continued aaggcattcc accactgctc ccattcatca gttccatagg ttggaatcta aaatacacaa 4440
acaattagaa tcagtagttt aacacattat acacttaaaa attttatatt taccttagag 4500
ctttaaatct ctgtaggtag tttgtccaat tatgtcacac cacagaagta aggttccttc 4560
acaaagatcc ggaccaaagc ggccatcgtg cctccccact cctgcagttc gggggcatgg 4620
atgcgcggat agccgctgct ggtttcctgg atgccgacgg atttgcactg ccggtagaac 4680
tccgcgaggt cgtccagcct caggcagcag ctgaaccaac tcgcgagggg atcgagcccg 4740
gggtgggcga agaactccag catgagatcc ccgcgctgga ggatcatcca gccggcgtcc 4800
cggaaaacga ttccgaagcc caacctttca tagaaggcgg cggtggaatc gaaatctcgt 4860
gatggcaggt tgggcgtcgc ttggtcggtc atttcgaacc ccagagtccc gctcagaaga 4920
actcgtcaag aaggcgatag aaggcgatgc gctgcgaatc gggagcggcg ataccgtaaa 4980
gcacgaggaa gcggtcagcc cattcgccgc caagctcttc agcaatatca cgggtagcca 5040
acgctatgtc ctgatagcgg tccgccacac ccagccggcc acagtcgatg aatccagaaa 5100
agcggccatt ttccaccatg atattcggca agcaggcatc gccatgggtc acgacgagat 5160
cctcgccgtc gggcatgcgc gccttgagcc tggcgaacag ttcggctggc gcgagcccct 5220
gatgctcttc gtccagatca tcctgatcga caagaccggc ttccatccga gtacgtgctc 5280
gctcgatgcg atgtttcgct tggtggtcga atgggcaggt agccggatca agcgtatgca 5340
gccgccgcat tgcatcagcc atgatggata ctttctcggc aggagcaagg tgagatgaca 5400
ggagatcctg ccccggcact tcgcccaata gcagccagtc ccttcccgct tcagtgacaa 5460
cgtcgagcac agctgcgcaa ggaacgcccg tcgtggccag ccacgatagc cgcgctgcct 5520
cgtcctgcag ttcattcagg gcaccggaca ggtcggtctt gacaaaaaga accgggcgcc 5580
cctgcgctga cagccggaac acggcggcat cagagcagcc gattgtctgt tgtgcccagt 5640
catagccgaa tagcctctcc acccaagcgg ccggagaacc tgcgtgcaat ccatcttgtt 5700
caatcatgcg aaacgatcct catcctgtct cttgatcaga tcttgatccc ctgcgccatc 5760
agatccttgg cggcaagaaa gccatccagt ttactttgca gggcttccca accttaccag 5820
agggcgcccc agctggcaat tccggttcgc ttgctgtcca taaaaccgcc cagtctagct 5880
atcgccatgt aagcccactg caagctacct gctttctctt tgcgcttgcg ttttcccttg 5940
tccagatagc ccagtagctg acattcatcc ggggtcagca ccgtttctgc ggactggctt 6000
tctacgtgtt ccgcttcctt tagcagccct tgcgccctga gtgcttgcgg cagcgtgaag 6060
ctttttgcaa aagcctaggc ctccaaaaaa gcctcctcac tacttctgga atagctcaga 6120
ggccgaggcg gcctcggcct ctgcataaat aaaaaaaatt agtcagccat ggggcggaga 6180
atgggcggaa ctgggcggag ttaggggcgg gatgggcgga gttaggggcg ggactatggt 6240
tgctgactaa ttgagatgca tgctttgcat acttctgcct gctggggagc ctggggactt 6300
tccacacctg gttgctgact aattgagatg catgctttgc atacttctgc ctgctgggga 6360
gcctggggac tttccacacc ctaactgaca cacattccac agctgcctcg cgcgtttcgg 6420
tgatgacggt gaaaacctct gacacatgca gctcccggag acggtcacag cttgtctgta 6480
agcggatgcc gggagcagac aagcccgtca gggcgcgtca gcgggtgttg gcgggtgtcg 6540
gggcgcagcc atgacccagt cacgtagcga tagcggagtg tatactggct taactatgcg 6600
gcatcagagc agattgtact gagagtgcac catatgcggt gtgaaatacc gcacagatgc 6660
gtaaggagaa aataccgcat caggcgctct tccgcttcct cgctcactga ctcgctgcgc 6720

-continued

```
tcggtcgttc ggctgcggcg agcggtatca gctcactcaa aggcggtaat acggttatcc   6780
acagaatcag gggataacgc aggaaagaac atgtgagcaa aaggccagca aaaggccagg   6840
aaccgtaaaa aggccgcgtt gctggcgttt ttccataggc tccgcccccc tgacgagcat   6900
cacaaaaatc gacgctcaag tcagaggtgg cgaaacccga caggactata aagataccag   6960
gcgtttcccc ctggaagctc cctcgtgcgc tctcctgttc cgaccctgcc gcttaccgga   7020
tacctgtccg cctttctccc ttcgggaagc gtggcgcttt ctcatagctc acgctgtagg   7080
tatctcagtt cggtgtaggt cgttcgctcc aagctgggct gtgtgcacga accccccgtt   7140
cagcccgacc gctgcgcctt atccggtaac tatcgtcttg agtccaaccc ggtaagacac   7200
gacttatcgc cactggcagc agccactggt aacaggatta gcagagcgag gtatgtaggc   7260
ggtgctacag agttcttgaa gtggtggcct aactacggct acactagaag gacagtattt   7320
ggtatctgcg ctctgctgaa gccagttacc ttcggaaaaa gagttggtag ctcttgatcc   7380
ggcaaacaaa ccaccgctgg tagcggtggt ttttttgttt gcaagcagca gattacgcgc   7440
agaaaaaaag gatctcaaga agatcctttg atcttttcta cggggtctga cgctcagtgg   7500
aacgaaaact cacgttaagg gattttggtc atgagattat caaaaaggat cttcacctag   7560
atccttttaa attaaaaatg aagttttaaa tcaatctaaa gtatatatga gtaaacttgg   7620
tctgacagtt accaatgctt aatcagtgag gcacctatct cagcgatctg tctatttcgt   7680
tcatccatag ttgcctgact ccccgtcgtg tagataacta cgatacggga gggcttacca   7740
tctggcccca gtgctgcaat gataccgcga gacccacgct caccggctcc agatttatca   7800
gcaataaacc agccagccgg aagggccgag cgcagaagtg gtcctgcaac tttatccgcc   7860
tccatccagt ctattaattg ttgccgggaa gctagagtaa gtagttcgcc agttaatagt   7920
ttgcgcaacg ttgttgccat tgctgcaggc atcgtggtgt cacgctcgtc gtttggtatg   7980
gcttcattca gctccggttc ccaacgatca aggcgagtta catgatcccc catgttgtgc   8040
aaaaaagcgg ttagctcctt cggtcctccg atcgttgtca gaagtaagtt ggccgcagtg   8100
ttatcactca tggttatggc agcactgcat aattctctta ctgtcatgcc atccgtaaga   8160
tgcttttctg tgactggtga gtactcaacc aagtcattct gagaatagtg tatgcggcga   8220
ccgagttgct cttgcccggc gtcaacacgg gataataccg cgccacatag cagaacttta   8280
aaagtgctca tcattggaaa acgttcttcg gggcgaaaac tctcaaggat cttaccgctg   8340
ttgagatcca gttcgatgta acccactcgt gcacccaact gatcttcagc atcttttact   8400
ttcaccagcg tttctgggtg agcaaaaaca ggaaggcaaa atgccgcaaa aaagggaata   8460
agggcgacac ggaaatgttg aatactcata ctcttccttt ttcaatatta ttgaagcatt   8520
tatcagggtt attgtctcat gagcggatac atatttgaat gtatttagaa aaataaacaa   8580
ataggggttc cgcgcacatt tccccgaaaa gtgccacctg acgtctaaga aaccattatt   8640
atcatgacat taacctataa aaataggcgt atcacgaggc cctttcgtct tcaagaattc   8700
gagctcggta cccatcagcc aaaaagcatg cctgccacac aacatcaatt tctggaaaac   8760
gctacactta attatttcta gtagaacagc tctttggttt gccaaaaaga atcacctata   8820
gtggcatcta agcacaaaaa ggagaaaaaa atcacaaaga aatgattgag aggcataata   8880
aaaattatca aaaaattatg agttttacga tttcatcttt ttccaagttg aaatcatagg   8940
gtggctttaa cacagtgaca aggaatgtgc atgctgccat tatggtgctc tgcctaaaat   9000
ggttggagcc ttgtcatgct acagagaaac tgtcatacag caggggggtgc caaatttcca   9060
tattttttta tatcattgag caggtgcaca gaagaccaga aagcactttc tatcaggctg   9120
```

-continued

```
gccttcctct tcctttccag tatgaagcaa aaactgccaa tgaaactagc aattgttaaa   9180
ttcctttttc aaacagtatt tgtgctatca gaacatagtg cattcaaaag tctagcctga   9240
gagaacaacc cagttttatt cattcctcct actacctctc tcattcccac tgtttgtgtt   9300
ctccctccca ttttaattgt ctatctagtc caaactaagc acacgatcca gtccacatta   9360
aacaacatgt tttcacttta agtcaaatac aagacacctt taatatcagc ccttgttcat   9420
aatcgtgctt ctagtgactt aatgtacatg tcacactgta ctgttgggtt ttgtgtctca   9480
tcatgaacaa tgttgtgaag gtattaagtg gagagtaagc agaattagat tcctctaatg   9540
atgcacaccc acactaagag cagaaataat attaaaaata gaaaaaaaag ttttacatga   9600
gatttcaaat acccaggtat gagctgcagt ttcttcaagt taaagcatcg aggttgtcag   9660
ttacactatt acaggaaaca tatgcagagt ttttatttta gtatattagt tttcacatat   9720
gtggaattac tattaaacta ttctttcttt tcaaatgctt accattgtaa atgagtttgt   9780
gactttgtgt aggtgagtgc acatgactct ggatgcctaa gaggactgaa gaagttggag   9840
ttataggtag ttttattcta cttgactgtt cagtgctaaa aatacaactg aggtccttta   9900
aactgctgtt catgaacttc ttaattgata tatctcatga gatctctaaa ctatttttat   9960
tatgacacgt ttcaccattt tcactgtaac gatttttatg ttttatatta atgtaactat  10020
atgacacttc ccaaaatccc catattcaca attgaactgt ttcaaagttt taccttgact  10080
tatgggaaat gaaaacccac attttataat tttaaaatga aatgtttatt ttatatttct  10140
gcaaatttca caaggaaaga ttagtcactg gtgtgtgaga gcagaggagc ataagagttc  10200
aggaatagaa tccattatga ttctggaggc aaggaagaac tgatgccaag gtttcagtat  10260
aagagcagta tccactggaa aggataaagt cactacatct gagcacagag caggacatct  10320
acataatgag tggtcactaa tgggccactg ttacactgtt atatgtataa ggctcaagaa  10380
tgagcactga ggctgtaagg tgtatgggtg aggacatcag gatgtaaacc cagctcaggt  10440
agaggactca gaggacagca cagtcagcat gaactaataa acatcagata agataaggca  10500
caagctcagc tatatagggt aagggatctt tgtaaatctg attgtgcatc cagtctagtt  10560
caatgtgact taggaagccc agtcatatgc aaatctagag aagactttag agtagaaatc  10620
tgaggctcac ctcacatacc agcaagcgag tgaccagtta gtcttaaggc accacttctt  10680
agacatcatg gcttgggtgt ggaccttgcc attcctgatg gcagctgccc aaagtaagac  10740
atcagaaaaa agagttccaa ggggaattga agcagttcca tgaatactca ccttcctgtg  10800
ttcttttcac aggtgtccag gcagaggtgc agctggtgga gtcaggagcc gaagtgaaaa  10860
agcctggggc ttcagtgaag gtgtcctgca aggcctctgg atacacattc actaattata  10920
ttatccactg ggtgaagcag gagcctggtc agggccttga atggattgga tattttaatc  10980
cttacaatca tggtactaag tacaatgaga agttcaaagg cagggccaca ctaactgcag  11040
acaaatccat cagcacagcc tacatggagc tcagcagcct gcgctctgag gacactgcgg  11100
tctactactg tgcaagatca ggaccctatg cctggtttga cacctggggc caagggacca  11160
cggtcaccgt ctcctcaggt aagaatggcc actctagggc ctttgttttc tgctgctgcc  11220
tgtgggattt catgagcatt gcaaagttgt cctcgggaca tgttccgagg ggacctgggc  11280
ggactggcca ggaggggacg ggcactgggg tgccttgagg atctgggagc ctctgtggat  11340
tttccgatgc ctttggaaaa tgggactgag gttgggtgcg tctgagacag taactcagcc  11400
tgggggcttg gtgaagatcg ccgcacagca gcgagtccgt gaaatatctt atttagactt  11460
```

-continued gtgaggtgcg ctgtgtgtca atttacatct taaatccttt attggctgga aagagaattg 11520
ttggagtggg tgaatccagc caggagggac gcggggggat cca 11563

<210> SEQ ID NO 38
<211> LENGTH: 11563
<212> TYPE: DNA
<213> ORGANISM: Artificial
<220> FEATURE:
<223> OTHER INFORMATION: Nucleotide sequence of the expression vector
HCVHQN73DSp20

<400> SEQUENCE: 38
ctagagaggt ctggtggagc ctgcaaaagt ccagctttca aaggaacaca gaagtatgtg 60
tatggaatat tagaagatgt tgcttttact cttaagttgg ttcctaggaa aaatagttaa 120
atactgtgac tttaaaatgt gagagggttt tcaagtactc atttttttaa atgtccaaaa 180
tttttgtcaa tcaatttgag gtcttgtttg tgtagaactg acattactta aagtttaacc 240
gaggaatggg agtgaggctc tctcataccc tattcagaac tgacttttaa caataataaa 300
ttaagtttaa aatattttta aatgaattga gcaatgttga gttggagtca agatggccga 360
tcagaaccag aacacctgca gcagctggca ggaagcaggt catgtggcaa ggctatttgg 420
ggaagggaaa ataaaaccac taggtaaact tgtagctgtg gtttgaagaa gtggttttga 480
aacactctgt ccagccccac caaaccgaaa gtccaggctg agcaaaacac cacctgggta 540
atttgcattt ctaaaataag ttgaggattc agccgaaact ggagaggtcc tcttttaact 600
tattgagttc aacctttttaa ttttagcttg agtagttcta gtttccccaa acttaagttt 660
atcgacttct aaaatgtatt taagctttct ggggcaggcc aggcctgacc ttggctttgg 720
ggcagggagg gggctaaggt gaggcaggtg gcgccagcca ggtgcacacc caatgcccat 780
gagcccagac actggacgct gaacctcgcg gacagttaag aacccagggg cctctgcgcc 840
ctgggcccag ctctgtccca caccgcggtc acatggcacc acctctcttg cagcctccac 900
caagggccca tcggtcttcc ccctggcacc ctcctccaag agcacctctg ggggcacagc 960
ggccctgggc tgcctggtca aggactactt ccccgaaccg gtgacggtgt cgtggaactc 1020
aggcgccctg accagcggcg tgcacacctt cccggctgtc ctacagtcct caggactcta 1080
ctccctcagc agcgtggtga ccgtgccctc cagcagcttg ggcacccaga cctacatctg 1140
caacgtgaat cacaagccca gcaacaccaa ggtggacaag agagttggtg agaggccagc 1200
acagggaggg agggtgtctg ctggaagcca ggctcagcgc tcctgcctgg acgcatcccg 1260
gctatgcagt cccagtccag ggcagcaagg caggccccgt ctgcctcttc acccggaggc 1320
ctctgcccgc cccactcatg ctcagggaga gggtcttctg gctttttccc caggctctgg 1380
gcaggcacag gctaggtgcc cctaacccag gccctgcaca caaaggggca ggtgctgggc 1440
tcagacctgc caagagccat atccgggagg accctgcccc tgacctaagc ccaccccaaa 1500
ggccaaactc tccactccct cagctcggac accttctctc ctcccagatt ccagtaactc 1560
ccaatcttct ctctgcagag cccaaatctt gtgacaaaac tcacacatgc ccaccgtgcc 1620
caggtaagcc agcccaggcc tcgccctcca gctcaaggcg ggacaggtgc cctagagtag 1680
cctgcatcca gggacaggcc ccagccgggt gctgacacgt ccacctccat ctcttcctca 1740
gcacctgaac tcctgggggg accgtcagtc ttcctcttcc ccccaaaacc caaggacacc 1800
ctcatgatct cccggacccc tgaggtcaca tgcgtggtgg tggacgtgag ccacgaagac 1860
cctgaggtca agttcaactg gtacgtggac ggcgtggagg tgcataatgc caagacaaag 1920

-continued

```
ccgcgggagg agcagtacaa cagcacgtac cgtgtggtca gcgtcctcac cgtcctgcac   1980

caggactggc tgaatggcaa ggagtacaag tgcaaggtct ccaacaaagc cctcccagcc   2040

cccatcgaga aaaccatctc caaagccaaa ggtgggaccc gtggggtgcg agggccacat   2100

ggacagaggc cggctcggcc caccctctgc cctgagagtg accgctgtac caacctctgt   2160

ccctacaggg cagccccgag aaccacaggt gtacaccctg cccccatccc gggaggagat   2220

gaccaagaac caggtcagcc tgacctgcct ggtcaaaggc ttctatccca gcgacatcgc   2280

cgtggagtgg gagagcaatg ggcagccgga gaacaactac aagaccacgc ctcccgtgct   2340

ggactccgac ggctccttct tcctctatag caagctcacc gtggacaaga gcaggtggca   2400

gcaggggaac gtcttctcat gctccgtgat gcatgaggct ctgcacaacc actacacgca   2460

gaagagcctc tccctgtccc cgggtaaatg agtgcgacgg ccggcaagcc cccgctcccc   2520

gggctctcgc ggtcgcacga ggatgcttgg cacgtacccc gtctacatac ttcccaggca   2580

cccagcatgg aaataaagca cccaccactg ccctgggccc ctgcgagact gtgatggttc   2640

tttccacggg tcaggccgag tctgaggcct gagtggcatg agggaggcag agcgggtccc   2700

actgtcccca cactggccca ggctgtgcag gtgtgcctgg gccgcctagg gtggggctca   2760

gccaggggct gccctcggca gggtggggga tttgccagcg tggccctccc tccagcagca   2820

gctgccctgg gctgggccac gagaagccct aggagcccct ggggacagac acacagcccc   2880

tgcctctgta ggagactgtc ctgtcctgtg agcgccctgt cctccgaccc cgatgcccac   2940

tcgggggcat gcctagtcca tgcgcgtagg gacaggccct ccctcaccca tctacccca    3000

cggcactaac ccctggcagc cctgcccagc ctcgcacccg catggggaca caaccgactc   3060

cggggacatg cactctcggg ccctgtggag ggactggtgc agatgcccac acacacactc   3120

agcccagacc cgttcaacaa accccgcact gaggttggtc gagcgggagt gcggccagag   3180

cctgcctcgg ccgtcaggga ggactcccgg gctcactcga aggaggtgcc accatttcag   3240

ctttggtagc ttttcttctt cttttaaatt ttctaaagct cattaattgt ctttgatgtt   3300

tcttttgtga tgacaataaa atatcctttt taagtcttgt acttcgtgat gggagccgcc   3360

ttcctgtgtc cacgcgcctc ctgcccccgg tgggaagcac ggtcaggagg aggctggtcc   3420

agctgcacct cgggggctcc ctgcactcgc cccccgcctc ctgcagccac acgcattgcc   3480

cgagcgaccc tccctggccc ctgtcactac atggacccct ggggcttctc ctcttttcta   3540

catggatgca gtttctcctc ctgctgggca cggtgctgcc tgccctggtc actctgcggg   3600

ggacagggcc tccagggaaa gctgggtcga ggctgggagc tggctcaggc tggccaggca   3660

gagccacagg gagggccttc cagaaccaac catggtccga agcgagaggt gggtgtcaga   3720

tccagacatg ataagataca ttgatgagtt tggacaaacc acaactagaa tgcagtgaaa   3780

aaaatgcttt atttgtgaaa tttgtgatgc tattgcttta tttgtaacca ttataagctg   3840

caataaacaa gttaacaaca acaattgcat tcattttatg tttcaggttc agggggaggt   3900

gtgggaggtt ttttaaagca agtaaaacct ctacaaatgt ggtatggctg attatgatct   3960

ctagtcaagg cactatacat caaatattcc ttattaaccc ctttacaaat taaaaagcta   4020

aaggtacaca atttttgagc atagttatta atagcagaca ctctatgcct gtgtggagta   4080

agaaaaaaca gtatgttatg attataactg ttatgcctac ttataaaggt tacagaatat   4140

ttttccataa ttttcttgta tagcagtgca gctttttcct ttgtggtgta aatagcaaag   4200

caagcaagag ttctattact aaacacagca tgactcaaaa aacttagcaa ttctgaagga   4260

aagtccttgg ggtcttctac ctttctcttc tttttggag gagtagaatg ttgagagtca    4320
```

-continued gcagtagcct catcatcact agatggcatt tcttctgagc aaaacaggtt ttcctcatta 4380
aaggcattcc accactgctc ccattcatca gttccatagg ttggaatcta aaatacacaa 4440
acaattagaa tcagtagttt aacacattat acacttaaaa attttatatt taccttagag 4500
ctttaaatct ctgtaggtag tttgtccaat tatgtcacac cacagaagta aggttccttc 4560
acaaagatcc ggaccaaagc ggccatcgtg cctccccact cctgcagttc gggggcatgg 4620
atgcgcggat agccgctgct ggtttcctgg atgccgacgg atttgcactg ccggtagaac 4680
tccgcgaggt cgtccagcct caggcagcag ctgaaccaac tcgcgagggg atcgagcccg 4740
gggtgggcga agaactccag catgagatcc ccgcgctgga ggatcatcca gccggcgtcc 4800
cggaaaacga ttccgaagcc caacctttca tagaaggcgg cggtggaatc gaaatctcgt 4860
gatggcaggt tgggcgtcgc ttggtcggtc atttcgaacc ccagagtccc gctcagaaga 4920
actcgtcaag aaggcgatag aaggcgatgc gctgcgaatc gggagcggcg ataccgtaaa 4980
gcacgaggaa gcggtcagcc cattcgccgc caagctcttc agcaatatca cgggtagcca 5040
acgctatgtc ctgatagcgg tccgccacac ccagccggcc acagtcgatg aatccagaaa 5100
agcggccatt ttccaccatg atattcggca agcaggcatc gccatgggtc acgacgagat 5160
cctcgccgtc gggcatgcgc gccttgagcc tggcgaacag ttcggctggc gcgagcccct 5220
gatgctcttc gtccagatca tcctgatcga caagaccggc ttccatccga gtacgtgctc 5280
gctcgatgcg atgtttcgct tggtggtcga atgggcaggt agccggatca agcgtatgca 5340
gccgccgcat tgcatcagcc atgatggata ctttctcggc aggagcaagg tgagatgaca 5400
ggagatcctg ccccggcact tcgcccaata gcagccagtc ccttcccgct tcagtgacaa 5460
cgtcgagcac agctgcgcaa ggaacgcccg tcgtggccag ccacgatagc cgcgctgcct 5520
cgtcctgcag ttcattcagg gcaccggaca ggtcggtctt gacaaaaaga accgggcgcc 5580
cctgcgctga cagccggaac acggcggcat cagagcagcc gattgtctgt tgtgcccagt 5640
catagccgaa tagcctctcc acccaagcgg ccggagaacc tgcgtgcaat ccatcttgtt 5700
caatcatgcg aaacgatcct catcctgtct cttgatcaga tcttgatccc ctgcgccatc 5760
agatccttgg cggcaagaaa gccatccagt ttactttgca gggcttccca accttaccag 5820
agggcgcccc agctggcaat tccggttcgc ttgctgtcca taaaaccgcc cagtctagct 5880
atcgccatgt aagcccactg caagctacct gctttctctt tgcgcttgcg ttttcccttg 5940
tccagatagc ccagtagctg acattcatcc ggggtcagca ccgtttctgc ggactggctt 6000
tctacgtgtt ccgcttcctt tagcagccct tgcgccctga gtgcttgcgg cagcgtgaag 6060
ctttttgcaa aagcctaggc ctccaaaaaa gcctcctcac tacttctgga atagctcaga 6120
ggccgaggcg gcctcggcct ctgcataaat aaaaaaaatt agtcagccat ggggcggaga 6180
atgggcggaa ctgggcggag ttaggggcgg gatgggcgga gttaggggcg ggactatggt 6240
tgctgactaa ttgagatgca tgctttgcat acttctgcct gctggggagc ctggggactt 6300
tccacacctg gttgctgact aattgagatg catgctttgc atacttctgc ctgctgggga 6360
gcctggggac tttccacacc ctaactgaca cacattccac agctgcctcg cgcgtttcgg 6420
tgatgacggt gaaaacctct gacacatgca gctcccggag acggtcacag cttgtctgta 6480
agcggatgcc gggagcagac aagcccgtca gggcgcgtca gcgggtgttg gcgggtgtcg 6540
gggcgcagcc atgacccagt cacgtagcga tagcggagtg tatactggct taactatgcg 6600
gcatcagagc agattgtact gagagtgcac catatgcggt gtgaaatacc gcacagatgc 6660

-continued

```
gtaaggagaa aataccgcat caggcgctct tccgcttcct cgctcactga ctcgctgcgc   6720
tcggtcgttc ggctgcggcg agcggtatca gctcactcaa aggcggtaat acggttatcc   6780
acagaatcag gggataacgc aggaaagaac atgtgagcaa aaggccagca aaaggccagg   6840
aaccgtaaaa aggccgcgtt gctggcgttt ttccataggc tccgcccccc tgacgagcat   6900
cacaaaaatc gacgctcaag tcagaggtgg cgaaacccga caggactata aagataccag   6960
gcgtttcccc ctggaagctc cctcgtgcgc tctcctgttc cgaccctgcc gcttaccgga   7020
tacctgtccg cctttctccc ttcgggaagc gtggcgcttt ctcatagctc acgctgtagg   7080
tatctcagtt cggtgtaggt cgttcgctcc aagctgggct gtgtgcacga accccccgtt   7140
cagcccgacc gctgcgcctt atccggtaac tatcgtcttg agtccaaccc ggtaagacac   7200
gacttatcgc cactggcagc agccactggt aacaggatta gcagagcgag gtatgtaggc   7260
ggtgctacag agttcttgaa gtggtggcct aactacggct acactagaag gacagtattt   7320
ggtatctgcg ctctgctgaa gccagttacc ttcggaaaaa gagttggtag ctcttgatcc   7380
ggcaaacaaa ccaccgctgg tagcggtggt ttttttgttt gcaagcagca gattacgcgc   7440
agaaaaaaag gatctcaaga agatcctttg atcttttcta cggggtctga cgctcagtgg   7500
aacgaaaact cacgttaagg gattttggtc atgagattat caaaaaggat cttcacctag   7560
atccttttaa attaaaaatg aagttttaaa tcaatctaaa gtatatatga gtaaacttgg   7620
tctgacagtt accaatgctt aatcagtgag gcacctatct cagcgatctg tctatttcgt   7680
tcatccatag ttgcctgact ccccgtcgtg tagataacta cgatacggga gggcttacca   7740
tctggcccca gtgctgcaat gataccgcga gacccacgct caccggctcc agatttatca   7800
gcaataaacc agccagccgg aagggccgag cgcagaagtg gtcctgcaac tttatccgcc   7860
tccatccagt ctattaattg ttgccgggaa gctagagtaa gtagttcgcc agttaatagt   7920
ttgcgcaacg ttgttgccat tgctgcaggc atcgtggtgt cacgctcgtc gtttggtatg   7980
gcttcattca gctccggttc ccaacgatca aggcgagtta catgatcccc catgttgtgc   8040
aaaaaagcgg ttagctcctt cggtcctccg atcgttgtca gaagtaagtt ggccgcagtg   8100
ttatcactca tggttatggc agcactgcat aattctctta ctgtcatgcc atccgtaaga   8160
tgcttttctg tgactggtga gtactcaacc aagtcattct gagaatagtg tatgcggcga   8220
ccgagttgct cttgcccggc gtcaacacgg gataataccg cgccacatag cagaacttta   8280
aaagtgctca tcattggaaa acgttcttcg gggcgaaaac tctcaaggat cttaccgctg   8340
ttgagatcca gttcgatgta acccactcgt gcacccaact gatcttcagc atcttttact   8400
ttcaccagcg tttctgggtg agcaaaaaca ggaaggcaaa atgccgcaaa aaagggaata   8460
agggcgacac ggaaatgttg aatactcata ctcttccttt ttcaatatta ttgaagcatt   8520
tatcagggtt attgtctcat gagcggatac atatttgaat gtatttagaa aaataaacaa   8580
ataggggttc cgcgcacatt tccccgaaaa gtgccacctg acgtctaaga aaccattatt   8640
atcatgacat taacctataa aaataggcgt atcacgaggc cctttcgtct tcaagaattc   8700
gagctcggta cccatcagcc aaaaagcatg cctgccacac aacatcaatt tctggaaaac   8760
gctacactta attatttcta gtagaacagc tctttggttt gccaaaaaga atcacctata   8820
gtggcatcta agcacaaaaa ggagaaaaaa atcacaaaga aatgattgag aggcataata   8880
aaaattatca aaaaattatg agttttacga tttcatcttt ttccaagttg aaatcatagg   8940
gtggctttaa cacagtgaca aggaatgtgc atgctgccat tatggtgctc tgcctaaaat   9000
ggttggagcc ttgtcatgct acagagaaac tgtcatacag caggggggtgc caaatttcca   9060
```

-continued

```
tatttttta tatcattgag caggtgcaca gaagaccaga aagcactttc tatcaggctg   9120
gccttcctct tcctttccag tatgaagcaa aaactgccaa tgaaactagc aattgttaaa   9180
ttccttttc aaacagtatt tgtgctatca gaacatagtg cattcaaaag tctagcctga   9240
gagaacaacc cagttttatt cattcctcct actacctctc tcattcccac tgtttgtgtt   9300
ctccctccca ttttaattgt ctatctagtc caaactaagc acacgatcca gtccacatta   9360
aacaacatgt tttcacttta agtcaaatac aagacacctt taatatcagc ccttgttcat   9420
aatcgtgctt ctagtgactt aatgtacatg tcacactgta ctgttgggtt ttgtgtctca   9480
tcatgaacaa tgttgtgaag gtattaagtg gagagtaagc agaattagat tcctctaatg   9540
atgcacaccc acactaagag cagaaataat attaaaaata gaaaaaaaag ttttacatga   9600
gatttcaaat acccaggtat gagctgcagt ttcttcaagt taaagcatcg aggttgtcag   9660
ttacactatt acaggaaaca tatgcagagt ttttatttta gtatattagt tttcacatat   9720
gtggaattac tattaaacta ttctttcttt tcaaatgctt accattgtaa atgagtttgt   9780
gactttgtgt aggtgagtgc acatgactct ggatgcctaa gaggactgaa gaagttggag   9840
ttataggtag ttttattcta cttgactgtt cagtgctaaa aatacaactg aggtccttta   9900
aactgctgtt catgaacttc ttaattgata tatctcatga gatctctaaa ctatttttat   9960
tatgacacgt ttcaccattt tcactgtaac gatttttatg ttttatatta atgtaactat  10020
atgacacttc ccaaaatccc catattcaca attgaactgt ttcaaagttt taccttgact  10080
tatgggaaat gaaaacccac attttataat tttaaaatga aatgtttatt ttatatttct  10140
gcaaatttca caaggaaaga ttagtcactg gtgtgtgaga gcagaggagc ataagagttc  10200
aggaatagaa tccattatga ttctggaggc aaggaagaac tgatgccaag gtttcagtat  10260
aagagcagta tccactggaa aggataaagt cactacatct gagcacagag caggacatct  10320
acataatgag tggtcactaa tgggccactg ttacactgtt atatgtataa ggctcaagaa  10380
tgagcactga ggctgtaagg tgtatgggtg aggacatcag gatgtaaacc cagctcaggt  10440
agaggactca gaggacagca cagtcagcat gaactaataa acatcagata agataaggca  10500
caagctcagc tatatagggt aagggatctt tgtaaatctg attgtgcatc cagtctagtt  10560
caatgtgact taggaagccc agtcatatgc aaatctagag aagactttag agtagaaatc  10620
tgaggctcac ctcacatacc agcaagcgag tgaccagtta gtcttaaggc accacttctt  10680
agacatcatg gcttgggtgt ggaccttgcc attcctgatg gcagctgccc aaagtaagac  10740
atcagaaaaa agagttccaa ggggaattga agcagttcca tgaatactca ccttcctgtg  10800
ttcttttcac aggtgtccag gcacaggtgc agctggtgga gtcaggagcc gaagtgaaaa  10860
agcctggggc ttcagtgaag gtgtcctgca aggcctctgg atacacattc actaattata  10920
ttatccactg ggtgaagcag gagcctggtc agggccttga atggattgga tattttaatc  10980
cttacaatca tggtactaag tacaatgaga agttcaaagg cagggccaca ctaactgcag  11040
acaaatccat cagcacagcc tacatggagc tcagcagcct gcgctctgag gacactgcgg  11100
tctactactg tgcaagatca ggaccctatg cctggtttga cacctggggc caagggacca  11160
cggtcaccgt ctcctcaggt aagaatggcc actctagggc ctttgttttc tgctgctgcc  11220
tgtgggattt catgagcatt gcaaagttgt cctcgggaca tgttccgagg ggacctgggc  11280
ggactggcca ggaggggacg ggcactgggg tgccttgagg atctgggagc ctctgtggat  11340
tttccgatgc ctttggaaaa tgggactgag gttgggtgcg tctgagacag taactcagcc  11400
```

-continued

```
tgggggcttg gtgaagatcg ccgcacagca gcgagtccgt gaaatatctt atttagactt  11460

gtgaggtgcg ctgtgtgtca atttacatct taaatccttt attggctgga aagagaattg  11520

ttggagtggg tgaatccagc caggagggac gcggggggat cca                    11563
```

<210> SEQ ID NO 39
<211> LENGTH: 8096
<212> TYPE: DNA
<213> ORGANISM: Artificial
<220> FEATURE:
<223> OTHER INFORMATION: Nucleotide sequence of expression vector LCVL2Sp20

<400> SEQUENCE: 39

```
ctagagtcct agagaggtct ggtggagcct gcaaaagtcc agctttcaaa ggaacacaga     60

agtatgtgta tggaatatta gaagatgttg cttttactct taagttggtt cctaggaaaa    120

atagttaaat actgtgactt taaaatgtga gagggttttc aagtactcat ttttttaaat    180

gtccaaaatt tttgtcaatc aatttgaggt cttgtttgtg tagaactgac attacttaaa    240

gtttaaccga ggaatgggag tgaggctctc tcatacccta ttcagaactg acttttaaca    300

ataataaatt aagtttaaaa tatttttaaa tgaattgagc aatgttgagt tggagtcaag    360

atggccgatc agaaccagaa cacctgcagc agctggcagg aagcaggtca tgtggcaagg    420

ctatttgggg aagggaaaat aaaaccacta ggtaaacttg tagctgtggt ttgaagaagt    480

ggttttgaaa cactctgtcc agccccacca aaccgaaagt ccaggctgag caaaacacca    540

cctgggtaat ttgcatttct aaaataagtt gaggattcag ccgaaactgg agaggtcctc    600

ttttaactta ttgagttcaa ccttttaatt ttagcttgag tagttctagt ttccccaaac    660

ttaagtttat cgacttctaa aatgtattta gaactcattt tcaaaattag gttatgtaag    720

aaattgaagg actttagtgt ctttaatttc taatatattt agaaaacttc ttaaaattac    780

tctattattc ttccctctga ttattggtct ccattcaatt cttttccaat acccgaagca    840

tttacagtga ctttgttcat gatctttttt agttgtttgt tttgccttac tattaagact    900

ttgacattct ggtcaaaacg gcttcacaaa tctttttcaa gaccactttc tgagtattca    960

ttttaggaga aatacttttt ttttaaatga atgcaattat ctaggacctg caggcatgct   1020

gttttctgtc tgtccctaac atgccctgtg attatccgca aacaacacac ccaagggcag   1080

aactttgtta cttaaacacc atcctgtttg cttctttcct caggaactgt ggctgcacca   1140

tctgtcttca tcttcccgcc atctgatgag cagttgaaat ctggaactgc ctctgttgtg   1200

tgcctgctga ataacttcta tcccagagag gccaaagtac agtggaaggt ggataacgcc   1260

ctccaatcgg gtaactccca ggagagtgtc acagagcagg acagcaagga cagcacctac   1320

agcctcagca gcaccctgac gctgagcaaa gcagactacg agaaacacaa agtctacgcc   1380

tgcgaagtca cccatcaggg cctgagctcg cccgtcacaa agagcttcaa caggggagag   1440

tgttagaggg agaagtgccc ccacctgctc ctcagttcca gcctgacccc ctcccatcct   1500

ttggcctctg accctttttc cacaggggac ctacccctat tgcggtcctc cagctcatct   1560

ttcacctcac ccccctcctc ctccttggct ttaattatgc taatgttgga ggagaatgaa   1620

taaataaagt gaatctttgc acctgtggtt tctctctttc ctcatttaat aattattatc   1680

tgttgtttta ccaactactc aatttctctt ataagggact aaatatgtag tcatcctaag   1740

gcgggatatc gagatctgaa gctgatccag acatgataag atacattgat gagtttggac   1800

aaaccacaac tagaatgcag tgaaaaaaat gctttatttg tgaaatttgt gatgctattg   1860
```

-continued

```
ctttatttgt aaccattata agctgcaata aacaagttaa caacaacaat tgcattcatt   1920
ttatgtttca ggttcagggg gaggtgtggg aggtttttta aagcaagtaa aacctctaca   1980
aatgtggtat ggctgattat gatctctagt caaggcacta tacatcaaat attccttatt   2040
aaccccttta caaattaaaa agctaaaggt acacaatttt tgagcatagt tattaatagc   2100
agacactcta tgcctgtgtg gagtaagaaa aaacagtatg ttatgattat aactgttatg   2160
cctacttata aaggttacag aatatttttc cataattttc ttgtatagca gtgcagcttt   2220
ttcctttgtg gtgtaaatag caaagcaagc aagagttcta ttactaaaca cagcatgact   2280
caaaaaactt agcaattctg aaggaaagtc cttggggtct tctacctttc tcttcttttt   2340
tggaggagta gaatgttgag agtcagcagt agcctcatca tcactagatg gcatttcttc   2400
tgagcaaaac aggttttcct cattaaaggc attccaccac tgctcccatt catcagttcc   2460
ataggttgga atctaaaata cacaaacaat tagaatcagt agtttaacac attatacact   2520
taaaaatttt atatttacct tagagcttta aatctctgta ggtagtttgt ccaattatgt   2580
cacaccacag aagtaaggtt ccttcacaaa gatccggacc aaagcggcca tcgtgcctcc   2640
ccactcctgc agttcggggg catggatgcg cggatagccg ctgctggttt cctggatgcc   2700
gacggatttg cactgccggt agaactccgc gaggtcgtcc agcctcaggc agcagctgaa   2760
ccaactcgcg aggggatcga gcatccccca tggtcttata aaaatgcata gctttaggag   2820
gggagcagag aacttgaaag catcttcctg ttagtctttc ttctcgtaga cttcaaactt   2880
atacttgatg cctttttcct cctggacctc agagaggacg cctgggtatt ctgggagaag   2940
tttatatttc cccaaatcaa tttctgggaa aaacgtgtca ctttcaaatt cctgcatgat   3000
ccttgtcaca aagagtctga ggtggcctgg ttgattcatg gcttcctggt aaacagaact   3060
gcctccgact atccaaacca tgtctacttt acttgccaat tccggttgtt caataagtct   3120
taaggcatca tccaaacttt tggcaagaaa atgagctcct cgtggtggtt ctttgagttc   3180
tctactgaga actatattaa ttctgtcctt taaaggtcga ttcttctcag gaatggagaa   3240
ccaggttttc ctacccataa tcaccagatt ctgtttacct tccactgaag aggttgtggt   3300
cattctttgg aagtacttga actcgttcct gagcggaggc cagggtcggt ctccgttctt   3360
gccaatcccc atattttggg acacggcgac gatgcagttc aatggtcgaa ccatgatggc   3420
agcggggata aaatcctacc agccttcacg ctaggattgc cgtcaagttt gggggtaccg   3480
agctcgaatt agctttttgc aaaagcctag gcctccaaaa aagcctcctc actacttctg   3540
gaatagctca gagggccgag gcggcctcgg cctctgcata aataaaaaaa attagtcagc   3600
catggggcgg agaatgggcg gaactgggcg gagttagggg cgggatgggc ggagttaggg   3660
gcgggactat ggttgctgac taattgagat gcatgctttg catacttctg cctgctgggg   3720
agcctgggga ctttccacac ctggttgctg actaattgag atgcatgctt tgcatacttc   3780
tgcctgctgg ggagcctggg gactttccac accctaactg acacacattc cacagctgcc   3840
tcgcgcgttt cggtgatgac ggtgaaaacc tctgacacat gcagctcccg gagacggtca   3900
cagcttgtct gtaagcggat gccgggagca gacaagcccg tcagggcgcg tcagcgggtg   3960
ttggcgggtg tcggggcgca gccatgaccc agtcacgtag cgatagcgga gtgtatactg   4020
gcttaactat gcggcatcag agcagattgt actgagagtg caccatatgc ggccgcatat   4080
gcggtgtgaa ataccgcaca gatgcgtaag gagaaaatac cgcatcaggc gctcttccgc   4140
ttcctcgctc actgactcgc tgcgctcggt cgttcggctg cggcgagcgg tatcagctca   4200
ctcaaaggcg gtaatacggt tatccacaga atcaggggat aacgcaggaa agaacatgtg   4260
```

-continued

```
agcaaaaggc cagcaaaagg ccaggaaccg taaaaaggcc gcgttgctgg cgtttttcca   4320
taggctccgc ccccctgacg agcatcacaa aaatcgacgc tcaagtcaga ggtggcgaaa   4380
cccgacagga ctataaagat accaggcgtt tccccctgga agctccctcg tgcgctctcc   4440
tgttccgacc ctgccgctta ccggatacct gtccgccttt ctcccttcgg gaagcgtggc   4500
gctttctcat agctcacgct gtaggtatct cagttcggtg taggtcgttc gctccaagct   4560
gggctgtgtg cacgaacccc ccgttcagcc cgaccgctgc gccttatccg gtaactatcg   4620
tcttgagtcc aacccggtaa gacacgactt atcgccactg gcagcagcca ctggtaacag   4680
gattagcaga gcgaggtatg taggcggtgc tacagagttc ttgaagtggt ggcctaacta   4740
cggctacact agaaggacag tatttggtat ctgcgctctg ctgaagccag ttaccttcgg   4800
aaaaagagtt ggtagctctt gatccggcaa acaaaccacc gctggtagcg gtggtttttt   4860
tgtttgcaag cagcagatta cgcgcagaaa aaaaggatct caagaagatc ctttgatctt   4920
ttctacgggg tctgacgctc agtggaacga aaactcacgt taagggattt tggtcatgag   4980
attatcaaaa aggatcttca cctagatcct tttaaattaa aaatgaagtt ttaaatcaat   5040
ctaaagtata tatgagtaaa cttggtctga cagttaccaa tgcttaatca gtgaggcacc   5100
tatctcagcg atctgtctat ttcgttcatc catagttgcc tgactccccg tcgtgtagat   5160
aactacgata cgggagggct taccatctgg ccccagtgct gcaatgatac cgcgagaccc   5220
acgctcaccg gctccagatt tatcagcaat aaaccagcca gccggaaggg ccgagcgcag   5280
aagtggtcct gcaactttat ccgcctccat ccagtctatt aattgttgcc gggaagctag   5340
agtaagtagt tcgccagtta atagtttgcg caacgttgtt gccattgctg caggcatcgt   5400
ggtgtcacgc tcgtcgtttg gtatggcttc attcagctcc ggttcccaac gatcaaggcg   5460
agttacatga tcccccatgt tgtgcaaaaa agcggttagc tccttcggtc ctccgatcgt   5520
tgtcagaagt aagttggccg cagtgttatc actcatggtt atggcagcac tgcataattc   5580
tcttactgtc atgccatccg taagatgctt ttctgtgact ggtgagtact caaccaagtc   5640
attctgagaa tagtgtatgc ggcgaccgag ttgctcttgc ccggcgtcaa cacgggataa   5700
taccgcgcca catagcagaa ctttaaaagt gctcatcatt ggaaaacgtt cttcggggcg   5760
aaaactctca aggatcttac cgctgttgag atccagttcg atgtaaccca ctcgtgcacc   5820
caactgatct tcagcatctt ttactttcac cagcgtttct gggtgagcaa aaacaggaag   5880
gcaaaatgcc gcaaaaaagg gaataagggc gacacggaaa tgttgaatac tcatactctt   5940
cctttttcaa tattattgaa gcatttatca gggttattgt ctcatgagcg gatacatatt   6000
tgaatgtatt tagaaaaata aacaaatagg ggttccgcgc acatttcccc gaaaagtgcc   6060
acctgacgtc taagaaacca ttattatcat gacattaacc tataaaaata ggcgtatcac   6120
gaggcccttt cgtcttcaag aattcagctg ctcgaggaag agctcaaacc catgctactc   6180
tctggcttga tggaagcaac gctttcatag ctgagctgtc ataaataata aagagatttt   6240
tttattaata ttgaaaagat gggttattta tgtaagactc tgtcttcatt ttaaaaacca   6300
caccttccag tagtattctg ttactgttct ggcaatcact gtgatcaaga agctacacgg   6360
tgagttgtgc ttctcagtcc taagggatac atctacaaga ggctcccata ctcgaagctc   6420
aggaaacatt gtagaaaagg aggcaaaaga ctgacagagc cagaggacca agaaatttgt   6480
tgtgaggttg tgtctcctac taacaatata agcaatatct ataaattgtt gatatcatgg   6540
ctactaaaat gtgagttgaa cgaggaggac acaaatgaac atgacaatca gaatgaggcc   6600
```

-continued

```
tctcacctgc aaaaaacact atagagaagc agataaagct gtcagcagaa gaggcgcacc   6660

tccttataga agaagcctac caggtttgat atatcagcct tgaaaaccta catagtattt   6720

acattatatc gagtctatga gacatattta gtaatgcata tgtatgtgtg tgtgtgcatg   6780

tatgtgtgta aatacatatg ttcatagaaa aatgtgtaaa aagagatcat gaatttaaga   6840

gagaactggg acaatttttt tcagggagtt gtaatcagga aagttaaggg aaaaatgttg   6900

taattaaaat tcaggctcag aaacaaacaa aggaaaagaa aaaaaaacaa caacaacaac   6960

aaaaaaacaa aacaaaggag aagctgtatg gccacaatag catctacagc taactgtgaa   7020

aggataatgg aacaagttat gtactgccta gagcagtatg atgcctaaat catctcgaca   7080

tggaggaaaa tagaacaaag acactctaca tagactatga tagaaatcaa aataaggtgt   7140

aagacataga acattagttt tgtttgttgt tcaaagagac tcacattccc acaaaaaaat   7200

ctgtgggatt ttacaggtct gcaataagct gctgacctga tgatttctgc agctgtgcct   7260

accctttgct gatttgcatg tacccaaagc atagcttact gacatgagga tttcttcata   7320

gtcaggtcac accctttgct ggagtcagaa tcacactgat cacacacagt catgagtgtg   7380

ctcactcagg tcctggcgtt gctgctgctg tggcttacag gtaatgaaga cagcactaga   7440

attttattga gcttcctgta cactgtgctg cttgtctctg tgaaaattct cttgtgaatt   7500

aatcatgtgg ggatctgttt tcaatttttc aattgtaggt acgcgttgtg acattctgct   7560

gacccagtct ccagccaccc tgtctctgag tccaggagaa agagccactt tctcctgcag   7620

ggccagtcag aacattggca caagcataca gtggtatcaa caaaaaacaa atggtgctcc   7680

aaggcttctc ataaggtctt cttctgagtc tatctctggg atcccttcca ggtttagtgg   7740

cagtggatca gggacagatt ttactcttac catcagcagt ctggagcctg aagattttgc   7800

agtgtattac tgtcaacaaa gtaatacctg gccattcacg ttcggccagg ggaccaagct   7860

tgaaatcaaa cgtaagtaga atccaaagtc tctttcttcc gttgtctatg tctgtggctt   7920

ctatgtctaa aaatgatgta taaaatctta ctctgaaacc agattctggc actctccaag   7980

gcaaagatac agagtaactc cgtaagcaaa gctgggaata ggctagacat gttctctgga   8040

gaatgaatgc cagtgtaata attaacacaa gtgatagttt cagaaatgct ctagtt       8096
```

<210> SEQ ID NO 40
<211> LENGTH: 11563
<212> TYPE: DNA
<213> ORGANISM: Artificial
<220> FEATURE:
<223> OTHER INFORMATION: Nucleotide sequence of expression vector HCVHESp20

<400> SEQUENCE: 40

```
ctagagaggt ctggtggagc ctgcaaaagt ccagctttca aaggaacaca gaagtatgtg     60

tatggaatat tagaagatgt tgcttttact cttaagttgg ttcctaggaa aaatagttaa    120

atactgtgac tttaaaatgt gagagggttt tcaagtactc atttttttaa atgtccaaaa    180

tttttgtcaa tcaatttgag gtcttgtttg tgtagaactg acattactta aagtttaacc    240

gaggaatggg agtgaggctc tctcataccc tattcagaac tgacttttaa caataataaa    300

ttaagtttaa aatattttta aatgaattga gcaatgttga gttggagtca agatggccga    360

tcagaaccag aacacctgca gcagctggca ggaagcaggt catgtggcaa ggctatttgg    420

ggaagggaaa ataaaaccac taggtaaact tgtagctgtg gtttgaagaa gtggttttga    480

aacactctgt ccagccccac caaaccgaaa gtccaggctg agcaaaacac cacctgggta    540
```

-continued

```
atttgcattt ctaaaataag ttgaggattc agccgaaact ggagaggtcc tcttttaact    600
tattgagttc aacctttaa ttttagcttg agtagttcta gtttccccaa acttaagttt    660
atcgacttct aaaatgtatt taagctttct ggggcaggcc aggcctgacc ttggctttgg    720
ggcagggagg gggctaaggt gaggcaggtg gcgccagcca ggtgcacacc caatgcccat    780
gagcccagac actggacgct gaacctcgcg gacagttaag aacccagggg cctctgcgcc    840
ctgggcccag ctctgtccca caccgcggtc acatggcacc acctctcttg cagcctccac    900
caagggccca tcggtcttcc ccctggcacc ctcctccaag agcacctctg gggcacagc    960
ggccctgggc tgcctggtca aggactactt ccccgaaccg gtgacggtgt cgtggaactc   1020
aggcgccctg accagcggcg tgcacacctt cccggctgtc ctacagtcct caggactcta   1080
ctccctcagc agcgtggtga ccgtgccctc cagcagcttg ggcacccaga cctacatctg   1140
caacgtgaat cacaagccca gcaacaccaa ggtggacaag agagttggtg agaggccagc   1200
acagggaggg agggtgtctg ctggaagcca ggctcagcgc tcctgcctgg acgcatcccg   1260
gctatgcagt cccagtccag ggcagcaagg caggccccgt ctgcctcttc acccggaggc   1320
ctctgcccgc cccactcatg ctcagggaga gggtcttctg gctttttccc caggctctgg   1380
gcaggcacag gctaggtgcc cctaacccag gccctgcaca caaaggggca ggtgctgggc   1440
tcagacctgc caagagccat atccgggagg accctgcccc tgacctaagc ccaccccaaa   1500
ggccaaactc tccactccct cagctcggac accttctctc ctcccagatt ccagtaactc   1560
ccaatcttct ctctgcagag cccaaatctt gtgacaaaac tcacacatgc ccaccgtgcc   1620
caggtaagcc agcccaggcc tcgccctcca gctcaaggcg ggacaggtgc cctagagtag   1680
cctgcatcca gggacaggcc ccagccgggt gctgacacgt ccacctccat ctcttcctca   1740
gcacctgaac tcctgggggg accgtcagtc ttcctcttcc ccccaaaacc caaggacacc   1800
ctcatgatct cccggacccc tgaggtcaca tgcgtggtgg tggacgtgag ccacgaagac   1860
cctgaggtca agttcaactg gtacgtggac ggcgtggagg tgcataatgc caagacaaag   1920
ccgcgggagg agcagtacaa cagcacgtac cgtgtggtca gcgtcctcac cgtcctgcac   1980
caggactggc tgaatggcaa ggagtacaag tgcaaggtct ccaacaaagc cctcccagcc   2040
cccatcgaga aaaccatctc caaagccaaa ggtgggaccc gtggggtgcg agggccacat   2100
ggacagaggc cggctcggcc caccctctgc cctgagagtg accgctgtac caacctctgt   2160
ccctacaggg cagccccgag aaccacaggt gtacaccctg cccccatccc gggaggagat   2220
gaccaagaac caggtcagcc tgacctgcct ggtcaaaggc ttctatccca gcgacatcgc   2280
cgtggagtgg gagagcaatg ggcagccgga gaacaactac aagaccacgc ctcccgtgct   2340
ggactccgac ggctccttct tcctctatag caagctcacc gtggacaaga gcaggtggca   2400
gcaggggaac gtcttctcat gctccgtgat gcatgaggct ctgcacaacc actacacgca   2460
gaagagcctc tccctgtccc cgggtaaatg agtgcgacgg ccggcaagcc cccgctcccc   2520
gggctctcgc ggtcgcacga ggatgcttgg cacgtacccc gtctacatac ttcccaggca   2580
cccagcatgg aaataaagca cccaccactg ccctgggccc ctgcgagact gtgatggttc   2640
tttccacggg tcaggccgag tctgaggcct gagtggcatg agggaggcag agcgggtccc   2700
actgtcccca cactggccca ggctgtgcag gtgtgcctgg gccgcctagg gtggggctca   2760
gccaggggct gccctcggca gggtggggga tttgccagcg tggccctccc tccagcagca   2820
gctgccctgg gctgggccac gagaagccct aggagcccct ggggacagac acacagcccc   2880
tgcctctgta ggagactgtc ctgtcctgtg agcgccctgt cctccgaccc cgatgcccac   2940
```

-continued

```
tcgggggcat gcctagtcca tgcgcgtagg gacaggccct ccctcaccca tctaccccca   3000
cggcactaac ccctggcagc cctgcccagc ctcgcacccg catggggaca caaccgactc   3060
cggggacatg cactctcggg ccctgtggag ggactggtgc agatgcccac acacacactc   3120
agcccagacc cgttcaacaa accccgcact gaggttggtc gagcgggagt gcggccagag   3180
cctgcctcgg ccgtcaggga ggactcccgg gctcactcga aggaggtgcc accatttcag   3240
ctttggtagc ttttcttctt cttttaaatt ttctaaagct cattaattgt ctttgatgtt   3300
tcttttgtga tgacaataaa atatcctttt taagtcttgt acttcgtgat gggagccgcc   3360
ttcctgtgtc cacgcgcctc ctgcccccgg tgggaagcac ggtcaggagg aggctggtcc   3420
agctgcacct cgggggctcc ctgcactcgc cccccgcctc ctgcagccac acgcattgcc   3480
cgagcgaccc tccctggccc ctgtcactac atggacccct ggggcttctc ctcttttcta   3540
catggatgca gtttctcctc ctgctgggca cggtgctgcc tgccctggtc actctgcggg   3600
ggacagggcc tccagggaaa gctgggtcga ggctgggagc tggctcaggc tggccaggca   3660
gagccacagg gagggccttc cagaaccaac catggtccga agcgagaggt gggtgtcaga   3720
tccagacatg ataagataca ttgatgagtt tggacaaacc acaactagaa tgcagtgaaa   3780
aaaatgcttt atttgtgaaa tttgtgatgc tattgcttta tttgtaacca ttataagctg   3840
caataaacaa gttaacaaca acaattgcat tcattttatg tttcaggttc agggggaggt   3900
gtgggaggtt ttttaaagca agtaaaacct ctacaaatgt ggtatggctg attatgatct   3960
ctagtcaagg cactatacat caaatattcc ttattaaccc ctttacaaat taaaaagcta   4020
aaggtacaca atttttgagc atagttatta atagcagaca ctctatgcct gtgtggagta   4080
agaaaaaaca gtatgttatg attataactg ttatgcctac ttataaaggt tacagaatat   4140
ttttccataa ttttcttgta tagcagtgca gctttttcct ttgtggtgta aatagcaaag   4200
caagcaagag ttctattact aaacacagca tgactcaaaa aacttagcaa ttctgaagga   4260
aagtccttgg ggtcttctac ctttctcttc ttttttggag gagtagaatg ttgagagtca   4320
gcagtagcct catcatcact agatggcatt tcttctgagc aaaacaggtt ttcctcatta   4380
aaggcattcc accactgctc ccattcatca gttccatagg ttggaatcta aaatacacaa   4440
acaattagaa tcagtagttt aacacattat acacttaaaa attttatatt taccttagag   4500
ctttaaatct ctgtaggtag tttgtccaat tatgtcacac cacagaagta aggttccttc   4560
acaaagatcc ggaccaaagc ggccatcgtg cctccccact cctgcagttc gggggcatgg   4620
atgcgcggat agccgctgct ggtttcctgg atgccgacgg atttgcactg ccggtagaac   4680
tccgcgaggt cgtccagcct caggcagcag ctgaaccaac tcgcgagggg atcgagcccg   4740
gggtgggcga agaactccag catgagatcc ccgcgctgga ggatcatcca gccggcgtcc   4800
cggaaaacga ttccgaagcc caacctttca tagaaggcgg cggtggaatc gaaatctcgt   4860
gatggcaggt tgggcgtcgc ttggtcggtc atttcgaacc ccagagtccc gctcagaaga   4920
actcgtcaag aaggcgatag aaggcgatgc gctgcgaatc gggagcggcg ataccgtaaa   4980
gcacgaggaa gcggtcagcc cattcgccgc caagctcttc agcaatatca cgggtagcca   5040
acgctatgtc ctgatagcgg tccgccacac ccagccggcc acagtcgatg aatccagaaa   5100
agcggccatt ttccaccatg atattcggca agcaggcatc gccatgggtc acgacgagat   5160
cctcgccgtc gggcatgcgc gccttgagcc tggcgaacag ttcggctggc gcgagcccct   5220
gatgctcttc gtccagatca tcctgatcga caagaccggc ttccatccga gtacgtgctc   5280
```

-continued

```
gctcgatgcg atgtttcgct tggtggtcga atgggcaggt agccggatca agcgtatgca   5340
gccgccgcat tgcatcagcc atgatggata ctttctcggc aggagcaagg tgagatgaca   5400
ggagatcctg ccccggcact tcgcccaata gcagccagtc ccttcccgct tcagtgacaa   5460
cgtcgagcac agctgcgcaa ggaacgcccg tcgtggccag ccacgatagc cgcgctgcct   5520
cgtcctgcag ttcattcagg gcaccggaca ggtcggtctt gacaaaaaga accgggcgcc   5580
cctgcgctga cagccggaac acggcggcat cagagcagcc gattgtctgt tgtgcccagt   5640
catagccgaa tagcctctcc acccaagcgg ccggagaacc tgcgtgcaat ccatcttgtt   5700
caatcatgcg aaacgatcct catcctgtct cttgatcaga tcttgatccc ctgcgccatc   5760
agatccttgg cggcaagaaa gccatccagt ttactttgca gggcttccca accttaccag   5820
agggcgcccc agctggcaat tccggttcgc ttgctgtcca taaaaccgcc cagtctagct   5880
atcgccatgt aagcccactg caagctacct gctttctctt tgcgcttgcg ttttcccttg   5940
tccagatagc ccagtagctg acattcatcc ggggtcagca ccgtttctgc ggactggctt   6000
tctacgtgtt ccgcttcctt tagcagccct tgcgccctga gtgcttgcgg cagcgtgaag   6060
ctttttgcaa aagcctaggc ctccaaaaaa gcctcctcac tacttctgga atagctcaga   6120
ggccgaggcg gcctcggcct ctgcataaat aaaaaaaatt agtcagccat ggggcggaga   6180
atgggcggaa ctgggcggag ttaggggcgg gatgggcgga gttaggggcg ggactatggt   6240
tgctgactaa ttgagatgca tgctttgcat acttctgcct gctggggagc ctggggactt   6300
tccacacctg gttgctgact aattgagatg catgctttgc atacttctgc ctgctgggga   6360
gcctggggac tttccacacc ctaactgaca cacattccac agctgcctcg cgcgtttcgg   6420
tgatgacggt gaaaacctct gacacatgca gctcccggag acggtcacag cttgtctgta   6480
agcggatgcc gggagcagac aagcccgtca gggcgcgtca gcgggtgttg gcgggtgtcg   6540
gggcgcagcc atgacccagt cacgtagcga tagcggagtg tatactggct taactatgcg   6600
gcatcagagc agattgtact gagagtgcac catatgcggt gtgaaatacc gcacagatgc   6660
gtaaggagaa aataccgcat caggcgctct tccgcttcct cgctcactga ctcgctgcgc   6720
tcggtcgttc ggctgcggcg agcggtatca gctcactcaa aggcggtaat acggttatcc   6780
acagaatcag gggataacgc aggaaagaac atgtgagcaa aaggccagca aaaggccagg   6840
aaccgtaaaa aggccgcgtt gctggcgttt ttccataggc tccgcccccc tgacgagcat   6900
cacaaaaatc gacgctcaag tcagaggtgg cgaaacccga caggactata aagataccag   6960
gcgtttcccc ctggaagctc cctcgtgcgc tctcctgttc cgaccctgcc gcttaccgga   7020
tacctgtccg cctttctccc ttcgggaagc gtggcgcttt ctcatagctc acgctgtagg   7080
tatctcagtt cggtgtaggt cgttcgctcc aagctgggct gtgtgcacga accccccgtt   7140
cagcccgacc gctgcgcctt atccggtaac tatcgtcttg agtccaaccc ggtaagacac   7200
gacttatcgc cactggcagc agccactggt aacaggatta gcagagcgag gtatgtaggc   7260
ggtgctacag agttcttgaa gtggtggcct aactacggct acactagaag gacagtattt   7320
ggtatctgcg ctctgctgaa gccagttacc ttcggaaaaa gagttggtag ctcttgatcc   7380
ggcaaacaaa ccaccgctgg tagcggtggt ttttttgttt gcaagcagca gattacgcgc   7440
agaaaaaaag gatctcaaga agatcctttg atcttttcta cggggtctga cgctcagtgg   7500
aacgaaaact cacgttaagg gattttggtc atgagattat caaaaaggat cttcacctag   7560
atccttttaa attaaaaatg aagttttaaa tcaatctaaa gtatatatga gtaaacttgg   7620
tctgacagtt accaatgctt aatcagtgag gcacctatct cagcgatctg tctatttcgt   7680
```

-continued

```
tcatccatag ttgcctgact ccccgtcgtg tagataacta cgatacggga gggcttacca   7740
tctggcccca gtgctgcaat gataccgcga gacccacgct caccggctcc agatttatca   7800
gcaataaacc agccagccgg aagggccgag cgcagaagtg gtcctgcaac tttatccgcc   7860
tccatccagt ctattaattg ttgccgggaa gctagagtaa gtagttcgcc agttaatagt   7920
ttgcgcaacg ttgttgccat tgctgcaggc atcgtggtgt cacgctcgtc gtttggtatg   7980
gcttcattca gctccggttc ccaacgatca aggcgagtta catgatcccc catgttgtgc   8040
aaaaaagcgg ttagctcctt cggtcctccg atcgttgtca gaagtaagtt ggccgcagtg   8100
ttatcactca tggttatggc agcactgcat aattctctta ctgtcatgcc atccgtaaga   8160
tgcttttctg tgactggtga gtactcaacc aagtcattct gagaatagtg tatgcggcga   8220
ccgagttgct cttgcccggc gtcaacacgg gataataccg cgccacatag cagaacttta   8280
aaagtgctca tcattggaaa acgttcttcg gggcgaaaac tctcaaggat cttaccgctg   8340
ttgagatcca gttcgatgta acccactcgt gcacccaact gatcttcagc atcttttact   8400
ttcaccagcg tttctgggtg agcaaaaaca ggaaggcaaa atgccgcaaa aaagggaata   8460
agggcgacac ggaaatgttg aatactcata ctcttccttt ttcaatatta ttgaagcatt   8520
tatcagggtt attgtctcat gagcggatac atatttgaat gtatttagaa aaataaacaa   8580
ataggggttc cgcgcacatt tccccgaaaa gtgccacctg acgtctaaga aaccattatt   8640
atcatgacat taacctataa aaataggcgt atcacgaggc cctttcgtct tcaagaattc   8700
gagctcggta cccatcagcc aaaaagcatg cctgccacac aacatcaatt tctggaaaac   8760
gctacactta attatttcta gtagaacagc tctttggttt gccaaaaaga atcacctata   8820
gtggcatcta agcacaaaaa ggagaaaaaa atcacaaaga aatgattgag aggcataata   8880
aaaattatca aaaaattatg agttttacga tttcatcttt ttccaagttg aaatcatagg   8940
gtggctttaa cacagtgaca aggaatgtgc atgctgccat tatggtgctc tgcctaaaat   9000
ggttggagcc ttgtcatgct acagagaaac tgtcatacag caggggggtgc caaatttcca   9060
tattttttta tatcattgag caggtgcaca gaagaccaga aagcactttc tatcaggctg   9120
gccttcctct tcctttccag tatgaagcaa aaactgccaa tgaaactagc aattgttaaa   9180
ttcctttttc aaacagtatt tgtgctatca gaacatagtg cattcaaaag tctagcctga   9240
gagaacaacc cagttttatt cattcctcct actacctctc tcattcccac tgtttgtgtt   9300
ctccctccca ttttaattgt ctatctagtc caaactaagc acacgatcca gtccacatta   9360
aacaacatgt tttcacttta agtcaaatac aagacacctt taatatcagc ccttgttcat   9420
aatcgtgctt ctagtgactt aatgtacatg tcacactgta ctgttgggtt ttgtgtctca   9480
tcatgaacaa tgttgtgaag gtattaagtg gagagtaagc agaattagat tcctctaatg   9540
atgcacaccc acactaagag cagaaataat attaaaaata gaaaaaaaag ttttacatga   9600
gatttcaaat acccaggtat gagctgcagt ttcttcaagt taaagcatcg aggttgtcag   9660
ttacactatt acaggaaaca tatgcagagt ttttatttta gtatattagt tttcacatat   9720
gtggaattac tattaaacta ttctttcttt tcaaatgctt accattgtaa atgagtttgt   9780
gactttgtgt aggtgagtgc acatgactct ggatgcctaa gaggactgaa gaagttggag   9840
ttataggtag ttttattcta cttgactgtt cagtgctaaa aatacaactg aggtccttta   9900
aactgctgtt catgaacttc ttaattgata tatctcatga gatctctaaa ctatttttat   9960
tatgacacgt ttcaccattt tcactgtaac gatttttatg ttttatatta atgtaactat  10020
```

-continued

```
atgacacttc ccaaaatccc catattcaca attgaactgt ttcaaagttt taccttgact  10080

tatgggaaat gaaaacccac attttataat tttaaaatga aatgtttatt ttatatttct  10140

gcaaatttca caaggaaaga ttagtcactg gtgtgtgaga gcagaggagc ataagagttc  10200

aggaatagaa tccattatga ttctggaggc aaggaagaac tgatgccaag gtttcagtat  10260

aagagcagta tccactggaa aggataaagt cactacatct gagcacagag caggacatct  10320

acataatgag tggtcactaa tgggccactg ttacactgtt atatgtataa ggctcaagaa  10380

tgagcactga ggctgtaagg tgtatgggtg aggacatcag gatgtaaacc cagctcaggt  10440

agaggactca gaggacagca cagtcagcat gaactaataa acatcagata agataaggca  10500

caagctcagc tatatagggt aagggatctt tgtaaatctg attgtgcatc cagtctagtt  10560

caatgtgact taggaagccc agtcatatgc aaatctagag aagactttag agtagaaatc  10620

tgaggctcac ctcacatacc agcaagcgag tgaccagtta gtcttaaggc accacttctt  10680

agacatcatg gcttgggtgt ggaccttgcc attcctgatg gcagctgccc aaagtaagac  10740

atcagaaaaa agagttccaa ggggaattga agcagttcca tgaatactca ccttcctgtg  10800

ttcttttcac aggtgtccag gcagaggtgc agctggtgga gtcaggagcc gaagtgaaaa  10860

agcctggggc ttcagtgaag gtgtcctgca aggcctctgg atacacattc actaattata  10920

ttatccactg ggtgaagcag gagcctggtc agggccttga atggattgga tattttaatc  10980

cttacaatca tggtactaag tacaatgaga agttcaaagg cagggccaca ctaactgcaa  11040

acaaatccat cagcacagcc tacatggagc tcagcagcct gcgctctgag gacactgcgg  11100

tctactactg tgcaagatca ggaccctatg cctggtttga cacctggggc caagggacca  11160

cggtcaccgt ctcctcaggt aagaatggcc actctagggc ctttgttttc tgctgctgcc  11220

tgtgggattt catgagcatt gcaaagttgt cctcgggaca tgttccgagg ggacctgggc  11280

ggactggcca ggaggggacg ggcactgggg tgccttgagg atctgggagc ctctgtggat  11340

tttccgatgc ctttggaaaa tgggactgag gttgggtgcg tctgagacag taactcagcc  11400

tgggggcttg gtgaagatcg ccgcacagca gcgagtccgt gaaatatctt atttagactt  11460

gtgaggtgcg ctgtgtgtca atttacatct taaatccttt attggctgga aagagaattg  11520

ttggagtggg tgaatccagc caggagggac gcggggggat cca                    11563
```

<210> SEQ ID NO 41
<211> LENGTH: 11563
<212> TYPE: DNA
<213> ORGANISM: Artificial
<220> FEATURE:
<223> OTHER INFORMATION: Nucleotide sequence of expression vector HCVHQSp20

<400> SEQUENCE: 41

```
ctagagaggt ctggtggagc ctgcaaaagt ccagctttca aaggaacaca gaagtatgtg     60

tatggaatat tagaagatgt tgcttttact cttaagttgg ttcctaggaa aaatagttaa    120

atactgtgac tttaaaatgt gagagggttt tcaagtactc atttttttaa atgtccaaaa    180

tttttgtcaa tcaatttgag gtcttgtttg tgtagaactg acattactta aagtttaacc    240

gaggaatggg agtgaggctc tctcataccc tattcagaac tgacttttaa caataataaa    300

ttaagtttaa aatattttta aatgaattga gcaatgttga gttggagtca agatggccga    360

tcagaaccag aacacctgca gcagctggca ggaagcaggt catgtggcaa ggctatttgg    420

ggaagggaaa ataaaaccac taggtaaact tgtagctgtg gtttgaagaa gtggttttga    480
```

-continued

```
aacactctgt ccagccccac caaaccgaaa gtccaggctg agcaaaacac cacctgggta    540
atttgcattt ctaaaataag ttgaggattc agccgaaact ggagaggtcc tcttttaact    600
tattgagttc aacctttttaa ttttagcttg agtagttcta gtttccccaa acttaagttt    660
atcgacttct aaaatgtatt taagctttct ggggcaggcc aggcctgacc ttggctttgg    720
ggcagggagg gggctaaggt gaggcaggtg gcgccagcca ggtgcacacc caatgcccat    780
gagcccagac actggacgct gaacctcgcg gacagttaag aacccagggg cctctgcgcc    840
ctgggcccag ctctgtccca caccgcggtc acatggcacc acctctcttg cagcctccac    900
caagggccca tcggtcttcc ccctggcacc ctcctccaag agcacctctg ggggcacagc    960
ggccctgggc tgcctggtca aggactactt ccccgaaccg gtgacggtgt cgtggaactc   1020
aggcgccctg accagcggcg tgcacacctt cccggctgtc ctacagtcct caggactcta   1080
ctccctcagc agcgtggtga ccgtgccctc cagcagcttg ggcacccaga cctacatctg   1140
caacgtgaat cacaagccca gcaacaccaa ggtggacaag agagttggtg agaggccagc   1200
acagggaggg agggtgtctg ctggaagcca ggctcagcgc tcctgcctgg acgcatcccg   1260
gctatgcagt cccagtccag ggcagcaagg caggccccgt ctgcctcttc acccggaggc   1320
ctctgcccgc cccactcatg ctcagggaga gggtcttctg gctttttccc caggctctgg   1380
gcaggcacag gctaggtgcc cctaacccag gccctgcaca caaaggggca ggtgctgggc   1440
tcagacctgc caagagccat atccgggagg accctgcccc tgacctaagc ccaccccaaa   1500
ggccaaactc tccactccct cagctcggac accttctctc ctcccagatt ccagtaactc   1560
ccaatcttct ctctgcagag cccaaatctt gtgacaaaac tcacacatgc ccaccgtgcc   1620
caggtaagcc agcccaggcc tcgccctcca gctcaaggcg ggacaggtgc cctagagtag   1680
cctgcatcca gggacaggcc ccagccgggt gctgacacgt ccacctccat ctcttcctca   1740
gcacctgaac tcctgggggg accgtcagtc ttcctcttcc ccccaaaacc caaggacacc   1800
ctcatgatct cccggacccc tgaggtcaca tgcgtggtgg tggacgtgag ccacgaagac   1860
cctgaggtca agttcaactg gtacgtggac ggcgtggagg tgcataatgc caagacaaag   1920
ccgcgggagg agcagtacaa cagcacgtac cgtgtggtca gcgtcctcac cgtcctgcac   1980
caggactggc tgaatggcaa ggagtacaag tgcaaggtct ccaacaaagc cctcccagcc   2040
cccatcgaga aaaccatctc caaagccaaa ggtgggaccc gtggggtgcg agggccacat   2100
ggacagaggc cggctcggcc caccctctgc cctgagagtg accgctgtac caacctctgt   2160
ccctacaggg cagccccgag aaccacaggt gtacaccctg cccccatccc gggaggagat   2220
gaccaagaac caggtcagcc tgacctgcct ggtcaaaggc ttctatccca gcgacatcgc   2280
cgtggagtgg gagagcaatg ggcagccgga gaacaactac aagaccacgc ctcccgtgct   2340
ggactccgac ggctccttct tcctctatag caagctcacc gtggacaaga gcaggtggca   2400
gcaggggaac gtcttctcat gctccgtgat gcatgaggct ctgcacaacc actacacgca   2460
gaagagcctc tccctgtccc cgggtaaatg agtgcgacgg ccggcaagcc cccgctcccc   2520
gggctctcgc ggtcgcacga ggatgcttgg cacgtacccc gtctacatac ttcccaggca   2580
cccagcatgg aaataaagca cccaccactg ccctgggccc ctgcgagact gtgatggttc   2640
tttccacggg tcaggccgag tctgaggcct gagtggcatg agggaggcag agcgggtccc   2700
actgtcccca cactggccca ggctgtgcag gtgtgcctgg gccgcctagg gtggggctca   2760
gccaggggct gccctcggca gggtggggga tttgccagcg tggccctccc tccagcagca   2820
gctgccctgg gctgggccac gagaagccct aggagcccct ggggacagac acacagcccc   2880
```

-continued

```
tgcctctgta ggagactgtc ctgtcctgtg agcgccctgt cctccgaccc cgatgcccac   2940
tcgggggcat gcctagtcca tgcgcgtagg gacaggccct ccctcaccca tctacccccca   3000
cggcactaac ccctggcagc cctgcccagc ctcgcacccg catggggaca caaccgactc   3060
cggggacatg cactctcggg ccctgtggag ggactggtgc agatgcccac acacacactc   3120
agcccagacc cgttcaacaa accccgcact gaggttggtc gagcgggagt gcggccagag   3180
cctgcctcgg ccgtcaggga ggactcccgg gctcactcga aggaggtgcc accatttcag   3240
ctttggtagc ttttcttctt cttttaaatt ttctaaagct cattaattgt ctttgatgtt   3300
tcttttgtga tgacaataaa atatcctttt taagtcttgt acttcgtgat gggagccgcc   3360
ttcctgtgtc cacgcgcctc ctgcccccgg tgggaagcac ggtcaggagg aggctggtcc   3420
agctgcacct cgggggctcc ctgcactcgc cccccgcctc ctgcagccac acgcattgcc   3480
cgagcgaccc tccctggccc ctgtcactac atggacccct ggggcttctc ctcttttcta   3540
catggatgca gtttctcctc ctgctgggca cggtgctgcc tgccctggtc actctgcggg   3600
ggacagggcc tccagggaaa gctgggtcga ggctgggagc tggctcaggc tggccaggca   3660
gagccacagg gagggccttc cagaaccaac catggtccga agcgagaggt gggtgtcaga   3720
tccagacatg ataagataca ttgatgagtt tggacaaacc acaactagaa tgcagtgaaa   3780
aaaatgcttt atttgtgaaa tttgtgatgc tattgcttta tttgtaacca ttataagctg   3840
caataaacaa gttaacaaca acaattgcat tcattttatg tttcaggttc agggggaggt   3900
gtgggaggtt ttttaaagca agtaaaacct ctacaaatgt ggtatggctg attatgatct   3960
ctagtcaagg cactatacat caaatattcc ttattaaccc ctttacaaat taaaaagcta   4020
aaggtacaca atttttgagc atagttatta atagcagaca ctctatgcct gtgtggagta   4080
agaaaaaaca gtatgttatg attataactg ttatgcctac ttataaaggt tacagaatat   4140
ttttccataa ttttcttgta tagcagtgca gctttttcct ttgtggtgta aatagcaaag   4200
caagcaagag ttctattact aaacacagca tgactcaaaa aacttagcaa ttctgaagga   4260
aagtccttgg ggtcttctac ctttctcttc ttttttggag gagtagaatg ttgagagtca   4320
gcagtagcct catcatcact agatggcatt tcttctgagc aaaacaggtt ttcctcatta   4380
aaggcattcc accactgctc ccattcatca gttccatagg ttggaatcta aaatacacaa   4440
acaattagaa tcagtagttt aacacattat acacttaaaa attttatatt taccttagag   4500
ctttaaatct ctgtaggtag tttgtccaat tatgtcacac cacagaagta aggttccttc   4560
acaaagatcc ggaccaaagc ggccatcgtg cctccccact cctgcagttc gggggcatgg   4620
atgcgcggat agccgctgct ggtttcctgg atgccgacgg atttgcactg ccggtagaac   4680
tccgcgaggt cgtccagcct caggcagcag ctgaaccaac tcgcgagggg atcgagcccg   4740
gggtgggcga agaactccag catgagatcc ccgcgctgga ggatcatcca gccggcgtcc   4800
cggaaaacga ttccgaagcc caacctttca tagaaggcgg cggtggaatc gaaatctcgt   4860
gatggcaggt tgggcgtcgc ttggtcggtc atttcgaacc ccagagtccc gctcagaaga   4920
actcgtcaag aaggcgatag aaggcgatgc gctgcgaatc gggagcggcg ataccgtaaa   4980
gcacgaggaa gcggtcagcc cattcgccgc caagctcttc agcaatatca cgggtagcca   5040
acgctatgtc ctgatagcgg tccgccacac ccagccggcc acagtcgatg aatccagaaa   5100
agcggccatt ttccaccatg atattcggca agcaggcatc gccatgggtc acgacgagat   5160
cctcgccgtc gggcatgcgc gccttgagcc tggcgaacag ttcggctggc gcgagcccct   5220
```

-continued

```
gatgctcttc gtccagatca tcctgatcga caagaccggc ttccatccga gtacgtgctc   5280

gctcgatgcg atgtttcgct tggtggtcga atgggcaggt agccggatca agcgtatgca   5340

gccgccgcat tgcatcagcc atgatggata ctttctcggc aggagcaagg tgagatgaca   5400

ggagatcctg ccccggcact tcgcccaata gcagccagtc ccttcccgct tcagtgacaa   5460

cgtcgagcac agctgcgcaa ggaacgcccg tcgtggccag ccacgatagc cgcgctgcct   5520

cgtcctgcag ttcattcagg gcaccggaca ggtcggtctt gacaaaaaga accgggcgcc   5580

cctgcgctga cagccggaac acggcggcat cagagcagcc gattgtctgt tgtgcccagt   5640

catagccgaa tagcctctcc acccaagcgg ccggagaacc tgcgtgcaat ccatcttgtt   5700

caatcatgcg aaacgatcct catcctgtct cttgatcaga tcttgatccc ctgcgccatc   5760

agatccttgg cggcaagaaa gccatccagt ttactttgca gggcttccca accttaccag   5820

agggcgcccc agctggcaat tccggttcgc ttgctgtcca taaaaccgcc cagtctagct   5880

atcgccatgt aagcccactg caagctacct gctttctctt tgcgcttgcg ttttcccttg   5940

tccagatagc ccagtagctg acattcatcc ggggtcagca ccgtttctgc ggactggctt   6000

tctacgtgtt ccgcttcctt tagcagccct tgcgccctga gtgcttgcgg cagcgtgaag   6060

ctttttgcaa aagcctaggc ctccaaaaaa gcctcctcac tacttctgga atagctcaga   6120

ggccgaggcg gcctcggcct ctgcataaat aaaaaaaatt agtcagccat ggggcggaga   6180

atgggcggaa ctgggcggag ttaggggcgg gatgggcgga gttaggggcg ggactatggt   6240

tgctgactaa ttgagatgca tgctttgcat acttctgcct gctggggagc ctggggactt   6300

tccacacctg gttgctgact aattgagatg catgctttgc atacttctgc ctgctgggga   6360

gcctggggac tttccacacc ctaactgaca cacattccac agctgcctcg cgcgtttcgg   6420

tgatgacggt gaaaacctct gacacatgca gctcccggag acggtcacag cttgtctgta   6480

agcggatgcc gggagcagac aagcccgtca gggcgcgtca gcgggtgttg gcgggtgtcg   6540

gggcgcagcc atgacccagt cacgtagcga tagcggagtg tatactggct taactatgcg   6600

gcatcagagc agattgtact gagagtgcac catatgcggt gtgaaatacc gcacagatgc   6660

gtaaggagaa aataccgcat caggcgctct tccgcttcct cgctcactga ctcgctgcgc   6720

tcggtcgttc ggctgcggcg agcggtatca gctcactcaa aggcggtaat acggttatcc   6780

acagaatcag gggataacgc aggaaagaac atgtgagcaa aaggccagca aaaggccagg   6840

aaccgtaaaa aggccgcgtt gctggcgttt ttccataggc tccgcccccc tgacgagcat   6900

cacaaaaatc gacgctcaag tcagaggtgg cgaaacccga caggactata aagataccag   6960

gcgtttcccc ctggaagctc cctcgtgcgc tctcctgttc cgaccctgcc gcttaccgga   7020

tacctgtccg cctttctccc ttcgggaagc gtggcgcttt ctcatagctc acgctgtagg   7080

tatctcagtt cggtgtaggt cgttcgctcc aagctgggct gtgtgcacga accccccgtt   7140

cagcccgacc gctgcgcctt atccggtaac tatcgtcttg agtccaaccc ggtaagacac   7200

gacttatcgc cactggcagc agccactggt aacaggatta gcagagcgag gtatgtaggc   7260

ggtgctacag agttcttgaa gtggtggcct aactacggct acactagaag gacagtattt   7320

ggtatctgcg ctctgctgaa gccagttacc ttcggaaaaa gagttggtag ctcttgatcc   7380

ggcaaacaaa ccaccgctgg tagcggtggt ttttttgttt gcaagcagca gattacgcgc   7440

agaaaaaaag gatctcaaga agatcctttg atcttttcta cggggtctga cgctcagtgg   7500

aacgaaaact cacgttaagg gattttggtc atgagattat caaaaaggat cttcacctag   7560

atccttttaa attaaaaatg aagttttaaa tcaatctaaa gtatatatga gtaaacttgg   7620
```

-continued

```
tctgacagtt accaatgctt aatcagtgag gcacctatct cagcgatctg tctatttcgt   7680
tcatccatag ttgcctgact ccccgtcgtg tagataacta cgatacggga gggcttacca   7740
tctggcccca gtgctgcaat gataccgcga gacccacgct caccggctcc agatttatca   7800
gcaataaacc agccagccgg aagggccgag cgcagaagtg gtcctgcaac tttatccgcc   7860
tccatccagt ctattaattg ttgccgggaa gctagagtaa gtagttcgcc agttaatagt   7920
ttgcgcaacg ttgttgccat tgctgcaggc atcgtggtgt cacgctcgtc gtttggtatg   7980
gcttcattca gctccggttc ccaacgatca aggcgagtta catgatcccc catgttgtgc   8040
aaaaaagcgg ttagctcctt cggtcctccg atcgttgtca gaagtaagtt ggccgcagtg   8100
ttatcactca tggttatggc agcactgcat aattctctta ctgtcatgcc atccgtaaga   8160
tgcttttctg tgactggtga gtactcaacc aagtcattct gagaatagtg tatgcggcga   8220
ccgagttgct cttgcccggc gtcaacacgg gataataccg cgccacatag cagaacttta   8280
aaagtgctca tcattggaaa acgttcttcg gggcgaaaac tctcaaggat cttaccgctg   8340
ttgagatcca gttcgatgta acccactcgt gcacccaact gatcttcagc atcttttact   8400
ttcaccagcg tttctgggtg agcaaaaaca ggaaggcaaa atgccgcaaa aaagggaata   8460
agggcgacac ggaaatgttg aatactcata ctcttccttt ttcaatatta ttgaagcatt   8520
tatcagggtt attgtctcat gagcggatac atatttgaat gtatttagaa aaataaacaa   8580
ataggggttc cgcgcacatt tccccgaaaa gtgccacctg acgtctaaga aaccattatt   8640
atcatgacat taacctataa aaataggcgt atcacgaggc cctttcgtct tcaagaattc   8700
gagctcggta cccatcagcc aaaaagcatg cctgccacac aacatcaatt tctggaaaac   8760
gctacactta attatttcta gtagaacagc tctttggttt gccaaaaaga atcacctata   8820
gtggcatcta agcacaaaaa ggagaaaaaa atcacaaaga aatgattgag aggcataata   8880
aaaattatca aaaaattatg agttttacga tttcatcttt ttccaagttg aaatcatagg   8940
gtggctttaa cacagtgaca aggaatgtgc atgctgccat tatggtgctc tgcctaaaat   9000
ggttggagcc ttgtcatgct acagagaaac tgtcatacag caggggggtgc caaatttcca   9060
tatttttttta tatcattgag caggtgcaca gaagaccaga aagcactttc tatcaggctg   9120
gccttcctct tcctttccag tatgaagcaa aaactgccaa tgaaactagc aattgttaaa   9180
ttcctttttc aaacagtatt tgtgctatca gaacatagtg cattcaaaag tctagcctga   9240
gagaacaacc cagttttatt cattcctcct actacctctc tcattcccac tgtttgtgtt   9300
ctccctccca ttttaattgt ctatctagtc caaactaagc acacgatcca gtccacatta   9360
aacaacatgt tttcacttta agtcaaatac aagacacctt taatatcagc ccttgttcat   9420
aatcgtgctt ctagtgactt aatgtacatg tcacactgta ctgttgggtt ttgtgtctca   9480
tcatgaacaa tgttgtgaag gtattaagtg gagagtaagc agaattagat tcctctaatg   9540
atgcacaccc acactaagag cagaaataat attaaaaata gaaaaaaaag ttttacatga   9600
gatttcaaat acccaggtat gagctgcagt ttcttcaagt taaagcatcg aggttgtcag   9660
ttacactatt acaggaaaca tatgcagagt ttttatttta gtatattagt tttcacatat   9720
gtggaattac tattaaacta ttctttcttt tcaaatgctt accattgtaa atgagtttgt   9780
gactttgtgt aggtgagtgc acatgactct ggatgcctaa gaggactgaa gaagttggag   9840
ttataggtag ttttattcta cttgactgtt cagtgctaaa aatacaactg aggtccttta   9900
aactgctgtt catgaacttc ttaattgata tatctcatga gatctctaaa ctatttttat   9960
```

-continued

```
tatgacacgt ttcaccattt tcactgtaac gatttttatg ttttatatta atgtaactat  10020

atgacacttc ccaaaatccc catattcaca attgaactgt ttcaaagttt taccttgact  10080

tatgggaaat gaaaacccac attttataat tttaaaatga aatgtttatt ttatatttct  10140

gcaaatttca caaggaaaga ttagtcactg gtgtgtgaga gcagaggagc ataagagttc  10200

aggaatagaa tccattatga ttctggaggc aaggaagaac tgatgccaag gtttcagtat  10260

aagagcagta tccactggaa aggataaagt cactacatct gagcacagag caggacatct  10320

acataatgag tggtcactaa tgggccactg ttacactgtt atatgtataa ggctcaagaa  10380

tgagcactga ggctgtaagg tgtatgggtg aggacatcag gatgtaaacc cagctcaggt  10440

agaggactca gaggacagca cagtcagcat gaactaataa acatcagata agataaggca  10500

caagctcagc tatatagggt aagggatctt tgtaaatctg attgtgcatc cagtctagtt  10560

caatgtgact taggaagccc agtcatatgc aaatctagag aagactttag agtagaaatc  10620

tgaggctcac ctcacatacc agcaagcgag tgaccagtta gtcttaaggc accacttctt  10680

agacatcatg gcttgggtgt ggaccttgcc attcctgatg gcagctgccc aaagtaagac  10740

atcagaaaaa agagttccaa ggggaattga agcagttcca tgaatactca ccttcctgtg  10800

ttcttttcac aggtgtccag gcacaggtgc agctggtgga gtcaggagcc gaagtgaaaa  10860

agcctggggc ttcagtgaag gtgtcctgca aggcctctgg atacacattc actaattata  10920

ttatccactg ggtgaagcag gagcctggtc agggccttga atggattgga tattttaatc  10980

cttacaatca tggtactaag tacaatgaga agttcaaagg cagggccaca ctaactgcaa  11040

acaaatccat cagcacagcc tacatggagc tcagcagcct gcgctctgag gacactgcgg  11100

tctactactg tgcaagatca ggaccctatg cctggtttga cacctggggc caagggacca  11160

cggtcaccgt ctcctcaggt aagaatggcc actctagggc ctttgttttc tgctgctgcc  11220

tgtgggattt catgagcatt gcaaagttgt cctcgggaca tgttccgagg ggacctgggc  11280

ggactggcca ggaggggacg ggcactgggg tgccttgagg atctgggagc ctctgtggat  11340

tttccgatgc ctttggaaaa tgggactgag gttgggtgcg tctgagacag taactcagcc  11400

tgggggcttg gtgaagatcg ccgcacagca gcgagtccgt gaaatatctt atttagactt  11460

gtgaggtgcg ctgtgtgtca atttacatct taaatccttt attggctgga aagagaattg  11520

ttggagtggg tgaatccagc caggagggac gcggggggat cca                   11563
```

<210> SEQ ID NO 42
<211> LENGTH: 33
<212> TYPE: DNA
<213> ORGANISM: Artificial
<220> FEATURE:
<223> OTHER INFORMATION: HuCD45LC-Mlu Primer

<400> SEQUENCE: 42

```
aaaacgcgtt gtgacattct gctgacccag tct                                 33
```

<210> SEQ ID NO 43
<211> LENGTH: 31
<212> TYPE: DNA
<213> ORGANISM: Artificial
<220> FEATURE:
<223> OTHER INFORMATION: HuCD45LC-Hind Primer

<400> SEQUENCE: 43

```
aaaaaagctt ggtcccctgg ccgaacgtga a                                   31
```

-continued

<210> SEQ ID NO 44
<211> LENGTH: 27
<212> TYPE: DNA
<213> ORGANISM: Artificial
<220> FEATURE:
<223> OTHER INFORMATION: HuCD45HCEup Primer

<400> SEQUENCE: 44
caggcagagg tgcagctggt ggagtca 27

<210> SEQ ID NO 45
<211> LENGTH: 27
<212> TYPE: DNA
<213> ORGANISM: Artificial
<220> FEATURE:
<223> OTHER INFORMATION: HuCD45HCQup Primer

<400> SEQUENCE: 45
caggcacagg tgcagctggt ggagtca 27

<210> SEQ ID NO 46
<211> LENGTH: 29
<212> TYPE: DNA
<213> ORGANISM: Artificial
<220> FEATURE:
<223> OTHER INFORMATION: HuCD45HClo Primer

<400> SEQUENCE: 46
aaatccttct agaactcacc tgaggagac 29

<210> SEQ ID NO 47
<211> LENGTH: 20
<212> TYPE: PRT
<213> ORGANISM: Artificial
<220> FEATURE:
<223> OTHER INFORMATION: Leader Sequence

<400> SEQUENCE: 47

```
Met Asp Trp Thr Trp Arg Val Phe Cys Leu Leu Ala Val Val Ala Pro
1               5                   10                  15

Gly Ala His Ser
            20
```

<210> SEQ ID NO 48
<211> LENGTH: 19
<212> TYPE: PRT
<213> ORGANISM: Artificial
<220> FEATURE:
<223> OTHER INFORMATION: Leader Sequence

<400> SEQUENCE: 48

```
Met Ala Trp Val Trp Thr Leu Pro Phe Leu Met Ala Ala Ala Gln Ser
1               5                   10                  15

Val Gln Ala
```

<210> SEQ ID NO 49
<211> LENGTH: 35
<212> TYPE: DNA
<213> ORGANISM: Artificial
<220> FEATURE:
<223> OTHER INFORMATION: aCD45H-N73D Primer

<400> SEQUENCE: 49
gccacactaa ctgcagacaa atccatcagc acagc 35